United States Patent
Deaton et al.

(10) Patent No.: US 11,149,035 B2
(45) Date of Patent: Oct. 19, 2021

(54) CHEMICAL COMPOUNDS AS H—PGDS INHIBITORS

(71) Applicant: GlaxoSmithKline Intellectual Property Development Limited, Middlesex (GB)

(72) Inventors: David Norman Deaton, Collegeville, PA (US); Barry George Shearer, Collegeville, PA (US); Mark Andrew Youngman, Collegeville, PA (US)

(73) Assignee: GLAXOSMITHKLINE INTELLECTUAL PROPERTY DFVELOPMENT LIMITED, Middlesex (GB)

( * ) Notice: Subject to any disclaimer, the term of this patent is extended or adjusted under 35 U.S.C. 154(b) by 0 days.

(21) Appl. No.: 16/621,927

(22) PCT Filed: Jun. 11, 2018

(86) PCT No.: PCT/IB2018/054206
§ 371 (c)(1),
(2) Date: Dec. 12, 2019

(87) PCT Pub. No.: WO2018/229629
PCT Pub. Date: Dec. 20, 2018

(65) Prior Publication Data
US 2020/0123152 A1  Apr. 23, 2020

Related U.S. Application Data

(60) Provisional application No. 62/518,779, filed on Jun. 13, 2017, provisional application No. 62/522,869, filed on Jun. 21, 2017.

(51) Int. Cl.
*C07D 471/04* (2006.01)
*A61P 21/00* (2006.01)
*A61P 11/06* (2006.01)

(52) U.S. Cl.
CPC ........... *C07D 471/04* (2013.01); *A61P 11/06* (2018.01); *A61P 21/00* (2018.01)

(58) Field of Classification Search
CPC ......... C07D 471/04; A61P 21/00; A61P 11/06
See application file for complete search history.

(56) References Cited

U.S. PATENT DOCUMENTS

| | | | |
|---|---|---|---|
| 2003/0232818 A1 | 12/2003 | Anderson et al. | |
| 2005/0288282 A1 | 12/2005 | Delorme et al. | |
| 2008/0146569 A1* | 6/2008 | Blake | A61P 11/02 514/235.5 |
| 2008/0306093 A1 | 12/2008 | Servant et al. | |
| 2010/0173888 A1* | 7/2010 | Thorarensen | A61P 43/00 514/210.18 |
| 2010/0234377 A1* | 9/2010 | Aicher | A61P 17/02 514/235.8 |
| 2011/0306597 A1* | 12/2011 | Crawforth | C07D 471/04 514/212.07 |
| 2019/0060282 A1* | 2/2019 | Ban | A61K 31/437 |
| 2019/0241554 A1* | 8/2019 | Deaton | C07D 205/04 |

FOREIGN PATENT DOCUMENTS

| | | |
|---|---|---|
| WO | WO2000073283 A1 | 12/2000 |
| WO | WO2002085908 A1 | 10/2002 |
| WO | WO2004014377 A1 | 2/2004 |
| WO | WO2004056744 A1 | 7/2004 |
| WO | WO2005035526 A1 | 4/2005 |
| WO | WO 2005/094805 A1 | 10/2005 |
| WO | WO 2009/153720 A1 | 12/2009 |
| WO | WO2011009540 A2 | 1/2011 |
| WO | WO2011135351 A1 | 11/2011 |
| WO | WO 2012/087872 A1 | 6/2012 |
| WO | WO2012154888 A1 | 11/2012 |
| WO | WO2013102145 A1 | 7/2013 |

(Continued)

OTHER PUBLICATIONS

Chan; Bioorg. Med. Chem. Lett. 1999, 9, 2583-2586. (Year: 1999).*
Edfeldt; Bioorg. Med. Chem. Lett. 2015, 25, 2496-2500. (Year: 2015).*
Saxty; Med. Chem. Commun., 2014,5, 134-141. (Year: 2014).*
National Center for Biotechnology Information. PubChem Compound Summary for CID 91010394, N-Cyclohexyl-1,8-naphthyridine-3-carboxamide. https://pubchem.ncbi.nlm.nih.gov/compound/N-Cyclohexyl-1_8-naphthyridine-3-carboxamide. Accessed Oct. 21, 2020. Create Date Mar. 17, 2015. (Year: 2015).*
Chemical Abstracts STN Registry Database, record for RN 250674-57-8, N-(2-Methoxyphenyl)-1,6-naphthyridine-3-carboxamide, Entered on Dec. 13, 1999. (Year: 1999).*

(Continued)

*Primary Examiner* — Daniel R Carcanague
(74) *Attorney, Agent, or Firm* — Nora L. Stein; Fang Qian; Duke M. Fitch

(57) ABSTRACT

A compound of formula (I)

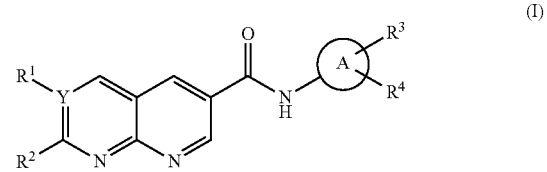

wherein $R^1$, $R^2$, $R^3$, $R^4$, X, Y, and A are as defined herein. The compounds of the present invention are inhibitors of hematopoietic prostaglandin D synthase (H-PGDS) and can be useful in the treatment of Duchenne muscular dystrophy. Accordingly, the invention is further directed to pharmaceutical compositions comprising a compound of the invention. The invention is still further directed to methods of inhibiting H-PGDS activity and treatment of disorders associated therewith using a compound of the invention or a pharmaceutical composition comprising a compound of the invention.

16 Claims, 2 Drawing Sheets

(56) References Cited

FOREIGN PATENT DOCUMENTS

| WO | WO2014018881 A1 | 1/2014 | |
|---|---|---|---|
| WO | WO2014018891 A1 | 1/2014 | |
| WO | WO2014165816 A1 | 10/2014 | |
| WO | WO2015086523 A1 | 6/2015 | |
| WO | WO2016009076 A1 | 1/2016 | |
| WO | WO2016116900 A1 | 7/2016 | |
| WO | WO 2017/103851 A1 | 6/2017 | |
| WO | WO 2017/146128 A1 | 8/2017 | |
| WO | WO-2019116256 A1 * | 6/2019 | .............. A61P 11/06 |

OTHER PUBLICATIONS

Abe, et al., *Gene*, 227:71-77 (1999).
Amir Hanna-Elias, et al., *Australian Journal of Chemistry*, 62(2):150 (2009).
Boie, et al., *Journal of Biological Chemistry*, 270:18910-18916 (1995).
Carron, et al., *ACS Med. Chem. Lett.*, 1:59-63 (2010).
Christ, et al., *J. Med. Chem.*, 53:5536-5548 (2010).
Hohwy, et al., *J. Med. Chem.*, 51:2178-2186 (2008).
Ikuko, et al., *J. Neuropath. Exp. Neur.*, 66:469-480 (2007).
Lewis, et al., *J. Immunology*, 129:1627-1631 (1982).
Mohri, et al., *American Journal of Pathology*, 174:1735-1744 (2009).
Mohri, et al., *Journal of Neuroscience*, 26:4383-4393 (2006).
Nakagawa, et al., *Clinica Chimica Acta*, 423:10-14 (2013).
Okinaga, et al., *Acta Neuropatholigica*, 104:377-384 (2002).
Papaliodis, et al., *JPET*, 327:665-672 (2008).
Redensek, et al., *Glia*, 59:603-614 (2011).
Tanaka, et al., *American J. Physiol. Cell Physiol.*, 301:C1360-C1367 (2011).
Urade, et al., *Vitamins and Hormones*, 58:89-120 (2000).
Weber, et al., *European Journal of Medicinal Chemistry*, 45:447-454 (2010).

* cited by examiner

CHEMICAL COMPOUNDS AS H—PGDS INHIBITORS

This application is a 371 of International Application No. PCT/IB2018/054206, filed 11 Jun. 2018, which claims priority to U.S. Provisional Application 62/518,779 filed on 13 Jun. 2017, and to U.S. Provisional Application 62/522,869 filed on 21 Jun. 2017, all of which are incorporated herein in their entireties.

FIELD OF THE INVENTION

The present invention relates to novel compounds, to the use of the compounds as Hematopoletic Prostaglandin D Synthase (H-PGDS) inhibitors, to pharmaceutical compositions comprising the compounds and to the use of the compounds in therapy, especially in the treatment of conditions for which a H-PGDS inhibitor is indicated, such as neurodegenerative diseases and musculoskeletal diseases including Duchenne Muscular Dystrophy, where $PGD_2$ is considered to play a pathological role, for the use of a compound in the manufacture of a medicament for the treatment of conditions in which an inhibitor of H-PGDS is indicated, and a method for the treatment or prophylaxis of disorders in which inhibition of H-PGDS is indicated, in a human.

BACKGROUND OF THE INVENTION

Prostaglandin $D_2$ ($PGD_2$) is a product of arachidonic acid metabolism, and is the major prostanoid mediator synthesised by mast cells in response to stimulation via multiple mechanisms and cellular activation pathways, including allergen-mediated cross-linking of high affinity IgE receptors (Lewis et al. (1982) Prostaglandin $D_2$ generation after activation of rat and human mast cells with anti-IgE. *J. Immunol.*, 129, 1627-1631). Other cells such as dendritic cells, $T_h2$ cells, and epithelial cells also produce $PGD_2$, but at lower levels than mast cells. $PGD_2$ mediates its effects via activation of the specific G-protein coupled receptors $DP_1$ (Bole et al. (1995) Molecular cloning and characterization of the human prostanoid DP receptor. *J. Biol. Chem.*, 270, 18910-18916) and $DP_2$ (CRTH2) (Abe et al. (1999), Molecular cloning, chromosome mapping and characterization of the mouse CRTH2 gene, a putative member of the leukocyte chemo-attractant receptor family. *Gene*, 227, 71-77) and also acts via the receptor for thromboxane $A_2$ ($TXA_2$), the TP receptor, on target cells.

Prostaglandin D synthase (PGDS) is the enzyme responsible for the catalytic isomerase conversion of prostaglandin endoperoxide $PGH_2$ to $PGD_2$. $PGD_2$ is generated by the action of either H-PGDS (hematopoietic-type or H-type) or L-PGDS (lipocalin-type or L-type) enzymes (Urade et al., (2000) Prostaglandin D synthase structure and function. *Vitamins and hormones*, 58, 89-120). H-PGDS activity is dependent on glutathione and plays an important role in the generation of $PGD_2$ by immune and inflammatory cells, including mast cells, antigen-presenting cells (e.g. dendritic cells), macrophages, and $T_h2$ cells, which are all key cells in the pathology of allergic disease. In contrast, L-type is glutathione-independent and is primarily located in the central nervous system, genital organs, and heart. These two isoforms of PGDS appear to have distinct catalytic properties, tertiary structure, and cellular and tissue distribution.

Using the small molecule inhibitor HQL-79, H-PGDS has been demonstrated to play a modulatory role in diseases such as Duchenne muscular dystrophy (Nakagawa et al. (2013) A prostaglandin $D_2$ metabolite is elevated in the urine of Duchenne muscular dystrophy patients and increases further from 8 years old, *Clinica Chimica Acta* 423, 10-14) and (Mohri et al. (2009), Inhibition of prostaglandin D synthase suppresses muscular necrosis, *Am. J. Pathol.* 174, 1735-1744) and (Okinaga et al. (2002), Induction of hematopoietic prostaglandin D synthase in hyalinated necrotic muscle fibers: its implication in grouped necrosis, *Acta Neuropathologica* 104, 377-84), spinal cord contusion injury (Redensek et al. (2011) Expression and detrimental role of hematopoietic prostaglandin D synthase in spinal cord contusion injury, *Glia* 59, 603-614), neuroinflammation (Mohri et al. (2006) Prostaglandin $D_2$-mediated microglia/astrocyte interaction enhances astrogliosis and demyelination in twitcher. *J. Neurosci.* 26, 4383-4393), and neurodegenerative disease (Ikuko et al. (2007) Hematopoietic prostaglandin D synthase and $DP_1$ receptor are selectively upregulated in microglia and astrocytes within senile plaques from human patients and in a mouse model of Alzheimer disease. *J. Neuropath. Exp. Neur.* 66, 469-480). H-PGDS has also been implicated to play a role in metabolic diseases such as diabetes and obesity, since $PGD_2$ is converted to 15-deoxy-$\Delta^{12,14}PGJ_2$, a potent ligand for PPARγ which is able to drive adipogenesis (Tanaka et al (2011) Mast cells function as an alternative modulator of adipogenesis through 15-deoxy-delta-12,14-prostaglandin $J_2$. *Am. J. Physiol. Cell Physiol.* 301, C1360-C1367). $PGD_2$ has been implicated to play a role in niacin-induced skin flushing (Papaliodis et al (2008) Niacin-induced "flush" involves release of prostaglandin $D_2$ from mast cells and serotonin from platelets: Evidence from human cells in vitro and an animal model. *JPET* 327:665-672).

Weber et al. (2010), Identification and characterisation of new inhibitors for the human hematopoietic prostaglandin $D_2$ synthase. *Eur. J. Med. Chem.* 45, 447-454, Carron et al. (2010), Discovery of an Oral Potent Selective Inhibitor of Hematopoietic Prostaglandin D Synthase (H-PGDS). *ACS Med. Chem. Lett.* 1, 59-63; Christ et al. (2010), Development and Characterization of New Inhibitors of the Human and Mouse Hematopoietic Prostaglandin $D_2$ Synthases, *J. Med. Chem.*, 53, 5536-5548; and Hohwy et al. (2008), Novel Prostaglandin D Synthase Inhibitors Generated by Fragment-Based Drug Design. *J. Med. Chem.*, 51, 2178-2186 are also of interest.

Based on this evidence, chemical inhibitors of H-PGDS which inhibit $PGD_2$ formation, simultaneously inhibit the biological actions of $PGD_2$ and its metabolites at multiple receptors and offer the potential for therapeutic benefit in the treatment of a range of diseases where $PGD_2$ is considered to play a pathological role.

International Patent Applications WO2005/094805, WO2007/007778, WO2007/041634, 2008/121670, WO2008/122787, WO2009/153720, WO2009/153721, WO2010/033977, WO2010/104024, WO2011/043359, WO2011044307, WO2011/090062, Japanese Patent Application 2007-51121 and US Patent Application 2008/0146569 disclose certain H-PGDS inhibitors and their use in the treatment of diseases associated with the activity of H-PGDS.

It is an object of the invention to provide further H-PGDS inhibitors, suitably for the treatment of Muscular Dystrophy.

SUMMARY OF THE INVENTION

The invention is directed to compounds according to Formula I:

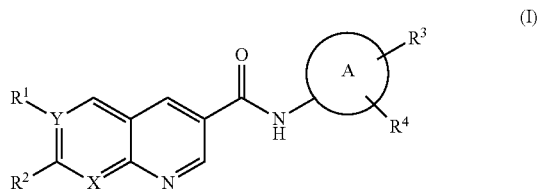

wherein $R^1$, $R^2$, $R^3$, $R^4$, X, Y, and A are as defined below.

Compounds of Formula (I) and their pharmaceutically acceptable salts have H-PGDS activity and are believed to be of use for the treatment or prophylaxis of certain disorders.

Accordingly, in another aspect of the invention there is provided a pharmaceutical composition comprising a compound of Formula (I) according to the first aspect, or a pharmaceutically acceptable salt thereof and one or more pharmaceutically acceptable carriers or excipients.

In some embodiments, the pharmaceutical composition is for the treatment or prophylaxis of a disorder in which inhibition of H-PGDS is beneficial.

In a further aspect, the invention provides a compound of Formula (I) or a pharmaceutically acceptable salt thereof according to the first aspect of the invention for use in therapy.

The invention also provides a compound of Formula (I) or a pharmaceutically acceptable salt thereof, for use in the treatment of a condition for which an H-PGDS inhibitor is indicated.

This invention also relates to a method of treating Duchenne muscular dystrophy, which comprises administering to a subject in need thereof an effective amount of a H-PGDS inhibiting compound of Formula (I).

This invention also relates to a method of treating congenital myotonia, which comprises administering to a subject in need thereof an effective amount of a H-PGDS inhibiting compound of Formula (I).

This invention also relates to a method of treating muscle injury, which comprises administering to a subject in need thereof an effective amount of a H-PGDS inhibiting compound of Formula (I).

This invention also relates to a method of treating tendon injury, which comprises administering to a subject in need thereof an effective amount of a H-PGDS inhibiting compound of Formula (I).

This invention also relates to a method of treating muscle lacerations, which comprises administering to a subject in need thereof an effective amount of a H-PGDS inhibiting compound of Formula (I).

This invention also relates to a method of treating chronic muscle strains, which comprises administering to a subject in need thereof an effective amount of a H-PGDS inhibiting compound of Formula (I).

This invention also relates to a method of treating myotonic dystrophy type I, which comprises administering to a subject in need thereof an effective amount of a H-PGDS inhibiting compound of Formula (I).

This invention also relates to a method of treating myotonic dystrophy type II, which comprises administering to a subject in need thereof an effective amount of a H-PGDS inhibiting compound of Formula (I).

This invention also relates to a method of treating asthma, which comprises administering to a subject in need thereof an effective amount of a H-PGDS inhibiting compound of Formula (I).

This invention also relates to a method of treating chronic obstructive pulmonary disease, which comprises administering to a subject in need thereof an effective amount of a H-PGDS inhibiting compound of Formula (I).

This invention also relates to a method of treating rheumatoid arthritis, which comprises administering to a subject in need thereof an effective amount of a H-PGDS inhibiting compound of Formula (I).

This invention also relates to a method of treating inflammatory bowel disease, which comprises administering to a subject in need thereof an effective amount of a H-PGDS inhibiting compound of Formula (I).

This invention also relates to a method of treating osteoarthritis, which comprises administering to a subject in need thereof an effective amount of a H-PGDS inhibiting compound of Formula (I).

This invention also relates to a method of treating psoriasis, which comprises administering to a subject in need thereof an effective amount of a H-PGDS inhibiting compound of Formula (I).

This invention also relates to a method of treating atopic dermatitis, which comprises administering to a subject in need thereof an effective amount of a H-PGDS inhibiting compound of Formula (I).

This invention also relates to a method of treating a muscle degenerative disorder, which comprises administering to a subject in need thereof an effective amount of a H-PGDS inhibiting compound of Formula (I).

This invention also relates to a method of treating muscular dystrophy, which comprises administering to a subject in need thereof an effective amount of a H-PGDS inhibiting compound of Formula (I).

Also included in the present invention are methods of co-administering the presently invented H-PGDS inhibiting compounds with further active ingredients.

The invention also relates to a compound of Formula (I) or a pharmaceutically acceptable salt thereof for use in the treatment of Duchenne muscular dystrophy.

The invention also relates to a compound of Formula (I) or a pharmaceutically acceptable salt thereof for use in the treatment of congenital myotonia.

The invention also relates to a compound of Formula (I) or a pharmaceutically acceptable salt thereof for use in the treatment of muscle injury.

The invention also relates to a compound of Formula (I) or a pharmaceutically acceptable salt thereof for use in the treatment of tendon injury.

The invention also relates to a compound of Formula (I) or a pharmaceutically acceptable salt thereof for use in the treatment of muscle lacerations.

The invention also relates to a compound of Formula (I) or a pharmaceutically acceptable salt thereof for use in the treatment of chronic muscle strains.

The invention also relates to a compound of Formula (I) or a pharmaceutically acceptable salt thereof for use in the treatment of myotonic dystrophy type I.

The invention also relates to a compound of Formula (I) or a pharmaceutically acceptable salt thereof for use in the treatment of myotonic dystrophy type II.

The invention also relates to a compound of Formula (I) or a pharmaceutically acceptable salt thereof for use in the treatment of asthma.

The invention also relates to a compound of Formula (I) or a pharmaceutically acceptable salt thereof for use in the treatment of chronic obstructive pulmonary disease.

The invention also relates to a compound of Formula (I) or a pharmaceutically acceptable salt thereof for use in the treatment of rheumatoid arthritis.

The invention also relates to a compound of Formula (I) or a pharmaceutically acceptable salt thereof for use in the treatment of inflammatory bowel disease.

The invention also relates to a compound of Formula (I) or a pharmaceutically acceptable salt thereof for use in the treatment of osteoarthritis.

The invention also relates to a compound of Formula (I) or a pharmaceutically acceptable salt thereof for use in the treatment of psoriasis.

The invention also relates to a compound of Formula (I) or a pharmaceutically acceptable salt thereof for use in the treatment of atopic dermatitis.

The invention also relates to a compound of Formula (I) or a pharmaceutically acceptable salt thereof for use in the treatment of a muscle degenerative disorder.

The invention also relates to a compound of Formula (I) or a pharmaceutically acceptable salt thereof for use in the treatment of muscular dystrophy.

The invention provides for the use of a compound of Formula (I) or a pharmaceutically acceptable salt thereof in the manufacture of a medicament for the treatment of conditions in which an inhibitor of H-PGDS is indicated.

The invention further provides a method for the treatment or prophylaxis of disorders in which inhibition of H-PGDS is indicated, in a human, which comprises administering a human in need thereof a therapeutically effective amount of a compound of Formula (I) or a pharmaceutically acceptable salt thereof.

DETAILED DESCRIPTION OF THE INVENTION

Figure 1:
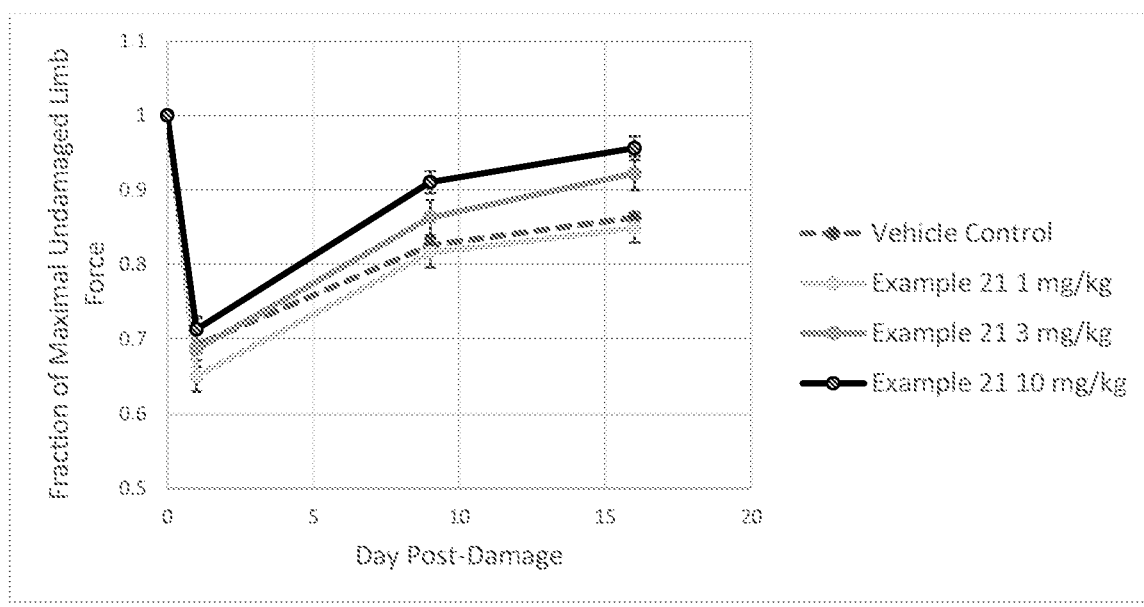
FIG. 1 depicts the protection and acceleration of functional repair dose response curves of H-PGDS inhibition using the compound of Example 21 following limb muscle injury in male C57Bl/6N mice.

This invention relates to compounds of Formula (I) and to the use of compounds of Formula (I) in the methods of the invention:

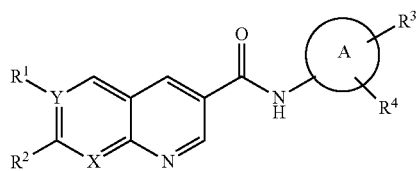

(I)

wherein:
either X is N and Y is C, X is CH and Y is N, or X is N and Y is N;

$R^1$ is absent or selected from hydrogen, fluoro, chloro, bromo, iodo, cyano, —$OR^5$, $C_{1-5}$alkyl, substituted $C_{1-5}$alkyl, $C_{3-5}$cycloalkyl, substituted $C_{3-5}$cycloalkyl, and heterocycloalkyl;

$R^2$ is selected from hydrogen, fluoro, chloro, bromo, iodo, cyano, —$OR^5$, —$SR^6$, $C_{1-5}$alkyl, substituted $C_{1-5}$alkyl, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —$NO_2$, —$NH_2$ and —CN), amino, —$NHR^7$, —$NR^7R^8$, azetidinyl, and azetidinyl (substituted with from 1 to 4 substituents independently selected from: fluoro, chloro, bromo, iodo, $C_{1-4}$alkyloxy, —OH, $C_{1-4}$alkyl, oxo, —COOH, —$NO_2$, —$NH_2$ and —CN), and heterocycloalkyl;

A is selected from:
$C_{4-7}$cycloalkyl,
a 4-, 5-, or 6-membered heterocycloalkyl containing one or two heteroatoms independently selected from O and N,
and
a 5-12 membered heteroaryl containing one or two heteroatoms, wherein at least one heteroatom is nitrogen and the second heteroatom, if present, is selected from N and S;

$R^3$ and $R^4$ are independently selected from:
hydrogen,
—$OS(O)_2NH_2$,
—$S(O)_2CH_3$,
—OH,
—C≡N,
F,
Cl,
Br,
I,
tetrazolyl,
methyl-tetrazolyl,
ethyl-tetrazolyl,
cycloalkyl,
cycloalkyl substituted with one or two substituents independently selected from; fluoro, —OH, —$OCH_3$, and —$CH_3$,
morpholinyl,
azetidinyl,
azetidinyl substituted with one or two substituents independently selected from: fluoro, chloro, bromo, iodo, —OH, —$CF_3$, and —$CH_3$,
pyridinyl,
pyridinyl substituted with —C≡N,
oxazolyl,
oxazolyl substituted with —$C(O)OCH_2CH_3$,
oxazolyl substituted with —C≡N,
—N(H)oxazolyl,
—N(H)oxazolyl substituted with —$C(O)OCH_2CH_3$,
—N(H)oxazolyl substituted with —C≡N,
—$N(H)S(O)_2CH_3$,
oxo,
$C_{1-8}$alkyl,
$C_{1-8}$alkyl substituted with from one to six substituents independently selected from: —OH, oxo, fluoro, chloro, bromo, iodo, $C_{1-4}$alkoxy, cycloalkyl, morpholinyl, methylpiperazinyl, —$NH_2$, —$N(H)C_{1-4}$alkyl, —$N(H)C_{1-4}$alkyl where alkyl is substituted with from 1 to 5 fluoro, —N($C_{1-4}$alkyl)$_2$, and —N($C_{1-4}$alkyl)$_2$ where the alkyls are independently substituted with from 1 to 7 fluoro, $C_{1-8}$alkoxy, $C_{1-8}$alkoxy substituted with from one to six substituents independently selected from: —OH, oxo, fluoro, chloro, bromo, iodo, $C_{1-4}$alkoxy, cycloalkyl, —NH$_2$, —N(H)$C_{1-4}$alkyl, —N(H)$C_{1-4}$alkyl where the alkyl is substituted with from 1 to 5 fluoro, —N($C_{1-4}$alkyl)$_2$, —N($C_{1-4}$alkyl)$_2$ where the alkyls are independently substituted with from 1 to 7 fluoro, —S(O)$_2$CH$_3$, —S(O)$_2$NH$_2$, and —S(O)$_2$N(H)$C_{1-4}$alkyl, dimethylamine oxide, N($C_{1-6}$alkyl)$_2$, where each alkyl is optionally substituted with from one to six substituents independently selected from: —OH, oxo, fluoro, chloro, bromo, iodo, and —S(O)$_2$CH$_3$, N(H)$C_{1-6}$alkyl, and N(H)$C_{1-6}$alkyl substituted with from one to six substituents independently selected from: —OH, oxo, fluoro, chloro, bromo, iodo, CF$_3$, CHF$_2$, CH$_2$F, and —S(O)$_2$CH$_3$;

$R^5$ is selected from hydrogen, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), $C_{1-6}$alkyl, and $C_{1-6}$alkyl (substituted with from 1 to 6 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN);

$R^6$ is selected from hydrogen, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), $C_{1-6}$alkyl, and $C_{1-6}$alkyl (substituted with from 1 to 6 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN);

$R^7$ is selected from aryl, heteroaryl, $C_{3-6}$cycloalkyl, heterocycloalkyl, —O$C_{1-6}$alkyl, —O$C_{1-6}$alkyl (substituted with from 1 to 6 substituents independently selected from: fluoro, chloro, oxo, and —OH), —$C_{1-6}$alkyl, and $C_{1-6}$alkyl (substituted with from 1 to 6 substituents independently selected from: fluoro, chloro, oxo, —OH, —O$C_{1-6}$alkyl, —COOH, —NH$_2$, —NHcycloalkyl, and —CN); and $R^8$ is selected from aryl, heteroaryl, $C_{3-6}$cycloalkyl, heterocycloalkyl, —O$C_{1-6}$alkyl, —O$C_{1-6}$alkyl (substituted with from 1 to 6 substituents independently selected from: fluoro, chloro, oxo, and —OH), —$C_{1-6}$alkyl, and $C_{1-6}$alkyl (substituted with from 1 to 6 substituents independently selected from: fluoro, chloro, oxo, —OH, —O$C_{1-6}$alkyl, —COOH, —NH$_2$, —NHcycloalkyl, and —CN);

provided $R^1$ is absent when Y is N, and provided $R^2$, $R^3$ and $R^4$ are not all hydrogen;

or a pharmaceutically acceptable salt thereof.

Suitably in the compounds of Formula (I), X is N and Y is C. Suitably in the compounds of Formula (I), X is CH and Y is N. Suitably in the compounds of Formula (I), X is N and Y is N.

Suitably in the compounds of Formula (I), $R^1$ is absent when Y is N, or selected from hydrogen, fluoro, chloro, bromo, iodo, cyano, —OR$^5$, $C_{1-5}$alkyl, substituted $C_{1-5}$alkyl, $C_{3-5}$cycloalkyl, substituted $C_{3-5}$cycloalkyl, and heterocycloalkyl;

where:

$R^5$ is selected from hydrogen, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), $C_{1-6}$alkyl, and $C_{1-6}$alkyl (substituted with from 1 to 6 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN).

Suitably in the compounds of Formula (I), $R^2$ is selected from hydrogen, fluoro, chloro, bromo, iodo, cyano, —OR$^5$, —SR$^6$, $C_{1-5}$alkyl, substituted $C_{1-5}$alkyl, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), amino, —NHR$^7$, —NR$^7$R$^8$, azetidinyl, and azetidinyl (substituted with from 1 to 4 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), and heterocycloalkyl;

where:

$R^5$ is selected from hydrogen, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), $C_{1-6}$alkyl, and $C_{1-6}$alkyl (substituted with from 1 to 6 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), $R^6$ is selected from hydrogen, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), $C_{1-6}$alkyl, and $C_{1-6}$alkyl (substituted with from 1 to 6 substituents independently selected from: fluoro, chloro, bromo, iodo, $C_{1-4}$alkyloxy, —OH, $C_{1-4}$alkyl, oxo, —COOH, —NO$_2$, —NH$_2$ and —CN), $R^7$ is selected from aryl, heteroaryl, $C_{3-6}$cycloalkyl, heterocycloalkyl, —O$C_{1-6}$alkyl, —O$C_{1-6}$alkyl (substituted with from 1 to 6 substituents independently selected from: fluoro, chloro, oxo, and —OH), —$C_{1-6}$alkyl, and $C_{1-6}$alkyl (substituted with from 1 to 6 substituents independently selected from: fluoro, chloro, oxo, —OH, —O$C_{1-6}$alkyl, —COOH, —NH$_2$, —NHcycloalkyl, and —CN), and $R^8$ is selected from aryl, heteroaryl, $C_{3-6}$cycloalkyl, heterocycloalkyl, —O$C_{1-6}$alkyl, —O$C_{1-6}$alkyl (substituted with from 1 to 6 substituents independently selected from: fluoro, chloro, oxo, and —OH), —$C_{1-6}$alkyl, and $C_{1-6}$alkyl (substituted with from 1 to 6 substituents independently selected from: fluoro, chloro, oxo, —OH, —O$C_{1-6}$alkyl, —COOH, —NH$_2$, —NHcycloalkyl, and —CN).

Suitably in the compounds of Formula (I), A is selected from:

$C_{4-7}$cycloalkyl, a 4-, 5-, or 6-membered heterocycloalkyl containing one or two heteroatoms independently selected from O and N, and
a 5-12 membered heteroaryl containing one or two heteroatoms, wherein at least one heteroatom is nitrogen and the second heteroatom, if present, is selected from N and S.

Suitably in the compounds of Formula (I), $R^3$ and $R^4$ are independently selected from:
hydrogen,
—$OS(O)_2NH_2$,
—$S(O)_2CH_3$,
—OH,
—C≡N,
F,
Cl,
Br,
I,
tetrazolyl,
methyl-tetrazolyl,
ethyl-tetrazolyl,
cycloalkyl,
cycloalkyl substituted with one or two substituents independently selected from; fluoro, —OH, —$OCH_3$, and —$CH_3$,
morpholinyl,
azetidinyl,
azetidinyl substituted with one or two substituents independently selected from: fluoro, chloro, bromo, iodo, —OH, —$CF_3$, and —$CH_3$,
pyridinyl,
pyridinyl substituted with —C≡N,
oxazolyl,
oxazolyl substituted with —$C(O)OCH_2CH_3$,
oxazolyl substituted with —C≡N,
—N(H)oxazolyl,
—N(H)oxazolyl substituted with —$C(O)OCH_2CH_3$,
—N(H)oxazolyl substituted with —C≡N,
—$N(H)S(O)_2CH_3$,
oxo,
$C_{1-8}$alkyl,
$C_{1-8}$alkyl substituted with from one to six substituents independently selected from: —OH, oxo, fluoro, chloro, bromo, iodo, $C_{1-4}$alkoxy, cycloalkyl, morpholinyl, methylpiperazinyl, —$NH_2$, —$N(H)C_{1-4}$alkyl, —$N(H)C_{1-4}$alkyl where alkyl is substituted with from 1 to 5 fluoro, —$N(C_{1-4}$alkyl$)_2$, and —$N(C_{1-4}$alkyl$)_2$ where the alkyls are independently substituted with from 1 to 7 fluoro,
$C_{1-8}$alkoxy,
$C_{1-8}$alkoxy substituted with from one to six substituents independently selected from: —OH, oxo, fluoro, chloro, bromo, iodo, $C_{1-4}$alkoxy, cycloalkyl, —$NH_2$, —$N(H)C_{1-4}$alkyl, —$N(H)C_{1-4}$alkyl where the alkyl is substituted with from 1 to 5 fluoro, —$N(C_{1-4}$alkyl$)_2$, —$N(C_{1-4}$alkyl$)_2$ where the alkyls are independently substituted with from 1 to 7 fluoro, —$S(O)_2CH_3$, —$S(O)_2NH_2$, and —$S(O)_2N(H)C_{1-4}$alkyl,
dimethylamine oxide,
$N(C_{1-6}$alkyl$)_2$, where each alkyl is optionally substituted with from one to six substituents independently selected from: —OH, oxo, fluoro, chloro, bromo, iodo, and —$S(O)_2CH_3$,
$N(H)C_{1-6}$alkyl, and
$N(H)C_{1-6}$alkyl substituted with from one to six substituents independently selected from: —OH, oxo, fluoro, chloro, bromo, iodo, and —$S(O)_2CH_3$.

Suitably in the compounds of Formula (I), $R^1$ is absent when Y is N, or selected from hydrogen, and chloro.

Suitably in the compounds of Formula (I), $R^2$ is selected from hydrogen, —$OR^5$, —$SR^6$, cyclopropyl, cyclobutyl, —$NHR^7$, azetidinyl, and azetidinyl substituted with 1 or 2 substituents independently selected from: fluoro, and —$CH_3$;
where:
$R^5$ is selected from hydrogen, $C_{1-2}$alkyl, and $C_{1-2}$alkyl substituted from 1 to 3 times by: fluoro,
$R^6$ is selected from hydrogen, and $C_{1-2}$alkyl,
$R^7$ is selected from $C_{1-2}$alkyl, and $C_{1-2}$alkyl substituted from 1 to 3 times by fluoro.

Suitably in the compounds of Formula (I), A is selected from: cyclohexyl, cyclobutyl, pyrrolidinyl, piperidinyl, spiro[3.3]heptanyl, and azetidinyl.

Suitably in the compounds of Formula (I), $R^3$ and $R^4$ are independently selected from:
hydrogen,
—OH,
F,
azetidinyl,
azetidinyl substituted one or two times by fluoro,
oxo,
$C_{1-6}$alkyl,
$C_{1-6}$alkyl substituted with from one to five substituents independently selected from: —OH, oxo, and fluoro,
$N(H)C_{1-3}$alkyl, and
$N(H)C_{1-3}$alkyl substituted with from one to five substituents independently selected from: —OH, and fluoro.

This invention relates to compounds of Formula (II) and to the use of compounds of Formula (II) in the methods of the invention:

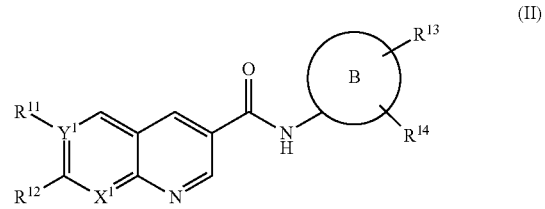

wherein:
either $X^1$ is N and $Y^1$ is C, $X^1$ is CH and $Y^1$ is N, or $X^1$ is N and $Y^1$ is N;
$R^{11}$ is absent or selected from hydrogen, fluoro, chloro, bromo, iodo, cyano, —$OR^{15}$, $C_{1-5}$alkyl, $C_{1-5}$alkyl substituted from 1 to 6 times by fluoro, $C_{3-5}$cycloalkyl, and $C_{3-5}$cycloalkyl substituted from 1 to 4 times by fluoro;
$R^{12}$ is selected from hydrogen, —$OR^{15}$, —$SR^{16}$, $C_{1-5}$alkyl, $C_{1-5}$alkyl substituted from 1 to 6 times by fluoro, $C_{3-5}$cycloalkyl, $C_{3-5}$cycloalkyl substituted from 1 to 4 times by fluoro, amino, —$NHR^{17}$, —$NR^{17}R^{18}$, azetidinyl, and azetidinyl (substituted with from 1 to 3 substituents independently selected from: fluoro, chloro, $C_{1-4}$alkyl, and $C_{1-4}$alkyl substituted from 1 to 4 times by fluoro);
B is selected from:
$C_{4-7}$cycloalkyl, and
a 4-, 5-, or 6-membered heterocycloalkyl containing one or two heteroatoms independently selected from O and N;
$R^{13}$ and $R^{14}$ are independently selected from:
hydrogen,
—OH,
—C≡N, F,
Cl,
$C_{3-6}$cycloalkyl,
$C_{3-6}$cycloalkyl substituted with one or two substituents independently selected from; fluoro, —OH, —OCH$_3$, and —CH$_3$,
azetidinyl,
azetidinyl substituted with one or two substituents independently selected from: fluoro, chloro, bromo, iodo, —OH, —CF$_3$, and —CH$_3$,
oxo,
$C_{1-6}$alkyl,
$C_{1-6}$alkyl substituted with from one to six substituents independently selected from: —OH, oxo, fluoro, chloro, bromo, iodo, $C_{1-4}$alkoxy, cycloalkyl, morpholinyl, methylpiperazinyl, —NH$_2$, —N(H)C$_{1-4}$alkyl, —N(H)C$_{1-4}$alkyl where alkyl is substituted with from 1 to 5 fluoro, —N(C$_{1-4}$alkyl)$_2$, and —N(C$_{1-4}$alkyl)$_2$ where the alkyls are independently substituted with from 1 to 7 fluoro,
$C_{1-8}$alkoxy,
$C_{1-8}$alkoxy substituted with from one to six substituents independently selected from: —OH, oxo, fluoro, chloro, bromo, iodo, $C_{1-4}$alkoxy, cycloalkyl, —NH$_2$, —N(H)C$_{1-4}$alkyl, —N(H)C$_{1-4}$alkyl where the alkyl is substituted with from 1 to 5 fluoro, —N(C$_{1-4}$alkyl)$_2$, —N(C$_{1-4}$alkyl)$_2$ where the alkyls are independently substituted with from 1 to 7 fluoro, —S(O)$_2$CH$_3$, —S(O)$_2$NH$_2$, and —S(O)$_2$N(H)C$_{1-4}$alkyl,
N(C$_{1-6}$alkyl)$_2$, where each alkyl is optionally substituted with from one to six substituents independently selected from: —OH, oxo, fluoro, chloro, bromo, iodo, and —S(O)$_2$CH$_3$,
N(H)C$_{1-6}$alkyl,
N(H)C$_{1-6}$alkyl substituted with from one to six substituents independently selected from: —OH, oxo, fluoro, chloro, bromo, iodo, and —S(O)$_2$CH$_3$;
$R^{15}$ is selected from: hydrogen, $C_{3-5}$cycloalkyl, $C_{3-5}$cycloalkyl substituted from 1 to 4 times by fluoro, $C_{1-5}$alkyl, and $C_{1-5}$alkyl substituted with from 1 to 6 substituents independently selected from: fluoro, chloro, $C_{1-3}$alkyloxy, —OH, oxo, —COOH, —NH$_2$ and —CN;
$R^{16}$ is selected from: hydrogen, $C_{3-5}$cycloalkyl, $C_{3-5}$cycloalkyl substituted from 1 to 4 times by fluoro, $C_{1-5}$alkyl, and $C_{1-5}$alkyl substituted with from 1 to 6 substituents independently selected from: fluoro, chloro, $C_{1-3}$alkyloxy, —OH, oxo, —COOH, —NH$_2$ and —CN;
$R^{17}$ is selected from: $C_{3-6}$cycloalkyl, —OC$_{1-6}$alkyl, —OC$_{1-6}$alkyl (substituted with from 1 to 6 substituents independently selected from: fluoro, chloro, oxo, and —OH), $C_{1-6}$alkyl, and $C_{1-6}$alkyl (substituted with from 1 to 6 substituents independently selected from: fluoro, chloro, oxo, and —OH);
and
$R^{18}$ is selected from: $C_{3-6}$cycloalkyl, —OC$_{1-6}$alkyl, —OC$_{1-6}$alkyl (substituted with from 1 to 6 substituents independently selected from: fluoro, chloro, oxo, and —OH), $C_{1-6}$alkyl, and $C_{1-6}$alkyl (substituted with from 1 to 6 substituents independently selected from: fluoro, chloro, oxo, and —OH);
provided $R^{11}$ is absent when $Y^1$ is N,
provided $R^{12}$, $R^{13}$ and $R^{14}$ are not all hydrogen;
or a pharmaceutically acceptable salt thereof.

Suitably in the compounds of Formula (II), $X^1$ is N and $Y^1$ is C. Suitably in the compounds of Formula (II), $X^1$ is CH and $Y^1$ is N. Suitably in the compounds of Formula (II), $X^1$ is N and $Y^1$ is N.

Suitably in the compounds of Formula (II), $R^{11}$ is absent when $Y^1$ is N or selected from: hydrogen, fluoro, chloro, bromo, iodo, cyano, $C_{1-5}$alkyl, cyclopropyl, cyclobutyl, cyclopentyl, and —OR$^{15}$, where $R^{15}$ is selected from: —CH$_3$, —CF$_3$, —CF$_2$H, —CH$_2$CF$_3$, —CH$_2$CH$_3$, $C_{3-5}$alkyl, $C_{1-5}$alkyl substituted from 1 to 6 times by fluoro, and cyclopropyl. Suitably in the compounds of Formula (II), $R^{11}$ is selected from: absent when $Y^1$ is N, hydrogen, and chloro.

Suitably in the compounds of Formula (II), $R^{12}$ is selected from: hydrogen, cyclopropyl, cyclobutyl, $C_{1-5}$alkyl, —OR$^{15}$, —SR$^{16}$, amino, —NHR$^{17}$, —NR$^{17}$R$^{18}$, azetidinyl, and azetidinyl substituted with from 1 to 3 substituents independently selected from: fluoro, chloro, $C_{1-4}$alkyl, and $C_{1-4}$alkyl substituted from 1 to 4 times by fluoro,
where:
$R^{15}$ is selected from: —CH$_3$, —CF$_3$, —CF$_2$H, —CH$_2$CF$_3$, —CH$_2$CH$_3$, $C_{3-5}$alkyl, $C_{1-5}$alkyl substituted from 1 to 6 times by fluoro, and cyclopropyl,
$R^{16}$ is selected from: —CH$_3$, —CF$_3$, —CF$_2$H, —CH$_2$CF$_3$, —CH$_2$CH$_3$, $C_{3-5}$alkyl, $C_{1-5}$alkyl substituted from 1 to 6 times by fluoro, and cyclopropyl,
$R^{17}$ is selected from: —CH$_3$, —CF$_3$, —CF$_2$H, —CH$_2$CF$_3$, —CH$_2$CH$_3$, —CH(CH$_3$)$_2$, and cyclopropyl, and
$R^{18}$ is selected from: —CH$_3$, —CF$_3$, —CF$_2$H, —CH$_2$CF$_3$, —CH$_2$CH$_3$, —CH(CH$_3$)$_2$, and cyclopropyl.

Suitably in the compounds of Formula (II), $R^{12}$ is selected from: hydrogen, azetidinyl, azetidinyl substituted by fluoro, azetidinyl (substituted by —CH$_3$), cyclopropyl, —NHCH$_2$CF$_3$, —NHCH$_2$CHF$_2$, —OCH$_3$, —OCH$_2$CF$_3$, and —OCH$_2$CH$_3$.

Suitably in the compounds of Formula (II), B is selected from:
$C_{4-7}$cycloalkyl, and
a 4-, 5-, or 6-membered heterocycloalkyl containing one or two heteroatoms independently selected from O and N Suitably in the compounds of Formula (II), $R^{13}$ and $R^{14}$ are independently selected from:
hydrogen,
—OH,
—C≡N,
F,
Cl,
$C_{3-6}$cycloalkyl,
cycloalkyl substituted with one or two substituents independently selected from; fluoro, —OH, —OCH$_3$, and —CH$_3$,
azetidinyl,
azetidinyl substituted with one or two substituents independently selected from: fluoro, chloro, bromo, iodo, —OH, —CF$_3$, and —CH$_3$,
oxo,
$C_{1-6}$alkyl,
$C_{1-6}$alkyl substituted with from one to six substituents independently selected from: —OH, oxo, fluoro, chloro, bromo, iodo, $C_{1-4}$alkoxy, cycloalkyl, morpholinyl, methylpiperazinyl, —NH$_2$, —N(H)C$_{1-4}$alkyl, —N(H)C$_{1-4}$alkyl where alkyl is substituted with from 1 to 5 fluoro, —N(C$_{1-4}$alkyl)$_2$, and —N(C$_{1-4}$alkyl)$_2$ where the alkyls are independently substituted with from 1 to 7 fluoro, $C_{1-8}$alkoxy, $C_{1-8}$alkoxy substituted with from one to six substituents independently selected from: —OH, oxo, fluoro, chloro, bromo, iodo, $C_{1-4}$alkoxy, cycloalkyl, —NH$_2$, —N(H)C$_{1-4}$alkyl, —N(H)C$_{1-4}$alkyl where the alkyl is substituted with from 1 to 5 fluoro, —N(C$_{1-4}$alkyl)$_2$, —N(C$_{1-4}$alkyl)$_2$ where the alkyls are independently substituted with from 1 to 7 fluoro, —S(O)$_2$CH$_3$, —S(O)$_2$NH$_2$, and —S(O)$_2$N(H)C$_{1-4}$alkyl, N(C$_{1-6}$alkyl)$_2$, where each alkyl is optionally substituted with from one to six substituents independently selected from: —OH, oxo, fluoro, chloro, bromo, iodo, and —S(O)$_2$CH$_3$, N(H)C$_{1-6}$alkyl, N(H)C$_{1-6}$alkyl substituted with from one to six substituents independently selected from: —OH, oxo, fluoro, chloro, bromo, iodo, and —S(O)$_2$CH$_3$.

Suitably in the compounds of Formula (II), $R^{13}$ and $R^{14}$ are independently selected from: hydrogen, —OH, —C(CH$_3$)$_2$OH, —CH$_3$, oxo, —C(O)C(CH$_3$)$_2$OH, —CHF$_2$, azetidinyl, azetidinyl substituted by fluoro, azetidinyl substituted 2 times by fluoro, —NHCH(CF$_3$)CH$_2$OH, —CF$_3$, and —NHCH(CHF$_2$)CH$_3$.

Suitably in the compounds of Formula (II), $R^{11}$ is absent when $Y^1$ is N, or selected from hydrogen, and chloro. Suitably in the compounds of Formula (II), $R^{12}$ is selected from hydrogen, —OR$^{15}$, —SR$^{16}$, cyclopropyl, cyclobutyl, —NHR$^{17}$, azetidinyl, and azetidinyl substituted with 1 or 2 substituents independently selected from: fluoro, and —CH$_3$;

where:

$R^{15}$ is selected from hydrogen, $C_{1-2}$alkyl, and $C_{1-2}$alkyl substituted from 1 to 3 times by: fluoro, $R^{16}$ is selected from hydrogen, and $C_{1-2}$alkyl, $R^{17}$ is selected from $C_{1-2}$alkyl, and $C_{1-2}$alkyl substituted from 1 to 3 times by fluoro.

Suitably in the compounds of Formula (II), B is selected from: cyclohexyl, cyclobutyl, pyrrolidinyl, piperidinyl, spiro[3.3]heptanyl, and azetidinyl.

Suitably in the compounds of Formula (II), $R^{13}$ and $R^{14}$ are independently selected from:

hydrogen,

—OH,

F, azetidinyl, azetidinyl substituted one or two times by fluoro, oxo, $C_{1-6}$alkyl, $C_{1-6}$alkyl substituted with from one to five substituents independently selected from: —OH, oxo, and fluoro, N(H)C$_{1-3}$alkyl, and N(H)C$_{1-3}$alkyl substituted with from one to five substituents independently selected from: —OH, and fluoro.

This invention relates to compounds of Formula (III) and to the use of compounds of Formula (III) in the methods of the invention:

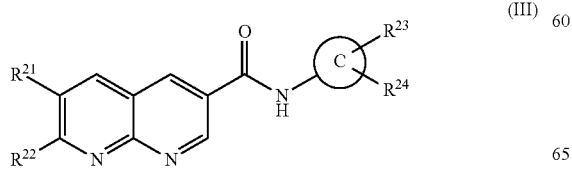

(III)

wherein:

$R^{21}$ is selected from: hydrogen and chloro;

$R^{22}$ is selected from hydrogen, —OR$^{25}$, —SR$^{26}$, cyclopropyl, cyclobutyl, —NHR$^{27}$ azetidinyl, and azetidinyl substituted with 1 or 2 substituents independently selected from: fluoro, and —CH$_3$;

where:

$R^{25}$ is selected from hydrogen, $C_{1-2}$alkyl, and $C_{1-2}$alkyl substituted from 1 to 3 times by: fluoro, $R^{26}$ is selected from hydrogen, and $C_{1-2}$alkyl, and $R^{27}$ is selected from $C_{1-2}$alkyl, and $C_{1-2}$alkyl substituted from 1 to 3 times by fluoro;

C is selected from: cyclohexyl, cyclobutyl, pyrrolidinyl, piperidinyl, spiro[3.3]heptanyl, and azetidinyl; and $R^{23}$ and $R^{24}$ are independently selected from:

hydrogen,

—OH,

F, azetidinyl, azetidinyl substituted one or two times by fluoro, oxo, $C_{1-6}$alkyl, $C_{1-6}$alkyl substituted with from one to five substituents independently selected from: —OH, oxo, and fluoro, N(H)C$_{1-3}$alkyl, and N(H)C$_{1-3}$alkyl substituted with from one to five substituents independently selected from: —OH, and fluoro;

provided $R^{22}$, $R^{23}$ and $R^{24}$ are not all hydrogen;

or a pharmaceutically acceptable salt thereof.

This invention relates to compounds of Formula (IV) and to the use of compounds of Formula (IV) in the methods of the invention:

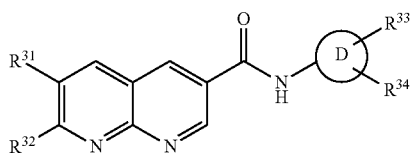

(IV)

wherein:

$R^{31}$ is selected from: hydrogen and chloro;

$R^{32}$ is selected from: hydrogen, azetidinyl, azetidinyl substituted by fluoro, azetidinyl substituted by —CH$_3$, cyclopropyl, —NHCH$_2$CF$_3$, —NHCH$_2$CHF$_2$, —OCH$_3$, —OCH$_2$CF$_3$, and —OCH$_2$CH$_3$;

D is selected from: cyclohexyl, cyclobutyl, pyrrolidinyl, piperidinyl, spiro[3.3]heptanyl, and azetidinyl; and $R^{33}$ and $R^{34}$ are independently selected from: hydrogen, —OH, —C(CH$_3$)$_2$OH, —CH$_3$, oxo, —C(O)C(CH$_3$)$_2$OH, —CHF$_2$, azetidinyl, azetidinyl substituted by fluoro, azetidinyl substituted 2 times by fluoro, —NHCH(CF$_3$)CH$_2$OH, —CF$_3$, and —NHCH(CHF$_2$)CH$_3$;

provided $R^{32}$, $R^{33}$ and $R^{34}$ are not all hydrogen;

or a pharmaceutically acceptable salt thereof.

This invention relates to compounds of Formula (V) and to the use of compounds of Formula (V) in the methods of the invention:

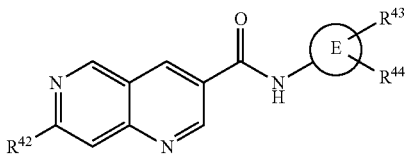

wherein:
R$^{42}$ is selected from hydrogen, —OR$^{45}$, —SR$^{46}$, cyclopropyl, cyclobutyl, —NHR$^{47}$, azetidinyl, and azetidinyl substituted with 1 or 2 substituents independently selected from: fluoro, and —CH$_3$;
where:
R$^{45}$ is selected from hydrogen, C$_{1-2}$alkyl, and C$_{1-2}$alkyl substituted from 1 to 3 times by: fluoro,
R$^{46}$ is selected from hydrogen, and C$_{1-2}$alkyl, and
R$^{47}$ is selected from C$_{1-2}$alkyl, and C$_{1-2}$alkyl substituted from 1 to 3 times by fluoro;
E is selected from: cyclohexyl, cyclobutyl, pyrrolidinyl, piperidinyl, spiro[3.3]heptanyl, and azetidinyl; and
R$^{43}$ and R$^{44}$ are independently selected from:
hydrogen,
—OH,
F,
azetidinyl,
azetidinyl substituted one or two times by fluoro,
oxo,
C$_{1-6}$alkyl,
C$_{1-6}$alkyl substituted with from one to five substituents independently selected from: —OH, oxo, and fluoro,
N(H)C$_{1-3}$alkyl, and
N(H)C$_{1-3}$alkyl substituted with from one to five substituents independently selected from: —OH, and fluoro;
provided R$^{42}$, R$^{43}$ and R$^{44}$ are not all hydrogen;
or a pharmaceutically acceptable salt thereof.

This invention relates to compounds of Formula (VI) and to the use of compounds of Formula (VI) in the methods of the invention:

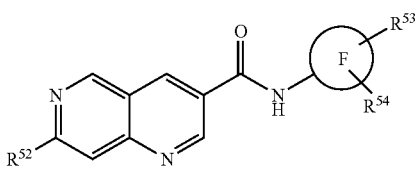

wherein:
R$^{52}$ is selected from: hydrogen, azetidinyl, azetidinyl substituted by fluoro, azetidinyl substituted by —CH$_3$, cyclopropyl, —NHCH$_2$CF$_3$, —NHCH$_2$CHF$_2$, —OCH$_3$, —OCH$_2$CF$_3$, and —OCH$_2$CH$_3$;
F is selected from: cyclohexyl, cyclobutyl, pyrrolidinyl, piperidinyl, spiro[3.3]heptanyl, and azetidinyl; and
R$^{53}$ and R$^{54}$ are independently selected from: hydrogen, —OH, —C(CH$_3$)$_2$OH, —CH$_3$, oxo, —C(O)C(CH$_3$)$_2$OH, —CHF$_2$, azetidinyl, azetidinyl substituted by fluoro, azetidinyl substituted 2 times by fluoro, —NHCH(CF$_3$)CH$_2$OH, —CF$_3$, and —NHCH(CHF$_2$)CH$_3$;
provided R$^{52}$, R$^{53}$ and R$^{54}$ are not all hydrogen;
or a pharmaceutically acceptable salt thereof.

Included in the compounds of Formula (I) and in the methods of the invention are:
N-(trans-4-(2-Hydroxypropan-2-yl)cyclohexyl)-1,6-naphthyridine-3-carboxamide;
N-(trans-4-(2-Hydroxypropan-2-yl)cyclohexyl)-1,8-naphthyridine-3-carboxamide;
7-(3-Fluoroazetidin-1-yl)-N-(trans-4-(2-hydroxypropan-2-yl)cyclohexyl)-1,6-naphthyridine-3-carboxamide;
7-(Azetidin-1-yl)-N-(trans-4-(2-hydroxypropan-2-yl)cyclohexyl)-1,6-naphthyridine-3-carboxamide;
7-(Azetidin-1-yl)-N-(trans-4-(2-hydroxypropan-2-yl)cyclohexyl)-1,8-naphthyridine-3-carboxamide;
7-(3-Fluoroazetidin-1-yl)-N-(trans-4-(2-hydroxypropan-2-yl)cyclohexyl)-1,8-naphthyridine-3-carboxamide;
N-(trans-4-(2-Hydroxypropan-2-yl)cyclohexyl)-7-(2-methylazetidin-1-yl)-1,8-naphthyridine-3-carboxamide;
N-(trans-4-(2-Hydroxypropan-2-yl)cyclohexyl)-7-((R)-2-methylazetidin-1-yl)-1,8-naphthyridine-3-carboxamide;
N-(trans-4-(2-Hydroxypropan-2-yl)cyclohexyl)-7-((S)-2-methylazetidin-1-yl)-1,8-naphthyridine-3-carboxamide;
7-Cyclopropyl-N-((trans)-4-(2-hydroxypropan-2-yl)cyclohexyl)-1,6-naphthyridine-3-carboxamide;
N-(trans-4-(2-Hydroxypropan-2-yl)cyclohexyl)-7-(2-methylazetidin-1-yl)-1,6-naphthyridine-3-carboxamide;
N-(trans-4-(2-Hydroxypropan-2-yl)cyclohexyl)-7-((R)-2-methylazetidin-1-yl)-1,6-naphthyridine-3-carboxamide;
N-(trans-4-(2-Hydroxypropan-2-yl)cyclohexyl)-7-((S)-2-methylazetidin-1-yl)-1,6-naphthyridine-3-carboxamide;
7-(Cyclopropylamino)-N-(trans-4-(2-hydroxypropan-2-yl)cyclohexyl)-1,6-naphthyridine-3-carboxamide;
7-(Azetidin-1-yl)-N-((1s,3s)-3-hydroxy-3-methylcyclobutyl)-1,6-naphthyridine-3-carboxamide;
7-((2,2-Difluoroethyl)amino)-N-(trans-4-(2-hydroxypropan-2-yl)cyclohexyl)-1,8-naphthyridine-3-carboxamide;
N-(trans-4-(2-Hydroxypropan-2-yl)cyclohexyl)-7-((2,2,2-trifluoroethyl)amino)-1,8-naphthyridine-3-carboxamide;
7-(Azetidin-1-yl)-N-((1s,3s)-3-hydroxy-3-methylcyclobutyl)-1,8-naphthyridine-3-carboxamide;
(S)-7-(Azetidin-1-yl)-N-(2-oxopyrrolidin-3-yl)-1,8-naphthyridine-3-carboxamide;
(S)-7-(Azetidin-1-yl)-N-(2-oxopyrrolidin-3-yl)-1,6-naphthyridine-3-carboxamide;
7-Cyclopropyl-N-((trans)-4-(2-hydroxypropan-2-yl)cyclohexyl)-1,8-naphthyridine-3-carboxamide;
7-((S)-2-Methylazetidin-1-yl)-N—((S)-2-oxopyrrolidin-3-yl)-1,6-naphthyridine-3-carboxamide;
N-((1s,3R)-3-Hydroxy-3-methylcyclobutyl)-7-((S)-2-methylazetidin-1-yl)-1,6-naphthyridine-3-carboxamide;
(S)—N-(1-(2-Hydroxy-2-methylpropanoyl)piperidin-4-yl)-7-(2-methylazetidin-1-yl)-1,6-naphthyridine-3-carboxamide;
7-(Azetidin-1-yl)-6-chloro-N-(trans-4-(2-hydroxypropan-2-yl)cyclohexyl)-1,8-naphthyridine-3-carboxamide;
N-(trans-3-(2-Hydroxypropan-2-yl)cyclobutyl)-7-((S)-2-methylazetidin-1-yl)-1,6-naphthyridine-3-carboxamide;
6-Chloro-7-cyclopropyl-N-((trans)-4-(2-hydroxypropan-2-yl)cyclohexyl)-1,8-naphthyridine-3-carboxamide;
N-((3S,4R)-4-Methyl-2-oxopyrrolidin-3-yl)-7-((S)-2-methylazetidin-1-yl)-1,6-naphthyridine-3-carboxamide;
(S)-7-Cyclopropyl-N-(2-oxopyrrolidin-3-yl)-1,6-naphthyridine-3-carboxamide;
7-Cyclopropyl-N-((1r,4r)-4-hydroxy-4-methylcyclohexyl)-1,6-naphthyridine-3-carboxamide;
7-Cyclopropyl-N-((1s,3s)-3-hydroxy-3-methylcyclobutyl)-1,6-naphthyridine-3-carboxamide;
7-Cyclopropyl-N-(trans-3-(2-hydroxypropan-2-yl)cyclobutyl)-1,6-naphthyridine-3-carboxamide;

7-Cyclopropyl-N-((1r,4r)-4-(difluoromethyl)-4-hydroxycyclohexyl)-1,6-naphthyridine-3-carboxamide;
7-Cyclopropyl-N-(6-(2-hydroxypropan-2-yl)spiro[3.3]heptan-2-yl)-1,6-naphthyridine-3-carboxamide;
7-Cyclopropyl-N-(trans-4-(3-fluoroazetidin-1-yl)cyclohexyl)-1,6-naphthyridine-3-carboxamide;
7-Cyclopropyl-N-((1s,4s)-4-(difluoromethyl)-4-hydroxycyclohexyl)-1,6-naphthyridine-3-carboxamide;
7-Cyclopropyl-N-((trans)-4-(((R)-1,1,1-trifluoro-3-hydroxypropan-2-yl)amino)cyclohexyl)-1,6-naphthyridine-3-carboxamide;
7-Cyclopropyl-N-(trans-4-(3,3-difluoroazetidin-1-yl)cyclohexyl)-1,6-naphthyridine-3-carboxamide;
7-Cyclopropyl-N-(trans-4-((1,1-difluoropropan-2-yl)amino)cyclohexyl)-1,6-naphthyridine-3-carboxamide;
7-Cyclopropyl-N-((1s,3s)-3-hydroxy-3-(trifluoromethyl)cyclobutyl)-1,6-naphthyridine-3-carboxamide;
7-Cyclopropyl-N-((1r,3r)-3-hydroxy-3-methylcyclobutyl)-1,6-naphthyridine-3-carboxamide;
7-Cyclopropyl-N-(cis-3-(((R)-1,1,1-trifluoro-3-hydroxypropan-2-yl)amino)cyclobutyl)-1,6-naphthyridine-3-carboxamide;
7-Cyclopropyl-N-(trans-3-(((R)-1,1,1-trifluoro-3-hydroxypropan-2-yl)amino)cyclobutyl)-1,6-naphthyridine-3-carboxamide;
(S)-7-Cyclopropyl-N-(2-oxopyrrolidin-3-yl)-1,8-naphthyridine-3-carboxamide;
7-Cyclopropyl-N-((1s,3s)-3-hydroxy-3-methylcyclobutyl)-1,8-naphthyridine-3-carboxamide;
7-Cyclopropyl-N-((1r,3r)-3-hydroxy-3-methylcyclobutyl)-1,8-naphthyridine-3-carboxamide;
7-Cyclopropyl-N-(trans-3-(2-hydroxypropan-2-yl)cyclobutyl)-1,8-naphthyridine-3-carboxamide;
7-Cyclopropyl-N-((1r,4r)-4-hydroxy-4-methylcyclohexyl)-1,8-naphthyridine-3-carboxamide;
7-Cyclopropyl-N-(6-(2-hydroxypropan-2-yl)spiro[3.3]heptan-2-yl)-1,8-naphthyridine-3-carboxamide;
N-(trans-4-(2-Hydroxypropan-2-yl)cyclohexyl)-7-methoxy-1,8-naphthyridine-3-carboxamide;
N-(trans-4-(2-Hydroxypropan-2-yl)cyclohexyl)-7-methoxy-1,6-naphthyridine-3-carboxamide;
7-Cyclopropyl-N-((1r,4r)-4-(difluoromethyl)-4-hydroxycyclohexyl)-1,8-naphthyridine-3-carboxamide;
7-Cyclopropyl-N-((1s,3s)-3-hydroxy-3-(trifluoromethyl)cyclobutyl)-1,8-naphthyridine-3-carboxamide;
7-Cyclopropyl-N-(trans-4-(3,3-difluoroazetidin-1-yl)cyclohexyl)-1,8-naphthyridine-3-carboxamide;
N-(trans-4-(2-Hydroxypropan-2-yl)cyclohexyl)-7-(2,2,2-trifluoroethoxy)-1,8-naphthyridine-3-carboxamide;
7-Ethoxy-N-(trans-4-(2-hydroxypropan-2-yl)cyclohexyl)-1,8-naphthyridine-3-carboxamide;
7-Cyclopropyl-N-(trans-4-((1,1-difluoropropan-2-yl)amino)cyclohexyl)-1,8-naphthyridine-3-carboxamide;
6-Chloro-N-(trans-4-(2-hydroxypropan-2-yl)cyclohexyl)-7-((S)-2-methylazetidin-1-yl)-1,8-naphthyridine-3-carboxamide;
6-Chloro-N-((1r,4S)-4-hydroxy-4-methylcyclohexyl)-7-((S)-2-methylazetidin-1-yl)-1,8-naphthyridine-3-carboxamide;
6-Chloro-7-((S)-2-methylazetidin-1-yl)-N—((S)-2-oxopyrrolidin-3-yl)-1,8-naphthyridine-3-carboxamide;
(S)-6-Chloro-N-(6-(2-hydroxypropan-2-yl)spiro[3.3]heptan-2-yl)-7-(2-methylazetidin-1-yl)-1,8-naphthyridine-3-carboxamide;
6-Chloro-N-(trans-4-(2-hydroxypropan-2-yl)cyclohexyl)-7-methoxy-1,8-naphthyridine-3-carboxamide;
6-Chloro-N-((1s,3R)-3-hydroxy-3-methylcyclobutyl)-7-((S)-2-methylazetidin-1-yl)-1,8-naphthyridine-3-carboxamide;
6-Chloro-N-((1r,3S)-3-hydroxy-3-methylcyclobutyl)-7-((S)-2-methylazetidin-1-yl)-1,8-naphthyridine-3-carboxamide;
6-Chloro-N-(trans-3-(2-hydroxypropan-2-yl)cyclobutyl)-7-((S)-2-methylazetidin-1-yl)-1,8-naphthyridine-3-carboxamide;
6-Chloro-N-((1s,3R)-3-hydroxy-3-(trifluoromethyl)cyclobutyl)-7-((S)-2-methylazetidin-1-yl)-1,8-naphthyridine-3-carboxamide;
6-Chloro-N-((3S,4R)-4-methyl-2-oxopyrrolidin-3-yl)-7-((S)-2-methylazetidin-1-yl)-1,8-naphthyridine-3-carboxamide;
7-Cyclopropyl-N-(cis-3-(((R)-1,1,1-trifluoro-3-hydroxypropan-2-yl)amino)cyclobutyl)-1,8-naphthyridine-3-carboxamide;
7-Cyclopropyl-N-(trans-3-(((R)-1,1,1-trifluoro-3-hydroxypropan-2-yl)amino)cyclobutyl)-1,8-naphthyridine-3-carboxamide;
N-(trans-4-(2-Hydroxypropan-2-yl)cyclohexyl)-2-(methylthio)pyrido[2,3-d]pyrimidine-6-carboxamide;
(S)-6-Chloro-7-cyclopropyl-N-(2-oxopyrrolidin-3-yl)-1,8-naphthyridine-3-carboxamide;
7-Cyclobutyl-N-(trans-4-(2-hydroxypropan-2-yl)cyclohexyl)-1,8-naphthyridine-3-carboxamide;
6-Chloro-7-cyclopropyl-N-(trans-3-(2-hydroxypropan-2-yl)cyclobutyl)-1,8-naphthyridine-3-carboxamide;
6-Chloro-7-cyclopropyl-N-((1r,4r)-4-hydroxy-4-methylcyclohexyl)-1,8-naphthyridine-3-carboxamide;
6-Chloro-7-cyclopropyl-N-((1r,3s)-3-hydroxy-3-methylcyclobutyl)-1,8-naphthyridine-3-carboxamide;
6-Chloro-7-cyclopropyl-N-((1s,3s)-3-hydroxy-3-methylcyclobutyl)-1,8-naphthyridine-3-carboxamide;
6-Chloro-7-cyclopropyl-N-((1s,3s)-3-hydroxy-3-(trifluoromethyl)cyclobutyl)-1,8-naphthyridine-3-carboxamide;
N—((S)-4,4-Dimethyl-2-oxopyrrolidin-3-yl)-7-((S)-2-methylazetidin-1-yl)-1,6-naphthyridine-3-carboxamide;
2-(Azetidin-1-yl)-N-((trans)-4-(2-hydroxypropan-2-yl)cyclohexyl)pyrido[2,3-d]pyrimidine-6-carboxamide;
N-((trans)-4-(2-Hydroxypropan-2-yl)cyclohexyl)-2-methoxypyrido[2,3-d]pyrimidine-6-carboxamide; and
2-Cyclopropyl-N-(trans-4-(2-hydroxypropan-2-yl)cyclohexyl)pyrido[2,3-d]pyrimidine-6-carboxamide;
and pharmaceutically acceptable salts thereof.

The skilled artisan will appreciate that salts, including pharmaceutically acceptable salts, of the compounds according to Formula (I) may be prepared. Indeed, in certain embodiments of the invention, salts including pharmaceutically-acceptable salts of the compounds according to Formula (I) may be preferred over the respective free or unsalted compound. Accordingly, the invention is further directed to salts, including pharmaceutically-acceptable salts, of the compounds according to Formula (I). The invention is further directed to free or unsalted compounds of Formula (I).

The salts, including pharmaceutically acceptable salts, of the compounds of the invention are readily prepared by those of skill in the art.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5- dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolidine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The compounds according to Formula (I) may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may be present in a substituent such as an alkyl group. Where the stereochemistry of a chiral center present in a compound of Formula (I), or in any chemical structure illustrated herein, if not specified the structure is intended to encompass all individual stereoisomers and all mixtures thereof. Thus, compounds according to Formula (I) containing one or more chiral centers may be used as racemic mixtures, enantiomerically enriched mixtures, or as enantiomerically pure individual stereoisomers.

The compounds according to Formula (I) and pharmaceutically acceptable salts thereof may contain isotopically-labelled compounds, which are identical to those recited in Formula (I) and following, but for the fact that one or more atoms are replaced by an atom having an atomic mass or mass number different from the atomic mass or mass number usually found in nature. Examples of such isotopes include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Isotopically-labelled compounds, for example those into which radioactive isotopes such as $^{3}H$ or $^{14}C$ are incorporated, are useful in drug and/or substrate tissue distribution assays. Tritium, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), both are useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds can generally be prepared by substituting a readily available isotopically labelled reagent for a non-isotopically labelled reagent.

The compounds according to Formula (I) may also contain double bonds or other centers of geometric asymmetry. Where the stereochemistry of a center of geometric asymmetry present in Formula (I), or in any chemical structure illustrated herein, is not specified, the structure is intended to encompass the trans (E) geometric isomer, the cis (Z) geometric isomer, and all mixtures thereof. Likewise, all tautomeric forms are also included in Formula (I) whether such tautomers exist in equilibrium or predominately in one form.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may have the ability to crystallize in more than one form, a characteristic, which is known as polymorphism ("polymorphs"). Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula (I) may exist in solvated and unsolvated forms. As used herein, the term "solvate" refers to a complex of variable stoichiometry formed by a solute (in this invention, a compound of Formula (I) or a salt) and a solvent. Such solvents, for the purpose of the invention, may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water.

It is also noted that the compounds of Formula (I) may form tautomers. Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. It is understood that all tautomers and mixtures of tautomers of the compounds of the present invention are included within the scope of the compounds of the present invention.

While aspects for each variable have generally been listed above separately for each variable this invention includes those compounds in which several or each aspect in Formula (I) is selected from each of the aspects listed above. Therefore, this invention is intended to include all combinations of aspects for each variable.

Definitions

It will be appreciated that the following definitions apply to each of the aforementioned formulae and to all instances of these terms, unless the context dictates otherwise.

"Alkyl" refers to a hydrocarbon chain having the specified number of "carbon atoms". For example, $C_1$-$C_6$ alkyl refers to an alkyl group having from 1 to 6 carbon atoms. Alkyl groups may be saturated, unsaturated, straight or branched. Representative branched alkyl groups have one, two, or three branches. Alkyl includes but is not limited to: methyl, ethyl, ethylene, ethynyl, propyl (n-propyl and isopropyl), butene, butyl (n-butyl, isobutyl, and t-butyl), pentyl and hexyl.

"Alkoxy" refers to an —O-alkyl group wherein "alkyl" is as defined herein. For example, $C_1$-$C_4$alkoxy refers to an alkoxy group having from 1 to 4 carbon atoms. Representative branched alkoxy groups have one, two, or three branches. Examples of such groups include methoxy, ethoxy, propoxy, t-butoxy and butoxy.

"Aryl" refers to an aromatic hydrocarbon ring system. Aryl groups are monocyclic, bicyclic, and tricyclic ring systems having a total of five to fourteen ring member atoms, wherein at least one ring system is aromatic and wherein each ring in the system contains 3 to 7 member atoms, such as but not limited to: phenyl, naphthalenyl, and biphenyl. Suitably aryl is phenyl.

"Cycloalkyl", unless otherwise defined, refers to a saturated or unsaturated non aromatic hydrocarbon ring system having from three to seven carbon atoms. Cycloalkyl groups are monocyclic or bicyclic ring systems. For example, $C_3$-$C_7$ cycloalkyl refers to a cycloalkyl group having from 3 to 7 member atoms. Examples of cycloalkyl as used herein include: cyclopropyl, cyclobutyl, cyclopentyl, cyclohexyl, cyclobutenyl, cyclopentenyl, cyclohexenyl, cycloheptyl and spiro heptanyl. Suitably "cycloalkyl" includes: cyclopropyl, cyclobutyl, cyclohexyl, and spiro heptanyl.

"Halogen" refers to the halogen radicals fluoro, chloro, bromo, and iodo.

"Heteroaryl" refers to a monocyclic aromatic 4 to 8 member ring containing from 1 to 7 carbon atoms and containing from 1 to 4 heteroatoms, provided that when the number of carbon atoms is 3, the aromatic ring contains at least two heteroatoms. Heteroaryl groups containing more than one heteroatom may contain different heteroatoms. Heteroaryl includes: pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, and tetrazinyl.

"Bicycloheteroaryl" refers to two fused rings, at least one of which is aromatic, containing from 1 to 6 heteroatoms as member atoms. Bicycloheteroaryl groups containing more than one heteroatom may contain different heteroatoms. Bicycloheteroaryl rings have from 6 to 11 member atoms. Bicycloheteroaryl includes: 1H-pyrrolo[3,2-c]pyridine, 1H-pyrazolo[4,3-c]pyridine, 1H-pyrazolo[3,4-d]pyrimidine, 1H-pyrrolo[2,3-d]pyrimidine, 7H-pyrrolo[2,3-d]pyrimidine, thieno[3,2-c]pyridine, thieno[2,3-d]pyrimidine, furo[2,3-c]pyridine, furo[2,3-d]pyrimidine, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzoxadiazolyl, imidazothiazolyl, benzimidazolyl, benzopyranyl, benzoxazolyl, benzofuranyl, isobenzofuranyl, benzothiazolyl, benzothienyl, imidazo[4.5-c]pyridine, imidazo[4.5-b]pyridine, furopyridinyl and napthyridinyl.

"Heterocycle" and "Heterocycloalkyl" refers to a saturated or unsaturated non-aromatic monocyclic ring system containing 4 to 7 member atoms, of which 1 to 6 are carbon atoms and from 1 to 4 are heteroatoms. Heterocycloalkyl groups containing more than one heteroatom may contain different heteroatoms. Heterocycle and heterocycloalkyl includes: pyrrolidinyl, tetrahydrofuranyl, dihydrofuranyl, pyranyl, tetrahydropyranyl, dihydropyranyl, tetrahydrothienyl, pyrazolidinyl, oxazolidinyl, oxetanyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, and azetidinyl. Suitably, "Heterocycle" and "Heterocycloalkyl" includes: pyrrolidinyl, piperidinyl, and azetidinyl.

"Heteroatom" refers to a nitrogen, sulfur or oxygen atom. The term "substituted" as used herein, unless otherwise defined, is meant that the subject chemical moiety has from one to six substituents, suitably from one to three substituents, selected from the group consisting of: fluoro, chloro, bromo, iodo, $C_{1-6}$alkoxy, CN, oxo, —OH, —COOH, —$NO_2$, and —$NH_2$.

Abbreviations

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl);
$Ac_2O$ (acetic anhydride);
ACN (acetonitrile);
AIBN (azobis(isobutyronitrile));
BINAP (2,2'-bis(diphenylphosphino)-1,1'-binaphthyl);
BMS (borane-dimethyl sulphide complex);
Bn (benzyl);
Boc (tert-Butoxycarbonyl);
$Boc_2O$ (di-tert-butyl dicarbonate);
BOP (Benzotriazole-1-yl-oxy-tris-(dimethylamino)-phosphonium hexafluorophosphate);
CAN (cerric ammonium nitrate);
Cbz (benzyloxycarbonyl);
CSI (chlorosulfonyl isocyanate);
CsF (cesium fluoride);
DABCO (1,4-Diazabicyclo[2.2.2]octane);
DAST (Diethylamino)sulfur trifluoride);

DBU (1,8-Diazabicyclo[5.4.0]undec-7-ene);
DCC (Dicyclohexyl Carbodiimide);
DCE (1,2-dichloroethane);
DDQ (2,3-Dichloro-5,6-dicyano-1,4-benzoquinone);
ATP (adenosine triphosphate);
Bis-pinacolatodiboron (4,4,4',4',5,5,5',5'-Octamethyl-2,2'-bi-1,3,2-dioxaborolane);
BSA (bovine serum albumin);
C18 (refers to 18-carbon alkyl groups on silicon in HPLC stationary phase);
$CH_3CN$ (acetonitrile);
Cy (cyclohexyl);
DCM (dichloromethane);
DIEA (Hünig's base, N,N-Diisopropylethylamine, N-ethyl-N-(1-methylethyl)-2-propanamine);
Dioxane (1,4-dioxane);
DMAP (4-dimethylaminopyridine);
DME (1,2-dimethoxyethane);
DMEDA (N,N'-dimethylethylenediamine);
DMF (N,N-dimethylformamide);
DMSO (dimethylsulfoxide);
DPPA (diphenyl phosphoryl azide);
EDC (N-(3-dimethylaminopropyl)-N'ethylcarbodiimide);
EDTA (ethylenediaminetetraacetic acid);
EtOAc (ethyl acetate);
EtOH (ethanol);
$Et_2O$ (diethyl ether);
HEPES (4-(2-hydroxyethyl)-1-piperazine ethane sulfonic acid);
HATU (O-(7-Azabenzotriazol-1-yl)-N,N,N',N'-tetramethyluronium hexafluorophosphate, 1-((dimethylamino)(dimethyliminio)methyl)-1H-[1,2,3]triazolo[4,5-b]pyridine 3-oxide hexafluorophosphate(V));
HOAt (1-hydroxy-7-azabenzotriazole);
HOBt (1-hydroxybenzotriazole);
HOAc (acetic acid);
HPLC (high pressure liquid chromatography);
HMDS (hexamethyldisilazide);
IPA (isopropyl alcohol);
Indoline (2,3-dihydro-1H-indole);
KHMDS (potassium hexamethyldisilazide);
LAH (lithium aluminum hydride);
LDA (lithium diisopropylamide);
LHMDS (lithium hexamethyldisilazide)
MeOH (methanol);
MTBE (methyl tert-butyl ether);
mCPBA (m-chloroperoxybenzoic acid);
NaHMDS (sodium hexamethyldisilazide);
NBS (N-bromosuccinimide);
PE (petroleum ether);
$Pd_2(dba)_3$ (Tris(dibenzylideneacetone)dipalladium(0);
$Pd(dppf)Cl_2$•DCM Complex([1,1'-Bis(diphenylphosphino)ferrocene]dichloropalladium(II)•dichloromethane complex);
PyBOP (benzotriazol-1-yl-oxytripyrrolidinophosphonium hexafluorophosphate);
PyBrOP (bromotripyrrolidinophosphonium hexafluorophosphate);
RP-HPLC (reverse phase high pressure liquid chromatography);
RT (room temperature);
Sat. (saturated)
SFC (supercritical fluid chromatography);
SGC (silica gel chromatography);
SM (starting material);
TLC (thin layer chromatography);
TEA (triethylamine);
TEMPO (2,2,6,6-Tetramethylpiperidine 1-oxyl, free radical);
TFA (trifluoroacetic acid); and
THF (tetrahydrofuran).

All references to ether are to diethyl ether and brine refers to a saturated aqueous solution of NaCl.

Compound Preparation

The compounds according to Formula (I) are prepared using conventional organic synthetic methods. A suitable synthetic route is depicted below in the following general reaction schemes. All of the starting materials are commercially available or are readily prepared from commercially available starting materials by those of skill in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Organic Synthesis* (4th ed.), John Wiley & Sons, NY (2006). In some instances, a substituent may be specifically selected to be reactive under the reaction conditions used. Under these circumstances, the reaction conditions convert the selected substituent into another substituent that is either useful as an intermediate compound or is a desired substituent in a target compound.

As used in the Schemes, "r" groups represent corresponding positional groups on any of Formulas I to VI.

In one method of preparation, 1,6-naphthyridines may be synthesized from pyridines as shown in Scheme 1. First, ipso displacement of the 4-chloro group of the dichloropyridine (commercially available) with para-methoxybenzylamine, followed by acid catalyzed cleavage of the protecting group affords the 4-aminopyridine ester. Subsequent reduction of the ester to the primary alcohol, followed by manganese dioxide oxidation gives the aminoaldehyde. Then, Lewis acid catalyzed condensation of this moiety with the acetal and cyclization/aromatization provides the 3-bromo-1,6-naphthyridine. After palladium catalyzed carbonylation, the resulting chloro-1,6-naphthyridine ester can be converted via Suzuki cross-couplings or chloride displacements to various 7-substituted-1,6-naphthyridine esters. Finally, ester hydrolyses and amide bond formations afford the desired 1,6-naphthyridine amides.

Scheme 1

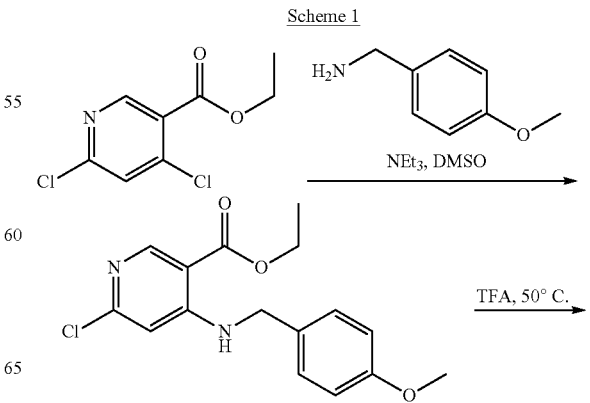

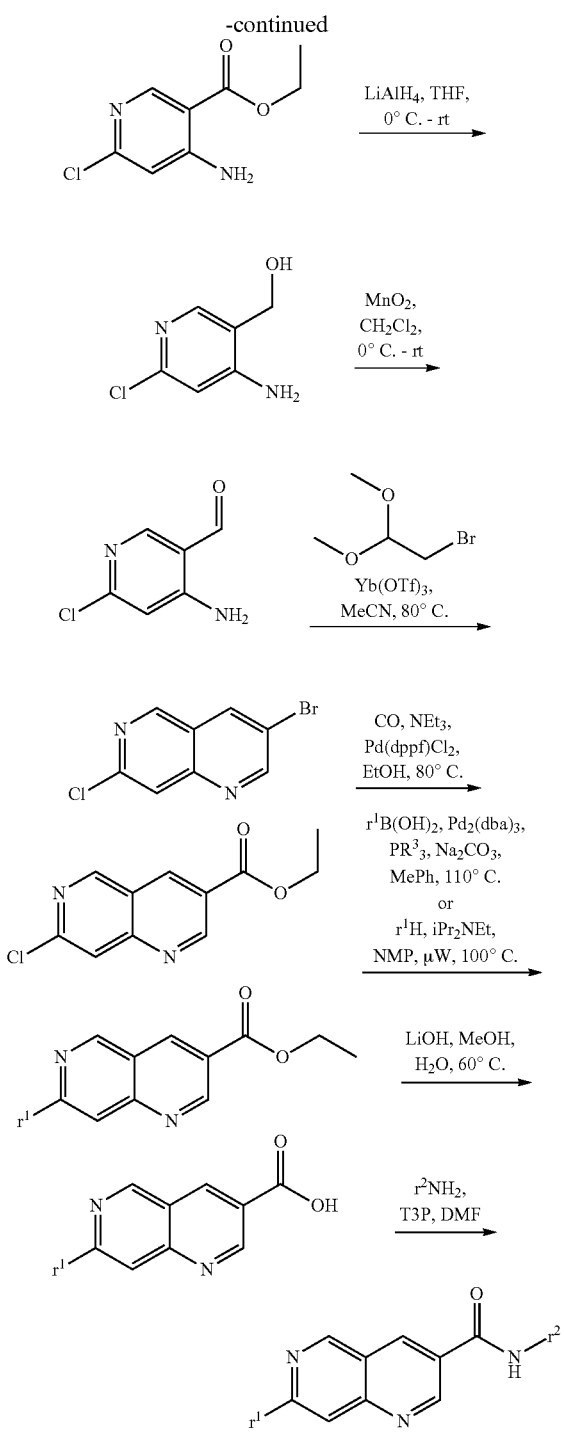

In another method of preparation, 1,8-naphthyridines may be synthesized from pyridines (commercially available) as shown in Scheme 2. First, condensation of the diaminopyridine with the dialdehyde with subsequent cyclization and aromatization provides the bromo-1,8-naphthyridine. Then, palladium catalyzed carbonylation and subsequent diazotization and chloride trapping gives the chloro-1,8-naphthyridine. This ester can be converted via Suzuki cross-couplings or chloride displacements to various 7-substituted-1,8-naphthyridine esters, which upon hydrolysis and amide bond formation afford the desired 1,8-naphthyridine amides.

In another method of preparation, 1,8-naphthyridines may be synthesized from pyridines (commercially available) as shown in Scheme 3. First, lithium aluminum hydride mediated reduction of the carboxylic acid to the primary alcohol, followed by manganese dioxide oxidation affords the aldehyde. Then, proline catalyzed addition of the aniline to the propiolate with subsequent condensation and elimination gives the 1,8-naphthyridine ester. This ester can be converted via Suzuki cross-couplings or chloride displacements to various 7-substituted-1,8-naphthyridine esters, which upon hydrolysis and amide bond formation afford the desired 1,8-naphthyridine amides.

Scheme 3

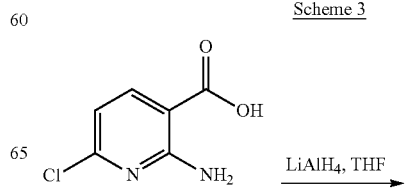

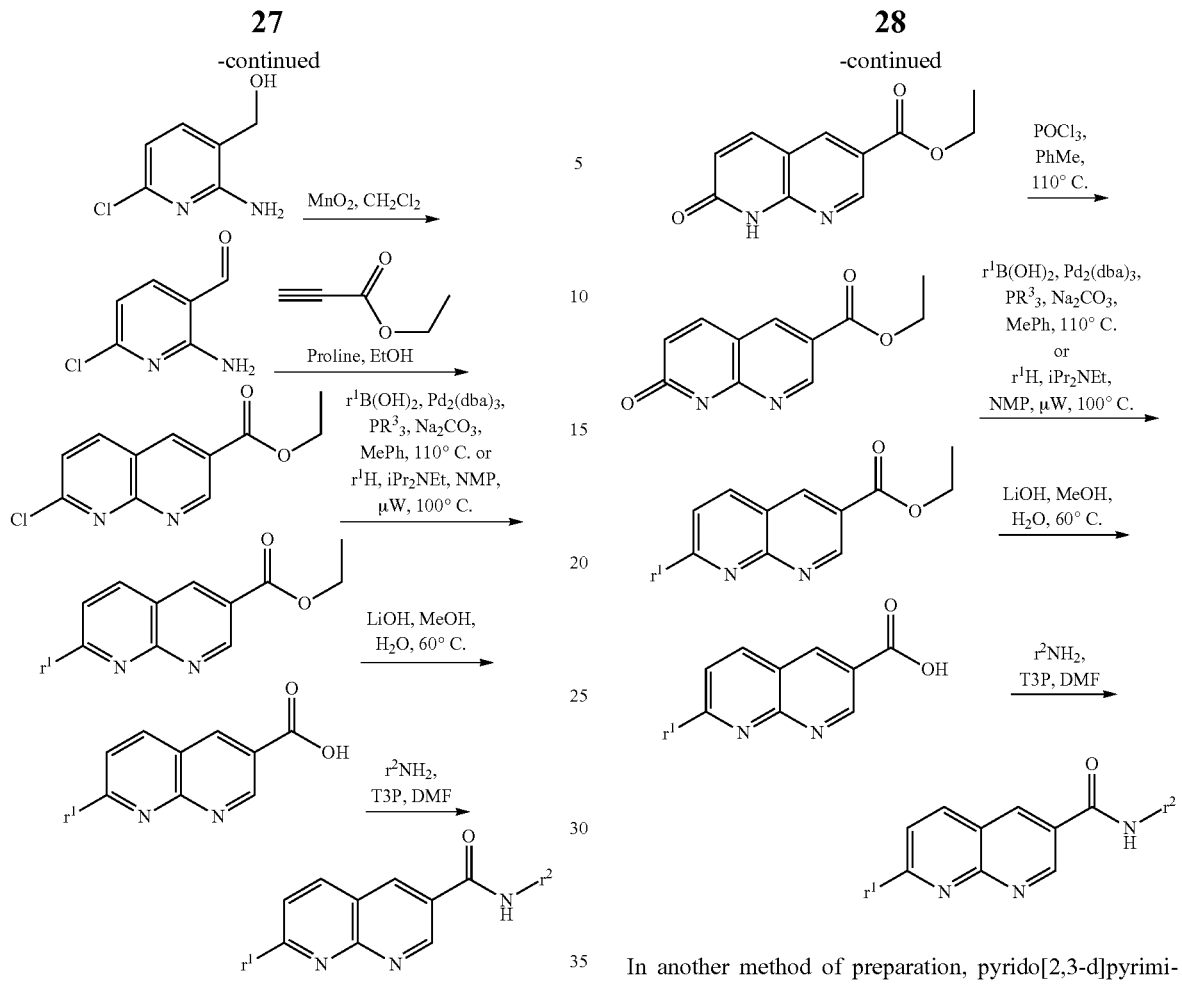

In another method of preparation, 1,8-naphthyridines may be synthesized from pyridines (commercially available) as shown in Scheme 4. First, chromium catalyzed partial reduction of the ester provides the aldehyde. Then, acid catalyzed condensation of the aniline with ethyl 3,3-diethoxypropanoate with subsequent cyclization and elimination gives the 1,8-naphthyridin-2(1H)-one. Treatment with phosphorus oxychloride then affords the 2-chloro-1,8-naphthyridine. This ester can be converted via Suzuki/Negishi cross-couplings or chloride displacements to various 7-substituted-1,8-naphthyridine esters, which upon hydrolysis and amide bond formation afford the desired 1,8-naphthyridine amides.

In another method of preparation, pyrido[2,3-d]pyrimidines may be synthesized from pyrimidines (commercially available) as shown in Scheme 5. First, displacement of the 4-chloro group of the pyrimidine with ammonia, followed by reduction of the ester to the primary alcohol, then oxidation affords the aldehyde. Subsequent condensation of the aldehyde with diethyl malonate with concomitant cyclization/aromatization gives 7-oxo-7,8-dihydropyrido[2,3-d]pyrimidine. Conversion of this compound to the chloride and palladium catalyzed reduction yields the pyrido[2,3-d]pyrimidine ester. Then, oxidation of the sulfide to the sulfone and subsequent displacement with nucleophiles gives various 7-substituted-pyrido[2,3-d]pyrimidine esters. Finally, ester hydrolyses and amide bond formations afford the desired pyrido[2,3-d]pyrimidine amides.

Scheme 4

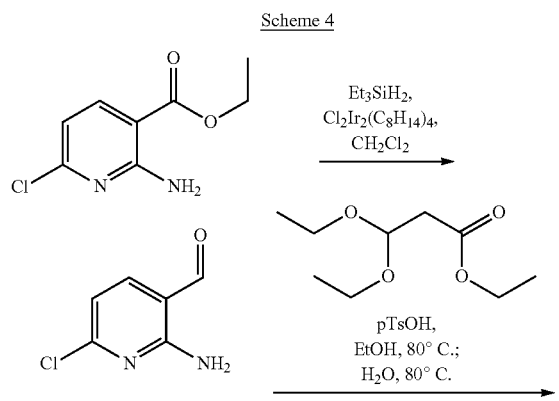

Scheme 5

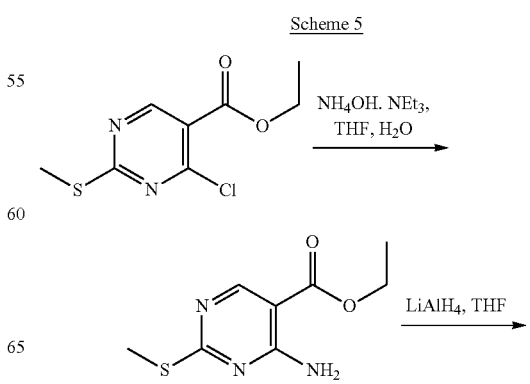

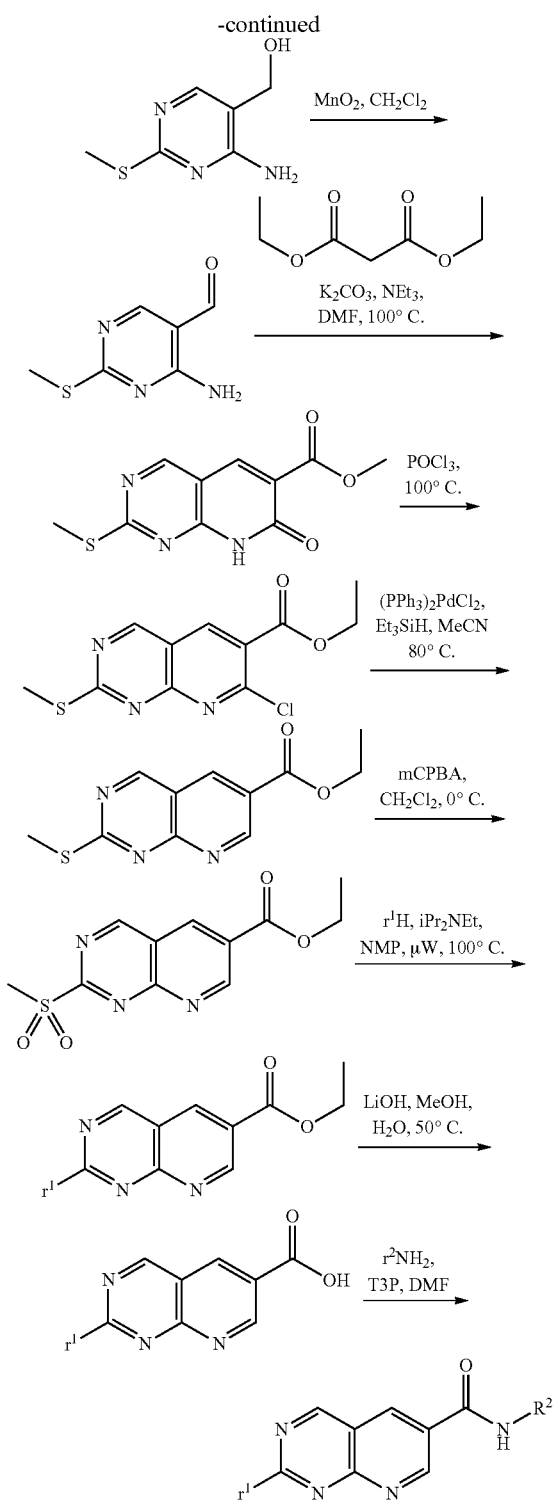

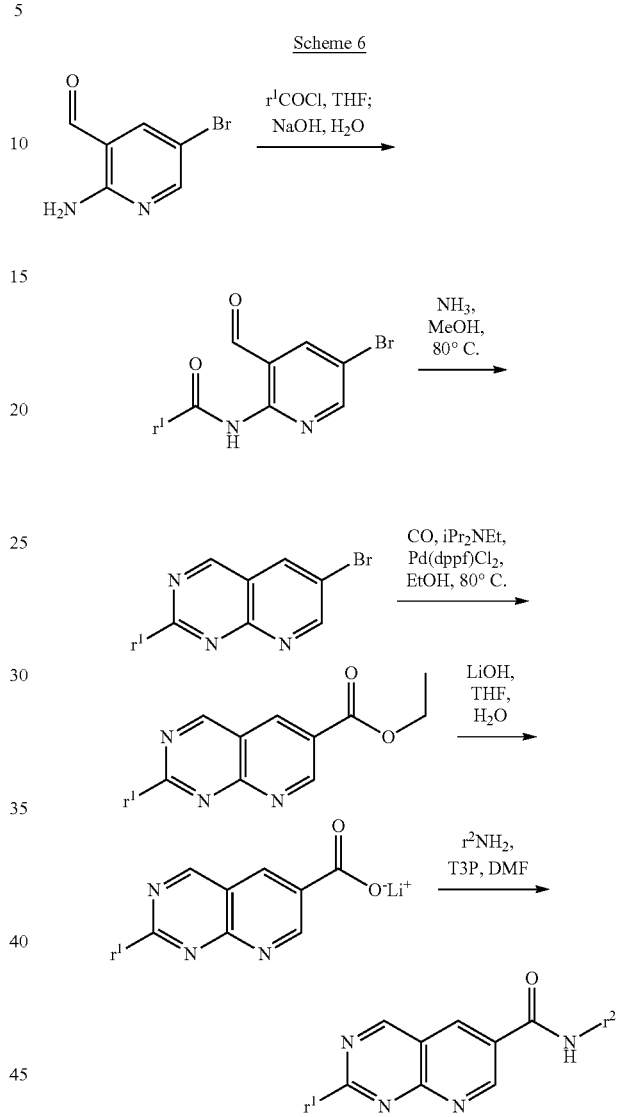

upon hydrolysis provides the lithium salt of the carboxylic acid. Finally, amide bond formations afford the desired pyrido[2,3-d]pyrimidine amides.

In another method of preparation, pyrido[2,3-d]pyrimidines may be synthesized from pyridines (commercially available) as shown in Scheme 6. First, acylation of the 2-aminopyridine with an acid chloride, followed by partial hydrolysis of the imide affords the amide. Then, condensation of the aldehyde with ammonia with subsequent cyclization gives the 6-bromopyrido[2,3-d]pyrimidines. Subsequent palladium catalyzed carbonylation with carbon monoxide and trapping with ethanol yields the ester, which In another method of preparation, 1,8-naphthyridines may be synthesized from pyridines (commercially available) as shown in Scheme 7. First, halogenation of the 2-aminopyridine with bromine provides the bromoaldehyde. Then, condensation of this aminoaldehyde with ketones, followed by cyclization and aromatization affords the 3-bromo-1,8-naphthyridines. Subsequent palladium catalyzed carbonylation with carbon monoxide gives various 7-substituted-1,8-naphthyridine esters, which upon hydrolysis and amide bond formation afford the desired 1,8-naphthyridine amides.

Scheme 7

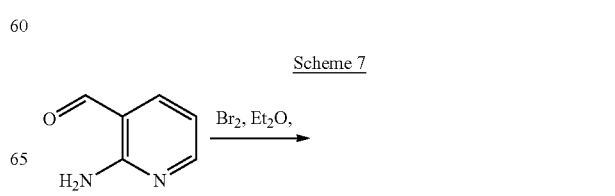

-continued

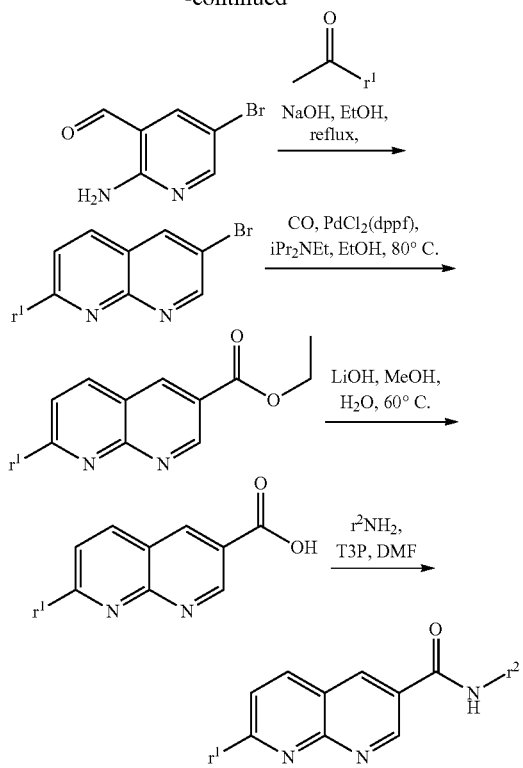

Methods of Use

The inventors have shown that inhibitors of Hematopoietic Prostaglandin D Synthase (H-PGDS) reduce muscle damage and preserve muscle function when administered prior to muscle injury in an in vivo assay for muscle function. Furthermore, the inventors have shown that when an H-PGDS inhibitor is administered after muscle damage in the same assay, recovery of muscle function is enhanced. These results support a role for the use of H-PGDS inhibitors in the treatment of muscle degenerative disorders and muscle injury.

In one aspect, the invention provides a method of treating a muscle degenerative disorder comprising administering to a human an H-PGDS inhibitor of Formula (I) or a pharmaceutically acceptable salt thereof.

In particular embodiments, the muscle degenerative disorder is muscular dystrophy, myotonic dystrophy, polymyositis, dermatomyositis, or inclusion body myositis.

For example, the compounds of Formula (I) or a pharmaceutically acceptable salt thereof may be used to treat a muscular dystrophy disorder selected from Duchenne MD, Becker MD, congenital MD (Fukuyama), Emery Dreifuss MD, limb girdle MD, and fascioscapulohumeral MD.

The compounds of Formula (I) or a pharmaceutically acceptable salt thereof may also be used to treat myotonic dystrophy type I (DM1 or Steinert's), myotonic dystrophy type II (DM2 or proximal myotonic myopathy), or congenital myotonia.

In some embodiments, the muscle injury is a surgery-related muscle injury, a traumatic muscle injury, a work-related skeletal muscle injury, or an overtraining-related muscle injury.

Non-limiting examples of surgery-related muscle injuries include muscle damage due to knee replacement, anterior cruciate ligament (ACL) repair, plastic surgery, hip replacement surgery, joint replacement surgery, tendon repair surgery, surgical repair of rotator cuff disease and injury, and amputation.

In one embodiment, the muscle injury is a surgery-related muscle injury and the treatment method provides for administration of at least one dose of an H-PGDS inhibitor of Formula (I) or a pharmaceutically acceptable salt thereof prior to the surgery (for example, within one day before the surgery) followed by periodic administration of a dose of the H-PGDS inhibitor during the recovery period.

In another embodiment, the muscle injury is a surgery-related muscle injury and the treatment method provides for administration of at least one high dose of an H-PGDS inhibitor of Formula (I) or a pharmaceutically acceptable salt thereof within one day to one week following the surgery.

In yet another embodiment, the muscle injury is a surgery-related muscle injury and the treatment method provides for administration of at least one high dose of an H-PGDS inhibitor of Formula (I) or a pharmaceutically acceptable salt thereof within one day to one week following the surgery, followed by periodic administration of a dose of the H-PGDS inhibitor during the recovery period.

Non-limiting examples of traumatic muscle injuries include battlefield muscle injuries, auto accident-related muscle injuries, and sports-related muscle injuries. Traumatic injury to the muscle can include lacerations, blunt force contusions, shrapnel wounds, muscle pulls or tears, burns, acute strains, chronic strains, weight or force stress injuries, repetitive stress injuries, avulsion muscle injury, and compartment syndrome.

In one embodiment, the muscle injury is a traumatic muscle injury and the treatment method provides for administration of at least one dose of an H-PGDS inhibitor of Formula (I) or a pharmaceutically acceptable salt thereof, immediately after the traumatic injury (for example, within one day of the injury) followed by periodic administration of a dose of the H-PGDS inhibitor during the recovery period.

Non-limiting examples of work-related muscle injuries include injuries caused by highly repetitive motions, forceful motions, awkward postures, prolonged and forceful mechanical coupling between the body and an object, and vibration.

Overtraining-related muscle injuries include unrepaired or under-repaired muscle damage coincident with a lack of recovery or lack of an increase of physical work capacity.

In an additional embodiment, the muscle injury is exercise or sports-induced muscle damage including exercise-induced delayed onset muscle soreness (DOMS).

In some embodiments, the invention encompasses a therapeutic combination in which the H-PGDS inhibitor of Formula (I) or a pharmaceutically acceptable salt thereof is administered in a subject in combination with the implantation of a biologic scaffold (e.g. a scaffold comprising extracellular matrix) that promotes muscle regeneration. Such scaffolds are known in the art. See, for example, Turner and Badylack (2012) *Cell Tissue Res.* 347(3):759-74 and U.S. Pat. No. 6,576,265. Scaffolds comprising non-cross-linked extracellular matrix material are preferred.

In another aspect, the invention provides a method of treating tendon damage where the method comprises administering a compound of Formula (I) or a pharmaceutically acceptable salt thereof to a subject in need thereof. In a particular embodiment, the invention includes a method of enhancing the formation of a stable tendon-bone interface. In a related embodiment, the invention provides a method of increasing the stress to failure of tendons, for example surgically-repaired tendons. In an additional embodiment, the invention provides a method of reducing fibrosis at the repair site for surgically-repaired tendons. In a particular embodiment, the invention provides a method of treating tendon damage associated with rotator cuff injury, or tendon damage associated with surgical repair of rotator cuff injury.

In another aspect, the invention provides a method of treating a disease state selected from: allergic diseases and other inflammatory conditions such as asthma, aspirin-exacerbated respiratory disease (AERD), cough, chronic obstructive pulmonary disease (including chronic bronchitis and emphysema), bronchoconstriction, allergic rhinitis (seasonal or perennial), vasomotor rhinitis, rhinoconjunctivitis, allergic conjunctivitis, food allergy, hypersensitivity lung diseases, eosinophilic syndromes including eosinophilic asthma, eosinophilic pneumonitis, eosinophilic oesophagitis, eosinophilic granuloma, delayed-type hypersensitivity disorders, atherosclerosis, rheumatoid arthritis, pancreatitis, gastritis, inflammatory bowel disease, osteoarthritis, psoriasis, sarcoidosis, pulmonary fibrosis, respiratory distress syndrome, bronchiolitis, sinusitis, cystic fibrosis, actinic keratosis, skin dysplasia, chronic urticaria, eczema and all types of dermatitis including atopic dermatitis or contact dermatitis in a subject in need thereof comprising administering to the subject a therapeutically effective amount of a compound of Formula (I) or a pharmaceutically acceptable salt thereof.

The methods of treatment of the invention comprise administering a safe and effective amount of a compound of Formula (I), or a pharmaceutically acceptable salt thereof to a mammal, suitably a human, in need thereof.

As used herein, "treat", and derivatives thereof, in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The term "treating" and derivatives thereof refers to therapeutic therapy. Therapeutic therapy is appropriate to alleviate symptoms or to treat at early signs of disease or its progression.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of Formula (I), or a pharmaceutically acceptable salt thereof, means an amount of the compound sufficient to treat the patient's condition but low enough to avoid serious side effects (at a reasonable benefit/risk ratio) within the scope of sound medical judgment. A safe and effective amount of the compound will vary with the particular route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient", and derivatives thereof refers to a human or other mammal, suitably a human.

The subject to be treated in the methods of the invention is typically a mammal in need of such treatment, preferably a human in need of such treatment.

Compositions

The pharmaceutically active compounds within the scope of this invention are useful as inhibitors of H-PGDS in mammals, particularly humans, in need thereof.

The present invention therefore provides a method of treating neurodegenerative diseases, musculoskeletal diseases and other conditions requiring H-PGDS inhibition, which comprises administering an effective amount of a compound of Formula (I) or a pharmaceutically acceptable salt thereof. The compounds of Formula (I) also provide for a method of treating the above indicated disease states because of their demonstrated ability to act as H-PGDS inhibitors. The drug may be administered to a patient in need thereof by any conventional route of administration, including, but not limited to, intravenous, intramuscular, oral, topical, subcutaneous, intradermal, intraocular and parenteral. Suitably, a H-PGDS inhibitor may be delivered directly to the brain by intrathecal or intraventricular route, or implanted at an appropriate anatomical location within a device or pump that continuously releases the H-PGDS inhibitor drug.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical compositions are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-500 mg/kg of active compound, preferably 0.001-100 mg/kg. When treating a human patient in need of a H-PGDS inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages, is preferred. Parenteral administration, at high dosages, however, also can be used when safe and convenient for the patient.

Optimal dosages to be administered may be readily determined by those skilled in the art, and will vary with the particular H-PGDS inhibitor in use, the strength of the preparation, the mode of administration, and the advancement of the disease condition. Additional factors depending on the particular patient being treated will result in a need to adjust dosages, including patient age, weight, diet, and time of administration.

When administered to prevent organ damage in the transportation of organs for transplantation, a compound of Formula (I) is added to the solution housing the organ during transportation, suitably in a buffered solution.

The method of this invention of inducing H-PGDS inhibitory activity in mammals, including humans, comprises administering to a subject in need of such activity an effective H-PGDS inhibiting amount of a pharmaceutically active compound of the present invention.

The invention also provides for the use of a compound of Formula (I) or a pharmaceutically acceptable salt thereof in the manufacture of a medicament for use as a H-PGDS inhibitor.

The invention also provides for the use of a compound of Formula (I) or a pharmaceutically acceptable salt thereof in the manufacture of a medicament for use in therapy.

The invention also provides for the use of a compound of Formula (I) or a pharmaceutically acceptable salt thereof in the manufacture of a medicament for treating musculoskeletal diseases such as Duchenne muscular dystrophy, spinal cord contusion injury, neuroinflammatory diseases such as multiple sclerosis or neurodegenerative diseases such as Alzheimer's disease or amyotrophic lateral sclerosis (ALS).

The invention also provides for a pharmaceutical composition for use as a H-PGDS inhibitor which comprises a compound of Formula (I) or a pharmaceutically acceptable salt thereof and a pharmaceutically acceptable carrier.

The invention also provides for a pharmaceutical composition for use in the treatment of cancer which comprises a compound of Formula (I) or a pharmaceutically acceptable salt thereof and a pharmaceutically acceptable carrier.

In addition, the pharmaceutically active compounds of the present invention can be co-administered with further active ingredients, such as other compounds known to treat cancer, or compounds known to have utility when used in combination with a H-PGDS inhibitor.

By the term "co-administration" as used herein is meant either simultaneous administration or any manner of separate sequential administration of a H-PGDS inhibiting compound, as described herein, and a further active agent or agents, known to be useful in the treatment of conditions in which a H-PGDS inhibitor is indicated. The term further active agent or agents, as used herein, includes any compound or therapeutic agent known to or that demonstrates advantageous properties when administered to a patient in need of H-PGDS inhibition. Preferably, if the administration is not simultaneous, the compounds are administered in a close time proximity to each other. Furthermore, it does not matter if the compounds are administered in the same dosage form, e.g. one compound may be administered by injection and another compound may be administered orally.

The invention also relates to the use of a compound of Formula (I) or a pharmaceutically acceptable salt thereof in the preparation of a medicament for the treatment of neurodegenerative diseases, musculoskeletal diseases and diseases associated with H-PGDS inhibition.

The invention also provides a pharmaceutical composition comprising from 0.5 to 1,000 mg of a compound of Formula (I) or pharmaceutically acceptable salt thereof and from 0.5 to 1,000 mg of a pharmaceutically acceptable excipient.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Examples

The following Examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

INTERMEDIATES

Intermediate 1

7-Cyclopropyl-1,6-naphthyridine-3-carboxylic acid

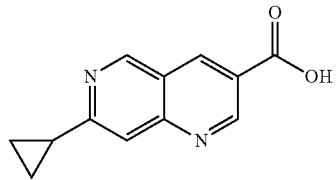 [SMILES: O=C(O)c1cnc2cc(C3CC3)ncc2c1]

A. Ethyl 6-chloro-4-((4-methoxybenzyl)amino)nicotinate

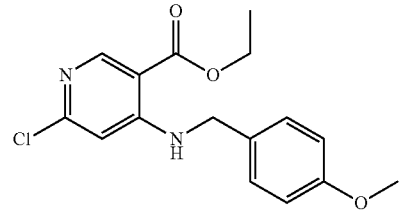 [SMILES: CCOC(=O)c1cnc(Cl)cc1NCc1ccc(OC)cc1]

Triethylamine (228 mL, 1636 mmol) was added to a solution of ethyl 4,6-dichloronicotinate (300 g, 1363 mmol) in dimethyl sulfoxide (3000 mL) at 0° C. Then, (4-methoxyphenyl)methanamine (187 g, 1363 mmol) was added and the reaction mixture was allowed to warm to room temperature and stirred for sixteen hours. The reaction mixture was quenched with ice cold water (2.5 L). The precipitated solid was filtered, washed with hexanes (3 L) and dried under vacuum to afford ethyl 6-chloro-4-((4-methoxybenzyl) amino)nicotinate (320 g, 737 mmol, 54% yield) as an off white solid. $^1$H NMR (400 MHz, CD$_3$SOCD$_3$) δ 1.31 (t, J=7 Hz, 3H), 3.78 (s, 3H), 4.28-4.39 (m, 2H), 4.46 (d, J=6 Hz, 2H), 6.76 (s, 1H), 6.90-7.00 (m, 2H), 7.28 (d, J=9 Hz, 2H), 8.47 (br t, J=6 Hz, 1H), 8.54 (s, 1H); LC-MS (LC-ES) M+H=321.

B. Ethyl 4-amino-6-chloronicotinate

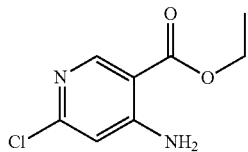

2,2,2-Trifluoroacetic acid (500 mL, 6490 mmol) was added to ethyl 6-chloro-4-((4-methoxybenzyl)amino)nicotinate (320 g, 737 mmol) at room temperature and stirred at 50° C. for sixteen hours. On completion, the reaction mixture was evaporated and quenched with saturated aqueous sodium bicarbonate solution (3000 mL), the precipitate was filtered and dried to give a impure material, which was purified via silica gel column chromatography, eluting with ethyl acetate:hexanes (1:4) to afford ethyl 4-amino-6-chloronicotinate (160 g, 727 mmol, 99% yield) as an off white solid. $^1$H NMR (400 MHz, CD$_3$SOCD$_3$) δ 1.31 (t, J=7 Hz, 3H), 4.27-4.36 (m, 2H), 6.76 (s, 1H), 7.45 (br s, 2H), 8.49 (s, 1H); LC-MS (LC-ES) M+H=201.

C. (4-Amino-6-chloropyridin-3-yl)methanol

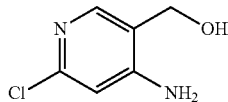

Ethyl 4-amino-6-chloronicotinate (50 g, 215 mmol) in tetrahydrofuran (500 mL) was added to a suspension of lithium aluminum hydride (16.31 g, 430 mmol) in tetrahydrofuran (500 mL) dropwise at 0° C. under a nitrogen atmosphere. The reaction mixture was allowed to warm to room temperature and stirred for five hours. On completion, the reaction mixture was quenched with 1N hydrochloric acid (1.5 L) slowly at 0° C. and filtered through a Celite® pad. The filtrate was evaporated under reduced pressure to obtain a solid that was washed with hexanes (1 L) and dried to afford (4-amino-6-chloropyridin-3-yl)methanol (38 g, 193 mmol, 90% yield) as an off white solid. $^1$H NMR (400 MHz, CD$_3$SOCD$_3$) δ 4.36 (d, J=5 Hz, 2H), 5.07 (t, J=5 Hz, 1H), 6.14 (br s, 2H), 6.53 (s, 1H), 7.79 (s, 1H); LC-MS (LC-ES) M+H=159.

D. 4-Amino-6-chloronicotinaldehyde

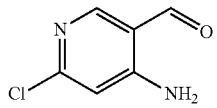

Manganese dioxide (230 g, 2648 mmol) was added to a solution of (4-amino-6-chloropyridin-3-yl)methanol (50 g, 265 mmol) in dichloromethane (3000 mL) at 0° C. under nitrogen. The resulting reaction mixture was allowed to warm to room temperature and stirred for sixteen hours. On completion, the reaction mixture was filtered through a Celite® pad and the residue was washed with dichloromethane and the filtrate was evaporated under reduced pressure. The solid was washed with pentane to afford 4-amino-6-chloronicotinaldehyde (41 g, 237 mmol, 89% yield) as an off white solid. $^1$H NMR (400 MHz, CD$_3$SOCD$_3$) δ 6.73 (s, 1H), 7.69-7.91 (m, 2H), 8.43 (s, 1H), 9.88 (s, 1H); LC-MS (LC-ES) M+H=157.

E. 3-Bromo-7-chloro-1,6-naphthyridine

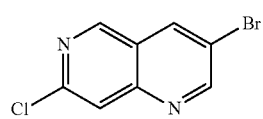 [SMILES: Clc1cc2ncc(Br)cc2cn1]

Ytterbium(III) trifluoromethanesulfonate (43.1 g, 69.5 mmol) was added to a solution of 4-amino-6-chloronicotinaldehyde (50 g, 278 mmol) in acetonitrile (500 mL) at 0° C. under argon. Then, 2-bromo-1,1-dimethoxyethane (98 mL, 833 mmol) was added and the resulting reaction mixture was heated to 80° C. and stirred for sixteen hours. On completion, the reaction mixture was filtered through a Celite® pad, the residue was washed with acetonitrile (500 mL) and the filtrate was evaporated under reduced pressure to give an impure material, which was purified via silica gel column chromatography, eluting with ethyl acetate:hexanes (1:4) to afford 3-bromo-7-chloro-1,6-naphthyridine (30 g, 98 mmol, 35% yield) as light yellow solid. $^1$H NMR (400 MHz, CDCl$_3$) δ 7.99 (s, 1H), 8.43 (m, 1H), 9.05 (s, 1H), 9.09 (d, J=2 Hz, 1H); LC-MS (LC-ES) M+H=243.

F. Ethyl 7-chloro-1,6-naphthyridine-3-carboxylate

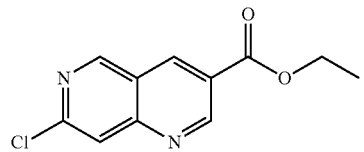 [SMILES: CCOC(=O)c1cnc2cc(Cl)ncc2c1]

Triethylamine (17.69 mL, 127 mmol) was added to a solution of 3-bromo-7-chloro-1,6-naphthyridine (20 g, 63.4 mmol, sold by Ryan Scientific, prepared as above, also prepared in Flynn, D. L.; et al. PCT Int. Appl. (2013), WO 2013134298 A1) in ethanol (400 mL) in an autoclave under carbon monoxide atmosphere (80 psi) at room temperature. Then, [1,1'-bis(diphenylphosphino)ferrocene]dichloropalladium(II) dichloromethane adduct (5.18 g, 6.34 mmol) was added and the reaction mixture was heated to 80° C. and stirred for 90 minutes. On completion, the reaction mixture was filtered through a Celite® pad, the residue was washed with ethanol (200 mL), and the solvent evaporated under reduced pressure to give an impure material, which was purified via silica gel column chromatography, eluting with ethyl acetate:hexanes (1:9) to afford ethyl 7-chloro-1,6-naphthyridine-3-carboxylate (10.7 g, 38.6 mmol, 61% yield) as an off white solid. $^1$H NMR (400 MHz, CDCl$_3$) δ 1.48 (t, J=7 Hz, 3H), 4.51 (q, J=7 Hz, 2H), 8.06 (s, 1H), 8.88-9.03 (m, 1H), 9.21 (s, 1H), 9.62 (d, J=2 Hz, 1H); LC-MS (LC-ES) M+H=237.

G. Ethyl 7-cyclopropyl-1,6-naphthyridine-3-carboxylate

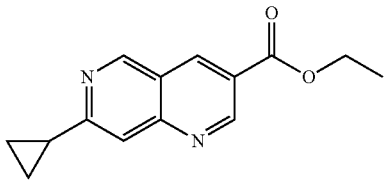 [SMILES: CCOC(=O)c1cnc2cc(C3CC3)ncc2c1]

Cyclopropylboronic acid (17.42 g, 203 mmol) was added to a solution of ethyl 7-chloro-1,6-naphthyridine-3-carboxylate (20 g, 67.6 mmol) in toluene (600 mL) at room temperature. Then, 2-dicyclohexylphosphino-2',6'-dimethoxybiphenyl (0.638 g, 1.555 mmol) was added, followed by the addition of tris(dibenzylideneacetone)dipalladium(0) (3.65 g, 3.99 mmol) and 2M aqueous sodium carbonate (42.3 mL, 85 mmol) and the reaction was purged with argon for 10 minutes. The reaction mixture was heated to 110° C. and stirred for sixteen hours. On completion, the reaction mixture was filtered through a Celite® pad, the residue was washed with ethyl acetate (200 mL), and the filtrate was evaporated under reduced pressure to give an impure material, which was purified via silica gel column chromatography, eluting with ethyl acetate:hexanes (1:4) to afford ethyl 7-cyclopropyl-1,6-naphthyridine-3-carboxylate (15 g, 61.4 mmol, 91% yield) as an off white solid. $^1$H NMR (400 MHz, CDCl$_3$) δ 1.05-1.24 (m, 4H), 1.46 (t, J=7 Hz, 3H), 2.26-2.36 (m, 1H), 4.48 (q, J=7 Hz, 2H), 7.78 (s, 1H), 8.84-8.93 (m, 1H), 9.21 (s, 1H), 9.54 (d, J=2 Hz, 1H); LC-MS (LC-ES) M+H=243.

H. 7-Cyclopropyl-1,6-naphthyridine-3-carboxylic acid

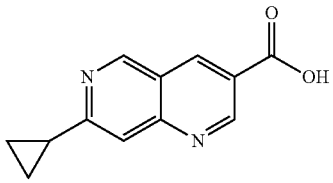 [SMILES: O=C(O)c1cnc2cc(C3CC3)ncc2c1]

A solution of sodium hydroxide (5.76 g, 144 mmol) in water (75 mL) was added to a solution of ethyl 7-cyclopropyl-1,6-naphthyridine-3-carboxylate (30 g, 120 mmol) in tetrahydrofuran (75 mL) at room temperature and the resulting reaction mixture was stirred for fifteen hours. On completion, the reaction mixture was concentrated (until tetrahydrofuran was removed) under vacuum, and then the reaction mixture was acidified with 1N hydrochloric acid solution. The precipitate was filtered, washed with water (250 mL), pentane (500 mL) and diethyl ether (500 mL), and dried to afford 7-cyclopropyl-1,6-naphthyridine-3-carboxylic acid (18 g, 84 mmol, 70% yield) as an off white solid. $^1$H NMR (400 MHz, CD$_3$SOCD$_3$) δ 0.96-1.22 (m, 4H), 2.25-2.40 (m, 1H), 7.89 (s, 1H), 9.06 (dd, J=2, 1 Hz, 1H), 9.43 (d, J=3 Hz, 2H), 13.57 (br s, 1H); LC-MS (LC-ES) M+H=215.

Intermediate 2

7-(3-Fluoroazetidin-1-yl)-1,6-naphthyridine-3-carboxylic acid ammonia salt

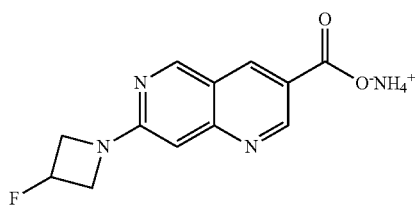

A. Ethyl 7-(3-fluoroazetidin-1-yl)-1,6-naphthyridine-3-carboxylate and Ethyl 7-(dimethylamino)-1,6-naphthyridine-3-carboxylate

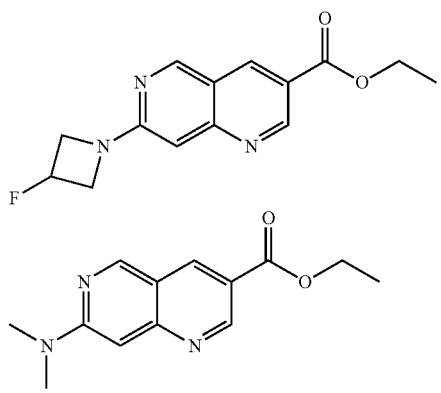

N,N-Diisopropylethylamine (1.259 mL, 7.23 mmol) was added to ethyl 7-chloro-1,6-naphthyridine-3-carboxylate (0.4278 g, 1.808 mmol, Intermediate 1F) in N,N-dimethylformamide (6.03 mL) at room temperature. Then 3-fluoroazetidin-1-ium chloride (0.605 g, 5.42 mmol) was added and the reaction mixture was heated at 100° C. in the microwave for three hours. The reaction mixture was diluted in dichloromethane, washed with saturated sodium bicarbonate, dried over magnesium sulfate, filtered, and concentrated. The residue was purified by silica gel chromatography, eluting with ethyl acetate:hexanes (2:3 to 4:1), then further purified by RP HPLC, eluting with acetonitrile:water with 0.1% ammonium hydroxide (30:70 to 80:20) and shaving fractions to give some pure ethyl 7-(3-fluoroazetidin-1-yl)-1,6-naphthyridine-3-carboxylate (0.0831 g, 0.287 mmol, 15.86% yield) as well as some impure material and some pure ethyl 7-(dimethylamino)-1,6-naphthyridine-3-carboxylate (0.0419 g, 0.162 mmol, 8.98% yield).

Ethyl 7-(3-fluoroazetidin-1-yl)-1,6-naphthyridine-3-carboxylate $^1$H NMR (400 MHz, CD$_3$SOCD$_3$) δ 1.35 (t, J=7 Hz, 3H), 4.18 (br dd, J=24, 11 Hz, 2H), 4.36 (q, J=7 Hz, 2H), 4.38-4.50 (m, 2H), 5.44-5.70 (m, 1H), 6.69 (s, 1H), 8.91 (s, 1H), 9.21 (s, 1H), 9.23 (s, 1H); LC-MS (LC-ES) M+H=276.

Ethyl 7-(dimethylamino)-1,6-naphthyridine-3-carboxylate $^1$H NMR (400 MHz, CD$_3$SOCD$_3$) δ 1.35 (t, J=7 Hz, 3H), 3.18 (s, 6H), 4.35 (q, J=7 Hz, 2H), 6.81 (s, 1H), 8.82 (s, 1H), 9.17 (s, 2H); LC-MS (LC-ES) M+H=246.

B. 7-(3-Fluoroazetidin-1-yl)-1,6-naphthyridine-3-carboxylic acid ammonia salt

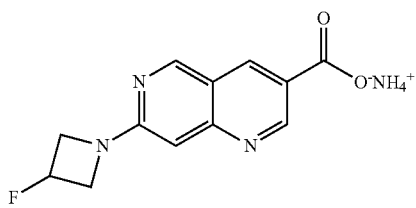

Lithium hydroxide (0.022 g, 0.906 mmol) was added to ethyl 7-(3-fluoroazetidin-1-yl)-1,6-naphthyridine-3-carboxylate (0.0831 g, 0.302 mmol) in methanol (1.20 mL) and water (0.30 mL) at room temperature and the reaction mixture was stirred sixteen hours at 60° C. The reaction mixture was concentrated. The reaction mixture was purified by RP HPLC eluting with acetonitrile:water with 0.1% ammonium hydroxide (0:100 to 60:40) to give 7-(3-fluoro-azetidin-1-yl)-1,6-naphthyridine-3-carboxylic acid ammonia salt (0.0579 g, 0.208 mmol, 69.0% yield).

$^1$H NMR (400 MHz, CD$_3$SOCD$_3$) δ 4.09 (br dd, J=25, 10 Hz, 2H), 4.02-4.44 (m, 2H), 5.42-5.66 (m, 1H), 6.65 (s, 1H), 8.54 (s, 1H), 9.01 (s, 1H), 9.28 (s, 1H); LC-MS (LC-ES) M+H=248.

Intermediate 3

7-(Azetidin-1-yl)-1,6-naphthyridine-3-carboxylic acid lithium salt

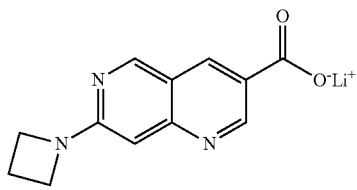

A. Ethyl 7-(azetidin-1-yl)-1,6-naphthyridine-3-carboxylate

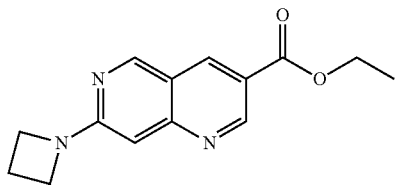

N,N-Diisopropylethylamine (1.502 mL, 8.62 mmol) was added to ethyl 7-chloro-1,6-naphthyridine-3-carboxylate (0.5102 g, 2.156 mmol, Intermediate 1F) in N-methyl-2-pyrrolidone (7.19 mL) at room temperature. Then, azetidine hydrochloride (0.605 g, 6.47 mmol) was added and the reaction mixture was heated at 100° C. in the microwave for five hours. The reaction mixture was diluted in dichloromethane, washed with saturated sodium bicarbonate, dried over magnesium sulfate, filtered, and concentrated. The resulting residue was purified by RP HPLC, eluting with acetonitrile:water with 0.1% ammonium hydroxide (5:95 to 100:0), then further purified by silica gel chromatography, eluting with ethyl acetate:hexanes (3:7 to 4:1) to give ethyl 7-(azetidin-1-yl)-1,6-naphthyridine-3-carboxylate (0.2198 g, 0.812 mmol, 37.6% yield).

$^1$H NMR (400 MHz, CD$_3$SOCD$_3$) δ 1.35 (t, J=7 Hz, 3H), 2.40 (p, J=7 Hz, 2H), 4.10 (t, J=7 Hz, 4H), 4.35 (q, J=7 Hz, 2H), 6.53 (s, 1H), 8.83 (s, 1H), 9.15 (s, 1H), 9.17 (s, 1H); LC-MS (LC-ES) M+H=258.

B. 7-(Azetidin-1-yl)-1,6-naphthyridine-3-carboxylic acid lithium salt

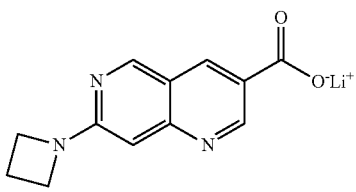

Lithium hydroxide (0.061 g, 2.56 mmol) was added to ethyl 7-(azetidin-1-yl)-1,6-naphthyridine-3-carboxylate (0.2198 g, 0.854 mmol) in methanol (3.42 mL) and water (0.854 mL) at room temperature and the reaction mixture was stirred sixteen hours at 60° C. Then, the reaction mixture was concentrated to give 7-(azetidin-1-yl)-1,6-naphthyridine-3-carboxylic acid lithium salt (0.2291 g, 0.854 mmol, 100% yield). $^1$H NMR (400 MHz, CD$_3$SOCD$_3$) δ 2.36 (p, J=7 Hz, 2H), 4.02 (t, J=7 Hz, 4H), 6.51 (s, 1H), 8.50 (s, 1H), 8.96 (s, 1H), 9.25 (s, 1H); LC-MS (LC-ES) M−H=230.

Intermediate 4

Sodium 7-cyclopropyl-1,8-naphthyridine-3-carboxylate

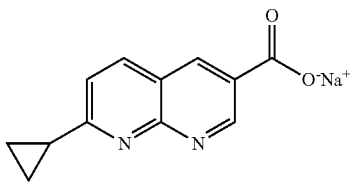

A. 6-Bromo-1,8-naphthyridin-2-amine

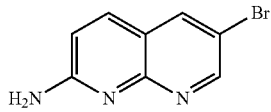

Phosphoric acid (60 mL, 183 mmol) was added to a mixture of pyridine-2,6-diamine (20 g, 183 mmol) and 2-bromomalonaldehyde (27.7 g, 183 mmol) at 0° C. under nitrogen. The resulting reaction mixture was heated to 120° C. and stirred for sixteen hours. On completion, the reaction mixture was quenched with 2M aqueous sodium hydroxide solution (150 mL). The precipitate was filtered, washed with water (1000 mL), and dried to give an impure material. This material was purified via neutral alumina column chromatography, eluting with methanol:dichloromethane (1:9) to afford 6-bromo-1,8-naphthyridin-2-amine (20 g, 69.4 mmol, 38% yield) as a yellow solid. $^1$H NMR (400 MHz, CD$_3$SOCD$_3$) δ 6.85 (d, J=9 Hz, 1H), 6.98 (br s, 2H), 7.90 (d, J=9 Hz, 1H), 8.32 (s, 1H), 8.68 (s, 1H); LC-MS (LC-ES) M+H=224.

B. Ethyl 7-amino-1,8-naphthyridine-3-carboxylate

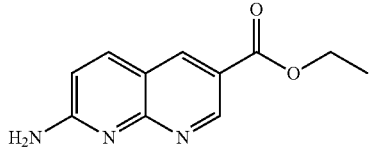 [SMILES: CCOC(=O)c1cnc2nc(N)ccc2c1]

Triethylamine (19.33 mL, 139 mmol) was added to a solution of 6-bromo-1,8-naphthyridin-2-amine (20 g, 69.4 mmol, sold by Aldrich, Reichardt, C.; Scheibelein, W. *Tetrahedron Lett.* 1977, 18, 2087-2090) in ethanol (200 mL) in an autoclave under carbon monoxide atmosphere (100 psi). Then, [1,1'-bis(diphenylphosphino)ferrocene]dichloropalladium(II) (5.07 g, 6.94 mmol) was added and the reaction mixture was heated to 100° C. and stirred for five hours. On completion, the reaction mixture was filtered through a Celite® pad that was washed with ethanol (500 mL). The filtrate was evaporated under reduced pressure to give a residue, which was purified via neutral alumina column chromatography, eluting with methanol:dichloromethane (1:9) to afford ethyl 7-amino-1,8-naphthyridine-3-carboxylate (10 g, 43.8 mmol, 63% yield) as an off white solid. $^1$H NMR (400 MHz, CD$_3$SOCD$_3$) δ 1.35 (t, J=7 Hz, 3H), 4.36 (q, J=7 Hz, 2H), 6.89 (d, J=9 Hz, 1H), 7.29 (s, 2H), 8.09 (d, J=9 Hz, 1H), 8.60 (d, J=2 Hz, 1H), 9.12 (d, J=2 Hz, 1H); LC-MS (LC-ES) M+H=218.

C. Ethyl 7-chloro-1,8-naphthyridine-3-carboxylate

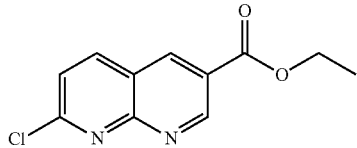 [SMILES: CCOC(=O)c1cnc2nc(Cl)ccc2c1]

Copper(II) chloride (5.71 g, 42.5 mmol) was added to a solution of ethyl 7-amino-1,8-naphthyridine-3-carboxylate (7.5 g, 28.3 mmol) in acetonitrile (150 mL) at 0° C. Then, isoamyl nitrite (5.72 mL, 42.5 mmol) was added and the resulting reaction mixture was heated to 80° C. and stirred for sixteen hours. On completion, the reaction mixture was quenched with water (100 mL) and extracted with ethyl acetate (3×100 mL). The combined organic layers were washed with brine (500 mL) and evaporated under reduced pressure to give an impure material, which was purified via neutral alumina column chromatography, eluting with ethyl acetate:petroleum ether (1:1) to afford ethyl 7-chloro-1,8-naphthyridine-3-carboxylate (1.2 g, 4.85 mmol, 17% yield) as light yellow solid. $^1$H NMR (400 MHz, CDCl$_3$) δ 1.47 (t, J=7 Hz, 3H), 4.41-4.61 (m, 2H), 7.58 (d, J=9 Hz, 1H), 8.25 (d, J=9 Hz, 1H), 8.88 (d, J=2 Hz, 1H), 9.66 (d, J=2 Hz, 1H); $^1$H NMR (400 MHz, CD$_3$SOCD$_3$) δ 1.38 (t, J=7 Hz, 3H), 4.43 (q, J=7 Hz, 2H), 7.86 (d, J=9 Hz, 1H), 8.77 (d, J=8 Hz, 1H), 9.17 (s, 1H), 9.48 (s, 1H); LC-MS (LC-ES) M+H=237.

Alternative Preparation

Ethyl 7-chloro-1,8-naphthyridine-3-carboxylate (Also Commercially Available)

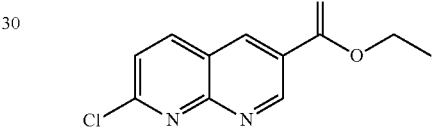

Sodium nitrite (1.210 g, 17.53 mmol) was added to ethyl 7-amino-1,8-naphthyridine-3-carboxylate (2 g, 8.77 mmol) at room temperature. Then, concentrated sulfuric acid (4.77 mL, 88 mmol) was added dropwise and the reaction mixture was stirred for sixteen hours. On completion, the reaction mixture was diluted with ice water (50 mL) and stirred for 10 minutes. The precipitate was filtered, washed with pentane (10 mL) and diethyl ether (10 mL), and dried under vacuum to afford ethyl 7-hydroxy-1,8-naphthyridine-3-carboxylate (1.8 g, 63% yield) as off white solid CH NMR (400 MHz, CD$_3$SOCD$_3$) δ 1.22-1.52 (t, J=7 Hz, 3H), 4.37 (q, J=7 Hz, 2H), 6.44-6.79 (m, 1H), 7.86-8.17 (m, 1H), 8.52-8.76 (m, 1H), 8.92-9.09 (m, 1H), 12.39-12.71 (br s, 1H); LC-MS (LC-ES) M+H=219. N,N-Diisopropylethylamine (2.3 mL, 13.33 mmol) was added to a solution of ethyl 7-hydroxy-1,8-naphthyridine-3-carboxylate (1.8 g, 6.67 mmol) in 1,4-dioxane (18 mL) at 0° C. Then, phosphorus oxychloride (2.48 mL, 26.7 mmol) was added and the resulting reaction mixture was heated to 80° C. and stirred for sixteen hours. On completion, the reaction mixture was diluted with ice cold water (50 mL) and extracted with ethyl acetate (2×50 mL). The combined organic layers were washed with brine (50 mL), dried over anhydrous sodium sulfate, filtered, and evaporated under reduced pressure to give an impure material, which was purified via neutral alumina column chromatography, eluting with ethyl acetate:petroleum ether (2:3) to afford ethyl 7-chloro-1,8-naphthyridine-3-carboxylate (900 mg, 3.66 mmol, 55% yield) as an off white solid. $^1$H NMR (400 MHz, CDCl$_3$) δ 1.37-1.52 (t, J=7 Hz, 3H), 4.48-4.59 (q, J=7 Hz, 2H), 7.58 (d, J=9 Hz, 1H), 8.26 (d, J=9 Hz, 1H), 8.88 (d, J=2 Hz, 1H), 9.66 (d, J=2 Hz, 1H); LC-MS (LC-ES) M+H=237.

D. Ethyl 7-cyclopropyl-1,8-naphthyridine-3-carboxylate

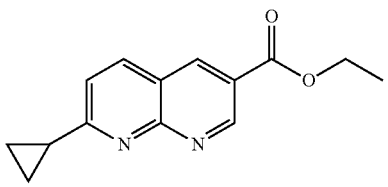 [SMILES: CCOC(=O)c1cnc2nc(C3CC3)ccc2c1]

Cyclopropylboronic acid (3.16 g, 36.8 mmol) was added to a solution of ethyl 7-chloro-1,8-naphthyridine-3-carboxylate (3 g, 12.27 mmol, available from FCH Group Reagents for Synthesis), dicyclohexyl(2',6'-dimethoxy-[1,1'-biphenyl]-2-yl)phosphine (0.504 g, 1.227 mmol), tris(dibenzylideneacetone)dipalladium(0) (2.247 g, 2.453 mmol), and 2M sodium carbonate (15.33 mL, 30.7 mmol) in toluene (30 mL) at room temperature under nitrogen and the reaction mixture was purged with argon for 10 min. The resulting reaction mixture was heated to 110° C. and stirred for sixteen hours. On completion, the reaction mixture was cooled, filtered through a Celite® pad, and the filtrate was evaporated under reduced pressure. The residue was purified via neutral alumina column chromatography, eluting with ethyl acetate:petroleum ether (1:1) to afford ethyl 7-cyclopropyl-1,8-naphthyridine-3-carboxylate (700 mg, 2.58 mmol, 21% yield) as an off white solid. $^1$H NMR (400 MHz, CDCl$_3$) δ 1.12-1.23 (m, 2H), 1.43-1.53 (m, 5H), 2.25-2.36 (m, 1H), 4.48 (q, J=7 Hz, 2H), 7.46 (d, J=8 Hz, 1H), 8.11 (d, J=8 Hz, 1H), 8.78 (d, J=2 Hz, 1H), 9.56 (d, J=2 Hz, 1H); LC-MS (LC-ES) M+H=243.

Alternative Method

Ethyl 7-cyclopropyl-1,8-naphthyridine-3-carboxylate

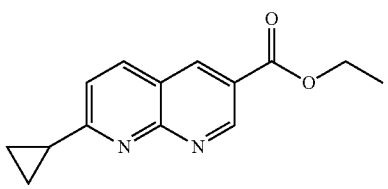 [SMILES: CCOC(=O)c1cnc2nc(C3CC3)ccc2c1]

Copper(I) iodide (4.04 mg, 0.021 mmol) was added to ethyl 7-chloro-1,8-naphthyridine-3-carboxylate (0.1005 g, 0.425 mmol, sold by FCH Group Reagents for Synthesis) in tetrahydrofuran (4.25 mL) at room temperature, followed by [1,1'-bis(diphenylphosphino)ferrocene]dichloropalladium (II)-dichloromethane adduct (3.47 mg, 4.25 μmol) and the reaction mixture was purged with nitrogen. Then, cyclopropylzinc(II) bromide (1.529 mL, 0.765 mmol) was added and the reaction mixture was stirred at room temperature for sixteen hours. Then, the reaction mixture was concentrated. The residue was purified by silica gel chromatography, eluting with methanol:dichloromethane (0:1 to 1:9) with acetonitrile:water with 0.1% ammonium hydroxide, then repurified by RP HPLC, eluting with acetonitrile:water with 0.1% ammonium hydroxide (5:95 to 100:0) to give ethyl 7-cyclopropyl-1,8-naphthyridine-3-carboxylate (0.0662 g, 0.238 mmol, 56.0% yield), containing a small amount of starting chloride. $^1$H NMR (400 MHz, CD$_3$SOCD$_3$) δ 1.12-1.22 (m, 4H), 3.37 (t, J=7 Hz, 3H), 2.34-2.44 (m, 1H), 4.40 (q, J=7 Hz, 2H), 7.69 (d, J=9 Hz, 1H), 8.51 (d, J=9 Hz, 1H), 9.00 (d, J=2 Hz, 1H), 9.36 (d, J=2 Hz, 1H); LC-MS (LC-ES) M+H=243.

E. Sodium 7-cyclopropyl-1,8-naphthyridine-3-carboxylate

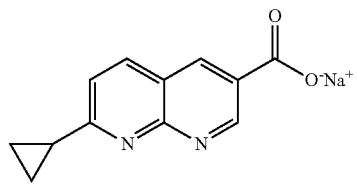

A solution of 2M sodium hydroxide (1.5 mL, 3.10 mmol) was added to a solution of ethyl 7-cyclopropyl-1,8-naphthyridine-3-carboxylate (700 mg, 2.58 mmol) in tetrahydrofuran (7 mL) at room temperature. The resulting reaction mixture was stirred for sixteen hours. On completion, the reaction mixture was evaporated under reduced pressure and toluene (3×20 mL) was added and distilled off to remove water, ultimately affording sodium 7-cyclopropyl-1,8-naphthyridine-3-carboxylate (500 mg, 1.93 mmol, 75% yield) as an off white solid. $^1$H NMR (400 MHz, CD$_3$SOCD$_3$) δ 1.11 (m, 4H), 2.22-2.35 (m, 1H), 7.50 (d, J=8 Hz, 1H), 8.31 (d, J=8 Hz, 1H), 8.59 (s, 1H), 9.36 (s, 1H); LC-MS (LC-ES) M−H=213.

Alternative Method

F. 7-cyclopropyl-1,8-naphthyridine-3-carboxylate

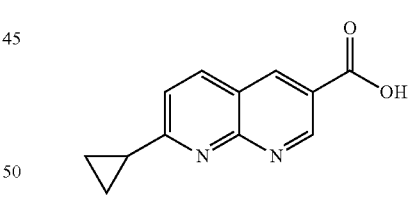

Sodium hydroxide (17.58 mL, 35.2 mmol) was added to a solution of ethyl 7-cyclopropyl-1,8-naphthyridine-3-carboxylate (7.1 g, 29.3 mmol) in tetrahydrofuran (30 mL) and reaction mixture was stirred for fifteen hours at 27 deg C. Then, the reaction mixture was concentrated, acidified with diluted hydrochloric acid and the precipitated solid was filtered, washed with water, and dried to give a crude solid. This material was washed with n-pentane (500 mL) and diethyl ether (500 mL), then dried to give 7-cyclopropyl-1, 8-naphthyridine-3-carboxylic acid (5.33 g, 23.89 mmol, 82% yield). $^1$H NMR (400 MHz, CD$_3$SOCD$_3$) δ 1.04-1.16 (m, 4H), 2.22-2.35 (m, 1H), 7.50 (d, J=8 Hz, 1H), 8.31 (d, J=8 Hz, 1H), 8.59 (s, 1H), 9.36 (s, 1H); LC-MS (LC-ES) M−H=213.

Alternative Method

A'. (2-Amino-6-chloropyridin-3-yl)methanol

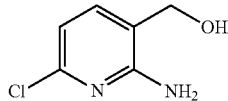

1M Borane·tetrahydrofuran complex (62 mL, 62.0 mmol) was added over 13 minutes to the 2-amino-6-chloronicotinic acid (3.47 g, 20.11 mmol) in tetrahydrofuran (100 mL) under nitrogen and the reaction mixture was stirred for one hour at 0° C., then the ice bath was removed. The reaction mixture was stirred for nineteen hours, then quenched with methanol and concentrated. The reaction mixture was taken up in methanol and concentrated (2×), then dissolved in dichloromethane and methanol and purified via silica gel chromatography, eluting with methanol:dichloromethane with 10% ammonium hydroxide (0:1 to 1:16) to give (2-amino-6-chloropyridin-3-yl)methanol (1.632 g, 10.29 mmol, 51%) as a cream solid. $^1$H NMR (400 MHz, CD$_3$SOCD$_3$) δ 4.28 (d, J=6 Hz, 1H), 5.19 (t, J=6 Hz, 2H), 6.13 (br s, 2H), 6.53 (d, J=8 Hz, 1H), 7.38 (d, J=8 Hz, 1H); LC-MS (LC-ES) M−H=159.

Alternative Method (2-Amino-6-chloropyridin-3-yl)methanol

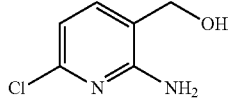

Lithium aluminum hydride (1M in tetrahydrofuran) (130 mL, 130 mmol) was added over 150 minutes to 2-amino-6-chloronicotinic acid (15.00 g, 87 mmol) in tetrahydrofuran (500 mL) under nitrogen, then the reaction mixture was stirred for eighteen hours. The reaction was quenched with sodium sulfate decahydrate, followed by methanol, and then the reaction mixture was concentrated. The residue was dissolved in dichloromethane and methanol and purified via silica gel chromatography, eluting with methanol:dichloromethane with 10% ammonium hydroxide (0:1 to 1:9) to give (2-amino-6-chloropyridin-3-yl)methanol (12.46 g, 79 mmol, 90%) as a yellow solid.

B'. 2-Amino-6-chloronicotinaldehyde

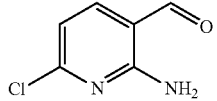

Manganese dioxide (activated, <10 micron) (4.473 g, 51.5 mmol) was added to the (2-amino-6-chloropyridin-3-yl)methanol (1.632 g, 10.29 mmol) in dichloromethane (100 mL) and the reaction mixture was stirred for one hour under sonication, then sixty-two hours without sonication. Then, Celite® was added to the reaction mixture and it was filtered. The filter cake was rinsed several times with dichloromethane and the combined organic layers were concentrated to give 2-amino-6-chloronicotinaldehyde (1.50 g, 9.58 mmol, 93%) as a yellow powder. $^1$H NMR (400 MHz, CD$_3$SOCD$_3$) δ 6.77 (d, J=8 Hz, 1H), 7.90 (br s, 2H), 8.04 (d, J=8 Hz, 1H), 9.83 (s, 1H); LC-MS (LC-ES) M−H=157.

Alternative Method

2-Amino-6-chloronicotinaldehyde

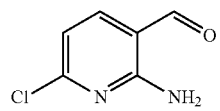

Chlorobis(cyclooctene)indium(I)dimer (0.116 g, 0.130 mmol) was added to diethylsilane (1.009 ml, 7.79 mmol) in dichloromethane (8.65 ml) under nitrogen at room temperature and the reaction mixture was stirred for five minutes. Then, ethyl 2-amino-6-chloronicotinate (0.5208 g, 2.60 mmol) was added and the reaction mixture was stirred for four hours. Then, the reaction mixture was quenched with 1.0 N hydrochloric acid and methanol and stirred for 20 minutes. The reaction mixture was neutralized with saturated sodium bicarbonate, extracted with dichloromethane, dried over magnesium sulfate, filtered, and concentrated. The residue was purified by silica gel chromatography, eluting with methanol:dichloromethane (0:1 to 1:9), then further purified by silica gel chromatography, eluting with ethyl acetate:hexanes (0:1 to 3:7) to give 2-amino-6-chloronicotinaldehyde (0.2754 g, 1.671 mmol, 64.4% yield). $^1$H NMR (400 MHz, CD$_3$SOCD$_3$) δ 6.76 (d, J=8 Hz, 1H), 7.90 (br s, 2H), 8.03 (d, J=8 Hz, 1H), 9.82 (s, 1H); LC-MS (LC-ES) M−H=157.

C. Ethyl 7-chloro-1,8-naphthyridine-3-carboxylate

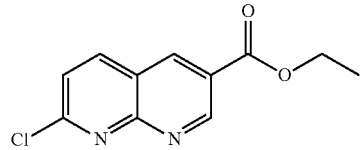 [SMILES: CCOC(=O)c1cnc2nc(Cl)ccc2c1]

L-Proline (0.667 g, 5.79 mmol) was added to the 2-amino-6-chloronicotinaldehyde (1.50 g, 9.58 mmol, sold by Aldrich) in ethanol (100 mL). Then, ethyl propiolate (1.17 mL, 11.54 mmol) was added and the reaction mixture was heated at 80° C. under nitrogen for forty-two hours. Then, additional ethyl propiolate (0.20 mL, 1.973 mmol) was added and the reaction mixture was stirred for five hours then concentrated. Methanol was added and the mixture was reconcentrated, triturated with methanol (15 mL), filtered, rinsed with methanol (5 mL), air-dried to give ethyl 7-chloro-1,8-naphthyridine-3-carboxylate (1.329 g, 5.62 mmol, 59%) as a tan powder which was carried on to the next step. $^1$H NMR (400 MHz, CD$_3$SOCD$_3$) δ 1.38 (t, J=7 Hz, 3H), 4.42 (q, J=7 Hz, 2H), 7.86 (d, J=9 Hz, 1H), 8.77 (d, J=9 Hz, 1H), 9.18 (d, J=2 Hz, 1H), 9.48 (d, J=2 Hz, 1H); LC-MS (LC-ES) M+H=237.

Alternative Method

Ethyl 7-chloro-1,8-naphthyridine-3-carboxylate

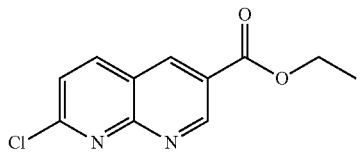 [SMILES: CCOC(=O)c1cnc2nc(Cl)ccc2c1]

Ethyl 3,3-diethoxypropanoate (0.771 ml, 3.96 mmol) was added to 2-amino-6-chloronicotinaldehyde (0.2481 g, 1.585 mmol) in ethanol (12.68 ml) at room temperature. Then, para-toluenesulfonic acid (0.014 g, 0.079 mmol) was added and the reaction mixture was heated at reflux for twenty-eight hours. Then, water (3.17 ml) was added and the reaction mixture was heated at 80° C. for eighty-two hours. The reaction mixture was concentrated and the residue was purified by silica gel chromatography, eluting with methanol:dichloromethane (0:1 to 1:9) to give ethyl 7-oxo-7,8-dihydro-1,8-naphthyridine-3-carboxylate (0.1472 g, 0.641 mmol, 40.4% yield). Yield could have been higher, but some material was spilled during transfer CH NMR (400 MHz, $CD_3SOCD_3$) δ 1.33 (t, J=7 Hz, 3H), 4.34 (q, J=7 Hz, 2H), 6.64 (dd, J=10, 2 Hz, 1H), 8.07 (d, J=10 Hz, 1H), 8.66 (d, J=2 Hz, 1H), 8.97 (d, J=2 Hz, 1H), 12.53 (brs, 1H); LC-MS (LC-ES) M+H=219). Phosphorus oxychloride (0.112 ml, 1.202 mmol) was added to ethyl 7-oxo-7,8-dihydro-1,8-naphthyridine-3-carboxylate (0.1311 g, 0.601 mmol) in toluene (6.01 ml) at room temperature and the reaction mixture was heated at 110° C. and stirred for three hours. Then, the reaction mixture was cooled to 0° C. and quenched with saturated sodium bicarbonate, extracted with dichloromethane, dried over magnesium sulfate, filtered, and concentrated. The residue was purified by silica gel chromatography, eluting with methanol:dichloromethane (0:1 to 1:9) to give ethyl 7-chloro-1,8-naphthyridine-3-carboxylate (0.1141 g, 0.458 mmol, 76% yield). $^1$H NMR (400 MHz, $CD_3SOCD_3$) δ 1.38 (t, J=7 Hz, 3H), 4.42 (q, J=7 Hz, 2H), 7.86 (d, J=9 Hz, 1H), 8.77 (d, J=9 Hz, 1H), 9.18 (d, J=2 Hz, 1H), 9.48 (d, J=2 Hz, 1H); LC-MS (LC-ES) M+H=237.

Alternative Method

A". 2-Amino-5-bromonicotinaldehyde

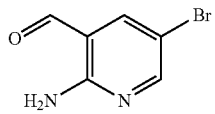

To a stirred solution of 2-aminonicotinaldehyde (500 mg, 4.09 mmol) in diethyl ether (15 mL) was added bromine (0.30 mL, 5.82 mmol) dropwise. The mixture was stirred for 30 minutes. The amber colored solids were collected via vacuum filtration and then partitioned between ethyl acetate and 1N aqueous sodium hydroxide. The organic layer was separated, washed with brine, dried over sodium sulfate, and filtered. Solvent was removed under reduced pressure and the remaining material was placed in vacuo to give 2-amino-5-bromonicotinaldehyde (637 mg, 3.17 mmol, 77% yield) as a dark yellow solid. $^1$H NMR (400 MHz, $CD_3SOCD_3$) δ 7.69 (br s, 2H), 8.23 (d, J=2 Hz, 1H), 8.30 (d, J=2 Hz, 1H), 9.81 (s, 1H); LC-MS (LC-ES) M+H=201.

B". 6-Bromo-2-cyclopropyl-1,8-naphthyridine

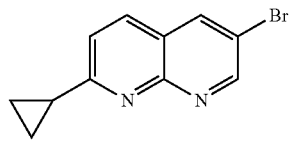 [SMILES: Brc1cnc2nc(C3CC3)ccc2c1]

To a stirred solution of 2-amino-5-bromonicotinaldehyde (634 mg, 3.15 mmol, sold by Combi-Blocks) and 1-cyclopropylethan-1-one (0.32 mL, 3.23 mmol) in ethanol (20 mL) was added 6M aqueous sodium hydroxide (0.50 mL, 3.00 mmol). The mixture was heated to reflux and stirred for 1 hour. Solvent was removed under reduced pressure and the remaining material was triturated with water. The resulting solid was collected via vacuum filtration, washed with water and dried overnight in vacuo to give 6-bromo-2-cyclopropyl-1,8-naphthyridine (631 mg, 2.53 mmol, 80% yield) as a brown solid. $^1$H NMR (400 MHz, $CD_3SOCD_3$) δ 1.08-1.16 (m, 4H), 2.30-2.38 (m, 1H), 7.62 (d, J=8 Hz, 1H), 8.27 (d, J=8 Hz, 1H), 8.71 (d, J=3 Hz, 1H), 9.00 (d, J=3 Hz, 1H); LC-MS (LC-ES) M+H=249.

D. Ethyl 7-cyclopropyl-1,8-naphthyridine-3-carboxylate

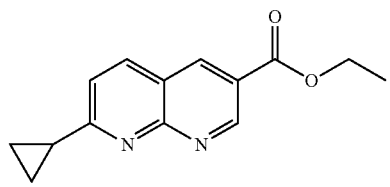 [SMILES: CCOC(=O)c1cnc2nc(C3CC3)ccc2c1]

A stirred mixture of 6-bromo-2-cyclopropyl-1,8-naphthyridine (100 mg, 0.401 mmol), [1,1'-bis(diphenylphosphino)ferrocene]dichloropalladium(II) dichloromethane adduct (50 mg, 0.061 mmol) and N,N-diisopropylethylamine (0.35 mL, 2.004 mmol) in ethanol (5 mL) was purged with nitrogen for 3 minutes, followed by purging with carbon monoxide for 5 minutes. The mixture was stirred under a carbon monoxide balloon and heated at 80° C. overnight. After cooling to room temperature, the mixture was filtered through a pad of Celite®, rinsing with ethanol. The filtrate was evaporated to dryness under reduced pressure and the remaining dark material was dissolved in a minimal amount of dichloromethane, loaded onto a pre-packed silica cartridge and purified by silica gel chromatography, eluting with ethyl acetate:ethanol (3:1):hexanes (1:19 to 1:4) to give ethyl 7-cyclopropyl-1,8-naphthyridine-3-carboxylate (74 mg, 0.305 mmol, 76% yield) as a beige solid. $^1$H NMR (400 MHz, $CD_3SOCD_3$) δ 1.12-1.22 (m, 4H), 3.37 (t, J=7 Hz, 3H), 2.34-2.42 (m, 1H), 4.40 (q, J=7 Hz, 2H), 7.68 (d, J=8 Hz, 1H), 8.51 (d, J=8 Hz, 1H), 8.99 (d, J=2 Hz, 1H), 9.36 (d, J=2 Hz, 1H); LC-MS (LC-ES) M+H=243.

Intermediate 5

7-(Azetidin-1-yl)-1,8-naphthyridine-3-carboxylic acid lithium salt

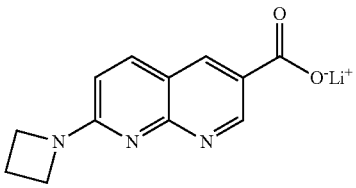

A. Ethyl 7-(azetidin-1-yl)-1,8-naphthyridine-3-carboxylate

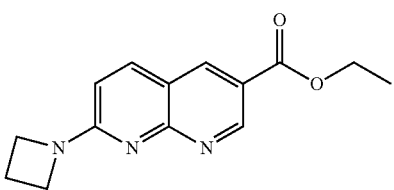 [SMILES: CCOC(=O)c1cnc2nc(N3CCC3)ccc2c1]

N,N-Diisopropylethylamine (1.35 mL, 7.75 mmol) was added to ethyl 7-chloro-1,8-naphthyridine-3-carboxylate (0.4588 g, 1.939 mmol, Intermediate 4C) in N-methyl-2-pyrrolidone (6.46 mL) at room temperature. Then, azetidine hydrochloride (0.544 g, 5.82 mmol) was added and the reaction mixture was heated at 100° C. in the microwave for one hour. The reaction mixture was diluted in dichloromethane, washed with saturated sodium bicarbonate, dried over magnesium sulfate, filtered, and concentrated. The resulting residue was purified by RP HPLC, eluting with acetonitrile:water with 0.1% ammonium hydroxide (5:95 to 100:0) to give ethyl 7-(azetidin-1-yl)-1,8-naphthyridine-3-carboxylate (0.4469 g, 1.650 mmol, 85% yield). $^1$H NMR (400 MHz, CD$_3$SOCD$_3$) δ 1.34 (t, J=7 Hz, 3H), 2.39 (p, J=7 Hz, 2H), 4.18 (t, J=7 Hz, 4H), 4.34 (q, J=7 Hz, 2H), 6.81 (d, J=9 Hz, 1H), 8.17 (d, J=9 Hz, 1H), 8.65 (s, 1H), 9.12 (s, 1H); LC-MS (LC-ES) M+H=258.

B. 7-(Azetidin-1-yl)-1,8-naphthyridine-3-carboxylic acid lithium salt

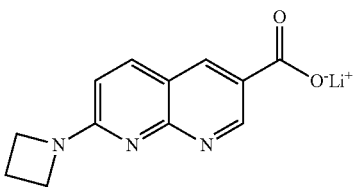

Lithium hydroxide (0.125 g, 5.21 mmol) was added to ethyl 7-(azetidin-1-yl)-1,8-naphthyridine-3-carboxylate (0.4469 g, 1.737 mmol) in methanol (6.95 mL) and water (1.737 mL) at room temperature and the reaction mixture was stirred three hours at 60° C. The reaction mixture was concentrated. The reaction mixture was purified by RP HPLC eluting with acetonitrile:water with 0.1% ammonium hydroxide (5:95 to 100:0), then further purified by silica gel chromatography, eluting with methanol:ethyl acetate (1:9 to 4:1) to give 7-(azetidin-1-yl)-1,8-naphthyridine-3-carboxylic acid lithium salt (0.4216 g, 1.696 mmol, 98% yield). $^1$H NMR (400 MHz, CD$_3$SOCD$_3$) δ 2.37 (p, J=7 Hz, 2H), 4.11 (t, J=7 Hz, 4H), 6.69 (d, J=9 Hz, 1H), 8.03 (d, J=9 Hz, 1H), 8.37 (s, 1H), 9.13 (s, 1H); LC-MS (LC-ES) M−H=230.

Intermediate 6

7-(3-Fluoroazetidin-1-yl)-1,8-naphthyridine-3-carboxylic acid lithium salt

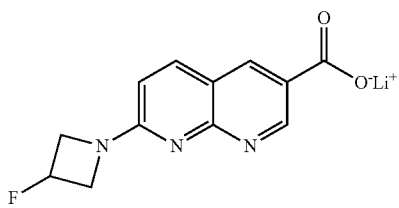

A. Ethyl 7-(3-fluoroazetidin-1-yl)-1,8-naphthyridine-3-carboxylate

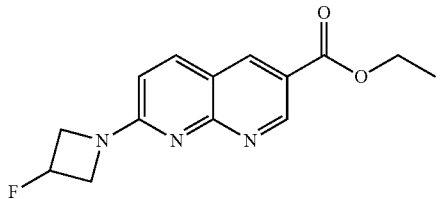 [SMILES: CCOC(=O)c1cnc2nc(N3CC(F)C3)ccc2c1]

N,N-Diisopropylethylamine (1.23 mL, 7.09 mmol) was added to ethyl 7-chloro-1,8-naphthyridine-3-carboxylate (0.4194 g, 1.772 mmol, Intermediate 4C) in N-methyl-2-pyrrolidone (5.91 mL) at room temperature. Then 3-fluoroazetidine hydrochloride (0.593 g, 5.32 mmol) was added and the reaction mixture was heated at 100° C. in the microwave for one hour. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:9) to give ethyl 7-(3-fluoroazetidin-1-yl)-1,8-naphthyridine-3-carboxylate (0.4561 g, 1.574 mmol, 89% yield).). $^1$H NMR (400 MHz, CD$_3$SOCD$_3$) δ 1.35 (t, J=7 Hz, 3H), 4.25 (br dd, J=24, 11 Hz, 2H), 4.35 (q, J=7 Hz, 2H), 4.46-4.60 (m, 2H), 5.46-5.68 (m, 1H), 6.91 (d, J=9 Hz, 1H), 8.25 (d, J=9 Hz, 1H), 8.71 (s, 1H), 9.16 (s, 1H); LC-MS (LC-ES)+H=276.

B. 7-(3-Fluoroazetidin-1-yl)-1,8-naphthyridine-3-carboxylic acid lithium salt

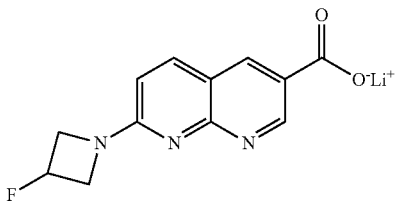

Lithium hydroxide (0.119 g, 4.97 mmol) was added to ethyl 7-(3-fluoroazetidin-1-yl)-1,8-naphthyridine-3-carboxylate (0.4561 g, 1.657 mmol) in methanol (6.6 mL) and water (1.7 mL) at room temperature and the reaction mixture was stirred three hours at 60° C. The reaction mixture was concentrated to give 7-(3-fluoroazetidin-1-yl)-1,8-naphthyridine-3-carboxylic acid lithium salt (0.4332 g, 1.619 mmol, 98% yield). $^1$H NMR (400 MHz, CD$_3$SOCD$_3$) δ 4.17 (br dd, J=24, 10 Hz, 2H), 4.38-4.54 (m, 2H), 5.44-5.66 (m, 1H), 6.79 (d, J=9 Hz, 1H), 8.11 (d, J=9 Hz, 1H), 8.44 (s, 1H), 9.18 (s, 1H); LC-MS (LC-ES) M+H=248.

Intermediate 7

7-(2-Methylazetidin-1-yl)-1,8-naphthyridine-3-carboxylic acid lithium salt

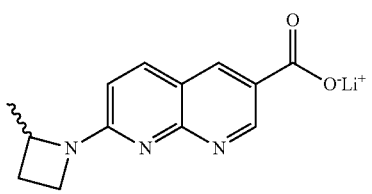

A. Ethyl 7-(2-methylazetidin-1-yl)-1,8-naphthyridine-3-carboxylate

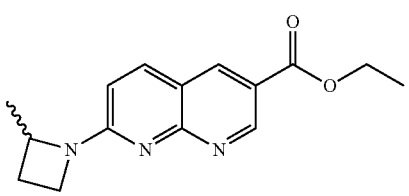 [SMILES: CCOC(=O)c1cnc2nc(N3CCC3C)ccc2c1]

N,N-Diisopropylethylamine (0.987 mL, 5.67 mmol) was added to ethyl 7-chloro-1,8-naphthyridine-3-carboxylate (0.3352 g, 1.416 mmol, Intermediate 4C) in N-methyl-2-pyrrolidone (4.72 mL) at room temperature. Then 2-methylazetidine hydrochloride (0.457 g, 4.25 mmol) was added and the reaction mixture was heated at 100° C. in the microwave for one hour. The reaction mixture was diluted in dichloromethane, washed with saturated sodium bicarbonate, dried over magnesium sulfate, filtered, and concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:19) to give ethyl 7-(2-methylazetidin-1-yl)-1,8-naphthyridine-3-carboxylate (0.3815 g, 1.336 mmol, 94% yield). $^1$H NMR (400 MHz, CD$_3$SOCD$_3$) δ 1.34 (t, J=7 Hz, 3H), 1.53 (d, J=6 Hz, 3H), 1.94-2.06 (m, 1H), 2.46-2.60 (m, 1H), 4.03 (q, J=7 Hz, 1H), 4.14 (q, J=6 Hz, 1H), 4.34 (q, J=7 Hz, 2H), 4.58 (h, J=6 Hz, 1H), 6.81 (d, J=9 Hz, 1H), 8.16 (d, J=9 Hz, 1H), 8.65 (s, 1H), 9.12 (s, 1H); LC-MS (LC-ES) M+H=272.

B. 7-(2-Methylazetidin-1-yl)-1,8-naphthyridine-3-carboxylic acid lithium salt

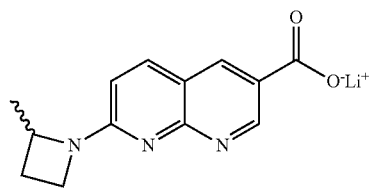

Lithium hydroxide (0.101 g, 4.22 mmol) was added to ethyl 7-(2-methylazetidin-1-yl)-1,8-naphthyridine-3-carboxylate (0.3815 g, 1.406 mmol) in methanol (5.6 mL) and water (1.4 mL) at room temperature and the reaction mixture was stirred three hours at 60° C. The reaction mixture was concentrated to give 7-(2-methylazetidin-1-yl)-1,8-naphthyridine-3-carboxylic acid lithium salt (0.3698 g, 1.404 mmol, 100% yield). $^1$H NMR (400 MHz, CD$_3$SOCD$_3$) δ 1.51 (d, J=6 Hz, 3H), 1.94-2.06 (m, 1H), 2.42-2.54 (m, 1H), 3.94 (q, J=8 Hz, 1H), 4.06 (q, J=8 Hz, 1H), 4.50 (h, J=6 Hz, 1H), 6.69 (d, J=9 Hz, 1H), 8.03 (d, J=9 Hz, 1H), 8.39 (s, 1H), 9.15 (s, 1H); LC-MS (LC-ES) M+H=244.

Intermediate 8

7-(2-Methylazetidin-1-yl)-1,6-naphthyridine-3-carboxylic acid lithium salt

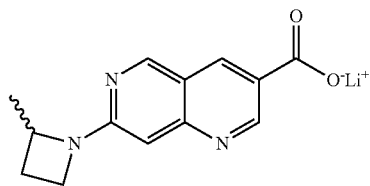

A. Ethyl 7-(2-methylazetidin-1-yl)-1,6-naphthyridine-3-carboxylate

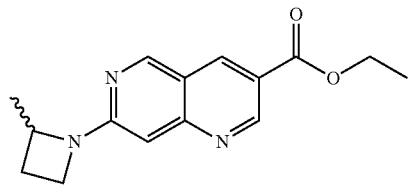 [SMILES: CCOC(=O)c1cnc2cc(N3CCC3C)ncc2c1]

N,N-Diisopropylethylamine (1.361 mL, 7.81 mmol) was added to ethyl 7-chloro-1,6-naphthyridine-3-carboxylate (0.4622 g, 1.953 mmol, Intermediate 1F) in N-methyl-2-pyrrolidone (6.51 mL) at room temperature. Then 2-methylazetidine hydrochloride (0.420 g, 3.91 mmol) was added and the reaction mixture was heated at 100° C. in the microwave for four hours. The reaction mixture was diluted in dichloromethane, washed with saturated sodium bicarbonate, dried over magnesium sulfate, filtered, and concentrated. The resulting residue was purified by RP HPLC, eluting with acetonitrile:water with 0.1% ammonium hydroxide (5:95 to 100:0), then further purified by silica gel chromatography, eluting with ethyl acetate:hexanes (1:4 to 3:2) to give ethyl 7-(2-methylazetidin-1-yl)-1,6-naphthyridine-3-carboxylate (0.2731 g, 0.956 mmol, 49.0% yield). $^1$H NMR (400 MHz, CD$_3$SOCD$_3$) δ 1.35 (t, J=7 Hz, 3H), 1.51 (d, J=6 Hz, 3H), 2.04 (p, J=8 Hz, 1H), 2.50 (p, J=8 Hz, 1H), 3.90 (q, J=8 Hz, 1H), 4.06 (q, J=5 Hz, 1H), 4.35 (q, J=7 Hz, 2H), 4.48 (h, J=7 Hz, 1H), 6.53 (s, 1H), 8.83 (s, 1H), 9.15 (s, 1H), 9.17 (s, 1H); LC-MS (LC-ES) M+H=272.

B. 7-(2-Methylazetidin-1-yl)-1,6-naphthyridine-3-carboxylic acid lithium salt

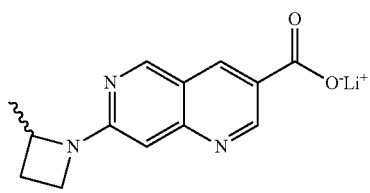

Lithium hydroxide (0.072 g, 3.02 mmol) was added to ethyl 7-(2-methylazetidin-1-yl)-1,6-naphthyridine-3-carboxylate (0.2731 g, 1.007 mmol) in methanol (4.0 mL) and water (1.0 mL) at room temperature and the reaction mixture was stirred three hours at 60° C. The reaction mixture was concentrated to give 7-(2-methylazetidin-1-yl)-1,6-naphthyridine-3-carboxylic acid lithium salt (0.2551 g, 0.969 mmol, 96% yield). $^1$H NMR (400 MHz, CD$_3$SOCD$_3$) δ 1.49 (d, J=6 Hz, 3H), 1.96-2.06 (m, 1H), 2.36-2.48 (m, 1H), 3.80 (q, J=8 Hz, 1H), 3.98 (q, J=8 Hz, 1H), 4.36 (h, J=7 Hz, 1H), 6.51 (s, 1H), 8.51 (s, 1H), 8.97 (s, 1H), 9.25 (s, 1H); LC-MS (LC-ES) M+H=244.

Intermediate 9

7-(Cyclopropylamino)-1,6-naphthyridine-3-carboxylic acid lithium salt

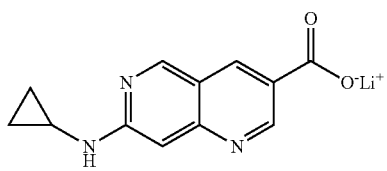

A. Ethyl 7-(cyclopropylamino)-1,6-naphthyridine-3-carboxylate

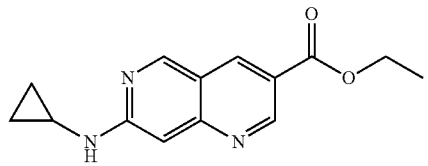 [SMILES: CCOC(=O)c1cnc2cc(NC3CC3)ncc2c1]

N,N-Diisopropylethylamine (1.2 mL, 7.13 mmol) was added to ethyl 7-chloro-1,6-naphthyridine-3-carboxylate (0.4220 g, 1.783 mmol, Intermediate 1F) in N-methyl-2-pyrrolidone (5.94 mL) at room temperature. Then cyclopropanamine (0.37 mL, 5.35 mmol) was added and the reaction mixture was heated at 100° C. in the microwave for nine hours. The reaction mixture was diluted with dichloromethane, washed with saturated sodium bicarbonate, dried over magnesium sulfate, filtered, and concentrated. The resulting residue was purified by RP HPLC, eluting with acetonitrile:water with 0.1% ammonium hydroxide (5:95 to 100:0), then further purified by silica gel chromatography, eluting with ethyl acetate:hexanes (1:4 to 3:2) to give ethyl 7-(cyclopropylamino)-1,6-naphthyridine-3-carboxylate (0.0896 g, 0.331 mmol, 18.6% yield). $^1$H NMR (400 MHz, CD$_3$SOCD$_3$) δ 0.53 (s, 2H), 0.81 (d, J=7 Hz, 2H), 1.35 (t, J=7 Hz, 3H), 2.52-2.64 (m, 1H), 4.36 (q, J=7 Hz, 2H), 6.86 (s, 1H), 7.64 (s, 1H), 8.81 (s, 1H), 9.09 (s, 1H), 9.18 (s, 1H); LC-MS (LC-ES) M+H=258.

B. 7-(Cyclopropylamino)-1,6-naphthyridine-3-carboxylic acid lithium salt

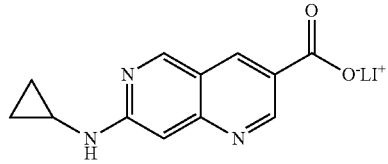

Lithium hydroxide (0.025 g, 1.045 mmol) was added to ethyl 7-(cyclopropylamino)-1,6-naphthyridine-3-carboxylate (0.0896 g, 0.348 mmol) in methanol (1.4 mL) and water (0.35 mL) at room temperature and the reaction mixture was stirred one hour at 60° C. The reaction mixture was concentrated to give 7-(cyclopropylamino)-1,6-naphthyridine-3-carboxylic acid lithium salt (0.0914 g, 0.341 mmol, 98% yield). $^1$H NMR (400 MHz, CD$_3$SOCD$_3$) δ 0.49 (s, 2 H), 0.76 (d, J=6 Hz, 2H), 3.15 (s, 1H), 6.82 (s, 1H), 7.06 (s, 1H), 8.48 (s, 1H), 8.89 (s, 1H), 9.24 (s, 1H); LC-MS (LC-ES) M+H=230.

Intermediate 10

(1s,3s)-3-Amino-1-methylcyclobutanol hydrochloride

A. tert-Butyl ((1s,3s)-3-hydroxy-3-methylcyclobutyl)carbamate

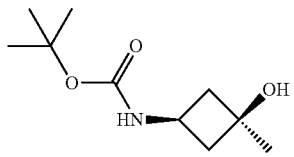

Cerium(III) chloride heptahydrate (10.06 g, 27.0 mmol) was dried at 140° C. under high vacuum for 17 h, and then was cooled to room temperature while remaining under vacuum. The solid was placed under a nitrogen atmosphere, cooled to 0° C. and tetrahydrofuran (60 mL) was added. The ice bath was removed, and the slurry was stirred for 1 hour, and then cooled to −78° C. A 1.6 M solution of methyllithium in diethyl ether (16.9 mL, 27.0 mmol) was added at a rate to keep the temperature below −70° C. After 90 minutes, tert-butyl (3-oxocyclobutyl)carbamate (2.50 g, 13.5 mmol) in tetrahydrofuran (15 mL) was added at a rate to keep the temperature below −70° C. After 3 hours, the mixture was allowed to slowly warm to room temperature. After stirring overnight, the mixture was poured into saturated aqueous ammonium chloride (100 mL) and water (100 mL), stirred 10 minutes and filtered. The filtrate was extracted with ethyl acetate (2×), and the combined organics were dried over magnesium sulfate, filtered, and concentrated. The residue was purified by silica gel chromatography, eluting with ethyl acetate:hexanes (1:4 to 1:0) to give tert-butyl (cis)-3-hydroxy-3-methylcyclobutyl)carbamate (1.05 g, 5.22 mmol, 39%) as a solid. $^1$H NMR (400 MHz, CDCl$_3$) δ 1.37 (s, 3H), 1.44 (s, 9H), 1.98 (td, J=9, 3 Hz, 2H), 2.46-2.54 (m, 2H), 3.72 (p, J=8 Hz, 1H), 4.68 (br s, 1H).

B. (1s,3s)-3-Amino-1-methylcyclobutanol hydrochloride

4N Hydrochloric acid in dioxane (5.8 mL, 23.3 mmol) was added to tert-butyl (cis)-3-hydroxy-3-methylcyclobutyl)carbamate (1.04 g, 5.17 mmol) in methanol (18.4 mL) at room temperature. The mixture was stirred overnight, more 4N hydrochloric acid in dioxane (1.30 mL, 5.17 mmol) was added, and after three hours, the solvent was removed in vacuo. The resulting residue was redissolved and concentrated with both dioxane and diethyl ether to give (cis)-3-amino-1-methylcyclobutanol hydrochloride (786 mg, 5.14 mmol, 99%). $^1$H NMR (400 MHz, CD$_3$SOCD$_3$) δ 1.14-1.24 (m, 3H), 1.88 (t, J=10 Hz, 2H), 2.10-2.20 (m, 2H), 3.42-3.55 (m, 1H), 4.85 (s, 1H).

Intermediate 11

(1r,3r)-3-Amino-1-methylcyclobutanol

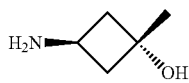

A. Methylenecyclobutanecarboxylic acid

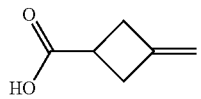

Potassium hydroxide (61 g, 1087 mmol) was added to a solution of 3-methylenecyclobutanecarbonitrile (25 g, 268 mmol) in a mixture of ethanol (150 mL) and water (150 mL) at 27° C. The reaction mixture was heated at 80° C. for sixteen hours. On completion, the reaction mixture was concentrated under reduced pressure to remove the ethanol. Ice water (250 mL) was added to the residue and the mixture was acidified with concentrated hydrochloric acid (pH=1) (250 mL), extracted with ethyl acetate (500 mL, 2X), dried over sodium sulfate, filtered, and concentrated under reduced pressure to afford 3-methylenecyclobutanecarboxylic acid (30 g, 252 mmol, 94% yield) as a colorless liquid. $^1$H NMR (400 MHz, CD$_3$SOCD$_3$) δ 2.82 (d, J=8 Hz, 4H), 3.04 (p, J=8 Hz, 1H), 4.76 (p, J=2 Hz, 2H), 12.20 (br s, 1H); LC-MS (LC-ES) M+H=113.

B. Benzyl (3-methylenecyclobutyl)carbamate

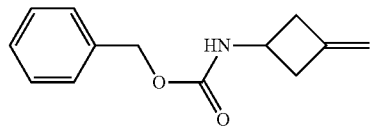 [SMILES: C=C1CC(NC(=O)OCc2ccccc2)C1]

Triethylamine (0.932 mL, 6.69 mmol) was added to a solution of 3-methylenecyclobutanecarboxylic acid (0.5 g, 4.46 mmol) in a mixture of acetonitrile (4.5 mL) and 1,4-dioxane (1.5 mL) at 27° C. Then, diphenyl phosphorazidate (1.227 mL, 5.35 mmol) was added and the reaction mixture was heated at 75° C. for one hour. Then, benzyl alcohol (5 mL, 48.1 mmol) was added at the same temperature. The resultant reaction mixture was stirred at 100° C. for sixteen hours. On completion, the reaction mixture was concentrated under reduced pressure to give an impure material. This material was purified via silica gel column chromatography, eluting with ethyl acetate:petroleum ether (3:1) to afford benzyl (3-methylenecyclobutyl)carbamate (650 mg, 2.96 mmol, 66.3% yield) as an off white solid. $^1$H NMR (400 MHz, CDCl$_3$) δ 2.49-2.65 (m, 2H), 3.01-3.05 (m, 2H), 4.16-4.33 (m, 1H), 4.80-4.89 (m, 2H), 4.95-5.02 (m, 1H), 5.10 (s, 2H), 7.29-7.45 (m, 5H); LC-MS (LC-ES) M+H=218.

C. Benzyl 1-oxaspiro[2.3]hexan-5-ylcarbamate

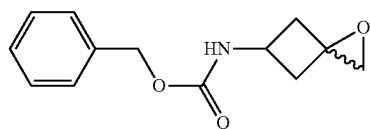 [SMILES: O=C(NC1CC2(CO2)C1)OCc1ccccc1]

3-Chloroperbenzoic acid (2.381 g, 13.8 mmol) was added to a solution of benzyl (3-methylenecyclobutyl)carbamate (2.8 g, 10.61 mmol) in dichloromethane (28 mL) portionwise at 0° C. The reaction mixture was allowed to warm to 27° C. and stirred for three hours. On completion, the reaction mixture was basified with saturated sodium bicarbonate solution (25 mL) and extracted with dichloromethane (50 mL, 2X). The organic layer was dried over sodium sulfate, filtered, and concentrated under reduced pressure to afford benzyl 1-oxaspiro[2.3]hexan-5-ylcarbamate (2.5 g, 7.81 mmol, 73% yield) as a colorless gum. $^1$H NMR (400 MHz, CDCl$_3$) δ 2.34-2.49 (m, 2H), 2.73 (br d, J=17 Hz, 4H), 4.06-4.37 (m, 1H), 5.10 (br s, 3H), 7.24-7.43 (m, 5H); LC-MS (LC-ES) M+H=234.

D. Benzyl (3-hydroxy-3-methylcyclobutyl)carbamate

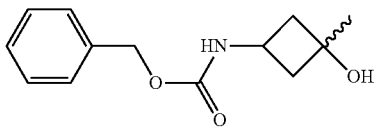 [SMILES: CC1(O)CC(NC(=O)OCc2ccccc2)C1]

Lithium triethyl borohydride (15.6 mL, 15.6 mmol) in tetrahydrofuran (1.0 M) was added to a solution of benzyl 1-oxaspiro[2.3]hexan-5-ylcarbamate (2.8 g, 12 mmol) in tetrahydrofuran (140 mL) at 0° C. The reaction mixture temperature was allowed to warm to 27° C. and stirred for one hour. On completion, the reaction mixture was quenched with water (500 mL) and extracted with ethyl acetate (300 mL, 2X). The combined organic layers were washed with brine (200 mL), dried over sodium sulfate, filtered, and concentrated under reduced pressure to give an impure material. This material was purified via silica gel column chromatography, eluting with ethyl acetate:petroleum ether (3:1) to afford benzyl (3-hydroxy-3-methylcyclobutyl)carbamate (2.5 g, 9.97 mmol, 83% yield, mixture of isomers) as a colorless gum. $^1$H NMR (400 MHz, CDCl$_3$) δ 1.38 (d, J=10 Hz, 3H), 2.00 (m, 2H), 2.44-2.59 (m, 2H), 3.72-3.81 (m, 1H), 4.25-4.34 (m, 1H), 4.80-5.01 (m, 1H), 5.08 (s, 2H), 7.29-7.51 (m, 5H); LC-MS (LC-ES) M+H=236.

E. Benzyl ((1s,3s)-3-hydroxy-3-methylcyclobutyl)carbamate and Benzyl ((1r,3r)-3-hydroxy-3-methylcyclobutyl)carbamate

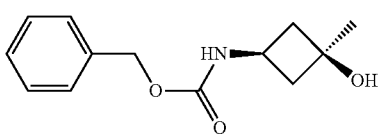

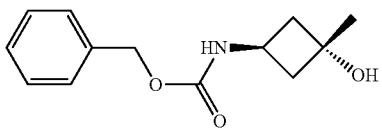

Benzyl (3-hydroxy-3-methylcyclobutyl)carbamate (2.5 g, mixture of isomers) was purified by chiral super critical fluid chromatography on a Lux Cellulose-2 column, eluting with methanol:carbon dioxide (1:1) to afford benzyl ((1s,3s)-3-hydroxy-3-methylcyclobutyl)carbamate (1 g, 4.13 mmol, 39% yield) as an off white solid and benzyl ((1r,3r)-3-hydroxy-3-methylcyclobutyl)carbamate (1 g, 4.16 mmol, 39% yield) as a gum.

Benzyl ((1s,3s)-3-hydroxy-3-methylcyclobutyl)carbamate $^1$H NMR (400 MHz, CDCl$_3$) δ 1.21 (s, 3H), 1.88-1.98 (m, 2H), 2.20-2.28 (m, 2H), 3.48-3.62 (m, 1H), 5.01 (s, 2H), 7.28-7.40 (m, 5H); LC-MS (LC-ES) M+H=236.

Benzyl ((1r,3r)-3-hydroxy-3-methylcyclobutyl)carbamate $^1$H NMR (400 MHz, CDCl$_3$) δ 1.23 (s, 3H), 1.82-1.96 (m, 2H), 2.16-2.27 (m, 2H), 3.94-4.11 (m, 1H), 4.77 (s, 1H), 4.99 (s, 2H), 7.26-7.40 (m, 5H), 7.49 (br d, J=7 Hz, 1H); LC-MS (LC-ES) M+H=236.

F. (1r,3r)-3-Amino-1-methylcyclobutanol

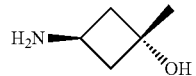

10% Palladium on carbon (0.442 g, 0.416 mmol) was added to a solution of benzyl ((1r,3r)-3-hydroxy-3-methylcyclobutyl)carbamate (1 g, 4.16 mmol) in ethanol (20 mL) at room temperature and stirred for five hours under a hydrogen atmosphere (balloon pressure). On completion, the reaction mixture was filtered through Celite® and the filtrate was evaporated under reduced pressure to afford (1r,3r)-3-amino-1-methylcyclobutanol (330 mg, 3.23 mmol, 78% yield) as a colorless liquid. $^1$H NMR (400 MHz, CD$_3$SOCD$_3$) δ 1.23 (s, 3H), 1.52-1.64 (m, 2H), 2.07-2.21 (m, 2H), 3.38-3.47 (m, 1H); LC-MS (LC-ES) M+H=102.

G. (1s,3s)-3-Amino-1-methylcyclobutanol

10% Palladium on carbon (0.439 g, 0.413 mmol) was added to a solution of benzyl ((1s,3s)-3-hydroxy-3-methylcyclobutyl)carbamate (1 g, 4.13 mmol) in ethanol (20 mL) at room temperature and stirred for five hours under a hydrogen atmosphere (balloon pressure). On completion, the reaction mixture was filtered through Celite® and the filtrate was evaporated under reduced pressure to afford (1s,3s)-3-amino-1-methylcyclobutanol (350 mg, 3.45 mmol, 84% yield) as an off white solid. $^1$H NMR (400 MHz, CD$_3$SOCD$_3$) δ 1.16 (s, 3H), 1.64-1.72 (m, 2H), 2.12-2.24 (m, 2H), 2.78-2.90 (m, 1H); LC-MS (LC-ES) M+H=102.

Intermediate 12

7-((2,2-Difluoroethyl)amino)-1,8-naphthyridine-3-carboxylic acid lithium salt

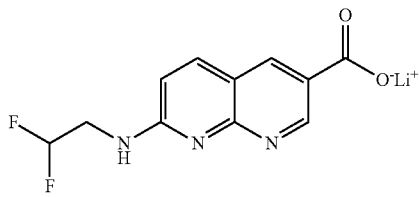

A. Ethyl 7-((2,2-difluoroethyl)amino)-1,8-naphthyridine-3-carboxylate

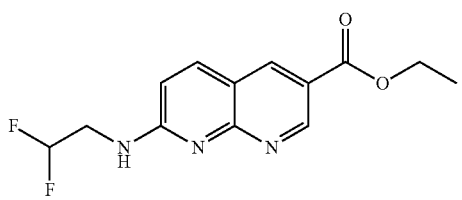 [SMILES: CCOC(=O)c1cnc2nc(NCC(F)F)ccc2c1]

N,N-Diisopropylethylamine (1.224 mL, 7.03 mmol) was added to ethyl 7-chloro-1,8-naphthyridine-3-carboxylate (0.4158 g, 1.757 mmol, Intermediate 4C) in N-methyl-2-pyrrolidone (5.86 mL) at room temperature. Then 2,2-difluoroethanamine (0.427 g, 5.27 mmol) was added and the reaction mixture was heated at 100° C. in the microwave for three hours. The reaction mixture was diluted in dichloromethane, washed with saturated sodium bicarbonate, dried over magnesium sulfate, filtered, and concentrated. The resulting residue was purified by RP HPLC, eluting with acetonitrile:water with 0.1% ammonium hydroxide (5:95 to 100:0) to give ethyl 7-((2,2-difluoroethyl)amino)-1,8-naphthyridine-3-carboxylate (0.4796 g, 1.620 mmol, 92% yield). $^1$H NMR (400 MHz, CD$_3$SOCD$_3$) δ 1.35 (t, J=7 Hz, 3H), 3.84-3.98 (m, 2H), 4.36 (q, J=7 Hz, 2H), 6.24 (t, J=56 Hz, 1H), 7.00 (d, J=9 Hz, 1H), 8.14 (d, J=9 Hz, 1H), 8.18 (br s, 1H), 8.66 (s, 1H), 9.14 (s, 1H); LC-MS (LC-ES) M+H=282.

B. 7-((2,2-Difluoroethyl)amino)-1,8-naphthyridine-3-carboxylic acid lithium salt

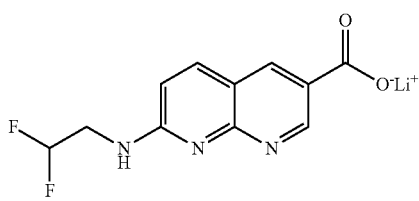

Lithium hydroxide (0.123 g, 5.12 mmol) was added to ethyl 7-((2,2-difluoroethyl)amino)-1,8-naphthyridine-3-carboxylate (0.4796 g, 1.705 mmol) in methanol (6.8 mL) and water (1.7 mL) at room temperature and the reaction mixture was stirred three hours at 60° C. The reaction mixture was concentrated to give 7-((2,2-difluoroethyl)amino)-1,8-naphthyridine-3-carboxylic acid lithium salt (0.4567 g, 1.668 mmol, 98% yield). $^1$H NMR (400 MHz, CD$_3$SOCD$_3$) δ 3.71 (t, J=16 Hz, 2H), 6.53 (t, J=57 Hz, 1H), 6.57 (d, J=9 Hz, 1H), 7.54 (d, J=7 Hz, 1H), 8.10 (s, 1H), 8.91 (s, 1H); LC-MS (LC-ES) M+H=254.

Intermediate 13

7-((2,2,2-Trifluoroethyl)amino)-1,8-naphthyridine-3-carboxylic acid lithium salt

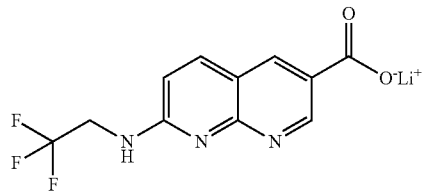

A. Ethyl 7-((2,2,2-trifluoroethyl)amino)-1,8-naphthyridine-3-carboxylate

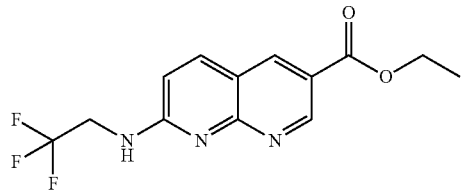 [SMILES: CCOC(=O)c1cnc2nc(NCC(F)(F)F)ccc2c1]

N,N-Diisopropylethylamine (1.199 mL, 6.88 mmol) was added to ethyl 7-chloro-1,8-naphthyridine-3-carboxylate (0.4071 g, 1.720 mmol, Intermediate 4C) in N-methyl-2-pyrrolidone (5.73 mL) at room temperature. Then 2,2,2-trifluoroethanamine (0.511 g, 5.16 mmol) was added and the reaction mixture was heated at 100° C. in the microwave for five hours. The reaction mixture was diluted in dichloromethane, washed with saturated sodium bicarbonate, dried over magnesium sulfate, filtered, and concentrated. The residue was purified by RP HPLC, eluting with acetonitrile:water with 0.1% ammonium hydroxide (5:95 to 100:0), then further purified by silica gel chromatography, eluting with ethyl acetate:hexanes (2:3 to 1:0) to give ethyl 7-((2,2,2-trifluoroethyl)amino)-1,8-naphthyridine-3-carboxylate (0.1719 g, 0.546 mmol, 31.7% yield). $^1$H NMR (400 MHz, CD$_3$SOCD$_3$) δ 1.36 (t, J=7 Hz, 3H), 4.36 (q, J=7 Hz, 2H), 4.36-4.46 (m, 2H), 7.04 (d, J=7 Hz, 1H), 8.20 (d, J=9 Hz, 1H), 8.34 (br s, 1H), 8.70 (s, 1H), 9.16 (s, 1H); LC-MS (LC-ES) M+H=300.

B. 7-((2,2,2-Trifluoroethyl)amino)-1,8-naphthyridine-3-carboxylic acid lithium salt

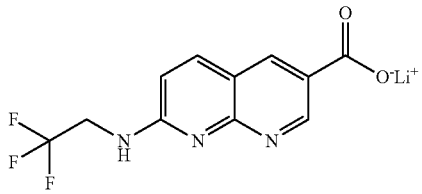

Lithium hydroxide (0.041 g, 1.723 mmol) was added to ethyl 7-((2,2,2-trifluoroethyl)amino)-1,8-naphthyridine-3-carboxylate (0.1719 g, 0.574 mmol) in methanol (2.3 mL) and water (0.57 mL) at room temperature and the reaction mixture was stirred sixteen hours at 60° C. The reaction mixture was concentrated to give 7-((2,2,2-trifluoroethyl)amino)-1,8-naphthyridine-3-carboxylic acid lithium salt (0.2390 g, 0.816 mmol, 142% yield). $^1$H NMR (400 MHz, CD$_3$SOCD$_3$) δ 4.35 (p, J=7 Hz, 2H), 6.90 (d, J=9 Hz, 1H), 7.83 (br s, 1H), 8.02 (d, J=9 Hz, 1H), 8.36 (s, 1H), 9.12 (s, 1H); LC-MS (LC-ES) M+H=272.

Intermediate 14

(S)-2-Methylazetidine hydrochloride

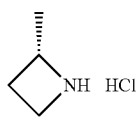

A. (R)-1-(tert-Butoxycarbonyl)azetidine-2-carboxylic acid

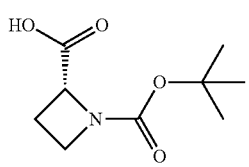

Di-tert-butyl dicarbonate (11.33 g, 51.9 mmol) in 1,4-dioxane (49.5 mL) was added to (R)-azetidine-2-carboxylic acid (5.00 g, 49.5 mmol) in 1,4-dioxane (49.5 mL) and water (49.5 mL) at 0° C. and the reaction mixture was stirred for two hours at room temperature. The reaction mixture was concentrated, diethyl ether added, 10% citric acid added, extracted with ethyl acetate, dried over magnesium sulfate, filtered, and concentrated to give (R)-1-(tert-butoxycarbonyl)azetidine-2-carboxylic acid (7.87 g, 37.2 mmol, 75% yield). $^1$H NMR (400 MHz, CD$_3$SOCD$_3$) δ 1.34 (s, 9H), 1.96-2.06 (m, 1H), 2.42-2.52 (m, 1H), 3.66-3.80 (m, 1H), 3.83 (q, J=8 Hz, 1H), 4.42 (dd, J=9, 5 Hz, 1H), 12.72 (br s, 1H); LC-MS (LC-ES) M−H=200.

B. (R)-tert-Butyl 2-(hydroxymethyl)azetidine-1-carboxylate

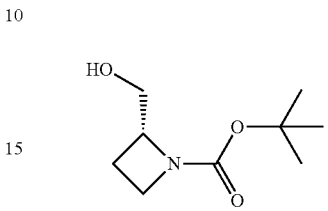

Trimethylsilyl chloride (13.52 mL, 156 mmol) was added slowly to 2.0 M lithium borohydride (39.1 mL, 78 mmol) in tetrahydrofuran at 0° C. and the reaction mixture was stirred for 30 minutes at room temperature. After cooling to 0° C., (R)-1-(tert-butoxycarbonyl)azetidine-2-carboxylic acid (7.87 g, 39.1 mmol) in tetrahydrofuran (78 mL) was added dropwise and the reaction was stirred for two hours at room temperature. The reaction mixture was quenched with methanol, followed by water, and then concentrated. The reaction mixture was extracted with ethyl acetate, washed with saturated sodium chloride, dried over magnesium sulfate, filtered, and concentrated. The resulting residue was purified by silica gel chromatography, eluting with ethyl acetate:hexanes (1:1) to give (R)-tert-butyl 2-(hydroxymethyl)azetidine-1-carboxylate (1.44 g, 7.31 mmol, 18.7% yield). $^1$H NMR (400 MHz, CD$_3$SOCD$_3$) δ 1.35 (s, 9H), 1.96-2.06 (m, 1H), 2.06-2.18 (m, 1H), 3.44-3.52 (m, 1H), 3.54-3.74 (m, 3H), 4.06-4.16 (m, 1H), 4.72 (t, J=6 Hz, 1H).

C. (R)-tert-Butyl 2-(((methylsulfonyl)oxy)methyl)azetidine-1-carboxylate

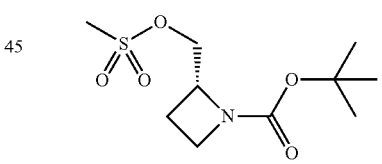

Triethylamine (1.286 mL, 9.23 mmol) was added to (R)-tert-butyl 2-(hydroxymethyl)azetidine-1-carboxylate (1.44 g, 7.69 mmol) in dichloromethane (15.4 mL) at 0° C., then methanesulfonyl chloride (0.595 mL, 7.69 mmol) was added dropwise and the reaction was stirred for sixteen hours at room temperature. The reaction mixture was treated with saturated sodium bicarbonate, extracted with dichloromethane, dried over magnesium sulfate, filtered, and concentrated. The resulting residue was purified by silica gel chromatography, eluting with ethyl acetate:hexanes (2:3) to give (R)-tert-butyl 2-(((methylsulfonyl)oxy)methyl)azetidine-1-carboxylate (1.95 g, 6.98 mmol, 91% yield). $^1$H NMR (400 MHz, CD$_3$SOCD$_3$) δ 1.37 (s, 9H), 2.00-2.10 (m, 1H), 2.20-2.32 (m, 1H), 3.20 (s, 3H), 3.60-3.76 (m, 2H), 4.22-4.30 (m, 1H), 4.36-4.44 (m, 2H); LC-MS (LC-ES) M−H=266.

D. (S)-tert-Butyl 2-methylazetidine-1-carboxylate

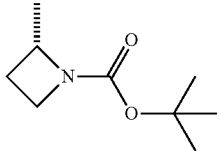

Lithium triethylborohydride (29.4 mL, 29.4 mmol) in tetrahydrofuran (1.0 M) was added to (R)-tert-butyl 2-(((methylsulfonyl)oxy)methyl)azetidine-1-carboxylate (1.95 g, 7.35 mmol) in tetrahydrofuran (7.35 mL) at 0° C. under nitrogen and the reaction mixture was stirred for three hours at room temperature, then the reaction mixture was quenched with water at 0° C., extracted with ethyl acetate, washed with 10% citric acid, washed with saturated sodium bicarbonate, dried over magnesium sulfate, filtered, and concentrated. The residue was purified by silica gel chromatography, eluting with ethyl acetate:hexanes (1:4) to give (S)-tert-butyl 2-methylazetidine-1-carboxylate (0.9826 g, 5.45 mmol, 74.2% yield). Care should be taken as the product is volatile. $^1$H NMR (400 MHz, CD$_3$SOCD$_3$) δ 1.27 (d, J=6 Hz, 3H), 1.35 (s, 9H), 1.66-1.80 (m, 1H), 2.18-2.34 (m, 1H), 3.64-3.80 (m, 2H), 4.14-4.26 (m, 1H).

E. (S)-2-Methylazetidine hydrochloride

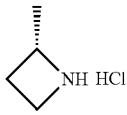

2.0 M Hydrochloric acid (11.48 mL, 22.95 mmol) in diethyl ether was added to (S)-tert-butyl 2-methylazetidine-1-carboxylate (0.9826 g, 5.74 mmol) at room temperature and the reaction mixture was stirred for sixteen hours. The reaction mixture was concentrated to give (S)-2-methylazetidine hydrochloride (0.6389 g, 2.67 mmol, 46.6% yield), contaminated with decomposition products. This product is low molecular weight and might be volatile and was carried forward without further purification. $^1$H NMR (400 MHz, CD$_3$SOCD$_3$) δ 1.41 (d, J=7 Hz, 3H), 2.04-2.16 (m, 1H), 2.36-2.48 (m, 1H), 3.71 (dt, J=10, 6 Hz, 1H), 3.81 (q, J=9 Hz, 1H), 4.41 (h, J=7 Hz, 1H), 8.70 (br s, 2H).

Alternative Method

A. (R)-Butane-1,3-diyldimethanesulfonate

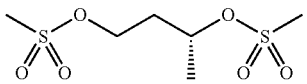

Triethylamine (23.20 mL, 166 mmol) was added to (R)-butane-1,3-diol (5.00 g, 55.5 mmol) in dichloromethane (111 mL) at 0° C., then methanesulfonyl chloride (10.31 mL, 133 mmol) was added dropwise and the reaction mixture was stirred for five hours at room temperature. The reaction mixture was treated with saturated ammonium chloride, extracted with dichloromethane, washed with saturated sodium chloride, dried over magnesium sulfate, filtered, and concentrated. The resulting residue was purified by silica gel chromatography, eluting with ethyl acetate:hexanes (2:3 to 1:0) to give (R)-butane-1,3-diyldimethanesulfonate. $^1$H NMR (400 MHz, CD$_3$SOCD$_3$) δ 1.38 (d, J=6 Hz, 3H), 2.03 (q, J=6 Hz, 2H), 3.18 (s, 6H), 4.27 (t, J=7 Hz, 2H), 4.81 (h, J=7 Hz, 1H); LC-MS (LC-ES) M-CH$_3$SO$_3$=151.

B. (S)-1-Benzyl-2-methylazetidine

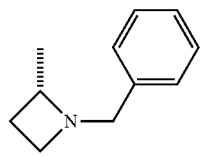

(R)-Butane-1,3-diyldimethanesulfonate (12.8 g, 52.0 mmol) was added to benzylamine (34.1 mL, 312 mmol) under nitrogen and the reaction mixture was stirred for sixteen hours at 50° C., after cooling, hexanes:methyl tert-butyl ether (1:1) was added to the reaction mixture. The resulting precipitate was removed by filtration and the organics were concentrated. The residue was purified by silica gel chromatography, eluting with methanol:ethyl acetate with 1% ammonium hydroxide (0:1 to 1:9) to give (S)-1-benzyl-2-methylazetidine (3.52 g, 20.74 mmol, 39.9% yield). $^1$H NMR (400 MHz, CD$_3$SOCD$_3$) δ 0.98 (d, J=6 Hz, 3H), 1.64 (p, J=9 Hz, 1H), 1.99 (q, J=9 Hz, 1H), 2.69 (q, J=8 Hz, 1H), 3.08-3.22 (m, 2H), 3.50 (ABq, J$_{AB}$=13 Hz, Δv$_{AB}$=9 Hz, 2H), 7.16-7.32 (m, 5H); LC-MS (LC-ES) M–H=162.

C. (2S)-1-Benzyl-2-methylazetidin-1-ium (7,7-dimethyl-2-oxobicyclo[2.2.1]heptan-1-yl)methanesulfonate

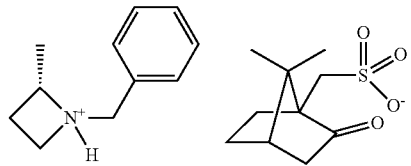

(S)-1-Benzyl-2-methylazetidine (3.52 g, 21.83 mmol) in ethanol (18.19 mL) was added to (1R)-10-camphorsulfonic acid (5.07 g, 21.83 mmol) in ethanol (18.19 mL) and the reaction mixture was stirred for sixteen hours at room temperature, and then concentrated. The residue was suspended in methyl tert-butyl ether (84 mL) and the solid was collected by filtration. The solid was dissolved in dichloromethane (7 mL) and ethyl acetate (11 mL) was added and stirred for 30 minutes, then filtered and dried to give (2S)-1-benzyl-2-methylazetidin-1-ium (7,7-dimethyl-2-oxobicyclo[2.2.1]heptan-1-yl)methanesulfonate (6.50 g, 15.69 mmol, 71.9% yield). $^1$H NMR (400 MHz, CD$_3$SOCD$_3$) δ 0.73 (s, 3H), 1.05 (s, 3H), 1.20 (d, J=6 Hz, 3H), 1.20-1.32 (m, 2H), 1.78 (d, J=18 Hz, 1H), 1.60-1.88 (m, 1H), 1.88-1.94 (m, 1H), 2.02-2.14 (m, 1H), 2.18-2.28 (m, 1H), 2.362.46 (m, 1H), 2.60 (ABq, J$_{AB}$=15 Hz, Δv$_{AB}$=200 Hz, 2H), 2.62-2.76 (m, 1H), 3.72-3.86 (m, 1H), 3.90-4.06

(m, 1H), 4.28-4.42 (m, 2H), 4.44-4.56 (m, 1H), 7.38-7.50 (m, 5H), 9.70 (br s, 1H); LC-MS (LC-ES) M−H=162.

D. (S)-2-Methylazetidin-1-ium (7,7-dimethyl-2-oxobicyclo[2.2.1]heptan-1-yl)methanesulfonate

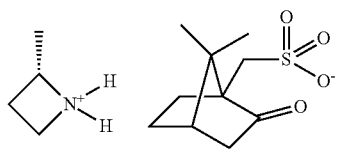

Palladium hydroxide on carbon (1.160 g, 1.652 mmol) was added to (2S)-1-benzyl-2-methylazetidin-1-ium (7,7-dimethyl-2-oxobicyclo[2.2.1]heptan-1-yl)methanesulfonate (6.50 g, 16.52 mmol) in methanol (55 mL) and tetrahydrofuran (55 mL) at 25° C. under nitrogen atmosphere. Then, the reaction vessel was fitted with a hydrogen balloon and the vessel was repeatedly evacuated and purged with hydrogen, then stirred for six days at 60° C. Then, the vessel was repeatedly evacuated and purged with nitrogen, filtered through Celite®, and concentrated to give (S)-2-methylazetidin-1-ium (7,7-dimethyl-2-oxobicyclo[2.2.1]heptan-1-yl)methanesulfonate (5.01 g, 15.69 mmol, 95% yield). $^1$H NMR (400 MHz, CD$_3$SOCD$_3$) δ 0.86 (s, 3H), 1.13 (s, 3H), 1.36-1.46 (m, 1H), 1.54 (d, J=7 Hz, 3H), 1.56-1.66 (m, 1H), 1.89 (d, J=18 Hz, 1H), 1.98-2.10 (m, 2H), 2.22-2.38 (m, 2H), 2.56-2.74 (m, 2H), 2.77 (d, J=15 Hz, 1H), 3.31 (d, J=15 Hz, 1H), 3.84-3.94 (m, 1H), 4.02 (q, J=10 Hz, 1H), 4.59 (h, J=8 Hz, 1H); LC-MS (LC-ES) 2M+H=143.

Intermediate 15

Lithium (S)-7-(2-methylazetidin-1-yl)-1,6-naphthyridine-3-carboxylate

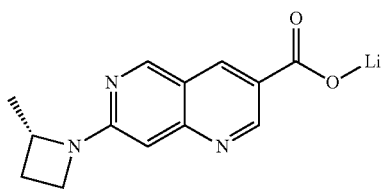

A. (S)-Ethyl 7-(2-methylazetidin-1-yl)-1,6-naphthyridine-3-carboxylate

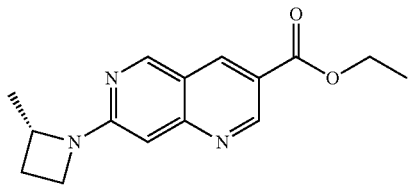 [SMILES: CCOC(=O)c1cnc2cc(N3CC[C@@H]3C)ncc2c1]

N,N-Diisopropylethylamine (1.196 mL, 6.86 mmol) was added to ethyl 7-chloro-1,6-naphthyridine-3-carboxylate (0.4061 g, 1.716 mmol, Intermediate 1F) in N-methyl-2-pyrrolidone (5.72 mL) at room temperature. Then (S)-2-methylazetidin-1-ium (7,7-dimethyl-2-oxobicyclo[2.2.1]heptan-1-yl)methanesulfonate (1.041 g, 3.43 mmol, Intermediate 14D alternative method) was added and the reaction mixture was heated at 100° C. in the microwave for six hours. The reaction mixture was diluted in dichloromethane, washed with saturated sodium bicarbonate, dried over magnesium sulfate, filtered, and concentrated. The resulting residue was purified by RP HPLC, eluting with acetonitrile:water with 0.1% ammonium hydroxide (5:95 to 100:0), then further purified by silica gel chromatography, eluting with ethyl acetate:hexanes (1:4 to 3:2) to give (S)-ethyl 7-(2-methylazetidin-1-yl)-1,6-naphthyridine-3-carboxylate (0.2439 g, 0.854 mmol, 49.8% yield). $^1$H NMR (400 MHz, CD$_3$SOCD$_3$) δ 1.35 (t, J=7 Hz, 3H), 1.51 (d, J=6 Hz, 3H), 2.04 (p, J=8 Hz, 1H), 2.50 (p, J=8 Hz, 1H), 3.90 (q, J=8 Hz, 1H), 4.07 (q, J=5 Hz, 1H), 4.36 (q, J=7 Hz, 2H), 4.48 (h, J=7 Hz, 1H), 6.54 (s, 1H), 8.83 (s, 1H), 9.15 (s, 1H), 9.18 (s, 1H); LC-MS (LC-ES) M+H=272.

B. Lithium (S)-7-(2-methylazetidin-1-yl)-1,6-naphthyridine-3-carboxylate

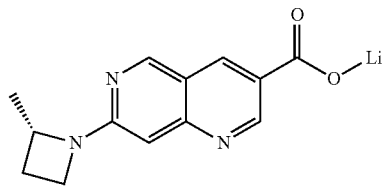

Lithium hydroxide (0.065 g, 2.70 mmol) was added to (S)-ethyl 7-(2-methylazetidin-1-yl)-1,6-naphthyridine-3-carboxylate (0.2439 g, 0.899 mmol) in methanol (3.60 mL) and water (0.89 mL) at room temperature and the reaction mixture was stirred three hours at 60° C. The reaction mixture was concentrated to give lithium (S)-7-(2-methylazetidin-1-yl)-1,6-naphthyridine-3-carboxylate (0.2308 g, 0.880 mmol, 98% yield). $^1$H NMR (400 MHz, CD$_3$SOCD$_3$) δ 1.50 (d, J=6 Hz, 3H), 2.03 (p, J=9 Hz, 1H), 2.36-2.48 (m, 1H), 3.80 (q, J=8 Hz, 1H), 3.99 (q, J=8 Hz, 1H), 4.36 (h, J=7 Hz, 1H), 6.52 (s, 1H), 8.52 (s, 1H), 8.97 (s, 1H), 9.26 (s, 1H); LC-MS (LC-ES) M+H=244.

Intermediate 16

1-(4-Aminopiperidin-1-yl)-2-hydroxy-2-methylpropan-1-one

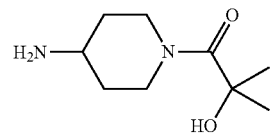

A. Benzyl (1-(2-hydroxy-2-methylpropanoyl)piperidin-4-yl)carbamate

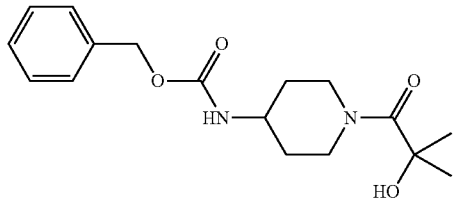 [SMILES: CC(C)(O)C(=O)N1CCC(NC(=O)OCc2ccccc2)CC1]

Benzyl piperidin-4-ylcarbamate (0.512 g, 2.183 mmol) was added to 2-hydroxy-2-methylpropanoic acid (0.2273 g, 2.183 mmol) in 1,4-dioxane (10.9 mL) at room temperature. Then, N,N-diisopropylethylamine (1.144 mL, 6.55 mmol) was added and the reaction mixture was stirred for five minutes. Then, 1-[bis(dimethylamino)methylene]-1H-1,2,3-triazolo[4,5-b]pyridinium 3-oxide hexafluorophosphate (0.830 g, 2.183 mmol) was added and the reaction mixture was stirred for sixteen hours. The reaction mixture was poured into saturated sodium bicarbonate, extracted with ethyl acetate (3×), dried over magnesium sulfate, filtered, and concentrated. The reaction mixture was purified by silica gel chromatography, eluting with ethyl acetate:hexanes (1:1 to 0:1) to give benzyl (1-(2-hydroxy-2-methylpropanoyl)piperidin-4-yl)carbamate (0.3151 g, 0.934 mmol, 42.8% yield). $^1$H NMR (400 MHz, CD$_3$SOCD$_3$) δ 1.28 (s, 6H), 1.28-1.36 (m, 2H), 1.74 (d, J=12 Hz, 2H), 2.60-3.24 (m, 2H), 3.48-3.62 (m, 1H), 4.10-4.70 (m, 2H), 5.00 (s, 2H), 5.33 (s, 1H), 7.26-7.40 (m, 6H); LC-MS (LC-ES) M+H=321.

B. 1-(4-Aminopiperidin-1-yl)-2-hydroxy-2-methylpropan-1-one

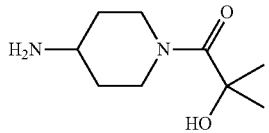

Palladium on carbon (0.105 g, 0.098 mmol) was added to benzyl (1-(2-hydroxy-2-methylpropanoyl)piperidin-4-yl) carbamate (0.3151 g, 0.984 mmol) in methanol (3.3 mL) at 25° C. under nitrogen atmosphere. Then, the reaction vessel was fitted with a hydrogen balloon and the vessel was repeatedly evacuated and purged with hydrogen, then stirred for sixteen hours. Then, the vessel was repeatedly evacuated and purged with nitrogen, filtered through Celite®, and concentrated to give 1-(4-aminopiperidin-1-yl)-2-hydroxy-2-methylpropan-1-one (0.1752 g, 0.894 mmol, 91% yield). $^1$H NMR (400 MHz, CD$_3$SOCD$_3$) δ 1.00-1.18 (m, 2H), 1.29 (s, 6H), 1.54 (br s, 2H), 1.67 (d, J=12 Hz, 2H), 2.76 (p, J=5 Hz, 1H), 2.54-3.18 (m, 2H), 4.02-4.72 (m, 2H), 5.28 (s, 1H); LC-MS (LC-ES) M+H=187.

Intermediate 17

2-(3-Aminocyclobutyl)propan-2-ol

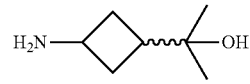

A. 3-(2-Hydroxypropan-2-yl)cyclobutanol

To a diethyl ether solution (30 mL) containing methyl magnesium bromide (7.63 mL of a 3.0 M diethyl ether solution) was added a diethyl ether solution (5 mL) containing ethyl 3-hydroxycyclobutane carboxylate (2.05 g, 6.94 mmol), dropwise. After two hours, the reaction was carefully quenched with 3 M aqueous hydrochloric acid. Magnesium sulfate was added until the evolution of gas stopped. The solution was filtered, and the solvent removed in vacuo yielding a viscous oil which was purified by silica gel chromatography, eluting with ethyl acetate:hexanes (1:1 to 1:0) to give 3-(2-hydroxypropan-2-yl)cyclobutanol (419 mg, 3.22 mmol, 46%). $^1$H NMR (CDCl$_3$) δ 1.13 (s, 6H), 1.74-1.86 (m, 4H), 2.23-2.39 (m, 2H), 2.66 (br s, 1H), 4.03-4.09 (m, 1H).

B. 3-(2-Hydroxypropan-2-yl)cyclobutyl 4-methylbenzenesulfonate

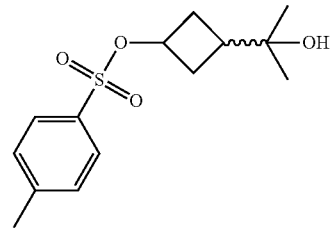 [SMILES: Cc1ccc(S(=O)(=O)OC2CC(C(C)(C)O)C2)cc1]

To a pyridine solution (15 mL) containing 3-(2-hydroxypropan-2-yl)cyclobutanol (415 mg, 3.19 mmol) cooled to 0° C. was added p-toluenesulfonyl chloride (638 mg, 3.35 mmol). The reaction was slowly allowed to warm to room temperature overnight, and the organics were taken up in diethyl ether. The solution was washed with water, saturated sodium bicarbonate and saturated sodium bisulfate, followed by drying over magnesium sulfate. After filtration, the solvent was removed in vacuo yielding 3-(2-hydroxypropan-2-yl)cyclobutyl 4-methylbenzenesulfonate (792 mg, 2.79 mmol, 87% yield) as a viscous oil, which was taken on crude. $^1$H NMR (CDCl$_3$) δ 1.08 (s, 6H), 1.71-1.88 (m, 1H), 1.98-2.11 (m, 2H), 2.12-2.23 (m, 2H), 2.45 (s, 3H), 4.65 (quin, J=8 Hz, 1H), 7.33 (d, J=8 Hz, 2H), 7.78 (d, J=8 Hz, 2H).

C. 2-(3-Azidocyclobutyl)propan-2-ol

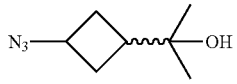

A DMF solution (40 mL) of 3-(2-hydroxypropan-2-yl)cyclobutyl 4-methylbenzenesulfonate (2.50 g, 8.79 mmol) and sodium azide (686 mg, 10.6 mmol) was heated to 90° C. overnight. Upon cooling, the organics were taken up in diethyl ether and washed with water (2×) and saturated sodium bicarbonate followed by drying over magnesium sulfate. After filtration, the solvent was carefully removed in vacuo yielding 2-(3-azidocyclobutyl)propan-2-ol (1.19 g, 7.67 mmol, 87% yield) as an oil which was taken on crude. $^1$H NMR (CDCl$_3$) δ 1.14 (s, 6H), 2.03-2.16 (m, 2H), 2.26-2.34 (m, 2H), 2.35-2.44 (m, 1H), 3.87-4.01 (m, 1H).

D. 2-(3-Aminocyclobutyl)propan-2-ol

To an ethanol solution (25 mL) containing 10% palladium on carbon (809 mg, wet Degussa) was added an ethanol solution (5 mL) of 2-(3-azidocyclobutyl)propan-2-ol (1.18 g, 7.60 mmol). The flask was then evacuated under vacuum and refilled with hydrogen via a balloon. This process was repeated twice more and then the reaction was stirred under 1 atmosphere of hydrogen overnight. The catalyst was removed under vacuum filtration through a plug of Celite®. The Celite® was rinsed with dichloromethane and the solvent removed in vacuo yielding 2-(3-aminocyclobutyl)propan-2-ol (920 mg, 5.55 mmol, 73% yield) as an oil. $^1$H NMR (CDCl$_3$) δ 1.12 (s, 6H), 1.66-1.77 (m, 2H), 2.16-2.28 (m, 2H), 2.27-2.42 (m, 1H), 3.40-3.52 (m, 1H).

Intermediate 18

6-Chloro-7-cyclopropyl-1,8-naphthyridine-3-carboxylic acid

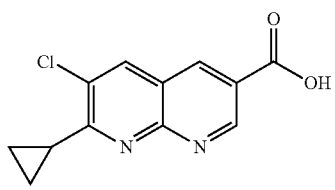 [SMILES: O=C(O)c1cnc2nc(C3CC3)c(Cl)cc2c1]

A. 6-Bromo-3-chloro-1,8-naphthyridin-2-amine

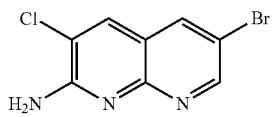

Hydrogen peroxide (51.6 mL, 505 mmol, 30 wt % in water) was added to a solution of 6-bromo-1,8-naphthyridin-2-amine (15 g, 63.1 mmol, Intermediate 4A) in concentrated hydrochloric acid (60 mL) at 27° C. in a sealed tube. The resultant reaction mixture was stirred for 30 h at 27° C. On completion, the reaction mixture was neutralized with 50% sodium hydroxide solution (100 mL) to pH=8. The precipitated solid compound was filtered and dried under vacuum to give impure material, which was purified via neutral alumina column chromatography, eluting with methanol:dichloromethane (1:99) to afford 6-bromo-3-chloro-1,8-naphthyridin-2-amine (6.5 g, 15.7 mmol, 24.9% yield) as an off-white solid. $^1$H NMR (400 MHz, CD$_3$SOCD$_3$) δ 7.31 (br s, 2H), 8.22-8.24 (m, 1H), 8.37 (d, J=3 Hz, 1H), 8.76 (d, J=3 Hz, 1H); LC-MS (LC-ES) M+H=258.

B. Ethyl 7-amino-6-chloro-1,8-naphthyridine-3-carboxylate

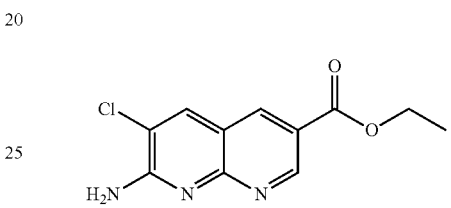

[1,1'-Bis(diphenylphosphino)ferrocene]dichloropalladium(II) dichloromethane adduct (1.283 g, 1.571 mmol) and triethylamine (4.38 mL, 31.4 mmol) were added to a solution of 6-bromo-3-chloro-1,8-naphthyridin-2-amine (6.5 g, 15.71 mmol) in ethanol (100 mL) in a steel bomb at 27° C. The reaction mixture was stirred at 100° C. under a carbon monoxide atmosphere (80 psi) for two hours. On completion, the reaction mixture was filtered through Celite® and the filtrate was concentrated under reduced pressure to give impure material. This material was purified via neutral alumina column chromatography, eluting with methanol:dichloromethane (1:19) to afford ethyl 7-amino-6-chloro-1,8-naphthyridine-3-carboxylate (2 g, 7.22 mmol, 45.9% yield) as an off-white solid. $^1$H NMR (400 MHz, CD$_3$SOCD$_3$) δ 1.35 (t, J=7 Hz, 3H), 4.37 (q, J=7 Hz, 2H), 7.60 (br s, 2H), 8.45 (s, 1H), 8.68 (d, J=2 Hz, 1H), 9.17 (d, J=2 Hz, 1H); LC-MS (LC-ES) M+H=252.

C. Ethyl 6-chloro-7-hydroxy-1,8-naphthyridine-3-carboxylate

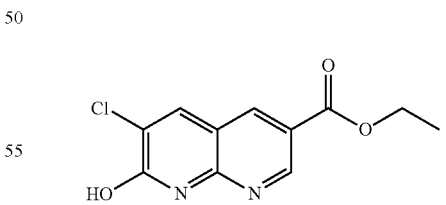

Aqueous sulfuric acid (~12 mL in 200 mL water) (200 mL, 400 mmol) was added dropwise to ethyl 7-amino-6-chloro-1,8-naphthyridine-3-carboxylate (4 g, 15.89 mmol) at 0° C., followed by the addition of 2M sodium nitrite in water (15.9 mL, 31.8 mmol) dropwise at 0° C. The resultant reaction mixture was allowed to warm to 27° C. and stirred for sixteen hours. On completion, the reaction mixture was filtered and dried under vacuum to give an impure material. This material was washed with diethyl ether (50 mL) and dried under vacuum to afford ethyl 6-chloro-7-hydroxy-1,8-naphthyridine-3-carboxylate (3.8 g, 10.17 mmol, 64% yield) as an off white solid. ¹H NMR (400 MHz, CD₃SOCD₃) δ 1.35 (t, J=7 Hz, 3H), 4.37 (q, J=7 Hz, 2H), 8.49 (s, 1H), 8.68 (d, J=2 Hz, 1H), 9.02 (d, J=2 Hz, 1H), 13.07 (br s, 1H); LC-MS (LC-ES) M+H=253.

D. Ethyl 6,7-dichloro-1,8-naphthyridine-3-carboxylate

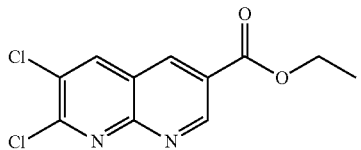 [SMILES: CCOC(=O)c1cnc2nc(Cl)c(Cl)cc2c1]

Phosphorous oxychloride (6.0 mL, 64.3 mmol) was added dropwise to a solution of ethyl 6-chloro-7-hydroxy-1,8-naphthyridine-3-carboxylate (5.6 g, 16.07 mmol) and N,N-diisopropylethylamine (5.61 mL, 32.1 mmol) in 1,4-dioxane (50 mL) at 0° C. The resulting reaction mixture was heated to 80° C. and stirred for five hours. On completion, the reaction mixture was quenched with ice water (250 mL) and extracted with ethyl acetate (300 mL, 2X). The combined organic layers were washed with brine (250 mL) and evaporated under reduced pressure to give an impure material, which was purified by neutral alumina column chromatography, eluting with ethyl acetate:petroleum ether (3:2) to afford ethyl 6,7-dichloro-1,8-naphthyridine-3-carboxylate (2.39 g, 8.37 mmol, 52.1% yield) as an off-white solid. ¹H NMR (400 MHz, CDCl₃) δ 1.47 (t, J=7 Hz, 3H), 4.51 (q, J=7 Hz, 2H), 8.38 (s, 1H), 8.82 (d, J=2 Hz, 1H), 9.64 (d, J=2 Hz, 1H); LC-MS (LC-ES) M+H=271.

E. Ethyl 6-chloro-7-cyclopropyl-1,8-naphthyridine-3-carboxylate

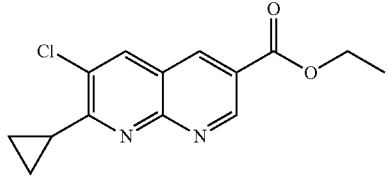 [SMILES: CCOC(=O)c1cnc2nc(C3CC3)c(Cl)cc2c1]

Potassium cyclopropyltrifluoroborate (0.157 g, 1.061 mmol) was added to ethyl 6,7-dichloro-1,8-naphthyridine-3-carboxylate (0.273 g, 1.007 mmol) at room temperature. Then cesium carbonate (0.988 g, 3.03 mmol) was added, followed by the addition of [1,1'-bis(diphenylphosphino)ferrocene]dichloropalladium (II)-dichloromethane adduct (0.083 g, 0.102 mmol). Then, toluene (20 mL) and water (2 mL) were added and nitrogen was bubbled through the reaction mixture for 5 minutes. Then, the reaction mixture was heated at 100° C. for five hours. The organics were decanted from the aqueous layer and the aqueous washed with dichloromethane. The combined organics were concentrated and the residue was purified by silica gel chromatography, eluting with (3:1 ethyl acetate:ethanol):hexanes (0:1 to 1:6) to give ethyl 6-chloro-7-cyclopropyl-1,8-naphthyridine-3-carboxylate (0.143 g, 0.543 mmol, 51% yield) as a lavender-gray solid. ¹H NMR (400 MHz, CD₃SOCD₃) δ 1.22-1.28 (m, 4H), 1.37 (t, J=7 Hz, 3H), 2.74 (p, J=6 Hz, 1H), 4.40 (q, J=7 Hz, 2H), 8.80 (s, 1H), 8.99 (d, J=2 Hz, 1H), 9.37 (d, J=2 Hz, 1H); LC-MS (LC-ES) M+H=277.

F. 6-Chloro-7-cyclopropyl-1,8-naphthyridine-3-carboxylic acid

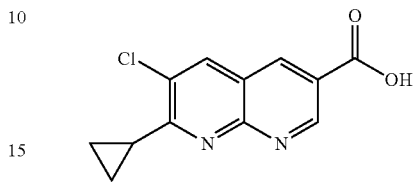

1N Sodium hydroxide (3.2 mL, 3.20 mmol) was added to a solution of ethyl 6-chloro-7-cyclopropyl-1,8-naphthyridine-3-carboxylate (0.448 g, 1.619 mmol, from three batches) in methanol (10 mL) and the reaction mixture was stirred for sixty-four hours. Upon consumption of the starting material, the reaction was quenched with 1N hydrochloric acid (3.2 mL), the solids were collected by filtration, washed with water (3×), air dried, and then dried under vacuum overnight to give 6-chloro-7-cyclopropyl-1,8-naphthyridine-3-carboxylic acid (0.382 g, 1.536 mmol, 95% yield) as a tan powder. ¹H NMR (400 MHz, CD₃SOCD₃) δ 1.20-1.28 (m, 4H), 2.74 (p, J=6 Hz, 1H), 8.78 (s, 1H), 8.96 (d, J=2 Hz, 1H), 9.36 (d, J=2 Hz, 1H), 13.67 (br s, 1H); LC-MS (LC-ES) M+H=249.

Intermediate 19

Lithium 7-(azetidin-1-yl)-6-chloro-1,8-naphthyridine-3-carboxylate

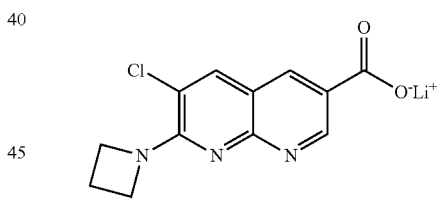

A. Ethyl 7-(azetidin-1-yl)-6-chloro-1,8-naphthyridine-3-carboxylate

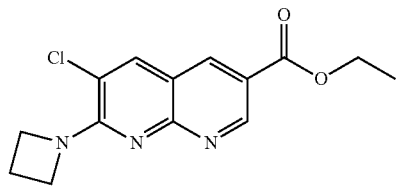

N,N-Diisopropylethylamine (0.264 mL, 1.515 mmol) was added to ethyl 6,7-dichloro-1,8-naphthyridine-3-carboxylate (0.1027 g, 0.379 mmol, Intermediate 18D) in N-methyl-2-pyrrolidone (1.263 mL) at room temperature. Then, azetidine hydrochloride (0.071 g, 0.758 mmol) was added and the reaction mixture was heated at 100° C. in the microwave for one hour. The reaction mixture was diluted in dichloromethane, washed with saturated sodium bicarbonate, dried over magnesium sulfate, filtered, and concentrated. The residue was purified by RP HPLC, eluting with acetonitrile:water with 0.1% ammonium hydroxide (5:95 to 100:0), then further purified by silica gel chromatography, eluting with ethyl acetate:hexanes (1:4 to 4:1) to give ethyl 7-(azetidin-1-yl)-6-chloro-1,8-naphthyridine-3-carboxylate (0.0783 g, 0.255 mmol, 67.3% yield). $^1$H NMR (400 MHz, CD$_3$SOCD$_3$) δ 1.34 (t, J=7 Hz, 3H), 2.33 (p, J=8 Hz, 2H), 4.35 (q, J=7 Hz, 2H), 4.38-4.54 (m, 4H), 8.40 (s, 1H), 8.68 (d, J=2 Hz, 1H), 9.15 (d, J=2 Hz, 1H); LC-MS (LC-ES) M+H=292.

B. Lithium 7-(azetidin-1-yl)-6-chloro-1,8-naphthyridine-3-carboxylate

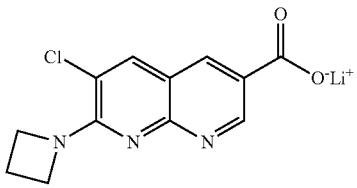

Lithium hydroxide (0.019 g, 0.805 mmol) was added to ethyl 7-(azetidin-1-yl)-6-chloro-1,8-naphthyridine-3-carboxylate (0.0783 g, 0.268 mmol) in methanol (1.1 mL) and water (0.27 mL) at room temperature and the reaction mixture was stirred three hours at 60° C. The reaction mixture was concentrated to give lithium 7-(azetidin-1-yl)-6-chloro-1,8-naphthyridine-3-carboxylate (0.0653 g, 0.230 mmol, 86% yield). $^1$H NMR (400 MHz, CD$_3$SOCD$_3$) δ 2.30 (p, J=8 Hz, 2H), 4.34 (t, J=8 Hz, 4H), 8.27 (s, 1H), 8.40 (d, J=2 Hz, 1H), 9.17 (d, J=2 Hz, 1H); LC-MS (LC-ES) M+H=264.

Intermediate 20

(3S,4R)-3-Amino-4-methylpyrrolidin-2-one

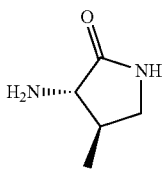

A. (S)-2-(1,3-dioxoisoindolin-2-yl)-3-methylbutanoyl chloride

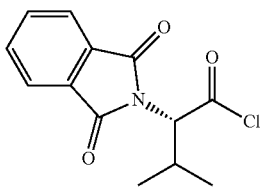 [SMILES: CC(C)[C@@H](C(=O)Cl)N1C(=O)c2ccccc2C1=O]

Thionyl chloride (3.12 mL, 42.8 mmol) was added to (S)-2-(1,3-dioxoisoindolin-2-yl)-3-methylbutanoic acid (10.57 g, 42.8 mmol) in tetrahydrofuran (214 mL) at room temperature and the reaction mixture was stirred for sixteen hours, then concentrated to give crude (S)-2-(1,3-dioxoisoindolin-2-yl)-3-methylbutanoyl chloride (11.36 g, 40.6 mmol, 95% yield), which was carried forward into the next reaction.

B. (S)-2-(1,3-Dioxoisoindolin-2-yl)-N-(5-methoxyquinolin-8-yl)-3-methylbutanamide

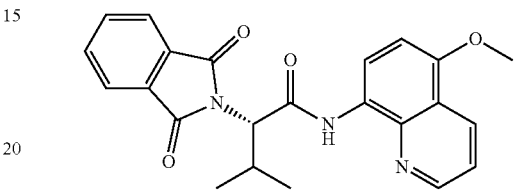

5-Methoxyquinolin-8-amine hydrochloride (5.57 g, 32.0 mmol) was added to (S)-2-(1,3-dioxoisoindolin-2-yl)-3-methylbutanoyl chloride (8.50 g, 32.0 mmol) in dichloromethane (160 mL) at room temperature. Then, 2,6-lutidine (7.45 mL, 64.0 mmol) was added and the reaction mixture was stirred for sixteen hours, then water was added and the reaction mixture was extracted with dichloromethane, washed with saturated sodium chloride, dried over magnesium sulfate, filtered, and concentrated. The reaction mixture was purified by silica gel chromatography, eluting with ethyl acetate:hexanes (3:7), then further purified by RP HPLC eluting with acetonitrile:water with 0.1% ammonium hydroxide (20:80 to 100:0) to give (S)-2-(1,3-dioxoisoindolin-2-yl)-N-(5-methoxyquinolin-8-yl)-3-methylbutanamide (9.47 g, 22.30 mmol, 69.7% yield). $^1$H NMR (400 MHz, CD$_3$SOCD$_3$) δ 0.90 (d, J=7 Hz, 3H), 1.11 (d, J=7 Hz, 3H), 2.92-3.06 (m, 1H), 3.95 (s, 3H), 4.72 (d, J=10 Hz, 1H), 7.03 (d, J=9 Hz, 1H), 7.59 (dd, J=8, 4 Hz, 1H), 7.84-7.96 (m, 4H), 8.40 (d, J=9 Hz, 1H), 8.54 (d, J=8 Hz, 1H), 8.86 (d, J=4 Hz, 1H), 10.20 (s, 1H); LC-MS (LC-ES) M+H=404.

C. 2-((3S,4R)-4-Methyl-2-oxopyrrolidin-3-yl)isoindoline-1,3-dione

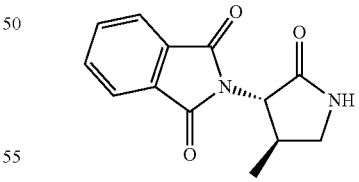

Iodobenzene diacetate (18.90 g, 58.7 mmol) was added to (S)-2-(1,3-dioxoisoindolin-2-yl)-N-(5-methoxyquinolin-8-yl)-3-methylbutanamide (9.47 g, 23.47 mmol) in toluene (235 mL) at room temperature and the reaction mixture was purged with nitrogen. Then, palladium(II) acetate (0.264 g, 1.174 mmol) was added and the reaction mixture was heated to 110° C. and stirred for five hours. The reaction mixture was cooled and concentrated. The resulting residue was purified by silica gel chromatography, eluting with acetone:hexanes (2:3) to give 8-((3S,4R)-3-(1,3-dioxoisoindolin-2- yl)-4-methyl-2-oxopyrrolidin-1-yl)-5-methoxyquinolin-7-yl acetate with 2-((3S,4R)-1-(5-methoxyquinolin-8-yl)-4-methyl-2-oxopyrrolidin-3-yl)isoindoline-1,3-dione (5.96 g, 6.92 mmol, 29.5% yield), which was carried forward to the next reaction. Ceric ammonium nitrate (22.77 g, 41.5 mmol) was added to 8-((3S,4R)-3-(1,3-dioxoisoindolin-2-yl)-4-methyl-2-oxopyrrolidin-1-yl)-5-methoxyquinolin-7-yl acetate with 2-((3S,4R)-1-(5-methoxyquinolin-8-yl)-4-methyl-2-oxopyrrolidin-3-yl)isoindoline-1,3-dione (5.96 g, 6.92 mmol) in acetonitrile (58 mL) and water (12 mL) at room temperature and the reaction mixture was stirred for sixteen hours. The reaction mixture was extracted with ethyl acetate, washed with saturated sodium chloride, dried over magnesium sulfate, filtered, and concentrated. The residue was purified by RP HPLC eluting with acetonitrile:water with 0.1% ammonium hydroxide (5:95 to 100:0) to give 2-((3S,4R)-4-methyl-2-oxopyrrolidin-3-yl)isoindoline-1,3-dione (0.6383 g, 2.483 mmol, 35.9% yield). $^1$H NMR (400 MHz, CD$_3$SOCD$_3$) δ 1.07 (d, J=7 Hz, 3H), 2.76-2.90 (m, 1H), 2.94 (t, J=9 Hz, 1H), 3.43 (t, J=9 Hz, 1H), 4.42 (d, J=9 Hz, 1H), 7.84-7.94 (m, 4H), 8.02 (br s, 1H); LC-MS (LC-ES) M+H=245.

D. (3S,4R)-3-Amino-4-methylpyrrolidin-2-one

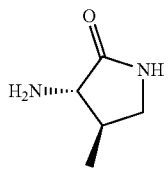

Hydrazine (0.116 mL, 3.69 mmol) was added to 2-((3S,4R)-4-methyl-2-oxopyrrolidin-3-yl)isoindoline-1,3-dione (0.3001 g, 1.229 mmol) in ethanol (12.3 mL) at room temperature and the reaction mixture was stirred for sixteen hours at reflux. The reaction mixture was concentrated. The resulting residue was purified by silica gel chromatography, eluting with methanol:dichloromethane (1:9 to 1:4) with 1% ammonium hydroxide to give (3S,4R)-3-amino-4-methylpyrrolidin-2-one (0.1240 g, 1.032 mmol, 84% yield). $^1$H NMR (400 MHz, CD$_3$SOCD$_3$) δ 1.06 (d, J=7 Hz, 3H), 1.66 (br s, 2H), 1.82-1.96 (m, 1H), 2.68 (t, J=9 Hz, 1H), 2.75 (d, J=10 Hz, 1H), 3.19 (dt, J=9, 2 Hz, 1H), 7.54 (br s, 1H); LC-MS (LC-ES) M+H=115.

Intermediate 21

(1r,4r)-4-Amino-1-methylcyclohexanol

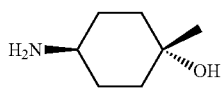

A. Benzyl ((1r,4r)-4-hydroxy-4-methylcyclohexyl)carbamate

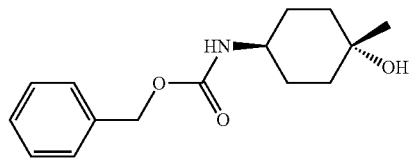 [SMILES: C[C@]1(O)CC[C@H](NC(=O)OCc2ccccc2)CC1]

Cerium(III) chloride heptahydrate (3.12 g, 8.39 mmol) was dried at 140° C. under high vacuum for 60 minutes, and then was cooled to room temperature while remaining under vacuum overnight. The solid was placed under a nitrogen atmosphere and tetrahydrofuran (16 mL) was added. The slurry was stirred for 90 minutes, and then cooled to −78° C. A 1.6 M solution of methyllithium in diethyl ether (5.10 mL, 8.16 mmol) was added. After 60 minutes, benzyl (4-oxocyclohexyl)carbamate (1.00 g, 4.05 mmol) in tetrahydrofuran (5 mL) was added. After 2 hours, the mixture was poured into saturated aqueous ammonium chloride (50 mL) and water (50 mL). The resulting mixture was extracted with ethyl acetate (3×20 mL), and the combined organics were dried over magnesium sulfate and concentrated. The residue was purified by silica gel chromatography, eluting with a 40%-70% ethyl acetate-heptane gradient, to give benzyl ((1r,4r)-4-hydroxy-4-methylcyclohexyl)carbamate as a white solid (524 mg, 1.99 mmol, 49%). $^1$H NMR (400 MHz, CDCl$_3$) δ 1.20-1.31 (m, 4H), 1.33-1.46 (m, 2H), 1.46-1.69 (m, 4H), 1.88-2.02 (m, 2H), 3.57-3.72 (m, 1H), 4.70 (br s, 1H), 5.09 (br s, 2H), 7.28-7.43 (m, 5H).

B. (1r,4r)-4-Amino-1-methylcyclohexanol

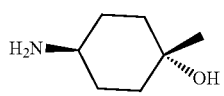

Palladium on carbon (217 mg, 0.20 mmol) was added to benzyl (trans-4-hydroxy-4-methylcyclohexyl)carbamate (524 mg, 1.99 mmol) under a nitrogen atmosphere with enough methanol to wet the catalyst. The reaction vessel was fitted with a hydrogen balloon, and the vessel was repeatedly evacuated and purged with hydrogen, then stirred for 1 h under a hydrogen atmosphere. The vessel was repeatedly evacuated and purged with nitrogen, filtered through Celite®, and concentrated to give the title compound (257 mg, 1.98 mmol, 100% yield) as a white solid. $^1$H NMR (400 MHz, CD$_3$SOCD$_3$) δ 1.08 (s, 3H), 1.09-1.19 (m, 2H), 1.26-1.38 (m, 2H), 1.45-1.56 (m, 2H), 1.59-1.72 (m, 2H), 2.59-2.66 (m, 1H).

Intermediate 22

(1s,4s)-4-Amino-1-(difluoromethyl)cyclohexan-1-ol

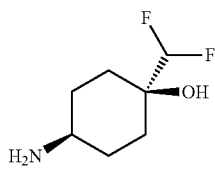 [SMILES: N[C@H]1CC[C@](O)(C(F)F)CC1]

A. (1s,4s)-4-(Dibenzylamino)-1-(difluoromethyl)cyclohexan-1-ol and (1r,4r)-4-(Dibenzylamino)-1-(difluoromethyl)cyclohexan-1-ol

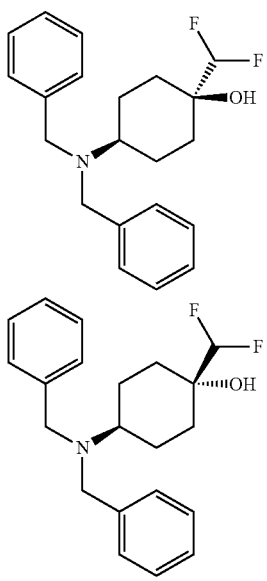

Cesium fluoride (0.155 g, 1.022 mmol) was added to 4-(dibenzylamino)cyclohexan-1-one (1 g, 3.41 mmol) and hexamethylphosphoramide (2.96 mL, 17.04 mmol) in tetrahydrofuran (8 mL). Then, (difluoromethyl)trimethylsilane (0.847 g, 6.82 mmol) was added. The resulting mixture was heated to reflux for 24 h. The mixture was cooled down a little bit (not quite rt yet) and tetrabutylammonium fluoride (3.41 mL, 3.41 mmol) was added and the mixture was stirred at room temperature for 1 h, then the mixture was poured into water (20 mL). The reaction mixture was extracted with ethyl acetate. The combined extracts were washed with water (2×) and brine, dried over sodium sulfate, filtered, and concentrated in vacuo. The residue was purified by silica gel chromatography, eluting with 0 to 30% ethyl acetate:hexanes to afford (1s,4s)-4-(dibenzylamino)-1-(difluoromethyl)cyclohexan-1-ol (352 mg, 1.019 mmol, 29.9% yield), which eluted first, and (1r,4r)-4-(dibenzylamino)-1-(difluoromethyl)cyclohexan-1-ol (560 mg, 1.621 mmol, 47.6% yield), both white solids. The stereochemistry was confirmed with 2D NMR and NOE.

(1s,4s)-4-(Dibenzylamino)-1-(difluoromethyl)cyclohexan-1-ol $^1$H NMR (400 MHz, CDCl$_3$) δ 1.38-1.48 (m, 2H), 1.72-1.82 (m, 2H), 1.82-1.90 (m, 4H), 2.50-2.60 (m, 1H), 3.69 (s, 4H), 5.44 (t, J=56 Hz, 1H), 7.23 (t, J=7 Hz, 2H), 7.31 (t, J=7 Hz, 4H), 7.39 (d, J=7 Hz, 4H); LC-MS (LC-ES) M+H=346.

(1r,4r)-4-(Dibenzylamino)-1-(difluoromethyl)cyclohexan-1-ol $^1$H NMR (400 MHz, CDCl$_3$) δ 1.42-1.48 (m, 2H), 1.62-1.74 (m, 2H), 1.82-1.92 (m, 2H), 2.04-2.12 (m, 2H), 2.68-2.76 (m, 1H), 3.66 (s, 4H), 5.77 (t, J=56 Hz, 1H), 7.24 (t, J=7 Hz, 2H), 7.31 (t, J=7 Hz, 4H), 7.35 (d, J=7 Hz, 4H); LC-MS (LC-ES) M+H=346.

B. (1s,4s)-4-Amino-1-(difluoromethyl)cyclohexan-1-ol

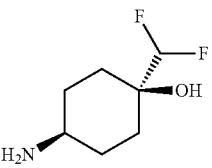 [SMILES: N[C@H]1CC[C@](O)(C(F)F)CC1]

(1s,4s)-4-(Dibenzylamino)-1-(difluoromethyl)cyclohexan-1-ol (330 mg, 0.955 mmol) was dissolved in ethanol (15 mL), palladium hydroxide on carbon (20%, 168 mg, 0.239 mmol) was added and the mixture was degassed under hydrogen balloon (3×) and then stirred under the hydrogen balloon overnight (16 h) at which time LC-MS showed the disappearance of the starting material. The mixture was filtered through Celite® and washed with methanol. The filtrate was concentrated in vacuo to afford (1s,4S)-4-amino-1-(difluoromethyl)cyclohexan-1-ol (137 mg, 0.829 mmol, 87% yield) as a white solid. $^1$H NMR (400 MHz, CD$_3$OD) δ 1.44-1.64 (m, 4H), 1.66-1.84 (m, 4H), 2.56-2.74 (m, 1H), 5.52 (t, J=56 Hz, 1H); LC-MS (LC-ES) M+H=166.

Intermediate 23

(1r,4r)-4-Amino-1-(difluoromethyl)cyclohexan-1-ol

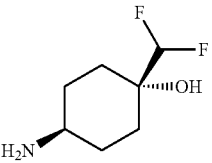

(1r,4r)-4-(Dibenzylamino)-1-(difluoromethyl)cyclohexan-1-ol (425 mg, 1.230 mmol) was dissolved in ethanol (7 mL), palladium hydroxide on carbon (20%, 216 mg, 0.308 mmol) was added and the mixture was degassed under hydrogen balloon (3×) and then stirred under the hydrogen balloon overnight (18 h) at which time LCMS showed the disappearance of the starting material. The mixture was filtered through Celite® and washed with ethanol. The filtrate was concentrated in vacuo to afford (1r,4r)-4-amino-1-(difluoromethyl)cyclohexan-1-ol (185 mg, 1.120 mmol, 91% yield) as a greenish solid. $^1$H NMR (400 MHz, CD$_3$OD) δ 1.44-1.54 (m, 4H), 1.82-1.96 (m, 4H), 2.96-3.04 (m, 1H), 5.67 (t, J=56 Hz, 1H); LC-MS (LC-ES) M+H=166.

Intermediate 24

2-(6-Aminospiro[3.3]heptan-2-yl)propan-2-ol

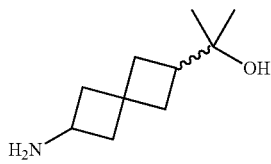

A. Methyl 3-methylenecyclobutanecarboxylate

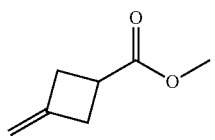

An ethanol/water solution (180 mL, 1:1) containing 3-methylenecyclobutanecarbonitrile (10.0 g, 107 mmol) and potassium hydroxide (24.1 g, 430 mmol) was heated to reflux for 8 hours. Upon cooling, the ethanol was removed under vacuum and the remaining liquid was cooled to 0° C. and acidified with concentrated hydrochloric acid. The organics were then extracted with diethyl ether (4X), dried over magnesium sulfate, and the solvent removed under vacuum affording 3-methylenecyclobutanecarboxylic acid (11.6 g, 103 mmol) as a light yellow oil. This material was dissolved in N,N-dimethylformamide (350 mL) and cesium carbonate (70.8 g, 217 mmol) and iodomethane (17.6 g, 124 mmol) were added at room temperature. The resulting heterogeneous solution was stirred overnight at room temperature. The solution was partitioned between diethyl ether and water. The organic layer was separated and the aqueous layer extracted with diethyl ether (3×). The combined organic layers were washed with water, dried over magnesium sulfate and the solvent removed under vacuum, yielding methyl 3-methylenecyclobutanecarboxylate (10.9 g, 86 mmol, 84% yield) as a light yellow liquid. $^1$H NMR (400 MHz, CDCl$_3$) δ 2.85-3.05 (m, 4H), 3.13 (m, 1H), 3.70 (s, 3H), 4.80 (m, 2H).

B. Methyl 6-oxospiro[3.3]heptane-2-carboxylate

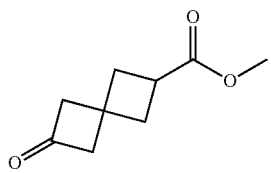

A solution of methyl 3-methylenecyclobutanecarboxylate (5.0 g, 39.6 mmol) was dissolved in dry methyl acetate (45 mL). Copper powder (2.77 g, 43.6 mmol) and zinc powder (5.70 g, 87 mmol) were added to the reaction and the resulting heterogeneous mixture was stirred at room temperature. Next, a solution of 2,2,2-trichloroacetyl chloride (4.86 mL, 43.6 mmol) and phosphorus oxychloride (0.369 mL, 3.96 mmol) in methyl acetate (45 mL) was added dropwise slowly over 2 hours. The reaction mixture was stirred for an additional 3 hours at room temperature. The reaction mixture was then cooled to 0° C. and an additional 2.2 equivalents of zinc (5.70 g, 87 mmol) powder was added. Next, a temperature probe was inserted into the reaction and acetic acid (22.69 mL, 396 mmol) was added dropwise keeping the internal temperature of the reaction mixture below 7° C. Total addition time was approximately 15-20 minutes. The reaction was warmed to room temperature and stirred overnight. The reaction mixture was then filtered through a pad of Celite® to remove the metals, rinsing with ethyl acetate. The filtrate was diluted with ethyl acetate (100 mL) and stirred vigorously while slowly adding saturated sodium bicarbonate (200 mL). The solution was transferred into a separatory funnel and the layers were separated. The aqueous extracts were then washed with ethyl acetate/ diethyl ether (1:1, 2×100 mL). The organics were combined, dried over magnesium sulfate, filtered, and the solvents removed under vacuum to afford a light brown oil. This material was purified by silica gel chromatography, eluting with 0-50% ethyl acetate in hexanes to afford methyl 6-oxospiro[3.3]heptane-2-carboxylate (4.10 g, 24.38 mmol, 61% yield) as a clear light yellow oil. $^1$H NMR (400 MHz, CDCl$_3$) δ 2.43 (m, 2H), 2.56 (m, 2H), 3.08 (m, 2H), 3.13 (m, 3H), 3.68 (s, 3H).

C. Methyl 6-(dibenzylamino)spiro[3.3]heptane-2-carboxylate

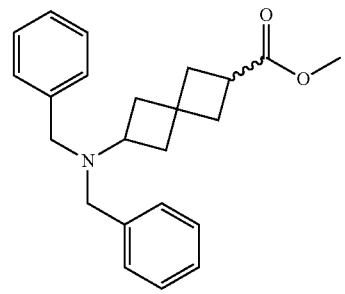 [SMILES: COC(=O)C1CC2(C1)CC(N(Cc1ccccc1)Cc1ccccc1)C2]

Methyl 6-oxospiro[3.3]heptane-2-carboxylate (3.89 g, 23.13 mmol) was dissolved in dry tetrahydrofuran (200 mL). Dibenzylamine (4.67 mL, 24.29 mmol) was added and the reaction mixture was stirred at room temperature for 10 minutes then cooled to 0° C. Next, sodium triacetoxyborohydride (7.35 g, 34.7 mmol) was added as a solid portion wise over 10 minutes. Glacial acetic acid (4-5 drops) was added and the ice bath removed, and the resulting reaction mixture was stirred at room temperature for 4 hours. Water (20 mL) was added, and then the reaction mixture was poured into diethyl ether (200 mL) and washed with saturated aqueous sodium bicarbonate (100 mL). The aqueous layer was washed with diethyl ether (1×100 mL), then the organic layers were combined, dried over magnesium sulfate, filtered, and the solvents removed under vacuum. Purification of the crude product by silica gel chromatography, eluting with 0-50% ethyl acetate in hexanes gradient elution afforded methyl 6-(dibenzylamino)spiro[3.3]heptane-2-carboxylate (5.00 g, 14.31 mmol, 62% yield) as a white solid. $^1$H NMR (400 MHz, CDCl$_3$) δ 1.83 (m, 2H), 1.97-2.31 (m, 6H), 2.98 (m, 2H), 3.43 (m, 4H), 3.64 (s, 3H), 7.18-7.32 (m, 10H); LC-MS (LC-ES) M+H=350.

D. 2-(6-(Dibenzylamino)spiro[3.3]heptan-2-yl)propan-2-ol

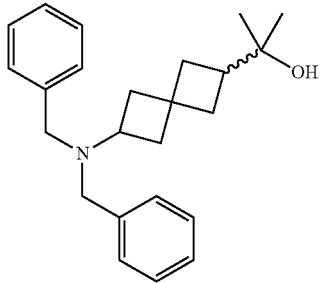 [SMILES: CC(C)(O)C1CC2(CC(N(Cc3ccccc3)Cc3ccccc3)C2)C1]

Methyl 6-(dibenzylamino)spiro[3.3]heptane-2-carboxylate (5.00 g, 14.31 mmol) was dissolved in anhydrous diethyl ether (200 mL) and cooled to 0° C. Methylmagnesium bromide (15.74 mL, 47.2 mmol) was added dropwise over 10 minutes and the resulting reaction mixture was stirred 30 minutes at 0° C., then warmed to room temperature and stirred an additional 70 minutes. The reaction was cooled to 0° C., and then quenched with 3N hydrochloric acid. The reaction mixture was poured into saturated sodium bicarbonate (150 mL) then extracted with diethyl ether (1×100 mL) and then ethyl acetate (1×100 mL). The organic layers were combined, dried over magnesium sulfate, filtered, and the solvents removed under vacuum. Purification of the crude product by silica gel chromatography, eluting with 0-100% ethyl acetate in hexanes afforded 2-(6-(dibenzylamino)spiro[3.3]heptan-2-yl)propan-2-ol (4.65 g, 13.30 mmol, 93% yield) as a white solid. $^1$H NMR (400 MHz, CDCl$_3$) δ 1.06 (s, 6H), 1.72-1.95 (m, 7H), 2.10-2.26 (m, 2H), 3.01 (quin, J=8 Hz, 1H), 3.45 (s, 4H), 7.20-7.33 (m, 10H); LC-MS (LC-ES) M+H=350.

E. 2-(6-Aminospiro[3.3]heptan-2-yl)propan-2-ol

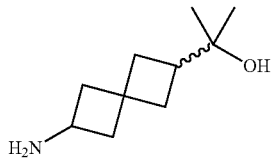

2-(6-(Dibenzylamino)spiro[3.3]heptan-2-yl)propan-2-ol (4.10 g, 11.73 mmol) was dissolved in absolute ethanol (100 mL) and placed in a glass pressure reactor. Palladium hydroxide on carbon (0.329 g, 2.346 mmol) was added and the system was purged with nitrogen and evacuated 3 times under vacuum, then placed under hydrogen gas (35 psi) and stirred overnight at room temperature. The reaction mixture was purged with nitrogen then was filtered through a pad of Celite®, rinsing with methanol, to remove the palladium catalyst. Removal of the solvent under vacuum afforded 2-(6-aminospiro[3.3]heptan-2-yl)propan-2-ol (2.17 g, 12.88 mmol, 110% yield) as a white solid. $^1$H NMR (400 MHz, CDCl$_3$) δ 1.07 (s, 6H), 1.57 (dd, J=11, 8 Hz, 1H), 1.67 (dd, J=10, 9 Hz, 1H), 1.73-1.95 (m, 5H), 2.14-2.27 (m, 2H), 2.41 (m, 1H), 3.30 (quin, J=8 Hz, 1H).

Intermediate 25 cis-4-(3-Fluoroazetidin-1-yl)cyclohexanamine

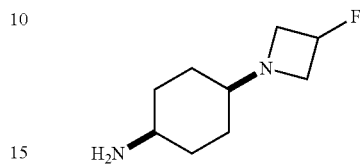

A. Benzyl (cis-4-(3-fluoroazetidin-1-yl)cyclohexyl)carbamate and Benzyl (trans-4-(3-fluoroazetidin-1-yl)cyclohexyl)carbamate

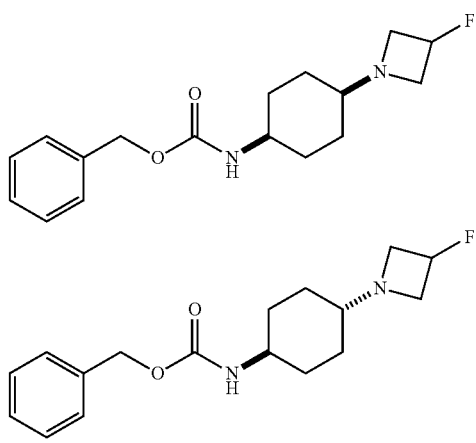

3-Fluoroazetidine hydrochloride (0.506 g, 4.54 mmol) was added to benzyl (4-oxocyclohexyl)carbamate (1.02 g, 4.12 mmol) in 1,2-dichloroethane (20.6 mL) at room temperature and stirred for 5 minutes, followed by acetic acid (0.012 g, 0.206 mmol) and 4 Å molecular sieves (4.0 g) and the reaction was stirred for two hours at room temperature. Then, sodium triacetoxyhydroborate (0.874 g, 4.12 mmol) was added, and the reaction mixture was stirred for sixty-six hours. The reaction mixture was filtered through Celite®, saturated sodium bicarbonate added, extracted with dichloromethane, dried over magnesium sulfate, filtered, and concentrated. The residue was purified by silica gel chromatography, eluting with methanol:ethyl acetate (0:1 to 1:9) to give benzyl (cis-4-(3-fluoroazetidin-1-yl)cyclohexyl)carbamate (0.5051 g, 1.236 mmol, 30.0% yield) and benzyl (trans-4-(3-fluoroazetidin-1-yl)cyclohexyl)carbamate (0.6475 g, 1.902 mmol, 46.1% yield).

Benzyl (cis-4-(3-fluoroazetidin-1-yl)cyclohexyl)carbamate $^1$H NMR (400 MHz, CD$_3$SOCD$_3$) δ 1.28-1.54 (m, 8H), 2.12-2.20 (m, 1H), 2.88-3.00 (m, 2H), 3.26-3.38 (m, 1H), 3.42-3.52 (m, 2H), 4.97 (s, 2H), 5.09 (dp, J=58, 5 Hz, 1H), 7.15 (d, J=8 Hz, 1H), 7.26-7.38 (m, 5H); LC-MS (LC-ES) M+H=307.

Benzyl (trans-4-(3-fluoroazetidin-1-yl)cyclohexyl)carbamate $^1$H NMR (400 MHz, CD$_3$SOCD$_3$) δ 0.91 (q, J=13 Hz, 2H), 1.13 (q, J=13 Hz, 2H), 1.68 (br d, J=12 Hz, 2H), 1.75 (br d, J=12 Hz, 2H), 1.92 (tt, J=11, 3 Hz, 1H), 2.92-3.04 (m, 2H), 3.14-3.26 (m, 1H), 3.42-3.52 (m, 2H), 4.98 (s, 2H), 5.07 (dp, J=58, 5 Hz, 1H), 7.14 (d, J=8 Hz, 1H), 7.26-7.38 (m, 5H); LC-MS (LC-ES) M+H=307.

B. cis-4-(3-Fluoroazetidin-1-yl)cyclohexanamine

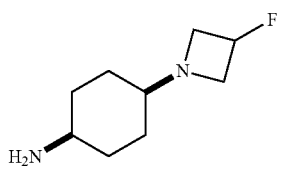 [SMILES: N[C@H]1CC[C@@H](N2CC(F)C2)CC1]

Palladium on carbon (0.018 g, 0.165 mmol) was added to benzyl (cis-4-(3-fluoroazetidin-1-yl)cyclohexyl)carbamate (0.5051 g, 1.649 mmol) in methanol (5.50 mL) at 25° C. under nitrogen atmosphere. Then, the reaction vessel was fitted with a hydrogen balloon and the vessel was repeatedly evacuated and purged with hydrogen, then stirred for sixteen hours. Then, the vessel was repeatedly evacuated and purged with nitrogen, filtered through Celite®, and concentrated to give cis-4-(3-fluoroazetidin-1-yl)cyclohexanamine (0.2627 g, 1.296 mmol, 79% yield). $^1$H NMR (400 MHz, CD$_3$SOCD$_3$) δ 1.24-1.48 (m, 8H), 2.10-2.16 (m, 1H), 2.21 (br s, 2H), 2.58-2.68 (m, 1H), 2.86-2.98 (m, 2H), 3.44-3.54 (m, 2H), 5.09 (dp, J=58, 5 Hz, 1H); LC-MS (LC-ES) M+H=173.

Intermediate 26 trans-4-(3-Fluoroazetidin-1-yl)cyclohexanamine

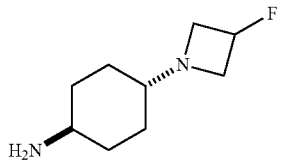 [SMILES: N[C@H]1CC[C@H](N2CC(F)C2)CC1]

Palladium on carbon (0.022 g, 0.211 mmol) was added to benzyl (trans-4-(3-fluoroazetidin-1-yl)cyclohexyl)carbamate (0.6475 g, 2.113 mmol, Intermediate 25A) in methanol (7.0 mL) at 25° C. under nitrogen atmosphere. Then, the reaction vessel was fitted with a hydrogen balloon and the vessel was repeatedly evacuated and purged with hydrogen, then stirred for seventeen hours. Then, the vessel was repeatedly evacuated and purged with nitrogen, filtered through Celite®, and concentrated to give trans-4-(3-fluoroazetidin-1-yl)cyclohexanamine (0.3991 g, 2.085 mmol, 99% yield). $^1$H NMR (400 MHz, CD$_3$SOCD$_3$) δ 0.82-1.04 (m, 4H), 1.58-1.74 (m, 6H), 1.84-1.94 (m, 1H), 2.38-2.50 (m, 1H), 2.90-3.02 (m, 2H), 3.42-3.52 (m, 2H), 5.06 (dp, J=58, 5 Hz, 1H); LC-MS (LC-ES) M+H=173.

Intermediate 27

(R)-Benzyl (3-(trifluoromethyl)-1-oxa-4-azaspiro[4.5]decan-8-yl)carbamate

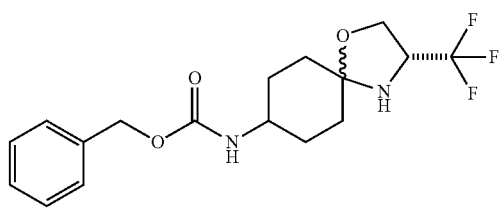 [SMILES: O=C(NC1CCC2(CC1)N[C@@H](C(F)(F)F)CO2)OCc1ccccc1]

(R)-2-Amino-3,3,3-trifluoropropan-1-ol hydrochloride (0.676 g, 4.08 mmol) was added to benzyl (4-oxocyclohexyl)carbamate (1.01 g, 4.08 mmol) in benzene (40.8 mL) at room temperature and the reaction was heated with a Dean-Stark trap for sixteen hours. Then, the reaction mixture was cooled, saturated sodium bicarbonate added, extracted with diethyl ether, dried over magnesium sulfate, filtered, and concentrated. The residue was purified by silica gel chromatography, eluting with ethyl acetate:hexanes (2:3) to give (R)-benzyl (3-(trifluoromethyl)-1-oxa-4-azaspiro[4.5]decan-8-yl)carbamate (1.21 g, 2.87 mmol, 70.3% yield) contaminated with 10% of starting ketone. $^1$H NMR (400 MHz, CD$_3$SOCD$_3$) δ 1.32-1.80 (m, 8H), 3.62-4.04 (m, 4H), 4.98 & 4.99 (s, 2H), 7.20 & 7.24 (d, J=8 Hz, 1H), 7.34-7.40 (m, 5H); LC-MS (LC-ES) M+H=359.

Intermediate 28

(R)-2-((trans-4-Aminocyclohexyl)amino)-3,3,3-trifluoropropan-1-ol

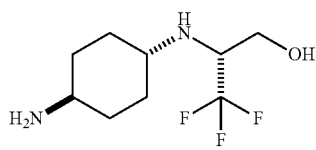 [SMILES: N[C@H]1CC[C@H](N[C@H](CO)C(F)(F)F)CC1]

A. Benzyl (cis-4-(((R)-1,1,1-trifluoro-3-hydroxypropan-2-yl)amino)cyclohexyl)carbamate and Benzyl (trans-4-(((R)-1,1,1-trifluoro-3-hydroxypropan-2-yl)amino)cyclohexyl)carbamate

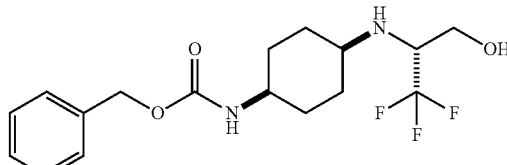

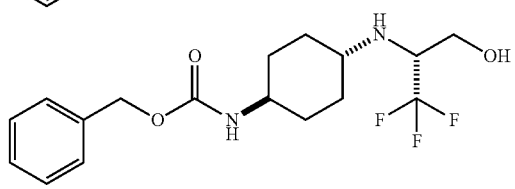

Sodium triacetoxyhydroborate (0.481 g, 2.269 mmol) was added to benzyl ((3R)-3-(trifluoromethyl)-1-oxa-4-azaspiro [4.5]decan-8-yl)carbamate (0.8130 g, 2.269 mmol, Intermediate 27) in 1,2-dichloroethane (11.3 mL) at room temperature, followed by acetic acid (6.81 mg, 0.113 mmol) and the reaction was stirred for sixty-four hours. The reaction mixture was diluted with saturated sodium bicarbonate, extracted with dichloromethane, dried over magnesium sulfate, filtered, and concentrated. The residue was purified by silica gel chromatography, eluting with ethyl acetate: hexanes (1:1) to give benzyl (cis-4-(((R)-1,1,1-trifluoro-3-hydroxypropan-2-yl)amino)cyclohexyl)carbamate (0.3625 g, 0.604 mmol, 26.6% yield) and benzyl (trans-4-(((R)-1,1,1-trifluoro-3-hydroxypropan-2-yl)amino)cyclohexyl)carbamate (0.3917 g, 1.033 mmol, 45.5% yield).

Benzyl (cis-4-(((R)-1,1,1-trifluoro-3-hydroxypropan-2-yl)amino)cyclohexyl)carbamate $^1$H NMR (400 MHz, CD$_3$SOCD$_3$) δ 1.40-1.70 (m, 8H), 2.34-2.46 (m, 1H), 3.12-3.26 (m, 1H), 3.34-3.44 (m, 1H), 3.44-3.52 (m, 1H), 3.58-3.66 (m, 1H), 4.97 (t, J=6 Hz, 1H), 4.99 (s, 2H), 7.20 (d, J=7 Hz, 1H), 7.26-7.38 (m, 5H); LC-MS (LC-ES) M+H=361.

Benzyl (trans-4-(((R)-1,1,1-trifluoro-3-hydroxypropan-2-yl)amino)cyclohexyl)carbamate $^1$H NMR (400 MHz, CD$_3$SOCD$_3$) δ 1.02 (q, J=13 Hz, 2H), 1.14 (q, J=13 Hz, 2H), 1.72-1.92 (m, 5H), 2.36-2.48 (m, 1H), 3.14-3.28 (m, 2H), 3.40-3.50 (m, 1H), 3.54-3.64 (m, 1H), 4.96 (t, J=6 Hz, 1H), 4.98 (s, 2H), 7.15 (d, J=8 Hz, 1H), 7.26-7.38 (m, 5H); LC-MS (LC-ES) M+H=361.

B. (R)-2-((trans-4-Aminocyclohexyl)amino)-3,3,3-trifluoropropan-1-ol

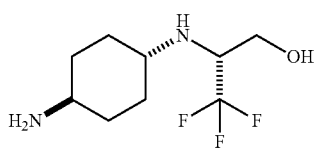

Palladium on carbon (0.012 g, 0.109 mmol) was added to benzyl (trans-4-(((R)-1,1,1-trifluoro-3-hydroxypropan-2-yl) amino)cyclohexyl)carbamate (0.3917 g, 1.087 mmol) in methanol (5.4 mL) at 25° C. under nitrogen atmosphere. Then, the reaction vessel was fitted with a hydrogen balloon and the vessel was repeatedly evacuated and purged with hydrogen, then stirred for sixteen hours. Then, the vessel was repeatedly evacuated and purged with nitrogen, filtered through Celite®, and concentrated to give (R)-2-((trans-4-aminocyclohexyl)amino)-3,3,3-trifluoropropan-1-ol (0.2481 g, 1.042 mmol, 96% yield). $^1$H NMR (400 MHz, CD$_3$SOCD$_3$) δ 0.92-1.06 (m, 4H), 1.62-1.88 (m, 7H), 2.36-2.50 (m, 2H), 3.16-3.28 (m, 1H), 3.40-3.50 (m, 1H), 3.54-3.64 (m, 1H), 4.96 (t, J=6 Hz, 1H); LC-MS (LC-ES) M+H=227.

Intermediate 29 cis-4-(3,3-Difluoroazetidin-1-yl)cyclohexanamine

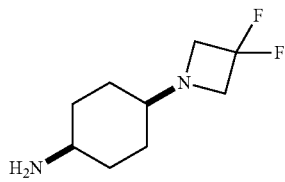 [SMILES: N[C@H]1CC[C@@H](N2CC(F)(F)C2)CC1]

A. Benzyl (cis-4-(3,3-difluoroazetidin-1-yl)cyclohexyl)carbamate and Benzyl (trans-4-(3,3-difluoroazetidin-1-yl)cyclohexyl)carbamate

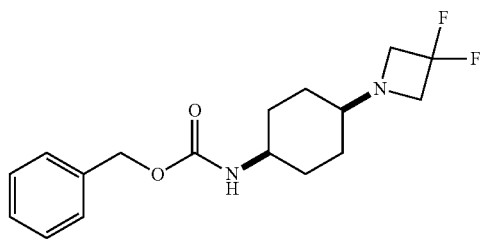

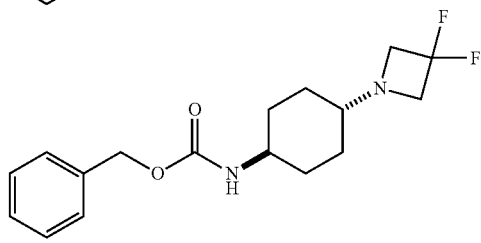

3,3-Difluoroazetidine hydrochloride (0.593 g, 4.58 mmol) was added to benzyl (4-oxocyclohexyl)carbamate (1.03 g, 4.17 mmol) in 1,2-dichloroethane (20.83 mL) at room temperature and stirred for 5 minutes, followed by acetic acid (0.013 g, 0.208 mmol) and 4 Å molecular sieves (4.0 g) and the reaction was stirred for two hours at room temperature. Then, sodium triacetoxyhydroborate (0.883 g, 4.17 mmol) was added, and the reaction mixture was stirred for sixteen hours. The reaction mixture was filtered through Celite®, saturated sodium bicarbonate added, extracted with dichloromethane, dried over magnesium sulfate, filtered, and concentrated. The residue was purified by silica gel chromatography, eluting with ethyl acetate:hexanes (2:3) to give benzyl (cis-4-(3,3-difluoroazetidin-1-yl)cyclohexyl) carbamate (0.3787 g, 1.109 mmol, 26.6% yield) and benzyl (trans-4-(3,3-difluoroazetidin-1-yl)cyclohexyl)carbamate (0.5901 g, 1.728 mmol, 41.5% yield).

Benzyl (cis-4-(3,3-difluoroazetidin-1-yl)cyclohexyl) carbamate $^1$H NMR (400 MHz, CD$_3$SOCD$_3$) δ 1.32-1.58 (m, 8H), 2.24-2.30 (m, 1H), 3.28-3.40 (m, 1H), 3.46 (t, J=12 Hz, 4H), 4.98 (s, 2H), 7.20 (d, J=8 Hz, 1H), 7.26-7.38 (m, 5H); LC-MS (LC-ES) M+H=325.

Benzyl (trans-4-(3,3-difluoroazetidin-1-yl)cyclohexyl)carbamate

¹H NMR (400 MHz, CD₃SOCD₃) δ 0.97 (q, J=13 Hz, 2H), 1.14 (dq, J=13, 3 Hz, 2H), 1.68 (br d, J=12 Hz, 2H), 1.76 (br d, J=12 Hz, 2H), 2.03 (t, J=10 Hz, 1H), 3.16-3.30 (m, 1H), 3.96 (t, J=12 Hz, 4H), 4.98 (s, 2H), 7.18 (d, J=8 Hz, 1H), 7.26-7.38 (m, 5H); LC-MS (LC-ES) M+H=325.

B. cis-4-(3,3-Difluoroazetidin-1-yl)cyclohexanamine

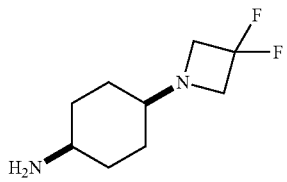 [SMILES: N[C@H]1CC[C@@H](N2CC(F)(F)C2)CC1]

Palladium on carbon (0.012 g, 0.117 mmol) was added to benzyl (cis-4-(3,3-difluoroazetidin-1-yl)cyclohexyl)carbamate (0.3787 g, 1.168 mmol) in methanol (5.8 mL) at 25° C. under nitrogen atmosphere. Then, the reaction vessel was fitted with a hydrogen balloon and the vessel was repeatedly evacuated and purged with hydrogen, then stirred for two hours. Then, the vessel was repeatedly evacuated and purged with nitrogen, filtered through Celite®, and concentrated to give cis-4-(3,3-difluoroazetidin-1-yl)cyclohexanamine (0.1968 g, 0.983 mmol, 84% yield). ¹H NMR (400 MHz, CD₃SOCD₃) δ 1.26-1.50 (m, 8H), 1.78-1.96 (m, 2H), 2.18-2.26 (m, 1H), 2.58-2.68 (m, 1H), 3.46 (t, J=12 Hz, 4H); LC-MS (LC-ES) M+H=191.

Intermediate 30 trans-4-(3,3-Difluoroazetidin-1-yl)cyclohexanamine

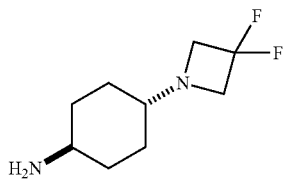 [SMILES: N[C@H]1CC[C@H](N2CC(F)(F)C2)CC1]

Palladium on carbon (0.019 g, 0.182 mmol) was added to benzyl (trans-4-(3,3-difluoroazetidin-1-yl)cyclohexyl)carbamate (0.5901 g, 1.819 mmol, Intermediate 29A) in methanol (9.1 mL) at 25° C. under nitrogen atmosphere. Then, the reaction vessel was fitted with a hydrogen balloon and the vessel was repeatedly evacuated and purged with hydrogen, then stirred for three hours. Then, the vessel was repeatedly evacuated and purged with nitrogen, filtered through Celite®, and concentrated to give trans-4-(3,3-difluoroazetidin-1-yl)cyclohexanamine (0.3403 g, 1.699 mmol, 93% yield). ¹H NMR (400 MHz, CD₃SOCD₃) δ 0.88-1.02 (m, 4H), 1.54 (br s, 2H), 1.68-1.74 (m, 4H), 1.96-2.06 (m, 1H), 2.40-2.52 (m, 1H), 3.48 (t, J=12 Hz, 4H); LC-MS (LC-ES) M+H=191.

Intermediate 31 trans-N1-(1,1-Difluoropropan-2-yl)cyclohexane-1,4-diamine

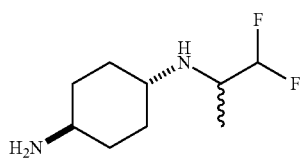

A. Benzyl (trans-4-((1,1-difluoropropan-2-yl)amino)cyclohexyl)carbamate

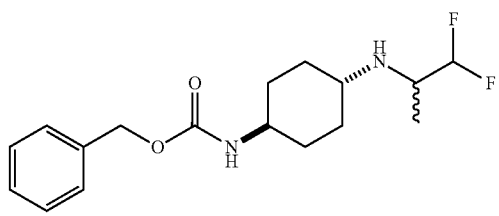 [SMILES: CC(N[C@H]1CC[C@H](NC(=O)OCc2ccccc2)CC1)C(F)F]

1,1-Difluoropropan-2-one (3.13 g, 33.3 mmol) was added to benzyl (trans-4-aminocyclohexyl)carbamate (7.52 g, 30.3 mmol) in 1,2-dichloroethane (151 mL) at room temperature and stirred for 5 minutes, followed by acetic acid (0.091 g, 1.514 mmol) and 4 Å molecular sieves (20.0 g) and the reaction was stirred for two hours at room temperature. Then, sodium triacetoxyhydroborate (6.42 g, 30.3 mmol) was added, and the reaction mixture was stirred for twenty hours. The reaction mixture was filtered through Celite®, saturated sodium bicarbonate added, extracted with dichloromethane, dried over magnesium sulfate, filtered, and concentrated. The residue was purified by silica gel chromatography, eluting with ethyl acetate:hexanes (1:1) to give benzyl (trans-4-((1,1-difluoropropan-2-yl)amino)cyclohexyl)carbamate (8.41 g, 24.48 mmol, 81% yield). ¹H NMR (400 MHz, CD₃SOCD₃) δ 0.99 (d, J=7 Hz, 3H), 0.94-1.06 (m, 2H), 1.08-1.22 (m, 2H), 1.45 (br s, 1H), 1.70-1.88 (m, 4H), 2.36-2.48 (m, 1H), 2.86-3.00 (m, 1H), 3.14-3.28 (m, 1H), 4.97 (s, 2H), 5.74 (dt, J=56, 4 Hz, 1H), 7.16 (d, J=8 Hz, 1H), 7.26-7.38 (m, 5H); LC-MS (LC-ES) M+H=327.

B. trans-N1-(1,1-Difluoropropan-2-yl)cyclohexane-1,4-diamine

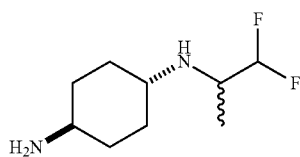

Palladium on carbon (0.137 g, 1.288 mmol) was added to benzyl (trans-4-((1,1-difluoropropan-2-yl)amino)cyclohexyl)carbamate (8.41 g, 25.8 mmol) in methanol (51.5 mL) at 25° C. under nitrogen atmosphere. Then, the reaction vessel was fitted with a hydrogen balloon and the vessel was repeatedly evacuated and purged with hydrogen, then stirred for six hours. Then, the vessel was repeatedly evacuated and purged with nitrogen, filtered through Celite®, and concentrated to give trans-N1-(1,1-difluoropropan-2-yl)cyclohexane-1,4-diamine (5.05 g, 24.95 mmol, 97% yield). $^1$H NMR (400 MHz, CD$_3$SOCD$_3$) δ 0.90-1.04 (m, 4H), 0.99 (d, J=7 Hz, 3H), 1.30-1.60 (m, 3H), 1.62-1.84 (m, 4H), 2.34-2.48 (m, 2H), 2.86-3.00 (m, 1H), 5.73 (dt, J=56, 4 Hz, 1H); LC-MS (LC-ES) M+H=193.

Intermediate 32

(R)-2((3-Aminocyclobutyl)amino)-3,3,3-trifluoropropan-1-ol

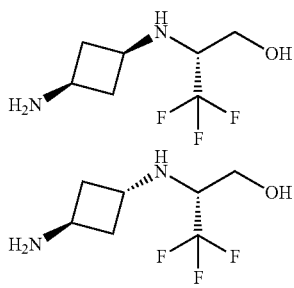

A. Benzyl (3-(((R)-1,1,1-trifluoro-3-hydroxypropan-2-yl)amino)cyclobutyl)carbamate

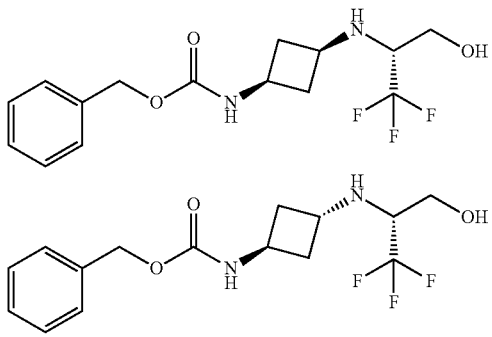

(R)-2-Amino-3,3,3-trifluoropropan-1-ol hydrochloride (415 mg, 2.509 mmol) was added to benzyl (3-oxocyclobutyl)carbamate (500 mg, 2.281 mmol) in benzene (20 mL) at room temperature. Then, the reaction mixture was heated at reflux with a Dean-Stark trap for twenty-four hours. Then, the reaction mixture was concentrated under vacuum to yield a white solid. This solid was dissolved in 1,2-dichloroethane (10 mL) and acetic acid (0.196 mL, 3.42 mmol) was added, followed by the addition of sodium triacetoxyborohydride (725 mg, 3.42 mmol) and the reaction mixture was stirred twenty-four hours. Then, the reaction mixture was diluted with dichloromethane (50 mL) and the dichloromethane layer was washed with saturated aqueous sodium bicarbonate (25 mL, 2X), dried over sodium sulfate, and concentrated. The residue was purified via silica gel chromatography, eluting with ethyl acetate:hexanes (0:1 to 1:0) to give a cis/trans mixture of benzyl (3-(((R)-1,1,1-trifluoro-3-hydroxypropan-2-yl)amino)cyclobutyl)carbamate (0.400 g, 1.004 mmol, 52.8% yield). $^1$H NMR (400 MHz, CD$_3$SOCD$_3$) δ 1.80-2.54 (m, 4H), 3.00-4.14 (m, 5H), 4.94-5.06 (m, 2H), 7.22-7.40 (m, 5H), 7.57 & 7.69 (d, J=7 Hz, 1H); LC-MS (LC-ES) M+H=333.

B. (R)-2-((3-Aminocyclobutyl)amino)-3,3,3-trifluoropropan-1-ol

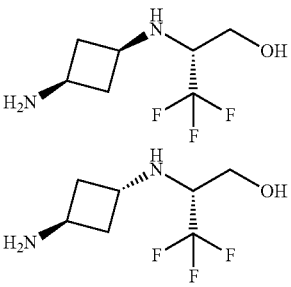

Benzyl (3-(((R)-1,1,1-trifluoro-3-hydroxypropan-2-yl)amino)cyclobutyl)carbamate (400 mg, 1.204 mmol) in methanol (8.0 mL) was added to a stirred suspension of palladium on carbon in methanol (4.0 mL) at room temperature. Then, the reaction mixture was stirred over the weekend under the atmosphere of hydrogen gas (balloon). Then, the reaction mixture was filtered through Celite®, which was rinsed with methanol, and concentrated under vacuum to yield a cis/trans mixture of (R)-2-((3-aminocyclobutyl)amino)-3,3,3-trifluoropropan-1-ol (0.230 g, 1.044 mmol, 87% yield) as an off white solid. $^1$H NMR (400 MHz, CD$_3$SOCD$_3$) δ 1.70-2.40 (m, 4H), 2.76-3.70 (m, 5H), 5.11 (br s, 1H), 7.83 (br s, 2H); LC-MS (LC-ES) M+H=199.

Intermediate 33

7-Methoxy-1,8-naphthyridine-3-carboxylic acid

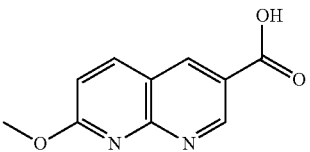

Sodium methoxide (25% in methanol, 1.15 mL, 5.03 mmol) was added to ethyl 7-chloro-1,8-naphthyridine-3-carboxylate (0.238 g, 1.006 mmol, Intermediate 4C) in methanol (10 mL) at room temperature and the reaction mixture was heated at 60° C. for two hours. The reaction mixture was concentrated and water (10 mL) was added. The reaction mixture was stirred for 75 minutes, then the reaction mixture was filtered through a pad of Celite® and the filter cake rinsed with water. The pH was adjusted to 4-5 with 1 N hydrochloric acid (4 mL). A fine, milky precipitate formed. An additional 1 N hydrochloric acid (1 mL) was added (pH=2), and the solids were filtered off and rinsed twice with water, air dried, then dried under vacuum to give 7-methoxy-1,8-naphthyridine-3-carboxylic acid (0.202 g, 989 mmol, 98% yield) as a tan powder. $^1$H NMR (400 MHz, CD$_3$SOCD$_3$) δ 4.05 (s, 3H), 7.23 (d, J=9 Hz, 1H), 8.50 (d, J=9 Hz, 1H), 8.95 (d, J=2 Hz, 1H), 9.31 (d, J=2 Hz, 1H), 13.46 (br s, 1H); LC-MS (LC-ES) M+H=205.

Intermediate 34

7-Methoxy-1,6-naphthyridine-3-carboxylic acid

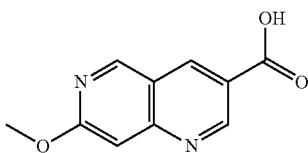

Sodium methoxide (25% in methanol, 1.15 mL, 5.03 mmol) was added to ethyl 7-chloro-1,6-naphthyridine-3-carboxylate (0.238 g, 1.006 mmol, Intermediate 1F) in methanol (10 mL) at room temperature and the reaction mixture was heated to 60° C. for seven hours. The reaction mixture was concentrated, then water (10 mL) was added and the reaction was stirred for 90 minutes. The reaction mixture was filtered through a pad of Celite® and the filter cake rinsed with water. The pH was adjusted to 5 with 1 N hydrochloric acid (4 mL). A fine, milky precipitate formed. An additional 1 N hydrochloric acid (1 mL) was added (pH=2). The solids were filtered off and rinsed with water (2×), air-dried, and then dried under vacuum to give 7-methoxy-1,6-naphthyridine-3-carboxylic acid (0.206 g, 1009 mmol, 100% yield) as a pale yellow powder. $^1$H NMR (400 MHz, CD$_3$SOCD$_3$) δ 4.02 (s, 3H), 7.29 (s, 1H), 9.07 (d, J=2 Hz, 1H), 9.35 (s, 1H), 9.36 (d, J=2 Hz, 1H), 13.54 (br s, 1H); LC-MS (LC-ES) M+H=205.

Intermediate 35

7-(2,2,2-Trifluoroethoxy)-1,8-naphthyridine-3-carboxylic acid and 7-Ethoxy-1,8-naphthyridine-3-carboxylic acid

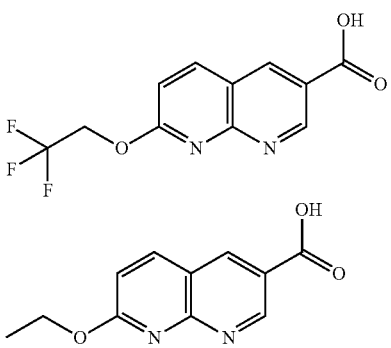

2,2,2-Trifluoroethan-1-ol (0.18 mL, 2.470 mmol) was added to sodium hydride (60% in mineral oil, 0.121 g, 3.03 mmol) in tetrahydrofuran (10 mL) under nitrogen. It bubbled gently. After 30 minutes, ethyl 7-chloro-1,8-naphthyridine-3-carboxylate (0.241 g, 1.018 mmol, Intermediate 4C) was added and the reaction mixture was stirred for nineteen hours. Water (2 mL) was added to the reaction mixture and it was allowed to stir for six hours. Then, the reaction mixture was partitioned between diethyl ether (25 mL) and water (15 mL) and the layers were separated. The aqueous layer was filtered through a pad of Celite®, gently concentrated to remove any remaining organics, and acidified with 1N hydrochloric acid (2 mL, pH=3-4). The precipitate was collected by filtration, rinsed with water (2×), and air-dried, then dried under vacuum to give a mixture of 7-(2,2,2-trifluoroethoxy)-1,8-naphthyridine-3-carboxylic acid and 7-ethoxy-1,8-naphthyridine-3-carboxylic acid (0.231 g, 65:35 ratio). LC-MS (LC-ES) M+H=219 and LC-MS (LC-ES) M+H=273.

Intermediate 36

Lithium (S)-6-chloro-7-(2-methylazetidin-1-yl)-1,8-naphthyridine-3-carboxylate

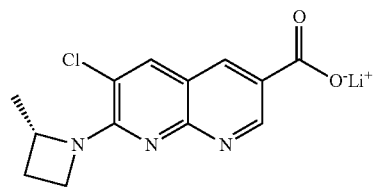

A. Ethyl (S)-6-chloro-7-(2-methylazetidin-1-yl)-1,8-naphthyridine-3-carboxylate

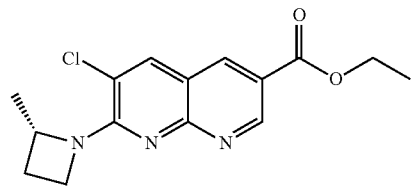 [SMILES: CCOC(=O)c1cnc2nc(N3CC[C@@H]3C)c(Cl)cc2c1]

N,N-Diisopropylethylamine (1.930 mL, 11.08 mmol) was added to ethyl 6,7-dichloro-1,8-naphthyridine-3-carboxylate (0.7511 g, 2.77 mmol, Intermediate 18D) in N-methyl-2-pyrrolidone (5.54 mL) at room temperature. Then (S)-2-methylazetidin-1-ium ((1R,4S)-7,7-dimethyl-2-oxobicyclo[2.2.1]heptan-1-yl)methanesulfonate (1.261 g, 4.16 mmol, Intermediate 14) was added and the reaction mixture was heated at 100° C. in the microwave for one hour. The reaction mixture was diluted in dichloromethane, washed with saturated sodium bicarbonate, dried over magnesium sulfate, filtered, and concentrated. The residue was purified by RP HPLC, eluting with acetonitrile:water with 0.1% ammonium hydroxide (5:95:100:0), then further purified by silica gel chromatography, eluting with ethyl acetate: hexanes (1:4 to 4:1) to give ethyl (S)-6-chloro-7-(2-methylazetidin-1-yl)-1,8-naphthyridine-3-carboxylate (0.7191 g, 2.234 mmol, 81% yield). $^1$H NMR (400 MHz, CD$_3$SOCD$_3$) δ 1.35 (t, J=7 Hz, 3H), 1.50 (d, J=6 Hz, 3H), 1.92-2.02 (m, 1H), 2.44-2.56 (m, 1H), 4.31 (dt, J=9, 7 Hz, 1H), 4.36 (q, J=7 Hz, 2H), 4.56 (dt, J=9, 6 Hz, 1H), 4.80 (h, J=6 Hz, 1H), 8.43 (s, 1H), 8.70 (d, J=2 Hz, 1H), 9.16 (d, J=2 Hz, 1H); LC-MS (LC-ES) M+H=306.

B. Lithium (S)-6-chloro-7-(2-methylazetidin-1-yl)-1,8-naphthyridine-3-carboxylate

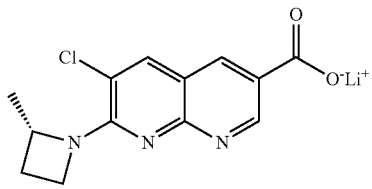

Lithium hydroxide (0.068 g, 2.82 mmol) was added to ethyl (S)-6-chloro-7-(2-methylazetidin-1-yl)-1,8-naphthyridine-3-carboxylate (0.7191 g, 2.352 mmol) in methanol (9.4 mL) and water (2.4 mL) at room temperature and the reaction mixture was stirred sixteen hours at 45° C. The reaction mixture was concentrated to give lithium (S)-6-chloro-7-(2-methylazetidin-1-yl)-1,8-naphthyridine-3-carboxylate (0.6877 g, 2.303 mmol, 98% yield). $^1$H NMR (400 MHz, CD$_3$SOCD$_3$) δ 1.45 (d, J=6 Hz, 3H), 1.90-2.00 (m, 1H), 2.38-2.50 (m, 1H), 4.11 (dt, J=9, 6 Hz, 1H), 4.47 (dt, J=9, 6 Hz, 1H), 4.74 (h, J=8 Hz, 1H), 8.30 (s, 1H), 8.41 (d, J=2 Hz, 1H), 9.17 (d, J=2 Hz, 1H); LC-MS (LC-ES) M+H=278.

Intermediate 37

6-Chloro-7-methoxy-1,8-naphthyridine-3-carboxylic acid

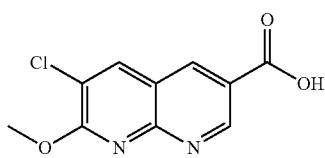 [SMILES: COc1nc2ncc(C(=O)O)cc2cc1Cl]

A. Methyl 6-chloro-7-methoxy-1,8-naphthyridine-3-carboxylate

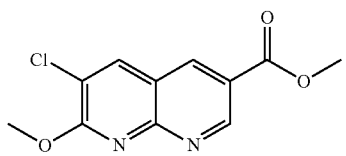

Sodium methoxide (25% in methanol, 0.65 mL, 2.84 mmol) was added to ethyl 6,7-dichloro-1,8-naphthyridine-3-carboxylate (0.154 g, 0.568 mmol, Intermediate 18D) in methanol (10 mL) at room temperature and stirred for twenty-four hours. It was combined with a smaller scale reaction and concentrated to 4 mL volume. The solids were filtered off and rinsed with methanol (2 mL) then air-dried, followed by drying under vacuum to give methyl 6-chloro-7-methoxy-1,8-naphthyridine-3-carboxylate (0.125 g, 0.495 mmol, 82% combined yield) as a tan powder. $^1$H NMR (400 MHz, CD$_3$SOCD$_3$) δ 3.95 (s, 3H), 4.15 (s, 3H), 8.80 (s, 1H), 8.98 (d, J=2 Hz, 1H), 9.35 (d, J=2 Hz, 1H); LC-MS (LC-ES) M+H=253.

B. 6-Chloro-7-methoxy-1,8-naphthyridine-3-carboxylic acid

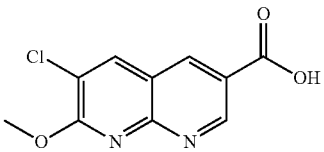 [SMILES: COc1nc2ncc(C(=O)O)cc2cc1Cl]

1N Sodium hydroxide (0.50 mL, 0.500 mmol) was added to the methyl 6-chloro-7-methoxy-1,8-naphthyridine-3-carboxylate (0.125 g, 0.495 mmol) in tetrahydrofuran (5 mL) at room temperature and the reaction mixture was stirred for five hours. Then, more 1N sodium hydroxide (0.50 mL, 0.500 mmol) was added and the reaction mixture was stirred for nineteen hours. The reaction mixture was acidified with 1N hydrochloric acid (1.0 mL) and a precipitate formed. The solids were filtered off and rinsed with water, and air-dried, then dried under vacuum to give 6-chloro-7-methoxy-1,8-naphthyridine-3-carboxylic acid (0.097 g, 0.406 mmol, 82% yield) as a cream colored powder. $^1$H NMR (400 MHz, CD$_3$SOCD$_3$) δ 4.14 (s, 3H), 8.78 (s, 1H), 8.93 (d, J=2 Hz, 1H), 9.33 (d, J=2 Hz, 1H), 13.58 (br s, 1H); LC-MS (LC-ES) M+H=239.

Intermediate 38

2-(Methylthio)pyrido[2,3-d]pyrimidine-6-carboxylic acid

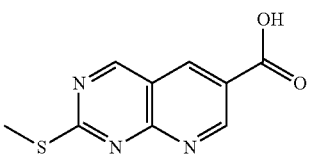

A. Ethyl 4-amino-2-(methylthio)pyrimidine-5-carboxylate

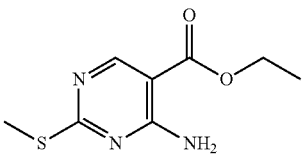

To a stirred solution of ethyl 4-chloro-2-(methylthio)pyrimidine-5-carboxylate (10 g, 43.0 mmol) in tetrahydrofuran (125 mL) was added triethylamine (20 mL, 143 mmol), followed by aqueous ammonium hydroxide (16 mL, 237 mmol). The mixture was stirred for 3 hours. Additional ammonium hydroxide (4 mL, 59.2 mmol) was added to the mixture and stirring was continued for 1 hour. The mixture was poured into water (125 mL) and the two layers were separated. The organic layer was washed with brine and evaporated under reduced pressure. The remaining solid was triturated with ethyl acetate:hexanes, collected via vacuum filtration, washed with hexane and dried in vacuo to give ethyl 4-amino-2-(methylthio)pyrimidine-5-carboxylate (4.74 g, 22.23 mmol, 51.7% yield) as a white solid. The filtrate was evaporated under reduced pressure and the remaining solid was triturated with 1:4 EtOAc-hexane, collected via vacuum filtration, washed with hexane and dried in vacuo to give ethyl 4-amino-2-(methylthio)pyrimidine-5-carboxylate (539 mg, 2.53 mmol, 5.9% yield) as a white solid. ¹H NMR (400 MHz, CD₃SOCD₃) δ 1.28 (t, J=7 Hz, 3H), 2.45 (s, 3H), 4.26 (q, J=7 Hz, 2H), 7.65 (br s, 1H), 8.03 (br s, 1H), 8.56 (s, 1H); LC-MS (LC-ES) M+H=214.

B. (4-Amino-2-(methylthio)pyrimidin-5-yl)methanol

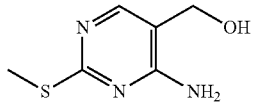

To a stirred, cooled (0° C.) solution of 1M lithium aluminum hydride (24 mL, 24.00 mmol) in tetrahydrofuran was added dropwise a solution of ethyl 4-amino-2-(methylthio)pyrimidine-5-carboxylate (4.73 g, 22.18 mmol) in tetrahydrofuran (75 mL) over 20 minutes. The mixture was warmed to room temperature and stirred for 30 minutes. The mixture was recooled to 0° C. and carefully quenched by the sequential addition of water (1 mL), 2N aqueous sodium hydroxide (1 mL) and water (3 mL). The ice bath was removed and stirring was continued for 10 minutes. The resulting suspension was filtered and the filter cake was washed with ethyl acetate (50 mL, 2X). Solvent was removed under reduced pressure and the remaining material was dried in vacuo to give (4-amino-2-(methylthio)pyrimidin-5-yl)methanol (3.07 g, 17.93 mmol, 81% yield) as a white solid. ¹H NMR (400 MHz, CD₃SOCD₃) δ 2.38 (s, 3H), 4.27 (dd, J=6, 1 Hz, 2H), 5.04 (t, J=6 Hz, 1H), 6.70 (br s, 2H), 7.88 (s, 1H); LC-MS (LC-ES) M+H=172.

C. 4-Amino-2-(methylthio)pyrimidine-5-carbaldehyde

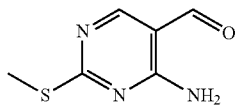

To a stirred solution of (4-amino-2-(methylthio)pyrimidin-5-yl)methanol (3.05 g, 17.81 mmol) in dichloromethane (150 mL) was added manganese dioxide (12.5 g, 144 mmol) and the mixture was stirred overnight. The mixture was filtered through a pad of Celite® and the filter cake was washed with dichloromethane (150 mL, 2X) and the filtrate was concentrated to give 4-amino-2-(methylthio)pyrimidine-5-carbaldehyde (1.76 g, 10.40 mmol, 58% yield) as a white solid. The Celite® filter cake was further washed with methanol (150 mL). This filtrate was evaporated to dryness to give 4-amino-2-(methylthio)pyrimidine-5-carbaldehyde (486 mg, 2.87 mmol, 16% yield) as a light gray solid. ¹H NMR (400 MHz, CD₃SOCD₃) δ 3.34 (s, 3H), 8.03 (br s, 1H), 8.31 (br s, 1H), 8.58 (s, 1H), 9.77 (s, 1H); LC-MS (LC-ES) M+H=170.

D. Ethyl 2-(methylthio)-7-oxo-7,8-dihydropyrido[2,3-d]pyrimidine-6-carboxylate

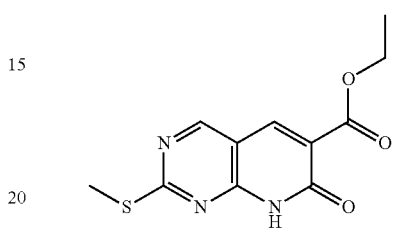

Diethyl malonate (2.40 mL, 15.73 mmol) was added to a stirred solution of 4-amino-2-(methylthio)pyrimidine-5-carbaldehyde (2.00 g, 11.82 mmol) in N,N-dimethylformamide (40 mL). Then, potassium carbonate (2.000 g, 14.47 mmol) was added and the reaction mixture was heated to 85° C. and stirred overnight. As starting material was still present, triethylamine (1.00 mL, 7.17 mmol) was added to the mixture with stirring continued overnight. Additional triethylamine (1.00 mL, 7.17 mmol) was added to the mixture and stirring was continued for 8 hours. Additional diethyl malonate (0.5 mL, 525 mg, 3.28 mmol) was added to the mixture and stirring was continued overnight. The reaction temperature was increased to 100° C. and stirring was continued for 1 hour. Additional diethyl malonate (0.5 mL, 525 mg, 3.28 mmol) was added, followed by triethylamine (1.00 mL, 7.17 mmol) and stirring was continued for 5 hours. Then the mixture was cooled to room temperature, poured into water (400 mL) and acidified with acetic acid (6 mL) to pH=4. Some solid precipitated and was collected via vacuum filtration. The filtrate was extracted with ethyl acetate (3×) and the combined organic layers were washed with brine, dried over sodium sulfate, filtered, and concentrated to give an orange solid. This material was combined with the previously collected tan solid and recrystallized from ethanol to give ethyl 2-(methylthio)-7-oxo-7,8-dihydropyrido[2,3-d]pyrimidine-6-carboxylate (903 mg, 3.40 mmol, 29% yield) as a tan solid. The mother liquor from the recrystallization was evaporated under reduced pressure. The remaining material was dissolved in a minimal amount of dichloromethane and purified via silica gel chromatography, eluting with ethyl acetate:hexanes (1:19 to 1:1) to give recovered starting material (230 mg) as a yellow solid. The aqueous layer from the previous workup contained solid material. This solid was collected via vacuum filtration, washed with water and dried in vacuo to give ethyl 2-(methylthio)-7-oxo-7,8-dihydropyrido[2,3-d]pyrimidine-6-carboxylate (496 mg, 1.87 mmol, 16% yield) as a tan solid. ¹H NMR (400 MHz, CD₃SOCD₃) δ 1.29 (t, J=7 Hz, 3H), 2.57 (s, 3H), 4.26 (q, J=7 Hz, 2H), 8.51 (s, 1H), 8.99 (s, 1H), 12.66 (br s, 1H); LC-MS (LC-ES) M+H=266.

E. Ethyl 7-chloro-2-(methylthio)pyrido[2,3-d]pyrimidine-6-carboxylate

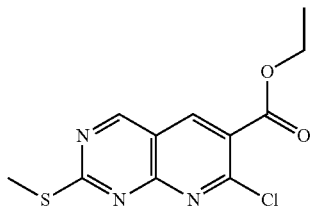 [SMILES: CCOC(=O)c1cc2cnc(SC)nc2nc1Cl]

A slurry of ethyl 2-(methylthio)-7-oxo-7,8-dihydropyrido[2,3-d]pyrimidine-6-carboxylate (0.795 g, 3.00 mmol) in phosphorus oxychloride (6 mL, 64.4 mmol) was heated to 100° C. and stirred for 4 hours. The mixture was still not homogeneous. Stirring was continued for 1 hour and the mixture became homogeneous. After cooling to room temperature, the mixture was carefully pipetted into rapidly stirring ice cold saturated aqueous sodium bicarbonate and carefully and slowly adjusted to pH=5 with saturated aqueous sodium bicarbonate. The mixture was stirred for 5 minutes and the resulting precipitate was collected via vacuum filtration, washed with water and dried in vacuo to give ethyl 7-chloro-2-(methylthio)pyrido[2,3-d]pyrimidine-6-carboxylate (681 mg, 2.40 mmol, 80% yield) as a tan solid. The filtrate was extracted with ethyl acetate (2×), washed with brine, dried over sodium sulfate, filtered, and concentrated to give ethyl 7-chloro-2-(methylthio)pyrido[2,3-d]pyrimidine-6-carboxylate (117 mg, 0.412 mmol, 14% yield) as a yellow solid. $^1$H NMR (400 MHz, CD$_3$SOCD$_3$) δ 1.36 (t, J=7 Hz, 3H), 2.65 (s, 3H), 4.40 (q, J=7 Hz, 2H), 9.10 (s, 1H), 9.51 (s, 1H); LC-MS (LC-ES) M+H=284.

F. Ethyl 2-(methylthio)pyrido[2,3-d]pyrimidine-6-carboxylate

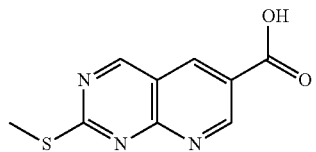

Acetonitrile (10 mL) was added to ethyl 7-chloro-2-(methylthio)pyrido[2,3-d]pyrimidine-6-carboxylate (678 mg, 2.390 mmol) and bis(triphenylphosphine)palladium(II) chloride (85 mg, 0.121 mmol) and the mixture was degassed by sparging with nitrogen for 15 minutes. Then, triethylsilane (0.50 mL, 3.13 mmol) was added to the mixture and it was heated to 80° C. and stirred overnight. After stirring at 80° C. for 19 hours, the mixture was cooled to room temperature and a solid precipitated. The solid was collected by vacuum filtration, washed with hexane and dried in vacuo to give ethyl 2-(methylthio)pyrido[2,3-d]pyrimidine-6-carboxylate (237 mg, 0.951 mmol, 39.8% yield) as a tan solid. The filtrate was evaporated to dryness, dissolved in a minimal amount of dichloromethane, containing enough methanol for complete solubilization, and purified by silica gel chromatography, eluting with ethyl acetate:hexanes (1:19 to 2:3) to give ethyl 2,7-bis(methylthio)pyrido[2,3-d]pyrimidine-6-carboxylate (101 mg, 0.342 mmol, 14% yield) as a yellow solid and ethyl 2-(methylthio)pyrido[2,3-d]pyrimidine-6-carboxylate (52 mg, 0.209 mmol, 9% yield) as a yellow solid. $^1$H NMR (400 MHz, CD$_3$SOCD$_3$) δ 1.38 (t, J=7 Hz, 3H), 2.66 (s, 3H), 4.41 (q, J=7 Hz, 2H), 9.13 (d, J=2 Hz, 1H), 9.51 (d, J=2 Hz, 1H), 9.65 (s, 1H); LC-MS (LC-ES) M+H=250.

G. 2-(Methylthio)pyrido[2,3-d]pyrimidine-6-carboxylic acid

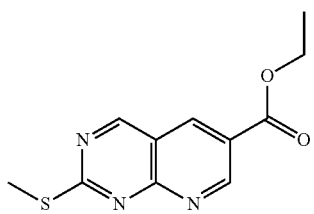 [SMILES: CCOC(=O)c1cnc2nc(SC)ncc2c1]

To a stirred suspension of ethyl 2-(methylthio)pyrido[2,3-d]pyrimidine-6-carboxylate (50 mg, 0.201 mmol) in tetrahydrofuran (1.5 mL) and methanol (0.5 mL) was added 1M aqueous lithium hydroxide (0.25 mL, 0.250 mmol). The mixture became homogeneous within a few minutes and was stirred for 1 hour, then concentrated. The remaining material was suspended in water (3 mL) and acidified with 1N aqueous hydrochloric acid. The solid was collected via vacuum filtration, washed with water and air dried. The filtrate was extracted with ethyl acetate and the organic layer was washed with brine, dried over sodium sulfate, filtered, and concentrated. The two isolated solids were combined, suspended in methanol, evaporated to dryness under reduced pressure, and placed in vacuo to give 2-(methylthio)pyrido[2,3-d]pyrimidine-6-carboxylic acid (33.5 mg, 0.151 mmol, 75% yield) as a yellow solid. $^1$H NMR (400 MHz, CD$_3$SOCD$_3$) δ 2.66 (s, 3H), 9.09 (d, J=2 Hz, 1H), 9.50 (d, J=2 Hz, 1H), 9.63 (s, 1H), 13.75 (br s, 1H); LC-MS (LC-ES) M+H=222.

Intermediate 39

7-Cyclobutyl-1,8-naphthyridine-3-carboxylic acid

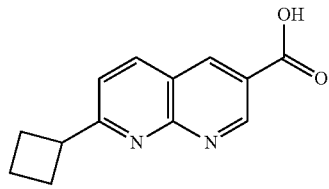 [SMILES: O=C(O)c1cnc2nc(C3CCC3)ccc2c1]

A. Ethyl 7-cyclobutyl-1,8-naphthyridine-3-carboxylate and Cyclobutyl 7-cyclobutyl-1,8-naphthyridine-3-carboxylate

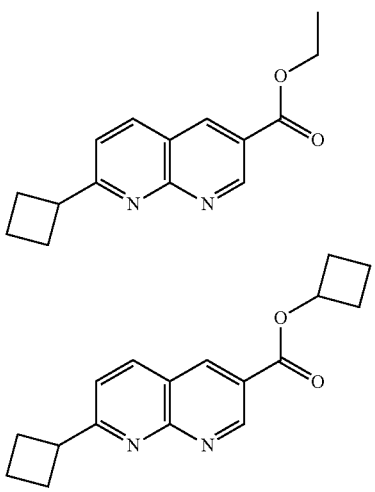

[1,1'-Bis(diphenylphosphino)ferrocene]dichloropalladium (II)-dichloromethane adduct (0.168 g, 0.206 mmol) was added to ethyl 7-chloro-1,8-naphthyridine-3-carboxylate (0.476 g, 2.011 mmol, Intermediate 4C), followed by tetrahydrofuran (20 mL) and the reaction mixture was purged with nitrogen. Then, cyclobutylzinc(II) bromide (4.5 mL, 2.250 mmol, 0.5 M in tetrahydrofuran) was added and the reaction mixture was heated at 60° C. for 90 minutes. Then, additional cyclobutylzinc(II) bromide (0.8 mL, 0.400 mmol, 0.5 M in tetrahydrofuran) was added. After 30 minutes, the reaction was allowed to cool to room temperature, combined with material from another reaction and purified via silica gel chromatography, eluting with (3:1 ethyl acetate:ethanol):hexanes (0:1 to 1:1 to 1:0) to give material that was further purified via silica gel chromatography, eluting with (9:1 methanol:ammonium hydroxide):dichloromethane (0:1 to 1:15) to give a mixture of ethyl 7-cyclobutyl-1,8-naphthyridine-3-carboxylate and cyclobutyl 7-cyclobutyl-1,8-naphthyridine-3-carboxylate (0.421 g, 1.643 mmol, 65% combined yield) as a tan-orange powder. LC-MS (LC-ES) M+H=257; LC-MS (LC-ES) M+H=283.

B. 7-Cyclobutyl-1,8-naphthyridine-3-carboxylic acid

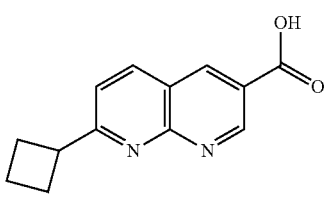 [SMILES: O=C(O)c1cnc2nc(C3CCC3)ccc2c1]

1N Sodium hydroxide (3.2 mL, 3.20 mmol) was added to the mixed ester ethyl/cyclobutyl 7-cyclobutyl-1,8-naphthyridine-3-carboxylate (0.421 g, 1.643 mmol) in methanol (10 mL) and the reaction mixture was stirred for 2.5 hours. Then, the reaction was quenched with 1N hydrochloric acid (3.2 mL) and concentrated to 6 mL volume. The solids were filtered off and rinsed with water, air-dried, and then dried under vacuum to give 7-cyclobutyl-1,8-naphthyridine-3-carboxylic acid (0.294 g, 1.288 mmol, 78% yield) as an orange-yellow powder. $^1$H NMR (400 MHz, CD$_3$SOCD$_3$) δ 1.84-1.96 (m, 1H), 2.00-2.14 (m, 1H), 2.32-2.48 (m, 4H), 3.91 (p, J=8 Hz, 1H), 7.59 (d, J=8 Hz, 1H), 8.53 (d, J=8 Hz, 1H), 8.98 (br s, 1H), 9.41 (d, J=2 Hz, 1H), 13.59 (br s, 1H); LC-MS (LC-ES) M+H=229.

Intermediate 40

(S)-3-Amino-4,4-dimethylpyrrolidin-2-one

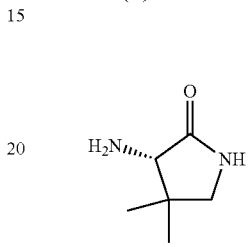

A. (R)-4,4-Dimethyl-2-oxotetrahydrofuran-3-yl trifluoromethanesulfonate

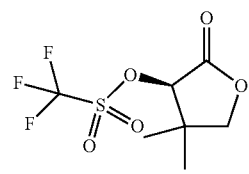 [SMILES: CC1(C)COC(=O)[C@@H]1OS(=O)(=O)C(F)(F)F]

Pyridine (2.8 mL, 34.6 mmol) was added to (R)-pantolactone (3.507 g, 26.9 mmol) in dichloromethane (27 mL) under nitrogen and the reaction mixture was cooled in a dry ice/acetone bath. Then, trifluoromethanesulfonic anhydride (5 mL, 29.7 mmol) was added over ~4 minutes. After two hours, the reaction mixture was allowed to warm to room temperature and stirred for seventeen hours. The reaction mixture was diluted with dichloromethane (50 mL), washed with 10% aqueous citric acid solution (25 mL, 2X) and brine (25 mL), dried over magnesium sulfate, filtered, and concentrated. Diethyl ether was added and the mixture was reconcentrated to give (R)-4,4-dimethyl-2-oxotetrahydrofuran-3-yl trifluoromethanesulfonate (6.905 g, 26.3 mmol, 98% yield) as a yellow-orange liquid. $^1$H NMR (400 MHz, CD$_3$SOCD$_3$) δ 1.06 (s, 3H), 1.19 (s, 3H), 4.19 (q, J=9 Hz, 2H), 5.95 (s, 1H); LC-MS (LC-ES) M+H=263.

B. (S)-3-Azido-4,4-dimethyldihydrofuran-2(3H)-one

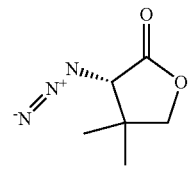

(R)-4,4-Dimethyl-2-oxotetrahydrofuran-3-yl trifluoromethanesulfonate (4.525 g, 17.26 mmol) in toluene (25 mL) was added to tetrabutylammonium azide (4.91 g, 17.26 mmol) in toluene (75 mL) at room temperature and the reaction mixture was stirred for seventeen hours, then partially concentrated. The mixture was diluted with water (100 mL) and extracted with diethyl ether (50 mL, 3X), then brine (25 mL) was added. Three layers formed. The middle and upper layers were pooled, dried over magnesium sulfate, filtered, and concentrated. The oil was absorbed directly onto silica gel and purified via silica gel chromatography, eluting with ethyl acetate:hexanes (0:1 to 1:1) to give (S)-3-azido-4,4-dimethyldihydrofuran-2(3H)-one (2.241 g, 14.44 mmol, 84% yield) as a cream-colored solid. $^1$H NMR (400 MHz, CD$_3$SOCD$_3$) δ 0.93 (s, 3H), 1.12 (s, 3H), 4.03 (q, J=9 Hz, 2H), 4.64 (s, 1H); LC-MS (LC-ES) M+H=156.

C. (S)-2-Azido-4-hydroxy-N-(4-methoxybenzyl)-3,3-dimethylbutanamide

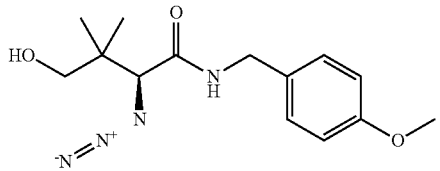

(4-Methoxyphenyl)methanamine (1.34 mL, 10.26 mmol) was added to (S)-3-azido-4,4-dimethyldihydrofuran-2(3H)-one (1.444 g, 9.31 mmol) in tetrahydrofuran (20 mL). Then, the reaction mixture was purged with nitrogen and heated to 60° C. and stirred for twenty-three hours. The reaction mixture was diluted with diethyl ether (100 mL), washed with 1N hydrochloric acid (25 mL, 2X) and brine (25 mL), dried over magnesium sulfate, filtered, and concentrated. Dichloromethane was added to the residue and the mixture was absorbed onto silica gel and purified via silica gel chromatography, eluting with ethyl acetate:hexanes (0:1 to 3:1) to give (S)-2-azido-4-hydroxy-N-(4-methoxybenzyl)-3,3-dimethylbutanamide (1.569 g, 5.37 mmol, 57.7% yield) as a colorless oil. $^1$H NMR (400 MHz, CD$_3$SOCD$_3$) δ 0.84 (s, 3H), 0.86 (s, 3H), 3.09 (dd, J=10, 5 Hz, 1H), 3.25 (dd, J=10, 5 Hz, 1H), 3.71 (s, 3H), 3.85 (s, 1H), 4.22 (dq, J=14, 6 Hz, 2H), 4.79 (t, J=5 Hz, 1H), 6.87 (d, J=9 Hz, 2H), 7.19 (d, J=9 Hz, 2H), 8.65 (br t, J=6 Hz, 1H); LC-MS (LC-ES) M+H=293.

D. (S)-3-Azido-1-(4-methoxybenzyl)-4,4-dimethylpyrrolidin-2-one

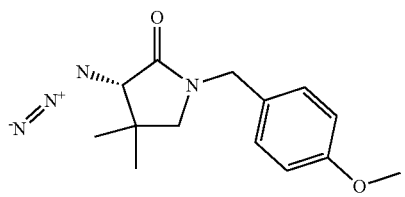

Triphenylphosphine (1.692 g, 6.45 mmol) was added to (S)-2-azido-4-hydroxy-N-(4-methoxybenzyl)-3,3-dimethylbutanamide (1.569 g, 5.37 mmol) in tetrahydrofuran (40 mL) and the reaction mixture was cooled to 0° C. Then, diisopropyl azodicarboxylate (1.25 mL, 6.43 mmol) in tetrahydrofuran (10 mL) was added over 18 minutes and the reaction mixture was allowed to warm to room temperature and stirred for five days. The reaction mixture was diluted with dichloromethane, absorbed onto silica gel, and purified via silica gel chromatography, eluting with ethyl acetate:hexanes (0:1 to 1:2) to give (S)-3-azido-1-(4-methoxybenzyl)-4,4-dimethylpyrrolidin-2-one (1.153 g, 4.20 mmol, 78% yield) as a yellow oil. $^1$H NMR (400 MHz, CD$_3$SOCD$_3$) δ 0.82 (s, 3H), 1.06 (s, 3H), 2.83 (d, J=10 Hz, 1H), 2.96 (d, J=10 Hz, 1H), 3.72 (s, 3H), 4.22 (s, 1H), 4.30 (ABq, J$_{AB}$=14 Hz, Δv$_{AB}$=52 Hz, 2H), 6.90 (d, J=9 Hz, 2H), 7.15 (d, J=9 Hz, 2H); LC-MS (LC-ES) M+H=275.

E. (S)-3-Azido-4,4-dimethylpyrrolidin-2-one

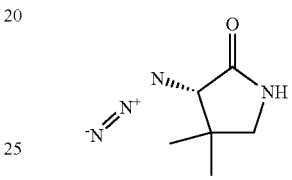

Ceric ammonium nitrate (6.913 g, 12.61 mmol) in water (10 mL) was added to (S)-3-azido-1-(4-methoxybenzyl)-4,4-dimethylpyrrolidin-2-one (1.153 g, 4.20 mmol) in acetonitrile (50 mL) at 0° C. and the reaction mixture was allowed to warm to room temperature and stirred for forty-three hours. The reaction mixture was partitioned between water (100 mL) and ethyl acetate (250 mL) and the layers were separated. The organics were washed with water (100 mL) and the aqueous layers were combined with the aqueous layers from another reaction and dichloromethane (25 mL) was added, forming an emulsion. The mixture was diluted with brine (50 mL), the clear aqueous layer was removed and sodium chloride was added to the remaining emulsion, followed by filtration over a pad of Celite®, and separation of the layers. All the organic layers were combined, dried over magnesium sulfate, filtered, and concentrated. The residue was dissolved in methanol (10 mL) and 4-methoxybenzylamine (0.10 mL, 0.765 mmol) was added. The reaction mixture was stirred 30 minutes then more 4-methoxybenzylamine (0.10 mL, 0.765 mmol) was added. After stirring for 3 days, more 4-methoxybenzylamine (0.10 mL, 0.765 mmol) was added. After five hours even more 4-methoxybenzylamine (0.10 mL, 0.765 mmol) was added and the reaction mixture was stirred two hours and then concentrated. Diethyl ether (10 mL) was added to the residue and the precipitate was removed by filtration and the filtrate was absorbed onto silica gel and purified via silica gel chromatography, eluting with (ethyl acetate:ethanol (3:1)):hexanes (0:1 to 1:0), then further purified via silica gel chromatography, eluting with ethyl acetate:hexanes (0:1 to 1:0) to give (S)-3-azido-4,4-dimethylpyrrolidin-2-one (0.409 g, 2.65 mmol, 61% yield) as a peach-tan powder. $^1$H NMR (400 MHz, CD$_3$SOCD$_3$) δ 0.91 (s, 3H), 1.09 (s, 3H), 2.88 (dd, J=10, 2 Hz, 1H), 2.97 (d, J=10 Hz, 1H), 4.04 (s, 1H), 8.01 (br s, 1H); LC-MS (LC-ES) M+H=155.

F. (S)-3-Amino-4,4-dimethylpyrrolidin-2-one

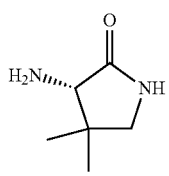

5% Palladium on carbon (0.097 g, 2.65 mmol) in a minimal amount of water was added to (S)-3-azido-4,4-dimethylpyrrolidin-2-one (0.409 g, 2.65 mmol) in ethanol (25 mL) under nitrogen. The reaction mixture was evacuated and back-filled with hydrogen and stirred for nineteen hours. The reaction mixture was purged with nitrogen, filtered through Celite®, washed with ethanol, and concentrated. The residue was dissolved in methanol and filtered over a syringe disk filter, and concentrated. Methanol was added and the mixture was concentrated again to give (S)-3-amino-4,4-dimethylpyrrolidin-2-one (0.335 g, 2.61 mmol, 99% yield) as a light tan solid. $^1$H NMR (400 MHz, CD$_3$SOCD$_3$) δ 0.82 (s, 3H), 1.03 (s, 3H), 1.48 (s, 2H), 2.81 (dd, J=9, 2 Hz, 1H), 2.88 (d, J=9 Hz, 1H), 2.94 (s, 1H), 7.53 (br s, 1H); LC-MS (LC-ES) M+H=129.

Intermediate 41

Lithium 2-(azetidin-1-yl)pyrido[2,3-d]pyrimidine-6-carboxylate

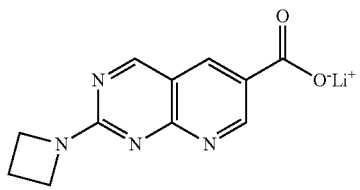

A. Ethyl 2-(methylsulfonyl)pyrido[2,3-d]pyrimidine-6-carboxylate

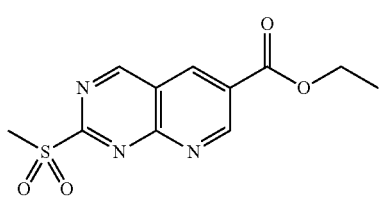 [SMILES: CCOC(=O)c1cnc2nc(S(C)(=O)=O)ncc2c1]

To a stirred, cooled (0° C.) solution of ethyl 2-(methylthio)pyrido[2,3-d]pyrimidine-6-carboxylate (200 mg, 0.802 mmol, Intermediate 38F) in dichloromethane (10 mL) was added 3-chloroperoxybenzoic acid (360 mg, 1.606 mmol). The mixture was stirred for three hours, then quenched with saturated aqueous sodium bicarbonate, extracted with dichloromethane (2×), washed with brine, dried over sodium sulfate, filtered, and concentrated to give impure ethyl 2-(methylsulfonyl)pyrido[2,3-d]pyrimidine-6-carboxylate (175 mg), which was carried forward into the next reaction. LC-MS (LC-ES) M+H=282.

B. Ethyl 2-(azetidin-1-yl)pyrido[2,3-d]pyrimidine-6-carboxylate

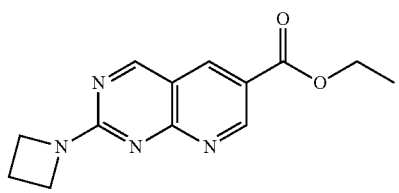 [SMILES: CCOC(=O)c1cnc2nc(N3CCC3)ncc2c1]

To crude ethyl 2-(methylsulfonyl)pyrido[2,3-d]pyrimidine-6-carboxylate (98 mg, 0.348 mmol) and azetidine hydrochloride (65 mg, 0.695 mmol) was added N-methyl-2-pyrrolidone (1.5 mL), followed by N,N-diisopropylethylamine (0.25 mL, 1.431 mmol), and the reaction mixture was heated with stirring in a microwave at 100° C. for two hours. After cooling to room temperature, the mixture was loaded onto a pre-packed Celite® cartridge and purified by reverse phase chromatography, eluting with acetonitrile:water with 0.1% ammonium hydroxide (0:1 to 4:1) to give ethyl 2-(azetidin-1-yl)pyrido[2,3-d]pyrimidine-6-carboxylate (10 mg, 0.039 mmol, 11.1% yield) as a yellow solid. $^1$H NMR (400 MHz, CD$_3$OD) δ 1.47 (t, J=7 Hz, 3H), 2.52 (p, J=8 Hz, 2H), 4.38 (t, J=8 Hz, 4H), 4.47 (q, J=7 Hz, 2H), 8.86 (d, J=2 Hz, 1H), 9.27 (s, 1H), 9.37 (d, J=2 Hz, 1H); LC-MS (LC-ES) M+H=259.

C. Lithium 2-(azetidin-1-yl)pyrido[2,3-d]pyrimidine-6-carboxylate

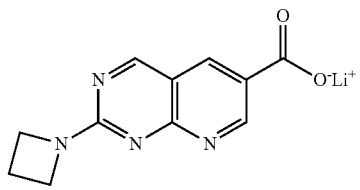

To a stirred solution of ethyl 2-(azetidin-1-yl)pyrido[2,3-d]pyrimidine-6-carboxylate (17 mg, 0.066 mmol) in methanol (1 mL) at room temperature was added 1M aqueous lithium hydroxide (0.20 mL, 0.200 mmol). The mixture was stirred for three hours, then methanol (1 mL) and 1M aqueous lithium hydroxide (0.1 mL, 0.100 mmol) were added and the reaction mixture was stirred for 90 minutes. Then, the reaction mixture was heated at 50° C. for 1 hour, cooled, and concentrated to give lithium 2-(azetidin-1-yl)pyrido[2,3-d]pyrimidine-6-carboxylate (25 mg, 0.106 mmol, 161% yield). $^1$H NMR (400 MHz, CD$_3$SOCD$_3$) δ 2.35 (p, J=8 Hz, 2H), 4.16 (t, J=8 Hz, 4H), 8.50 (d, J=2 Hz, 1H), 9.23 (s, 1H), 9.29 (d, J=2 Hz, 1H); LC-MS (LC-ES) M+H=231.

Intermediate 42

2-Methoxypyrido[2,3-d]pyrimidine-6-carboxylic acid

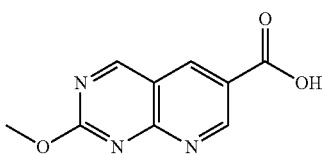

A. Ethyl 2-(methylsulfinyl)pyrido[2,3-d]pyrimidine-6-carboxylate

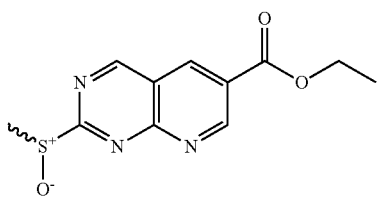 [SMILES: CCOC(=O)c1cnc2nc([S+](C)[O-])ncc2c1]

To a stirred, cooled (0° C.) solution of ethyl 2-(methylthio)pyrido[2,3-d]pyrimidine-6-carboxylate (200 mg, 0.802 mmol, Intermediate 38F) in dichloromethane (10 mL) was added 3-chloroperoxybenzoic acid (370 mg, 1.651 mmol). The mixture was stirred for 30 minutes. The mixture was poured into saturated aqueous sodium bicarbonate and extracted with dichloromethane (2×). The combined organic layers were washed with brine, dried over sodium sulfate, filtered, and concentrated to give crude ethyl 2-(methylsulfinyl)pyrido[2,3-d]pyrimidine-6-carboxylate, containing some ethyl 2-(methylsulfonyl)pyrido[2,3-d]pyrimidine-6-carboxylate (155 mg) which was carried forward to the next reaction. $^1$H NMR (400 MHz, CD$_3$SOCD$_3$) δ 1.40 (t, J=7 Hz, 3H), 3.00 (s, 3H), 4.46 (q, J=7 Hz, 2H), 9.36 (d, J=2 Hz, 1H), 9.73 (d, J=2 Hz, 1H), 10.04 (s, 1H); LC-MS (LC-ES) M+H=266.

B. Methyl 2-methoxypyrido[2,3-d]pyrimidine-6-carboxylate

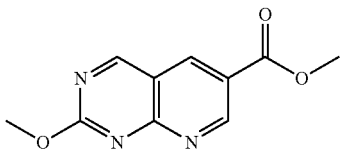

To a stirred solution of crude ethyl 2-(methylsulfinyl)pyrido[2,3-d]pyrimidine-6-carboxylate (154 mg, 0.581 mmol) in methanol (5 mL) was added 25% sodium methoxide (1 mL, 4.37 mmol) in methanol. A precipitate formed immediately upon addition of the sodium methoxide. The mixture was stirred for 20 minutes, then filtered and the collected solid was washed with a small amount of methanol and dried in vacuo to give methyl 2-methoxypyrido[2,3-d]pyrimidine-6-carboxylate (47 mg, 0.214 mmol, 37% yield) as a white solid. $^1$H NMR (400 MHz, CD$_3$SOCD$_3$) δ 3.10 (s, 3H), 3.25 (s, 3H), 8.32 (d, J=2 Hz, 1H), 8.66 (d, J=2 Hz, 1H), 8.88 (s, 1H); LC-MS (LC-ES) M+H=220.

C. 2-Methoxypyrido[2,3-d]pyrimidine-6-carboxylic acid

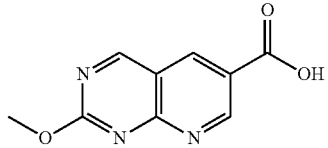

To a stirred suspension of methyl 2-methoxypyrido[2,3-d]pyrimidine-6-carboxylate (45 mg, 0.205 mmol) in tetrahydrofuran (1.5 mL) and methanol (0.5 mL) was added 1M aqueous lithium hydroxide (0.25 mL, 0.250 mmol). The mixture eventually became homogeneous and was stirred for 1 hour. The solvent was removed under reduced pressure. The remaining material was suspended in water, acidified with 1N aqueous hydrochloric acid and extracted with ethyl acetate (2×). The combined organic layers were washed with brine, dried over sodium sulfate, filtered, and concentrated to give 2-methoxypyrido[2,3-d]pyrimidine-6-carboxylic acid (18 mg, 0.088 mmol, 43% yield) as a white solid. $^1$H NMR (400 MHz, CD$_3$SOCD$_3$) δ 4.09 (s, 3H), 9.10 (d, J=2 Hz, 1H), 9.49 (d, J=2 Hz, 1H), 9.71 (s, 1H), 13.68 (br s, 1H); LC-MS (LC-ES) M+H=206.

Intermediate 43

Lithium 2-cyclopropylpyrido[2,3-d]pyrimidine-6-carboxylate

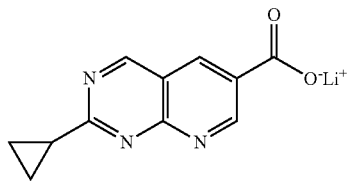

A. N-(5-Bromo-3-formylpyridin-2-yl)cyclopropanecarboxamide

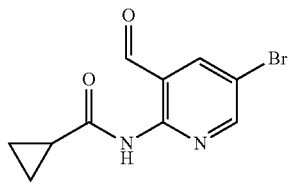 [SMILES: O=Cc1cc(Br)cnc1NC(=O)C1CC1]

Cyclopropanecarbonyl chloride (1 mL, 11.02 mmol) was added to a stirred solution of 2-amino-5-bromonicotinaldehyde (1 g, 4.97 mmol) and pyridine (2 mL, 24.73 mmol) in dichloromethane (20 mL) and the mixture was stirred for 30 minutes. The mixture was evaporated to dryness under reduced pressure and placed in vacuo for 15 minutes to give a brown foam. This material was dissolved in tetrahydrofuran (30 mL) and methanol (10 mL) and then 1N aqueous sodium hydroxide (15 mL, 15.00 mmol) was added dropwise. The mixture was stirred for 10 minutes and the mixture was concentrated under reduced pressure. The remaining material was triturated with water to give a solid which was collected via vacuum filtration, washed with water and dried in vacuo overnight to give N-(5-bromo-3-formylpyridin-2-yl)cyclopropanecarboxamide (1.21 g, 4.50 mmol, 90% yield) as a tan solid. $^1$H NMR (400 MHz, CD$_3$SOCD$_3$) δ 0.80-0.92 (m, 4H), 1.98-2.08 (m, 1H), 8.19 (d, J=2 Hz, 1H), 8.76 (d, J=2 Hz, 1H), 9.56 (s, 1H), 11.27 (br s, 1H); LC-MS (LC-ES) M+H=269.

B. 6-Bromo-2-cyclopropylpyrido[2,3-d]pyrimidine

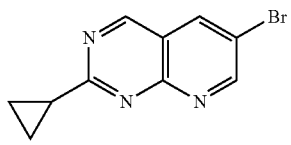 [SMILES: Brc1cnc2nc(C3CC3)ncc2c1]

7M Ammonia (30 mL, 210 mmol) in methanol was added to N-(5-bromo-3-formylpyridin-2-yl)cyclopropanecarboxamide (1.20 g, 4.46 mmol) suspended in methanol (20 mL). The mixture quickly became homogeneous. The reaction vessel was sealed and the mixture was heated at 80° C. overnight, then, the mixture was cooled and concentrated under reduced pressure. The remaining material was dissolved in dichloromethane and purified via silica gel chromatography, eluting with ethyl acetate:hexanes (1:9 to 9:1) to give 6-bromo-2-cyclopropylpyrido[2,3-d]pyrimidine (745 mg, 2.98 mmol, 66.8% yield) as a yellow solid. $^1$H NMR (400 MHz, CD$_3$SOCD$_3$) δ 1.14-1.22 (m, 4H), 2.36-2.44 (m, 1H), 8.87 (d, J=3 Hz, 1H), 9.24 (d, J=3 Hz, 1H), 9.51 (s, 1H); LC-MS (LC-ES) M+H=250.

C. Ethyl 2-cyclopropylpyrido[2,3-d]pyrimidine-6-carboxylate

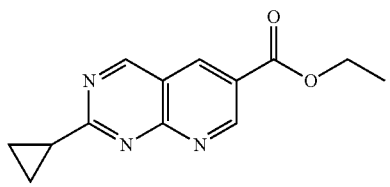 [SMILES: CCOC(=O)c1cnc2nc(C3CC3)ncc2c1]

A stirred mixture of 6-bromo-2-cyclopropylpyrido[2,3-d]pyrimidine (100 mg, 0.400 mmol), [1,1'-bis(diphenylphosphino)ferrocene]dichloropalladium(II) dichloromethane adduct (50 mg, 0.061 mmol) and N,N-diisopropylethylamine (0.35 mL, 2.004 mmol) in ethanol (5 mL) was purged with nitrogen for 3 minutes, followed by purging with carbon monoxide for 5 minutes. The mixture was stirred under a carbon monoxide balloon and heated at 80° C. overnight. After cooling to room temperature, the mixture was filtered through a pad of Celite®, rinsing with ethanol. The filtrate was evaporated to dryness under reduced pressure and the remaining dark material was dissolved in a minimal amount of dichloromethane and purified via silica chromatography, eluting with ethyl acetate:ethanol (3:1): hexanes (1:19 to 1:1) to give ethyl 2-cyclopropylpyrido[2,3-d]pyrimidine-6-carboxylate (63 mg, 0.259 mmol, 64.8% yield) as a white solid. $^1$H NMR (400 MHz, CD$_3$SOCD$_3$) δ 1.20-1.26 (m, 4H), 1.38 (t, J=7 Hz, 3H), 2.38-2.48 (m, 1H), 4.41 (q, J=7 Hz, 2H), 9.15 (d, J=2 Hz, 1H), 9.55 (d, J=2 Hz, 1H), 9.73 (s, 1H); LC-MS (LC-ES) M+H=244.

D. Lithium 2-cyclopropylpyrido[2,3-d]pyrimidine-6-carboxylate

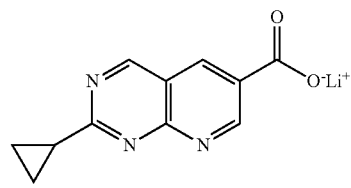

To a stirred solution of ethyl 2-cyclopropylpyrido[2,3-d]pyrimidine-6-carboxylate (62 mg, 0.255 mmol) in methanol (4 mL) was added 1M aqueous lithium hydroxide (0.80 mL, 0.800 mmol). The mixture was stirred for two hours, then concentrated, slurried with methanol and reconcentrated (2×) to give crude lithium 2-cyclopropylpyrido[2,3-d]pyrimidine-6-carboxylate (77 mg, 0.348 mmol, >100% yield) which was carried forward to the next reaction. $^1$H NMR (400 MHz, CD$_3$SOCD$_3$) δ 1.10-1.18 (m, 4H), 2.32-2.42 (m, 1H), 8.74 (d, J=2 Hz, 1H), 9.54 (s, 1H), 9.55 (d, J=2 Hz, 1H); LC-MS (LC-ES) M+H=216.

EXAMPLES

Example 1

N-(trans-4-(2-Hydroxypropan-2-yl)cyclohexyl)-1,6-naphthyridine-3-carboxamide

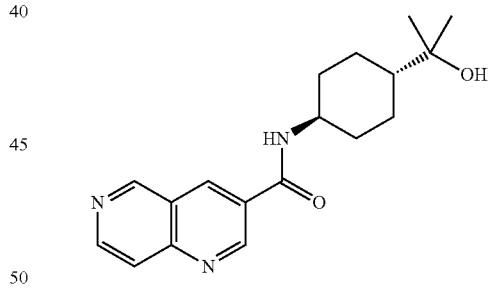

N,N-Di-iso-propylethylamine (0.471 mL, 2.70 mmol) was added to 1,6-naphthyridine-3-carboxylic acid (0.0783 g, 0.450 mmol) in 1,4-dioxane (2.248 mL) at room temperature. Then, 2-(trans-4-aminocyclohexyl)propan-2-ol (0.078 g, 0.495 mmol) was added and the reaction mixture was stirred for five minutes. Then, n-propylphosphonic acid anhydride (0.535 mL, 0.899 mmol) was added and the reaction mixture was stirred for sixty-six hours. The reaction mixture was poured into saturated sodium bicarbonate, extracted with ethyl acetate (3×), dried over magnesium sulfate, filtered, and concentrated. The residue was purified by silica gel chromatography, eluting with methanol:ethyl acetate (1:4) to give N-(trans-4-(2-hydroxypropan-2-yl)cyclohexyl)-1,6-naphthyridine-3-carboxamide (0.0410 g, 0.124 mmol, 27.6% yield). $^1$H NMR (400 MHz, CD$_3$SOCD$_3$) δ 1.05 (s, 6H), 1.06-1.26 (m, 3H), 1.33 (q, J=12

Hz, 2H), 1.85 (br d, J=11 Hz, 2H), 1.96 (br d, J=10 Hz, 2H), 3.76 (qt, J=8, 4 Hz, 1H), 4.05 (s, 1H), 7.97 (d, J=6 Hz, 1H), 8.68 (d, J=8 Hz, 1H), 8.81 (d, J=6 Hz, 1H), 8.99 (d, J=2 Hz, 1H), 9.46 (d, J=2 Hz, 1H), 9.50 (s, 1H); LC-MS (LC-ES) M+H=314.

Example 2

N-(trans-4-(2-Hydroxypropan-2-yl)cyclohexyl)-1,8-naphthyridine-3-carboxamide

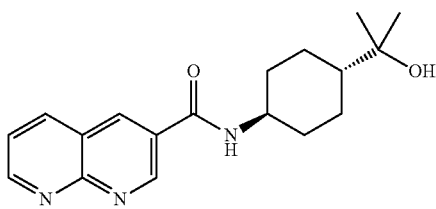 [SMILES: CC(C)(O)[C@H]1CC[C@H](NC(=O)c2cnc3ncccc3c2)CC1]

N,N-Di-iso-propylethylamine (0.629 mL, 3.60 mmol) was added to 1,8-naphthyridine-3-carboxylic acid (0.1046 g, 0.601 mmol) in 1,4-dioxane (3.00 mL) at room temperature. Then, 2-(trans-4-aminocyclohexyl)propan-2-ol (0.142 g, 0.901 mmol) was added and the reaction mixture was stirred for five minutes. Then, n-propylphosphonic acid anhydride (0.715 mL, 1.201 mmol) was added and the reaction mixture was stirred for sixteen hours. The reaction mixture was poured into saturated sodium bicarbonate, extracted with ethyl acetate (3×), dried over magnesium sulfate, filtered, and concentrated. The residue was purified by silica gel chromatography, eluting with methanol:ethyl acetate (1:4) to give N-(trans-4-(2-hydroxypropan-2-yl)cyclohexyl)-1,8-naphthyridine-3-carboxamide (0.0449 g, 0.136 mmol, 22.66% yield). $^1$H NMR (400 MHz, CD$_3$SOCD$_3$) δ 1.05 (s, 6H), 1.04-1.26 (m, 3H), 1.33 (q, J=12 Hz, 2H), 1.85 (br d, J=11 Hz, 2H), 1.96 (br d, J=10 Hz, 2H), 3.76 (qt, J=8, 4 Hz, 1H), 4.04 (s, 1H), 7.71 (dd, J=8, 4 Hz, 1H), 8.58 (dd, J=8, 2 Hz, 1H), 8.63 (d, J=8 Hz, 1H), 8.88 (d, J=2 Hz, 1H), 9.15 (dd, J=4, 2 Hz, 1H), 9.42 (d, J=2 Hz, 1H); LC-MS (LC-ES) M+H=314.

Example 3

7-(3-Fluoroazetidin-1-yl)-N-(trans-4-(2-hydroxypropan-2-yl)cyclohexyl)-1,6-naphthyridine-3-carboxamide

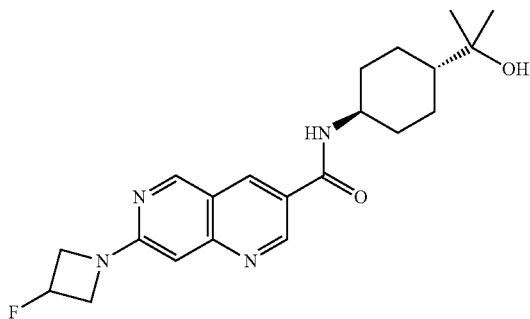 [SMILES: CC(C)(O)[C@H]1CC[C@H](NC(=O)c2cnc3cc(N4CC(F)C4)ncc3c2)CC1]

N,N-Diisopropylethylamine (0.230 mL, 1.315 mmol) was added to 7-(3-fluoroazetidin-1-yl)-1,6-naphthyridine-3-carboxylic acid ammonia salt (0.0579 g, 0.219 mmol, Intermediate 2) in N,N-dimethylformamide (0.730 mL) at room temperature. Then, 2-(trans-4-aminocyclohexyl)propan-2-ol (0.041 g, 0.263 mmol) was added and the reaction mixture was stirred for five minutes. Then, n-propylphosphonic acid anhydride (0.261 mL, 0.438 mmol) was added and the reaction mixture was stirred for sixty-four hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-(3-fluoroazetidin-1-yl)-N-(trans-4-(2-hydroxypropan-2-yl)cyclohexyl)-1,6-naphthyridine-3-carboxamide (0.0622 g, 0.153 mmol, 69.8% yield). $^1$H NMR (400 MHz, CD$_3$SOCD$_3$) δ 1.04 (s, 6H), 1.06-1.24 (m, 3H), 1.30 (q, J=13 Hz, 2H), 1.83 (br d, J=12 Hz, 2H), 1.92 (br d, J=12 Hz, 2H), 3.64-3.78 (m, 1H), 4.03 (s, 1H), 4.14 (br dd, J=24, 10 Hz, 2H), 4.34-4.48 (m, 2H), 5.38-5.68 (m, 1H), 6.70 (s, 1H), 8.42 (d, J=7 Hz, 1H), 8.73 (s, 1H), 9.09 (s, 1H), 9.21 (s, 1H); LC-MS (LC-ES) M+H=387.

Example 4

7-(Azetidin-1-yl)-N-(trans-4-(2-hydroxypropan-2-yl)cyclohexyl)-1,6-naphthyridine-3-carboxamide

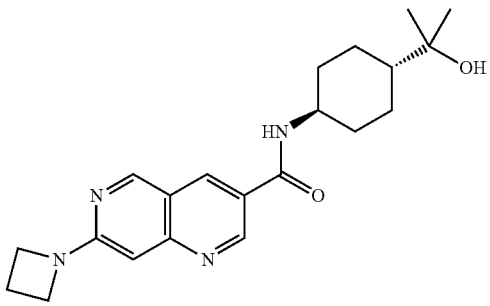 [SMILES: CC(C)(O)[C@H]1CC[C@H](NC(=O)c2cnc3cc(N4CCC4)ncc3c2)CC1]

N,N-Diisopropylethylamine (0.265 mL, 1.517 mmol) was added to 7-(azetidin-1-yl)-1,6-naphthyridine-3-carboxylic acid lithium salt (0.0597 g, 0.253 mmol, Intermediate 3) in N,N-dimethylformamide (0.843 mL) at room temperature. Then, 2-(trans-4-aminocyclohexyl)propan-2-ol (0.048 g, 0.303 mmol) was added and the reaction mixture was stirred for five minutes. Then, n-propylphosphonic acid anhydride (0.301 mL, 0.506 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 3:7) to give 7-(azetidin-1-yl)-N-(trans-4-(2-hydroxypropan-2-yl)cyclohexyl)-1,6-naphthyridine-3-carboxamide (0.0514 g, 0.133 mmol, 52.4% yield). $^1$H NMR (400 MHz, CD$_3$SOCD$_3$) δ 1.04 (s, 6H), 1.04-1.24 (m, 3H), 1.29 (q, J=12 Hz, 2H), 1.83 (br d, J=12 Hz, 2H), 1.91 (br d, J=12 Hz, 2H), 2.39 (p, J=7 Hz, 2H), 3.64-3.78 (m, 1H), 4.03 (s, 1H), 4.08 (t, J=7 Hz, 4H), 6.54 (s, 1H), 8.38 (d, J=7 Hz, 1H), 8.69 (s, 1H), 9.04 (s, 1H), 9.17 (s, 1H); LC-MS (LC-ES) M+H=369.

Example 5

7-(Azetidin-1-yl)-N-(trans-4-(2-hydroxypropan-2-yl)cyclohexyl)-1,8-naphthyridine-3-carboxamide

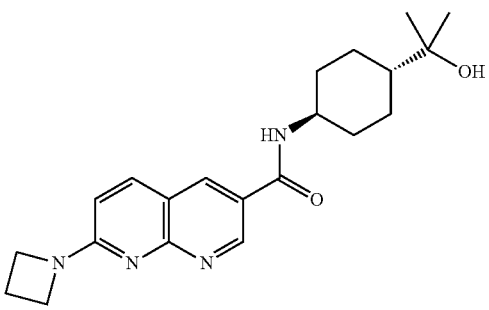

N,N-Diisopropylethylamine (0.298 mL, 1.707 mmol) was added to 7-(azetidin-1-yl)-1,8-naphthyridine-3-carboxylic acid lithium salt (0.0672 g, 0.285 mmol, Intermediate 5) in N,N-dimethylformamide (0.948 mL) at room temperature. Then, 2-(trans-4-aminocyclohexyl)propan-2-ol (0.054 g, 0.341 mmol) was added and the reaction mixture was stirred for five minutes. Then, n-propylphosphonic acid anhydride (0.339 mL, 0.569 mmol) was added and the reaction mixture was stirred for sixty-six hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-(azetidin-1-yl)-N-(trans-4-(2-hydroxypropan-2-yl)cyclohexyl)-1,8-naphthyridine-3-carboxamide (0.0648 g, 0.167 mmol, 58.7% yield). $^1$H NMR (400 MHz, CD$_3$SOCD$_3$) δ 1.04 (s, 6H), 1.04-1.24 (m, 3H), 1.30 (q, J=11 Hz, 2H), 1.83 (br d, J=11 Hz, 2H), 1.92 (br d, J=11 Hz, 2H), 2.39 (p, J=7 Hz, 2H), 3.66-3.78 (m, 1H), 4.02 (s, 1H), 4.16 (t, J=7 Hz, 4H), 6.78 (d, J=9 Hz, 1H), 8.08 (d, J=9 Hz, 1H), 8.31 (d, J=7 Hz, 1H), 8.51 (s, 1H), 9.10 (s, 1H); LC-MS (LC-ES) M+H=369.

Example 6

7-(3-Fluoroazetidin-1-yl)-N-(trans-4-(2-hydroxypropan-2-yl)cyclohexyl)-1,8-naphthyridine-3-carboxamide

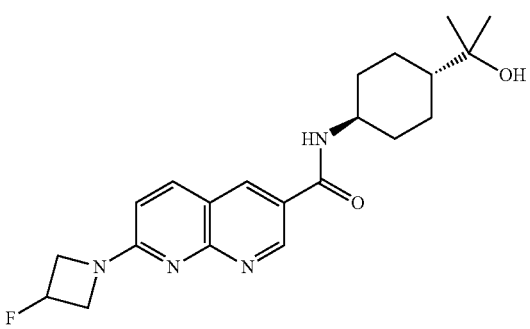 [SMILES: CC(C)(O)[C@H]1CC[C@H](NC(=O)c2cnc3nc(N4CC(F)C4)ccc3c2)CC1]

N,N-Diisopropylethylamine (0.278 mL, 1.591 mmol) was added to 7-(3-fluoroazetidin-1-yl)-1,8-naphthyridine-3-carboxylic acid lithium salt (0.0674 g, 0.265 mmol, Intermediate 6) in N,N-dimethylformamide (0.88 mL) at room temperature. Then, 2-(trans-4-aminocyclohexyl)propan-2-ol (0.050 g, 0.318 mmol) was added and the reaction mixture was stirred for five minutes. Then, n-propylphosphonic acid anhydride (0.316 mL, 0.530 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-(3-fluoroazetidin-1-yl)-N-(trans-4-(2-hydroxypropan-2-yl)cyclohexyl)-1,8-naphthyridine-3-carboxamide (0.0748 g, 0.184 mmol, 69.3% yield). $^1$H NMR (400 MHz, CD$_3$SOCD$_3$) δ 1.04 (s, 6H), 1.04-1.24 (m, 3H), 1.30 (q, J=12 Hz, 2H), 1.83 (br d, J=11 Hz, 2H), 1.92 (br d, J=11 Hz, 2H), 3.66-3.78 (m, 1H), 4.03 (s, 1H), 4.22 (br dd, J=24, 11 Hz, 2H), 4.42-4.58 (m, 2H), 5.46-5.68 (m, 1H), 6.88 (d, J=9 Hz, 1H), 8.14 (d, J=9 Hz, 1H), 8.36 (d, J=8 Hz, 1H), 8.56 (s, 1H), 9.13 (s, 1H); LC-MS (LC-ES) M+H=387.

Example 7

N-(trans-4-(2-Hydroxypropan-2-yl)cyclohexyl)-7-(2-methylazetidin-1-yl)-1,8-naphthyridine-3-carboxamide

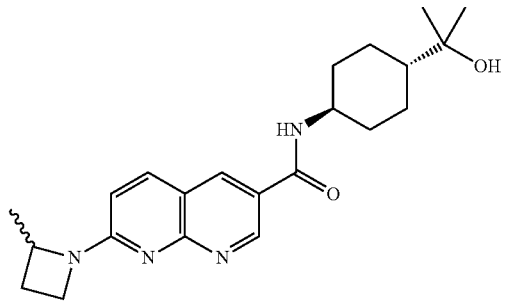 [SMILES: CC1CCN1c1ccc2cc(C(=O)N[C@H]3CC[C@H](C(C)(C)O)CC3)cnc2n1]

N,N-Diisopropylethylamine (0.444 mL, 2.54 mmol) was added to 7-(2-methylazetidin-1-yl)-1,8-naphthyridine-3-carboxylic acid lithium salt (0.1061 g, 0.424 mmol, Intermediate 7) in N,N-dimethylformamide (1.4 mL) at room temperature. Then, 2-(trans-4-aminocyclohexyl)propan-2-ol (0.080 g, 0.509 mmol) was added and the reaction mixture was stirred for five minutes. Then, n-propylphosphonic acid anhydride (0.505 mL, 0.848 mmol) was added and the reaction mixture was stirred for sixty-four hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give N-(trans-4-(2-hydroxypropan-2-yl)cyclohexyl)-7-(2-methylazetidin-1-yl)-1,8-naphthyridine-3-carboxamide (0.0514 g, 0.128 mmol, 30.1% yield). $^1$H NMR (400 MHz, CD$_3$SOCD$_3$) δ 1.04 (s, 6H), 1.04-1.24 (m, 3H), 1.30 (q, J=12 Hz, 2H), 1.52 (d, J=6 Hz, 3H), 1.83 (br d, J=12 Hz, 2H), 1.91 (br d, J=11 Hz, 2H), 1.96-2.06 (m, 1H), 2.46-2.58 (m, 1H), 3.64-3.78 (m, 1H), 4.00 (q, J=8 Hz, 1H), 4.03 (s, 1H), 4.11 (q, J=8 Hz, 1H), 4.56 (h, J=7 Hz, 1H), 6.79 (d, J=9 Hz, 1H), 8.07 (d, J=9 Hz, 1H), 8.32 (d, J=8 Hz, 1H), 8.52 (s, 1H), 9.09 (s, 1H); LC-MS (LC-ES) M+H=383.

Example 8 & 9

N-(trans-4-(2-Hydroxypropan-2-yl)cyclohexyl)-7-((R)-2-methylazetidin-1-yl)-1,8-naphthyridine-3-carboxamide and N-(trans-4-(2-Hydroxypropan-2-yl)cyclohexyl)-7-((S)-2-methylazetidin-1-yl)-1,8-naphthyridine-3-carboxamide

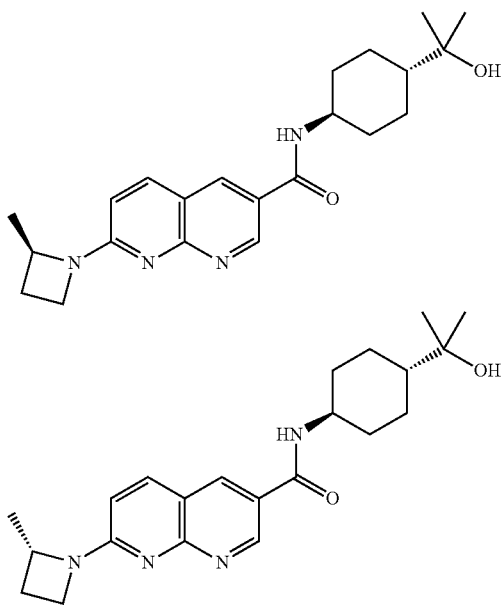

Racemic N-(trans-4-(2-hydroxypropan-2-yl)cyclohexyl)-7-(2-methylazetidin-1-yl)-1,8-naphthyridine-3-carboxamide (0.1238 g, 0.324 mmol, Example 7) was separated into its enantiomers on a chiral IC column eluting with methanol:hexanes (3:2) with 1% diethylamine to give N-(trans-4-(2-hydroxypropan-2-yl)cyclohexyl)-7-((R)-2-methylazetidin-1-yl)-1,8-naphthyridine-3-carboxamide (0.028 g, 0.070 mmol, 21.49% yield) as the first diastereomer (>99% ee) to elute and N-(trans-4-(2-hydroxypropan-2-yl)cyclohexyl)-7-((S)-2-methylazetidin-1-yl)-1,8-naphthyridine-3-carboxamide (0.035 g, 0.087 mmol, 26.9% yield) as the last diastereomer to elute (86.6% ee). The structures were assigned by vibrational circular dichroism.

N-(trans-4-(2-Hydroxypropan-2-yl)cyclohexyl)-7-((R)-2-methylazetidin-1-yl)-1,8-naphthyridine-3-carboxamide $^1$H NMR (400 MHz, CD$_3$SOCD$_3$) δ 1.04 (s, 6H), 1.04-1.24 (m, 3H), 1.30 (q, J=12 Hz, 2H), 1.52 (d, J=6 Hz, 3H), 1.83 (br d, J=12 Hz, 2H), 1.91 (br d, J=11 Hz, 2H), 1.96-2.06 (m, 1H), 2.46-2.58 (m, 1H), 3.64-3.78 (m, 1H), 4.00 (q, J=8 Hz, 1H), 4.02 (s, 1H), 4.11 (q, J=8 Hz, 1H), 4.56 (h, J=6 Hz, 1H), 6.79 (d, J=9 Hz, 1H), 8.07 (d, J=9 Hz, 1H), 8.31 (d, J=8 Hz, 1H), 8.52 (s, 1H), 9.10 (s, 1H); LC-MS (LC-ES) M+H=383.

N-(trans-4-(2-Hydroxypropan-2-yl)cyclohexyl)-7-((S)-2-methylazetidin-1-yl)-1,8-naphthyridine-3-carboxamide $^1$H NMR (400 MHz, CD$_3$SOCD$_3$) δ 1.04 (s, 6H), 1.04-1.24 (m, 3H), 1.30 (q, J=12 Hz, 2H), 1.52 (d, J=6 Hz, 3H), 1.83 (br d, J=11 Hz, 2H), 1.91 (br d, J=12 Hz, 2H), 1.96-2.06 (m, 1H), 2.46-2.58 (m, 1H), 3.64-3.78 (m, 1H), 4.00 (q, J=8 Hz, 1H), 4.02 (s, 1H), 4.11 (q, J=8 Hz, 1H), 4.56 (h, J=6 Hz, 1H), 6.78 (d, J=9 Hz, 1H), 8.07 (d, J=9 Hz, 1H), 8.31 (d, J=8 Hz, 1H), 8.51 (s, 1H), 9.09 (s, 1H); LC-MS (LC-ES) M+H=383.

Example 10

7-Cyclopropyl-N-((trans)-4-(2-hydroxypropan-2-yl)cyclohexyl)-1,6-naphthyridine-3-carboxamide

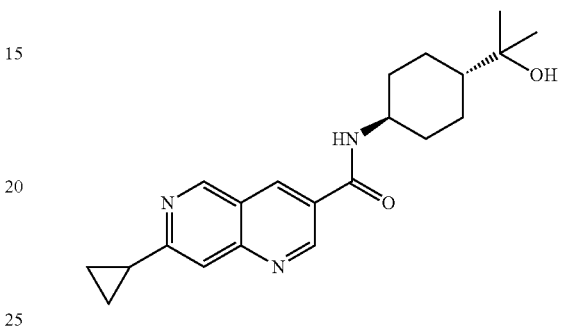

To a stirring suspension of 7-cyclopropyl-1,6-naphthyridine-3-carboxylic acid (214 mg, 0.999 mmol) (Intermediate 1) in N,N-dimethylformamide (13.3 mL) was added N,N-diisopropylethylamine (0.262 mL, 1.498 mmol) followed by 1-[bis(dimethylamino)methylene]-1H-1,2,3-triazolo[4,5-b]pyridinium 3-oxide hexafluorophosphate (475 mg, 1.249 mmol) in one portion. After 5 minutes, 2-((trans)-4-aminocyclohexyl)propan-2-ol (236 mg, 1.498 mmol) and N,N-diisopropylethylamine (0.262 mL, 1.498 mmol) were added. The reaction was stirred at room temperature over the weekend. Water was added to the vessel in attempts to crash out the product, to no avail. The solution was concentrated in vacuo to give a crude solid. The residue was purified using silica gel chromatography, eluting with 0-10% methanol:dichloromethane to give 7-cyclopropyl-N-((trans)-4-(2-hydroxypropan-2-yl)cyclohexyl)-1,6-naphthyridine-3-carboxamide (318 mg, 0.900 mmol, 90% yield). $^1$H NMR (400 MHz, CD$_3$OD) δ 1.09-1.53 (m, 15H), 1.92-2.19 (m, 4H), 2.26-2.43 (m, 1H), 3.85-3.99 (m, 1H), 7.80 (s, 1H), 8.65 (d, J=8 Hz, 1H), 8.82-8.92 (m, 1H), 9.28 (s, 1H), 9.39 (d, J=2 Hz, 1H); LC-MS (LC-ES) M+H=354.

Example 11

N-(trans-4-(2-Hydroxypropan-2-yl)cyclohexyl)-7-(2-methylazetidin-1-yl)-1,6-naphthyridine-3-carboxamide

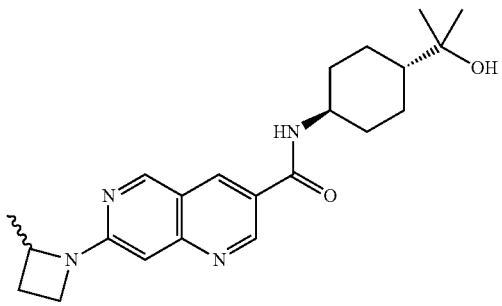 [SMILES: CC1CCN1c1cc2ncc(C(=O)N[C@H]3CC[C@H](C(C)(C)O)CC3)cc2cn1]

N,N-Diisopropylethylamine (0.426 mL, 2.441 mmol) was added to 7-(2-methylazetidin-1-yl)-1,6-naphthyridine-3-carboxylic acid lithium salt (0.1018 g, 0.407 mmol, Intermediate 8) in N,N-dimethylformamide (1.36 mL) at room temperature. Then, 2-(trans-4-aminocyclohexyl)propan-2-ol (0.077 g, 0.488 mmol) was added and the reaction mixture was stirred for five minutes. Then, n-propylphosphonic acid anhydride (0.484 mL, 0.814 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:9) to give N-(trans-4-(2-hydroxypropan-2-yl)cyclohexyl)-7-(2-methylazetidin-1-yl)-1,6-naphthyridine-3-carboxamide (0.1064 g, 0.264 mmol, 64.9% yield). $^1$H NMR (400 MHz, CD$_3$SOCD$_3$) δ 1.04 (s, 6H), 1.04-1.24 (m, 3H), 1.30 (q, J=12 Hz, 2H), 1.50 (d, J=6 Hz, 3H), 1.83 (br d, J=12 Hz, 2H), 1.92 (br d, J=11 Hz, 2H), 2.04 (p, J=9 Hz, 1H), 2.42-2.54 (m, 1H), 3.66-3.78 (m, 1H), 3.86 (q, J=8 Hz, 1H), 4.02 (s, 1H), 4.04 (q, J=6 Hz, 1H), 4.44 (h, J=7 Hz, 1H), 6.54 (s, 1H), 8.38 (d, J=7 Hz, 1H), 8.69 (s, 1H), 9.05 (s, 1H), 9.17 (s, 1H); LC-MS (LC-ES) M+H=383.

Example 12 & 13

N-(trans-4-(2-Hydroxypropan-2-yl)cyclohexyl)-7-((R)-2-methylazetidin-1-yl)-1,6-naphthyridine-3-carboxamide and N-(trans-4-(2-Hydroxypropan-2-yl)cyclohexyl)-7-((S)-2-methylazetidin-1-yl)-1,6-naphthyridine-3-carboxamide

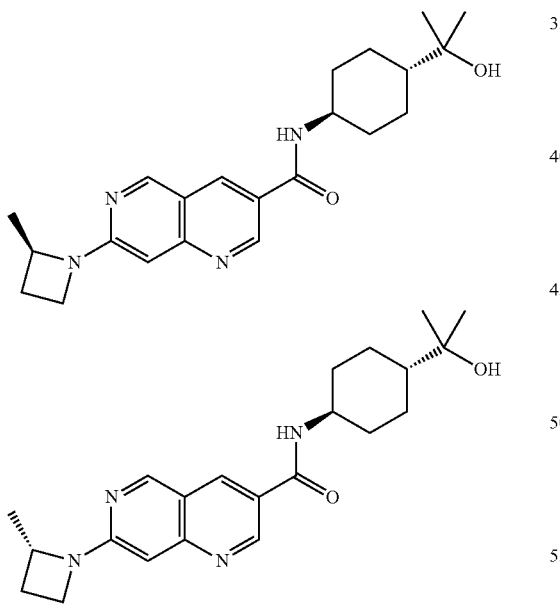

Racemic N-(trans-4-(2-hydroxypropan-2-yl)cyclohexyl)-7-(2-methylazetidin-1-yl)-1,6-naphthyridine-3-carboxamide (0.0971 g, 0.254 mmol, Example 11) was separated into its enantiomers on a chiral IC column eluting with methanol:hexanes (3:2) with 1% diethylamine to give N-(trans-4-(2-hydroxypropan-2-yl)cyclohexyl)-7-((R)-2-methylazetidin-1-yl)-1,6-naphthyridine-3-carboxamide (0.0201 g, 0.050 mmol, 19.67% yield) as the first diastereomer (>99% ee) to elute and N-(trans-4-(2-hydroxypropan-2-yl)cyclohexyl)-7-((S)-2-methylazetidin-1-yl)-1,6-naphthyridine-3-carboxamide (0.0230 g, 0.057 mmol, 22.50% yield) as the last diastereomer to elute (96.6% ee). The structures were assigned by analogy to Examples 8 & 9.

N-(trans-4-(2-Hydroxypropan-2-yl)cyclohexyl)-7-((R)-2-methylazetidin-1-yl)-1,6-naphthyridine-3-carboxamide $^1$H NMR (400 MHz, CD$_3$SOCD$_3$) δ 1.04 (s, 6H), 1.04-1.24 (m, 3H), 1.30 (q, J=12 Hz, 2H), 1.51 (d, J=6 Hz, 3H), 1.83 (br d, J=12 Hz, 2H), 1.92 (br d, J=12 Hz, 2H), 2.04 (p, J=8 Hz, 1H), 2.42-2.54 (m, 1H), 3.66-3.78 (m, 1H), 3.87 (q, J=8 Hz, 1H), 4.01 (s, 1H), 4.04 (q, J=5 Hz, 1H), 4.44 (h, J=6 Hz, 1H), 6.54 (s, 1H), 8.38 (d, J=7 Hz, 1H), 8.68 (s, 1H), 9.05 (s, 1H), 9.17 (s, 1H); LC-MS (LC-ES) M+H=383.

N-(trans-4-(2-Hydroxypropan-2-yl)cyclohexyl)-7-((S)-2-methylazetidin-1-yl)-1,6-naphthyridine-3-carboxamide $^1$H NMR (400 MHz, CD$_3$SOCD$_3$) δ 1.04 (s, 6H), 1.04-1.24 (m, 3H), 1.30 (q, J=12 Hz, 2H), 1.50 (d, J=6 Hz, 3H), 1.83 (br d, J=12 Hz, 2H), 1.92 (br d, J=11 Hz, 2H), 2.04 (p, J=9 Hz, 1H), 2.42-2.54 (m, 1H), 3.66-3.78 (m, 1H), 3.87 (q, J=8 Hz, 1H), 4.02 (s, 1H), 4.04 (q, J=5 Hz, 1H), 4.44 (h, J=6 Hz, 1H), 6.54 (s, 1H), 8.38 (d, J=8 Hz, 1H), 8.68 (s, 1H), 9.05 (s, 1H), 9.17 (s, 1H); LC-MS (LC-ES) M+H=383.

Example 14

7-(Cyclopropylamino)-N-(trans-4-(2-hydroxypropan-2-yl)cyclohexyl)-1,6-naphthyridine-3-carboxamide

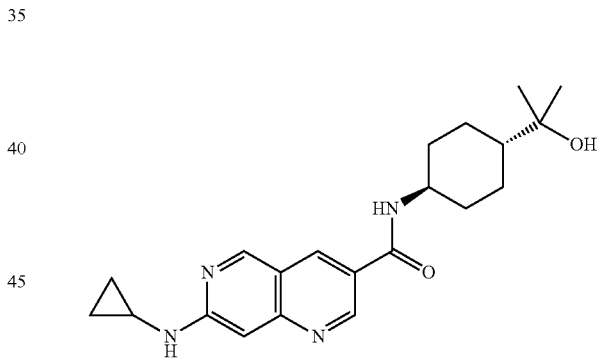

N,N-Diisopropylethylamine (0.210 mL, 1.204 mmol) was added to 7-(cyclopropylamino)-1,6-naphthyridine-3-carboxylic acid lithium salt (0.0474 g, 0.201 mmol, Intermediate 9) in N,N-dimethylformamide (0.67 mL) at room temperature. Then, 2-(trans-4-aminocyclohexyl)propan-2-ol (0.041 g, 0.261 mmol) was added and the reaction mixture was stirred for five minutes. Then, n-propylphosphonic acid anhydride (0.239 mL, 0.401 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:dichloromethane (0:1 to 3:7) to give 7-(cyclopropylamino)-N-(trans-4-(2-hydroxypropan-2-yl)cyclohexyl)-1,6-naphthyridine-3-carboxamide (0.0232 g, 0.060 mmol, 29.8% yield). $^1$H NMR (400 MHz, CD$_3$SOCD$_3$) δ 0.52 (s, 2H), 0.79 (d, J=6 Hz, 2H), 1.04 (s, 6H), 1.04-1.24 (m, 3H), 1.30 (q, J=12

Hz, 2H), 1.83 (br d, J=11 Hz, 2H), 1.92 (br d, J=11 Hz, 2H), 2.46-2.60 (m, 1H), 3.66-3.80 (m, 1H), 4.02 (s, 1H), 6.85 (s, 1H), 7.42 (s, 1H), 8.37 (d, J=7 Hz, 1H), 8.66 (s, 1H), 8.97 (s, 1H), 9.17 (s, 1H); LC-MS (LC-ES) M+H=369.

Example 15

7-(Azetidin-1-yl)-N-((1s,3s)-3-hydroxy-3-methylcyclobutyl)-1,6-naphthyridine-3-carboxamide

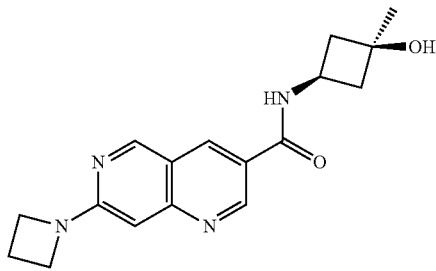 [SMILES: C[C@]1(O)C[C@@H](NC(=O)c2cnc3cc(N4CCC4)ncc3c2)C1]

N,N-Diisopropylethylamine (0.301 mL, 1.722 mmol) was added to 7-(azetidin-1-yl)-1,6-naphthyridine-3-carboxylic acid lithium salt (0.0678 g, 0.287 mmol, Intermediate 3) in N,N-dimethylformamide (0.96 mL) at room temperature. Then, (1s,3s)-3-amino-1-methylcyclobutanol hydrochloride (0.047 g, 0.344 mmol, Intermediate 10) was added and the reaction mixture was stirred for five minutes. Then, n-propylphosphonic acid anhydride (0.342 mL, 0.574 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0) to give 7-(azetidin-1-yl)-N-((1s,3s)-3-hydroxy-3-methylcyclobutyl)-1,6-naphthyridine-3-carboxamide (0.0370 g, 0.113 mmol, 39.2% yield). $^1$H NMR (400 MHz, CD$_3$SOCD$_3$) δ 1.27 (s, 3H), 2.11 (t, J=10 Hz, 2H), 2.30 (t, J=8 Hz, 2H), 2.39 (p, J=7 Hz, 2H), 4.02 (h, J=7 Hz, 1H), 4.08 (t, J=7 Hz, 4H), 4.97 (s, 1H), 6.54 (s, 1H), 8.71 (s, 1H), 8.74 (d, J=9 Hz, 1H), 9.03 (s, 1H), 9.18 (s, 1H); LC-MS (LC-ES) M+H=313.

Example 16

7-((2,2-Difluoroethyl)amino)-N-(trans-4-(2-hydroxypropan-2-yl)cyclohexyl)-1,8-naphthyridine-3-carboxamide

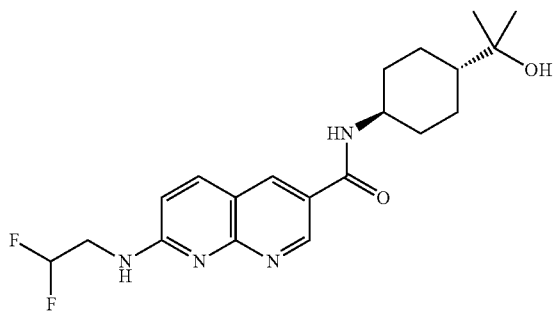 [SMILES: CC(C)(O)[C@H]1CC[C@H](NC(=O)c2cnc3nc(NCC(F)F)ccc3c2)CC1]

N,N-Diisopropylethylamine (0.269 mL, 1.543 mmol) was added to 7-((2,2-difluoroethyl)amino)-1,8-naphthyridine-3-carboxylic acid lithium salt (0.0669 g, 0.257 mmol, Intermediate 12) in N,N-dimethylformamide (0.86 mL) at room temperature. Then, 2-(trans-4-aminocyclohexyl)propan-2-ol (0.049 g, 0.309 mmol) was added and the reaction mixture was stirred for five minutes. Then, n-propylphosphonic acid anhydride (0.306 mL, 0.514 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-((2,2-difluoroethyhamino)-N-(trans-4-(2-hydroxypropan-2-yl)cyclohexyl)-1,8-naphthyridine-3-carboxamide (0.0611 g, 0.148 mmol, 57.5% yield). $^1$H NMR (400 MHz, CD$_3$SOCD$_3$) δ 1.04 (s, 6H), 1.04-1.24 (m, 3H), 1.31 (q, J=11 Hz, 2H), 1.83 (br d, J=12 Hz, 2H), 1.92 (br d, J=12 Hz, 2H), 3.66-3.80 (m, 1H), 3.91 (br t, J=15 Hz, 2H), 4.01 (s, 1H), 6.23 (t, J=57 Hz, 1H), 6.98 (d, J=9 Hz, 1H), 8.00 (br s, 1H), 8.04 (d, J=9 Hz, 1H), 8.32 (d, J=8 Hz, 1H), 8.52 (s, 1H), 9.10 (s, 1H); LC-MS (LC-ES) M+H=393.

Example 17

N-(trans-4-(2-Hydroxypropan-2-yl)cyclohexyl)-7-((2,2,2-trifluoroethyl)amino)-1,8-naphthyridine-3-carboxamide

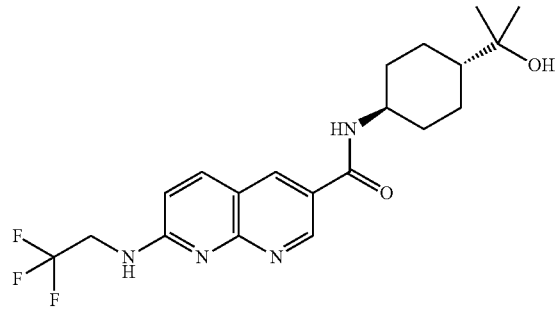 [SMILES: CC(C)(O)[C@H]1CC[C@H](NC(=O)c2cnc3nc(NCC(F)(F)F)ccc3c2)CC1]

N,N-Diisopropylethylamine (0.216 mL, 1.234 mmol) was added to 7-((2,2,2-trifluoroethyl)amino)-1,8-naphthyridine-3-carboxylic acid lithium salt (0.0572 g, 0.206 mmol, Intermediate 13) in N,N-dimethylformamide (0.69 mL) at room temperature. Then, 2-(trans-4-aminocyclohexyl)propan-2-ol (0.039 g, 0.247 mmol) was added and the reaction mixture was stirred for five minutes. Then, n-propylphosphonic acid anhydride (0.245 mL, 0.411 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give N-(trans-4-(2-hydroxypropan-2-yl)cyclohexyl)-7-((2,2,2-trifluoroethyl)amino)-1,8-naphthyridine-3-carboxamide (0.0219 g, 0.051 mmol, 24.65% yield). $^1$H NMR (400 MHz, CD$_3$SOCD$_3$) δ 1.04 (s, 6H), 1.04-1.24 (m, 3H), 1.30 (q, J=12 Hz, 2H), 1.83 (br d, J=13 Hz, 2H), 1.92 (br d, J=11 Hz, 2H), 3.66-3.78 (m, 1H), 4.02 (s, 1H), 4.38 (p, J=8 Hz, 2H), 7.01 (d, J=9 Hz, 1H), 8.09 (d, J=9 Hz, 1H), 8.17 (t, J=7 Hz, 1H), 8.36 (d, J=8 Hz, 1H), 8.55 (s, 1H), 9.12 (s, 1H); LC-MS (LC-ES) M+H=411.

Example 18

7-(Azetidin-1-yl)-N-((1s,3s)-3-hydroxy-3-methylcyclobutyl)-1,8-naphthyridine-3-carboxamide

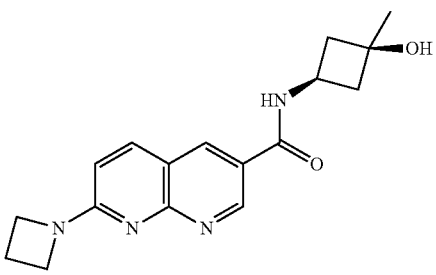 [SMILES: C[C@]1(O)C[C@@H](NC(=O)c2cnc3nc(N4CCC4)ccc3c2)C1]

N,N-Diisopropylethylamine (0.321 mL, 1.837 mmol) was added to 7-(azetidin-1-yl)-1,8-naphthyridine-3-carboxylic acid lithium salt (0.0723 g, 0.306 mmol, Intermediate 5) in N,N-dimethylformamide (1.02 mL) at room temperature. Then, (1s,3s)-3-amino-1-methylcyclobutanol hydrochloride (0.059 g, 0.429 mmol, Intermediate 10) was added and the reaction mixture was stirred for five minutes. Then, n-propylphosphonic acid anhydride (0.364 mL, 0.612 mmol) was added and the reaction mixture was stirred for sixty-four hours. The reaction mixture was concentrated. The resulting residue was purified by RP HPLC, eluting with acetonitrile:water with 0.1% ammonium hydroxide (5:95 to 100:0) to give 7-(azetidin-1-yl)-N-((1s,3s)-3-hydroxy-3-methylcyclobutyl)-1,8-naphthyridine-3-carboxamide (0.0611 g, 0.186 mmol, 60.7% yield). $^1$H NMR (400 MHz, CD$_3$SOCD$_3$) δ 1.27 (s, 3H), 2.11 (t, J=8 Hz, 2H), 2.30 (t, J=8 Hz, 2H), 2.39 (p, J=7 Hz, 2H), 3.99 (h, J=8 Hz, 1H), 4.16 (t, J=7 Hz, 4H), 4.96 (br s, 1H), 6.78 (d, J=9 Hz, 1H), 8.07 (d, J=9 Hz, 1H), 8.53 (s, 1H), 8.69 (d, J=5 Hz, 1H), 9.11 (s, 1H); LC-MS (LC-ES) M+H=313.

Example 19

(S)-7-(Azetidin-1-yl)-N-(2-oxopyrrolidin-3-yl)-1,8-naphthyridine-3-carboxamide

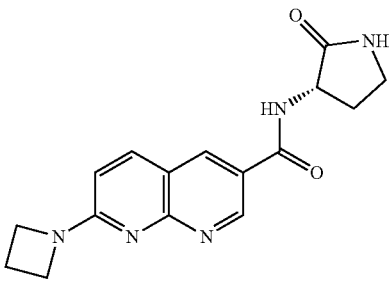 [SMILES: O=C(N[C@H]1CCNC1=O)c1cnc2nc(N3CCC3)ccc2c1]

N,N-Diisopropylethylamine (0.299 mL, 1.712 mmol) was added to 7-(azetidin-1-yl)-1,8-naphthyridine-3-carboxylic acid lithium salt (0.0674 g, 0.285 mmol, Intermediate 5) in N,N-dimethylformamide (0.951 mL) at room temperature. Then, (S)-3-aminopyrrolidin-2-one (0.040 g, 0.400 mmol) was added and the reaction mixture was stirred for five minutes. Then, n-propylphosphonic acid anhydride (0.340 mL, 0.571 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0) to give (S)-7-(azetidin-1-yl)-N-(2-oxopyrrolidin-3-yl)-1,8-naphthyridine-3-carboxamide (0.0578 g, 0.176 mmol, 61.8% yield). $^1$H NMR (400 MHz, CD$_3$SOCD$_3$) δ 2.01 (p, J=11 Hz, 1H), 2.30-2.44 (m, 3H), 3.25 (q, J=9 Hz, 2H), 4.17 (t, J=7 Hz, 4H), 4.59 (q, J=9 Hz, 1H), 6.79 (d, J=9 Hz, 1H), 7.85 (s, 1H), 8.09 (d, J=9 Hz, 1H), 8.55 (s, 1H), 8.79 (d, J=8 Hz, 1H), 9.12 (s, 1H); LC-MS (LC-ES) M+H=312.

Example 20

(S)-7-(Azetidin-1-yl)-N-(2-oxopyrrolidin-3-yl)-1,6-naphthyridine-3-carboxamide

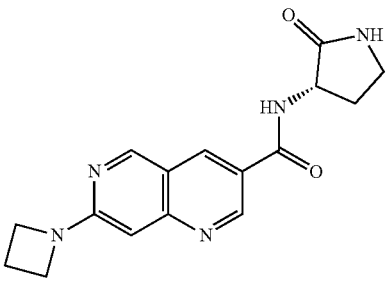 [SMILES: O=C(N[C@H]1CCNC1=O)c1cnc2cc(N3CCC3)ncc2c1]

N,N-Diisopropylethylamine (0.209 mL, 1.194 mmol) was added to 7-(azetidin-1-yl)-1,6-naphthyridine-3-carboxylic acid lithium salt (0.0470 g, 0.199 mmol, Intermediate 3) in N,N-dimethylformamide (0.663 mL) at room temperature. Then, (S)-3-aminopyrrolidin-2-one (0.028 g, 0.279 mmol) was added and the reaction mixture was stirred for five minutes. Then, n-propylphosphonic acid anhydride (0.237 mL, 0.398 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0) to give (S)-7-(azetidin-1-yl)-N-(2-oxopyrrolidin-3-yl)-1,6-naphthyridine-3-carboxamide (0.0358 g, 0.109 mmol, 54.9% yield). $^1$H NMR (400 MHz, CD$_3$SOCD$_3$) δ 2.01 (p, J=10 Hz, 1H), 2.32-2.44 (m, 3H), 3.25 (q, J=9 Hz, 2H), 4.09 (t, J=7 Hz, 4H), 4.59 (q, J=9 Hz, 1H), 6.55 (s, 1H), 7.86 (s, 1H), 8.73 (s, 1H), 8.85 (d, J=8 Hz, 1H), 9.06 (s, 1H), 9.20 (s, 1H); LC-MS (LC-ES) M+H=312.

Example 21

7-Cyclopropyl-N-((trans)-4-(2-hydroxypropan-2-yl)cyclohexyl)-1,8-naphthyridine-3-carboxamide

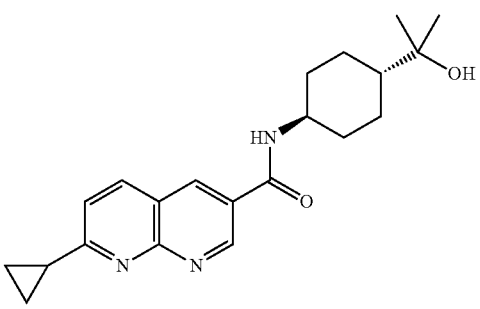 [SMILES: CC(C)(O)[C@H]1CC[C@H](NC(=O)c2cnc3nc(C4CC4)ccc3c2)CC1]

N,N-Diisopropylethylamine (1.977 mL, 11.32 mmol) was added to 7-cyclopropyl-1,8-naphthyridine-3-carboxylic acid (0.6061 g, 2.83 mmol, Intermediate 4) in dichloromethane (14.15 mL) at room temperature. Then, 2-(trans-4-aminocyclohexyl)propan-2-ol (0.667 g, 4.24 mmol) was added and the reaction mixture was stirred for five minutes. Then, n-propylphosphonic acid anhydride (3.03 ml, 5.09 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-cyclopropyl-N-(trans-4-(2-hydroxypropan-2-yl)cyclohexyl)-1,8-naphthyridine-3-carboxamide (0.5820 g, 1.564 mmol, 55.3% yield). $^1$H NMR (400 MHz, $CD_3SOCD_3$) δ 1.04 (s, 6H), 1.06-1.24 (m, 7H), 1.32 (q, J=11 Hz, 2H), 1.83 (br d, J=11 Hz, 2H), 1.93 (br d, J=11 Hz, 2H), 2.32-2.40 (m, 1H), 3.75 (dtt, J=8, 4, 4 Hz, 1H), 4.06 (s, 1H), 7.63 (d, J=9 Hz, 1H), 8.39 (d, J=8 Hz, 1H), 8.57 (br d, J=8 Hz, 1H), 8.78 (d, J=2 Hz, 1H), 9.32 (d, J=2 Hz, 1H); LC-MS (LC-ES) M+H=354.

Example 22

7-((S)-2-Methylazetidin-1-yl)-N—((S)-2-oxopyrrolidin-3-yl)-1,6-naphthyridine-3-carboxamide

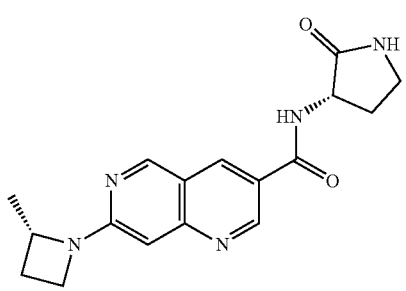 [SMILES: C[C@H]1CCN1c1cc2ncc(C(=O)N[C@H]3CCNC3=O)cc2cn1]

N,N-Diisopropylethylamine (0.293 mL, 1.678 mmol) was added to lithium (S)-7-(2-methylazetidin-1-yl)-1,6-naphthyridine-3-carboxylate (0.0697 g, 0.280 mmol, Intermediate 15) in N,N-dimethylformamide (0.93 mL) at room temperature. Then, (S)-3-aminopyrrolidin-2-one (0.039 g, 0.392 mmol) was added and the reaction mixture was stirred for five minutes. Then, n-propylphosphonic acid anhydride (0.333 mL, 0.559 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0) to give 7-((S)-2-methylazetidin-1-yl)-N—((S)-2-oxopyrrolidin-3-yl)-1,6-naphthyridine-3-carboxamide (0.0520 g, 0.152 mmol, 54.3% yield). $^1$H NMR (400 MHz, $CD_3SOCD_3$) δ 1.51 (d, J=6 Hz, 3H), 1.94-2.12 (m, 2H), 2.32-2.44 (m, 1H), 2.44-2.54 (m, 1H), 3.20-3.32 (m, 2H), 3.88 (q, J=8 Hz, 1H), 4.05 (q, J=8 Hz, 1H), 4.45 (q, J=7 Hz, 1H), 4.59 (q, J=9 Hz, 1H), 6.55 (s, 1H), 7.86 (s, 1H), 8.73 (s, 1H), 8.86 (d, J=8 Hz, 1H), 9.06 (s, 1H), 9.20 (s, 1H); LC-MS (LC-ES) M+H=326.

Example 23

N-((1s,3R)-3-Hydroxy-3-methylcyclobutyl)-7-((S)-2-methylazetidin-1-yl)-1,6-naphthyridine-3-carboxamide

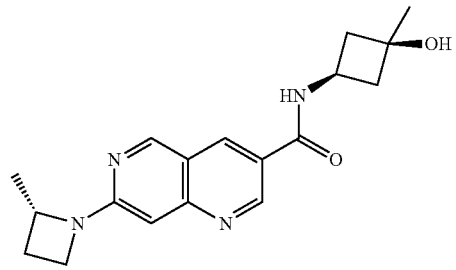 [SMILES: C[C@H]1CCN1c1cc2ncc(C(=O)N[C@H]3C[C@@](C)(O)C3)cc2cn1]

N,N-Diisopropylethylamine (0.264 mL, 1.510 mmol) was added to lithium (S)-7-(2-methylazetidin-1-yl)-1,6-naphthyridine-3-carboxylate (0.0627 g, 0.252 mmol, Intermediate 15) in N,N-dimethylformamide (0.84 mL) at room temperature. Then, (1s,3s)-3-amino-1-methylcyclobutanol (0.036 g, 0.352 mmol, Intermediate 10) was added and the reaction mixture was stirred for five minutes. Then, n-propylphosphonic acid anhydride (0.300 mL, 0.503 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0) to give N-((1s,3R)-3-hydroxy-3-methylcyclobutyl)-7-((S)-2-methylazetidin-1-yl)-1,6-naphthyridine-3-carboxamide (0.0534 g, 0.155 mmol, 61.8% yield). $^1$H NMR (400 MHz, $CD_3SOCD_3$) δ 1.28 (s, 3H), 1.51 (d, J=6 Hz, 3H), 2.05 (p, J=8 Hz, 1H), 2.12 (t, J=9 Hz, 2H), 2.31 (t, J=8 Hz, 2H), 2.44-2.54 (m, 1H), 3.87 (q, J=8 Hz, 1H), 3.94-4.08 (m, 2H), 4.44 (q, J=6 Hz, 1H), 4.96 (s, 1H), 6.54 (s, 1H), 8.71 (s, 1H), 8.74 (d, J=6 Hz, 1H), 9.04 (s, 1H), 9.18 (s, 1H); LC-MS (LC-ES) M+H=327.

Example 24

(S)—N-(1-(2-Hydroxy-2-methylpropanoyl)piperidin-4-yl)-7-(2-methylazetidin-1-yl)-1,6-naphthyridine-3-carboxamide

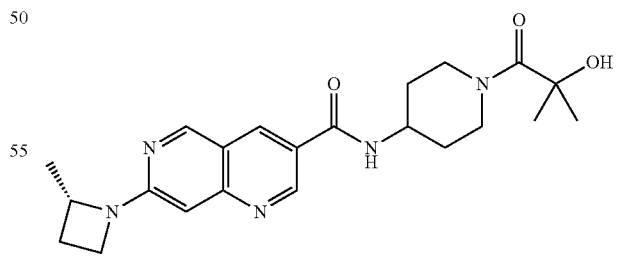

N,N-Diisopropylethylamine (0.192 mL, 1.100 mmol) was added to lithium (S)-7-(2-methylazetidin-1-yl)-1,6-naphthyridine-3-carboxylate (0.0685 g, 0.275 mmol, Intermediate 15) in N,N-dimethylformamide (1.374 mL) at room temperature. Then, 1-[bis(dimethylamino)methylene]-1H-1,2,3-triazolo[4,5-b]pyridinium 3-oxide hexafluorophosphate (0.115 g, 0.302 mmol) was added and the reaction mixture was stirred for five minutes. Then, 1-(4-aminopiperidin-1-yl)-2-hydroxy-2-methylpropan-1-one (0.051 g, 0.275 mmol, Intermediate 16) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with ethyl acetate:hexanes (3:2 to 1:0) to give (S)—N-(1-(2-hydroxy-2-methylpropanoyl)piperidin-4-yl)-7-(2-methylazetidin-1-yl)-1,6-naphthyridine-3-carboxamide (0.0636 g, 0.147 mmol, 53.4% yield). $^1$H NMR (400 MHz, CD$_3$SOCD$_3$) δ 1.33 (s, 6H), 1.40-1.50 (m, 2H), 1.51 (d, J=6 Hz, 3H), 1.86 (br d, J=13 Hz, 2H), 2.05 (t, J=9 Hz, 1H), 2.44-2.54 (m, 1H), 2.70-3.24 (m, 2H), 3.87 (q, J=7 Hz, 1H), 4.00-4.14 (m, 2H), 4.44 (h, J=7 Hz, 1H), 4.26-4.90 (m, 2H), 5.36 (s, 1H), 6.55 (s, 1H), 8.47 (d, J=7 Hz, 1H), 8.70 (s, 1H), 9.05 (s, 1H), 9.18 (s, 1H); LC-MS (LC-ES) M+H=412.

Example 25

7-(Azetidin-1-yl)-6-chloro-N-(trans-4-(2-hydroxypropan-2-yl)cyclohexyl)-1,8-naphthyridine-3-carboxamide

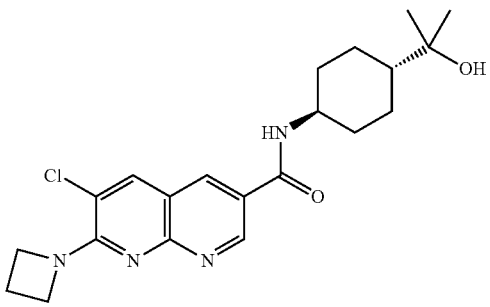 [SMILES: CC(C)(O)[C@H]1CC[C@H](NC(=O)c2cnc3nc(N4CCC4)c(Cl)cc3c2)CC1]

N,N-Diisopropylethylamine (0.169 mL, 0.969 mmol) was added to lithium 7-(azetidin-1-yl)-6-chloro-1,8-naphthyridine-3-carboxylate (0.0653 g, 0.242 mmol, Intermediate 19) in N,N-dimethylformamide (0.81 mL) at room temperature. Then, 2-(trans-4-aminocyclohexyl)propan-2-ol (0.050 g, 0.315 mmol) was added and the reaction mixture was stirred for five minutes. Then, n-propylphosphonic acid anhydride (0.288 mL, 0.484 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-(azetidin-1-yl)-6-chloro-N-(trans-4-(2-hydroxypropan-2-yl)cyclohexyl)-1,8-naphthyridine-3-carboxamide (0.0312 g, 0.074 mmol, 30.4% yield). $^1$H NMR (400 MHz, CD$_3$SOCD$_3$) δ 1.03 (s, 6H), 1.04-1.24 (m, 3H), 1.30 (q, J=12 Hz, 2H), 1.82 (br d, J=12 Hz, 2H), 1.91 (br d, J=10 Hz, 2H), 2.32 (p, J=8 Hz, 2H), 3.66-3.78 (m, 1H), 4.05 (s, 1H), 4.41 (t, J=7 Hz, 4H), 8.30 (s, 1H), 8.43 (d, J=8 Hz, 1H), 8.52 (d, J=2 Hz, 1H), 9.13 (d, J=2 Hz, 1H); LC-MS (LC-ES) M+H=403.

Example 26

N-(trans-3-(2-Hydroxypropan-2-yl)cyclobutyl)-7-((S)-2-methylazetidin-1-yl)-1,6-naphthyridine-3-carboxamide

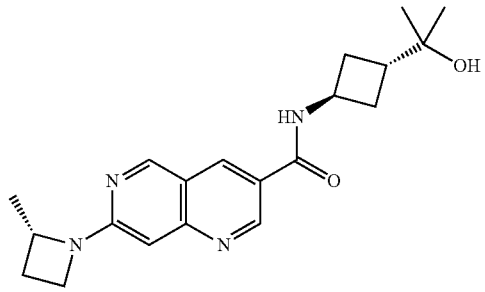 [SMILES: C[C@H]1CCN1c1cc2ncc(C(=O)N[C@H]3C[C@H](C(C)(C)O)C3)cc2cn1]

N,N-Diisopropylethylamine (0.202 mL, 1.157 mmol) was added to lithium (S)-7-(2-methylazetidin-1-yl)-1,6-naphthyridine-3-carboxylate (0.0721 g, 0.289 mmol, Intermediate 15) in N,N-dimethylformamide (0.96 mL) at room temperature. Then, 2-(trans-3-aminocyclobutyl)propan-2-ol (0.049 g, 0.376 mmol) was added and the reaction mixture was stirred for five minutes. Then, n-propylphosphonic acid anhydride (0.344 mL, 0.579 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give N-(trans-3-(2-hydroxypropan-2-yl)cyclobutyl)-7-((S)-2-methylazetidin-1-yl)-1,6-naphthyridine-3-carboxamide (0.0262 g, 0.070 mmol, 24.27% yield). $^1$H NMR (400 MHz, CD$_3$SOCD$_3$) δ 1.04 (s, 6H), 1.50 (d, J=6 Hz, 3H), 1.96-2.12 (m, 3H), 2.16-2.36 (m, 4H), 3.87 (q, J=8 Hz, 1H), 4.00-4.10 (m, 1H), 4.25 (s, 1H), 4.28-4.38 (m, 1H), 4.40-4.48 (m, 1H), 6.55 (s, 1H), 8.72 (d, J=2 Hz, 1H), 8.81 (d, J=7 Hz, 1H), 9.06 (s, 1H), 9.19 (d, J=2 Hz, 1H); LC-MS (LC-ES) M+H=355.

Example 27

6-Chloro-7-cyclopropyl-N-((trans)-4-(2-hydroxypropan-2-yl)cyclohexyl)-1,8-naphthyridine-3-carboxamide

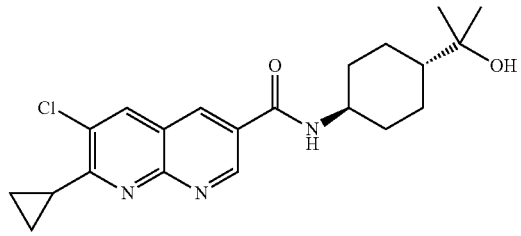 [SMILES: CC(C)(O)[C@H]1CC[C@H](NC(=O)c2cnc3nc(C4CC4)c(Cl)cc3c2)CC1]

2-(trans-4-Aminocyclohexyl)propan-2-ol (0.040 g, 0.254 mmol) and the N,N-diisopropylethylamine (0.06 mL, 0.344 mmol) were added to the 6-chloro-7-cyclopropyl-1,8-naphthyridine-3-carboxylic acid (0.063 g, 0.253 mmol, Intermediate 18) in N,N-dimethylformamide (2.5 mL). Then, 1-[bis (dimethylamino)methylene]-1H-1,2,3-triazolo[4,5-b]pyridinium 3-oxide hexafluorophosphate (0.116 g, 0.305 mmol) was added and the reaction mixture was stirred for 100 minutes. Then the reaction mixture was concentrated. Dichloromethane and methanol were added to the residue and the mixture was purified by silica gel chromatography, eluting with (ethyl acetate:ethanol (3:1):hexanes (3:1) to give a solid that was triturated/sonicated with ethyl acetate to give 6-chloro-7-cyclopropyl-N-((trans)-4-(2-hydroxypropan-2-yl)cyclohexyl)-1,8-naphthyridine-3-carboxamide (0.82 g, 0.211 mmol, 83% yield) as a white powder. $^1$H NMR (400 MHz, CD$_3$SOCD$_3$) δ 1.04 (s, 6H), 1.06-1.26 (m, 7H),1.31 (q, J=12 Hz, 2H), 1.83 (br d, J=11 Hz, 2H), 1.93 (br d, J=10 Hz, 2H), 2.68-2.78 (m, 1H), 3.68-3.80 (m, 1H), 4.06 (s, 1H), 8.64 (d, J=8 Hz, 1H), 8.68 (s, 1H), 8.77 (d, J=2 Hz, 1H), 9.34 (d, J=2 Hz, 1H); LC-MS (LC-ES) M+H=388.

Example 28

N-((3S,4R)-4-Methyl-2-oxopyrrolidin-3-yl)-7-((S)-2-methylazetidin-1-yl)-1,6-naphthyridine-3-carboxamide

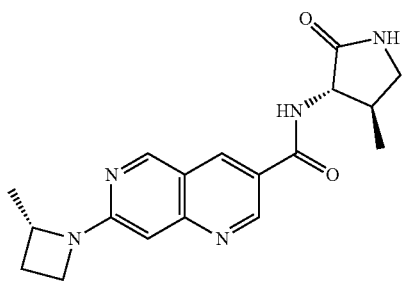 [SMILES: C[C@@H]1CNC(=O)[C@H]1NC(=O)c1cnc2cc(N3CC[C@@H]3C)ncc2c1]

N,N-Diisopropylethylamine (0.274 mL, 1.570 mmol) was added to lithium (S)-7-(2-methylazetidin-1-yl)-1,6-naphthyridine-3-carboxylate (0.0978 g, 0.392 mmol, Intermediate 15) in N,N-dimethylformamide (1.3 mL) at room temperature. Then, (3S,4R)-3-amino-4-methylpyrrolidin-2-one (0.049 g, 0.432 mmol, Intermediate 20) was added and the reaction mixture was stirred for five minutes. Then, n-propylphosphonic acid anhydride (0.467 mL, 0.785 mmol) was added and the reaction mixture was stirred for sixty-four hours. The reaction mixture was concentrated. The resulting residue was purified by RP HPLC, eluting with acetonitrile:water with 0.1% ammonium hydroxide (5:95 to 100:0) to give N-((3S,4R)-4-methyl-2-oxopyrrolidin-3-yl)-7-((S)-2-methylazetidin-1-yl)-1,6-naphthyridine-3-carboxamide (0.0497 g, 0.139 mmol, 35.4% yield). $^1$H NMR (400 MHz, CDCl$_3$) δ 1.09 (d, J=7 Hz, 3H), 1.51 (d, J=6 Hz, 3H), 2.00-2.10 (m, 1H), 2.36-2.54 (m, 2H), 2.88 (t, J=9 Hz, 1H), 3.28-3.36 (m, 1H), 3.88 (q, J=8 Hz, 1H), 4.04 (dt, J=9, 5 Hz, 1H), 4.29 (dd, J=11, 8 Hz, 1H), 4.45 (h, J=8 Hz, 1H), 6.56 (s, 1H), 7.85 (s, 1H), 8.74 (d, J=2 Hz, 1H), 8.82 (d, J=9 Hz, 1H), 9.07 (s, 1H), 9.21 (d, J=2 Hz, 1H); LC-MS (LC-ES) M+H=340.

Example 29

(S)-7-Cyclopropyl-N-(2-oxopyrrolidin-3-yl)-1,6-naphthyridine-3-carboxamide

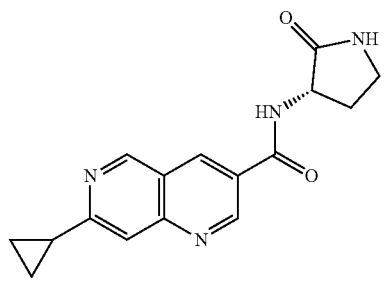 [SMILES: O=C(N[C@H]1CCNC1=O)c1cnc2cc(C3CC3)ncc2c1]

1-[Bis(dimethylamino)methylene]-1H-1,2,3-triazolo[4,5-b]pyridinium 3-oxide hexafluorophosphate (200 mg, 0.525 mmol) was added to a stirred solution of 7-cyclopropyl-1,6-naphthyridine-3-carboxylic acid (75 mg, 0.350 mmol, Intermediate 1) in N,N-dimethylformamide (1.5 mL) at room temperature. Then N,N-diisopropylethylamine (0.092 mL, 0.525 mmol) was added. After stirring for 15 minutes, (S)-3-aminopyrrolidin-2-one (52.6 mg, 0.525 mmol) was added to the reaction mixture, followed by the addition of N,N-diisopropylethylamine (0.092 mL, 0.525 mmol) and the reaction mixture was stirred for eight hours. Then, the reaction mixture was concentrated under vacuum. The resulting residue was triturated with acetonitrile to give (S)-7-cyclopropyl-N-(2-oxopyrrolidin-3-yl)-1,6-naphthyridine-3-carboxamide (0.075 g, 0.240 mmol, 68.7% yield) as an off white solid. $^1$H NMR (400 MHz, CD$_3$SOCD$_3$) δ 1.00-1.14 (m, 4H), 2.03 (quin, J=11 Hz, 1H), 2.30-2.44 (m, 2H), 3.20-3.30 (m, 2H), 4.62 (q, J=10 Hz, 1H), 7.87 (s, 1H), 7.94 (s, 1H), 8.93 (d, J=2 Hz, 1H), 9.10 (d, J=8 Hz, 1H), 9.34 (s, 1H), 9.40 (d, J=2 Hz, 1H); LC-MS (LC-ES) M+H=297.

Example 30

7-Cyclopropyl-N-((1r,4r)-4-hydroxy-4-methylcyclohexyl)-1,6-naphthyridine-3-carboxamide

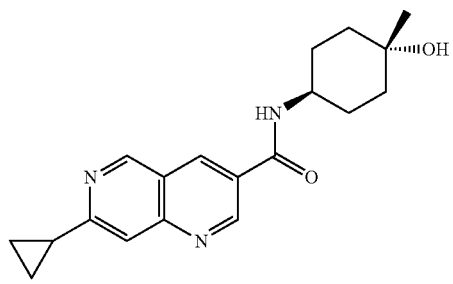 [SMILES: C[C@]1(O)CC[C@H](NC(=O)c2cnc3cc(C4CC4)ncc3c2)CC1]

N,N-Diisopropylethylamine (0.092 mL, 0.525 mmol) was added to a stirred solution of 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo [4,5-b]pyridinium 3-oxide hexafluorophosphate (200 mg, 0.525 mmol) was added. After stirring for 15 minutes, (1r,4r)-4-amino-1-methylcyclohexan-1-ol (67.9 mg, 0.525 mmol, Intermediate 21, Astatech) was added, followed by the addition of N,N-diisopropylethylamine (0.092 mL, 0.525 mmol) and the reaction mixture was stirred for eight hours. The reaction mixture was concentrated under vacuum. The resulting semisolid residue was triturated with acetonitrile to give 7-cyclopropyl-N-((1r,4r)-4-hydroxy-4-methylcyclohexyl)-1,6-naphthyridine-3-carboxamide (0.055 g, 0.161 mmol, 45.9% yield) as an off white solid. $^1$H NMR (400 MHz, CD$_3$SOCD$_3$) δ 1.00-1.10 (m, 4H), 1.16 (s, 3H), 1.38-1.54 (m, 4H), 1.56-1.68 (m, 2H), 1.74-1.86 (m, 2H), 2.34 (quin, J=6 Hz, 1H), 3.80-3.92 (m, 1H), 4.32 (s, 1H), 7.86 (s, 1H), 8.57 (d, J=8 Hz, 1H), 8.88 (d, J=2 Hz, 1H), 9.33 (s, 1H), 9.36 (d, J=2 Hz, 1H); LC-MS (LC-ES) M+H=326.

Example 31

7-Cyclopropyl-N-((1s,3s)-3-hydroxy-3-methylcyclobutyl)-1,6-naphthyridine-3-carboxamide

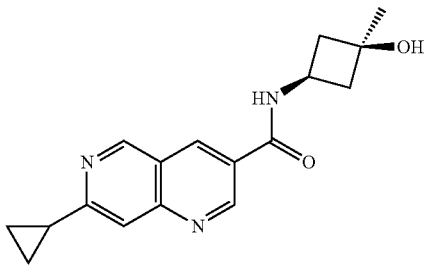 [SMILES: C[C@]1(O)C[C@@H](NC(=O)c2cnc3cc(C4CC4)ncc3c2)C1]

N,N-Diisopropylethylamine (0.122 mL, 0.700 mmol) was added to a stirred solution of 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, (1s,3s)-3-amino-1-methylcyclobutan-1-ol hydrochloride (72.3 mg, 0.525 mmol, Intermediate 10, Astatech) was added, followed by the addition of N,N-diisopropylethylamine (0.122 mL, 0.700 mmol) and the reaction mixture was stirred for fifteen hours. Then, the reaction mixture was concentrated to dryness under vacuum. The resulting residue was triturated with acetonitrile to give 7-cyclopropyl-N-((1s,3s)-3-hydroxy-3-methylcyclobutyl)-1,6-naphthyridine-3-carboxamide (0.050 g, 0.160 mmol, 45.6% yield) as an off white solid. $^1$H NMR (400 MHz, CD$_3$SOCD$_3$) δ 1.00-1.12 (m, 4H), 1.28 (s, 3H), 2.12 (dt, J=9, 2 Hz, 2H), 2.26-2.38 (m, 3H), 4.02 (sex, J=8 Hz, 1H), 5.03 (s, 1H), 7.85 (s, 1H), 8.92 (d, J=2 Hz, 1H), 8.98 (d, J=7 Hz, 1H), 9.32 (s, 1H), 9.38 (d, J=2 Hz, 1H); LC-MS (LC-ES) M+H=298.

Example 32

7-Cyclopropyl-N-(trans-3-(2-hydroxypropan-2-yl)cyclobutyl)-1,6-naphthyridine-3-carboxamide

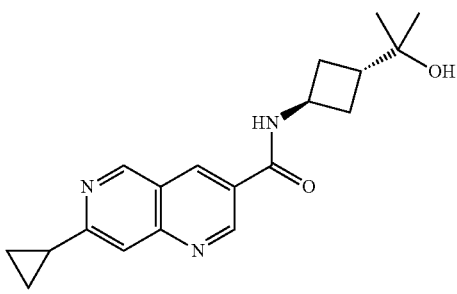 [SMILES: CC(C)(O)[C@H]1C[C@H](NC(=O)c2cnc3cc(C4CC4)ncc3c2)C1]

N,N-Diisopropylethylamine (0.122 mL, 0.700 mmol) was added to a stirred solution of 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, 2-(trans-3-aminocyclobutyl)propan-2-ol hydrochloride (87 mg, 0.525 mmol) was added, followed by the addition of N,N-diisopropylethylamine (0.122 mL, 0.700 mmol) and the reaction mixture was stirred for fifteen hours. Then the reaction mixture was concentrated under vacuum to dryness. The resulting residue was triturated with acetonitrile to yield 7-cyclopropyl-N-(trans-3-(2-hydroxypropan-2-yl)cyclobutyl)-1,6-naphthyridine-3-carboxamide (0.050 g, 0.149 mmol, 42.6% yield) as an off white solid. $^1$H NMR (400 MHz, CD$_3$SOCD$_3$) δ 1.05 (s, 6H), 1.00-1.10 (m, 4H), 2.02-2.12 (m, 2H), 2.20-2.38 (m, 4H), 4.27 (s, 1H), 4.37 (sex, J=7 Hz, 1H), 7.86 (s, 1H), 8.92 (d, J=2 Hz, 1H), 9.00 (d, J=7 Hz, 1H), 9.33 (s, 1H), 9.39 (d, J=2 Hz, 1H); LC-MS (LC-ES) M+H=326.

Example 33

7-Cyclopropyl-N-((1r,4r)-4-(difluoromethyl)-4-hydroxycyclohexyl)-1,6-naphthyridine-3-carboxamide

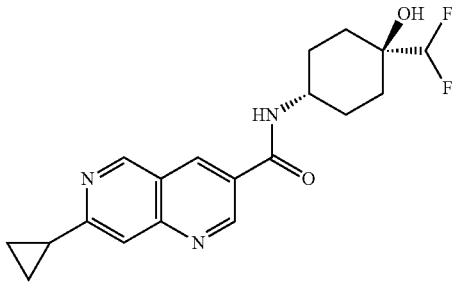 [SMILES: O=C(N[C@H]1CC[C@@](O)(C(F)F)CC1)c1cnc2cc(C3CC3)ncc2c1]

N,N-Diisopropylethylamine (0.092 mL, 0.525 mmol) was added to 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, (1r,4r)-4-amino-1-(difluoromethyl)cyclohexan-1-ol (87 mg, 0.525 mmol, Intermediate 23) was added, followed by the addition of N,N-diisopropylethylamine (0.092 mL, 0.525 mmol) and the reaction mixture was stirred for fifteen hours. Then, the reaction mixture was concentrated to dryness under vacuum. The resulting residue was purified by silica gel chromatography, eluting with methanol:dichloromethane (0:1 to 1:6) to give 7-cyclopropyl-N-((1r,4r)-4-(difluoromethyl)-4-hydroxycyclohexyl)-1,6-naphthyridine-3-carboxamide (0.050 g, 0.133 mmol, 37.9% yield) as an off white solid. $^1$H NMR (400 MHz, CD$_3$SOCD$_3$) δ 1.02-1.10 (m, 4H), 1.38-1.50 (m, 2H), 1.62-1.76 (m, 2H), 1.78-1.94 (m, 4H), 2.30-2.40 (m, 1H), 4.02-4.12 (m, 1H), 5.08 (s, 1H), 5.73 (t, J=56 Hz, 1H), 7.86 (s, 1H), 8.52 (d, J=7 Hz, 1H), 8.87 (d, J=2 Hz, 1H), 9.34 (s, 1H), 9.34 (d, J=2 Hz, 1H); LC-MS (LC-ES) M+H=362.

Example 34

Racemic 7-Cyclopropyl-N-(6-(2-hydroxypropan-2-yl)spiro[3.3]heptan-2-yl)-1,6-naphthyridine-3-carboxamide

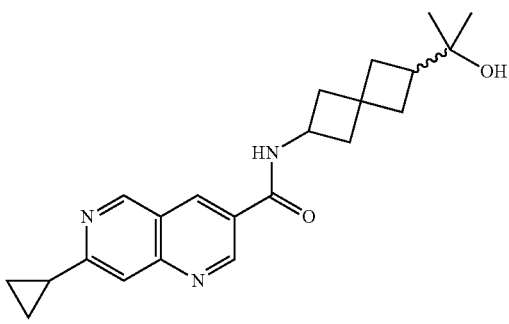 [SMILES: CC(C)(O)C1CC2(CC(NC(=O)c3cnc4cc(C5CC5)ncc4c3)C2)C1]

N,N-Diisopropylethylamine (0.061 mL, 0.350 mmol) was added to a stirred solution of 7-cyclopropyl-1,6-naphthyridine-3-carboxylic acid (50 mg, 0.233 mmol, Intermediate 1) in N,N-dimethylformamide (1.0 mL) at room temperature. Then, 1-[bis(dimethylamino)methylene]-1H-1,2,3-triazolo[4,5-b]pyridinium 3-oxide hexafluorophosphate (133 mg, 0.350 mmol) was added. After stirring for 15 minutes, 2-(6-aminospiro[3.3]heptan-2-yl)propan-2-ol (43.5 mg, 0.257 mmol, Intermediate 24) was added, followed by the addition of N,N-diisopropylethylamine (0.061 mL, 0.350 mmol) and the reaction mixture was stirred for fifteen hours. Then, the reaction mixture was concentrated under vacuum to dryness. The resulting residue was triturated with acetonitrile to yield racemic 7-cyclopropyl-N-(6-(2-hydroxypropan-2-yl)spiro[3.3]heptan-2-yl)-1,6-naphthyridine-3-carboxamide (0.045 g, 0.117 mmol, 50.1% yield) as an off white solid. $^1$H NMR (400 MHz, CD$_3$SOCD$_3$) δ 0.94 (s, 3H), 0.95 (s, 3H), 1.02-1.10 (m, 4H), 1.66-1.76 (m, 1H), 1.86-2.02 (m, 4H), 2.06-2.22 (m, 3H), 2.30-2.46 (m, 2H), 4.01 (s, 1H), 4.33 (sex, J=8 Hz, 1H), 7.85 (s, 1H), 8.89 (d, J=2 Hz, 1H), 8.94 (d, J=8 Hz, 1H), 9.32 (s, 1H), 9.36 (d, J=2 Hz, 1H); LC-MS (LC-ES) M+H=366.

Example 35

7-Cyclopropyl-N-(trans-4-(3-fluoroazetidin-1-yl)cyclohexyl)-1,6-naphthyridine-3-carboxamide

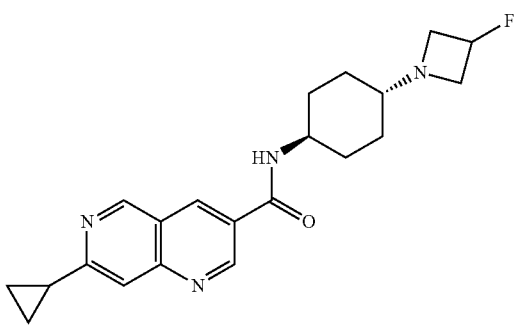 [SMILES: O=C(N[C@H]1CC[C@H](N2CC(F)C2)CC1)c1cnc2cc(C3CC3)ncc2c1]

N,N-Diisopropylethylamine (0.092 mL, 0.525 mmol) was added to 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, trans-4-(3-fluoroazetidin-1-yl)cyclohexan-1-amine (0.0724 g, 0.420 mmol, Intermediate 26) was added, followed by the addition of N,N-diisopropylethylamine (0.092 mL, 0.525 mmol) and the reaction mixture was stirred for fifteen hours. Then, the reaction mixture was concentrated under vacuum to dryness. The resulting residue was purified via reverse phase chromatography, eluting with acetonitrile:water with 0.1% ammonium hydroxide (0:1 to 1:0) to give 7-cyclopropyl-N-(trans-4-(3-fluoroazetidin-1-yl)cyclohexyl)-1,6-naphthyridine-3-carboxamide (0.070 g, 0.180 mmol, 51.6% yield) as an off white solid. $^1$H NMR (400 MHz, CD$_3$SOCD$_3$) δ 1.01 (q, J=13 Hz, 2H), 1.02-1.10 (m, 4H), 1.35 (q, J=14 Hz, 2H), 1.77 (br d, J=11 Hz, 2H), 1.88 (br d, J=10 Hz, 2H), 1.96-2.08 (m, 1H), 2.30-2.38 (m, 1H), 2.96-3.10 (m, 2H), 3.46-3.58 (m, 2H), 3.70-3.82 (m, 1H), 5.10 (dquin, J=58, 5 Hz, 1H), 7.86 (s, 1H), 8.63 (d, J=8 Hz, 1H), 8.88 (d, J=2 Hz, 1H), 9.33 (s, 1H), 9.37 (d, J=2 Hz, 1H); LC-MS (LC-ES) M+H=369.

Example 36

7-Cyclopropyl-N-((1s,4s)-4-(difluoromethyl)-4-hydroxycyclohexyl)-1,6-naphthyridine-3-carboxamide

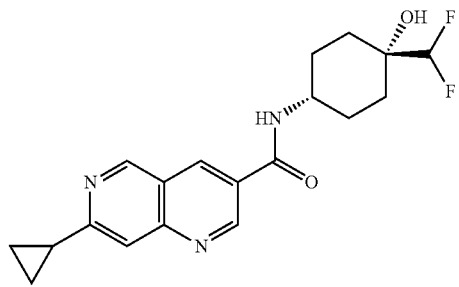 [SMILES: O=C(N[C@H]1CC[C@](O)(C(F)F)CC1)c1cnc2cc(C3CC3)ncc2c1]

N,N-Diisopropylethylamine (0.092 mL, 0.525 mmol) was added to 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, (1s,4s)-4-amino-1-(difluoromethyl)cyclohexan-1-ol (69.4 mg, 0.420 mmol, Intermediate 22) was added, followed by the addition of N,N-diisopropylethylamine (0.092 mL, 0.525 mmol) and the reaction mixture was stirred for eight hours. Then, the reaction mixture was concentrated to dryness under vacuum. The resulting residue was purified via reverse phase chromatography, eluting with acetonitrile:water with 0.1% ammonium hydroxide (0:1 to 1:0) to give 7-cyclopropyl-N-((1s,4s)-4-(difluoromethyl)-4-hydroxycyclohexyl)-1,6-naphthyridine-3-carboxamide (0.080 g, 0.210 mmol, 60.1% yield) as an off white solid. $^1$H NMR (400 MHz, CD$_3$SOCD$_3$) δ 1.02-1.10 (m, 4H), 1.40-1.52 (m, 2H), 1.60-1.82 (m, 6H), 2.28-2.38 (m, 1H), 3.81 (sex, J=7 Hz, 1H), 5.10 (s, 1H), 5.69 (t, J=57 Hz, 1H), 7.85 (s, 1H), 8.71 (d, J=8 Hz, 1H), 8.92 (d, J=2 Hz, 1H), 9.32 (s, 1H), 9.39 (d, J=2 Hz, 1H); LC-MS (LC-ES) M+H=362.

Example 37

7-Cyclopropyl-N-((trans)-4-(((R)-1,1,1-trifluoro-3-hydroxypropan-2-yl)amino)cyclohexyl)-1,6-naphthyridine-3-carboxamide

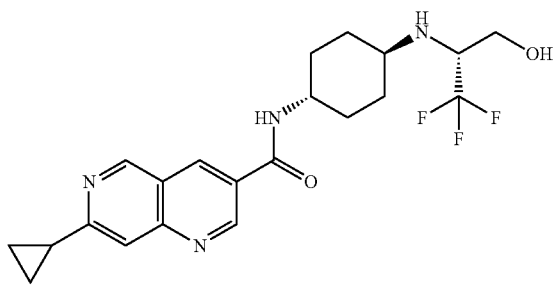 [SMILES: O=C(N[C@H]1CC[C@H](N[C@H](CO)C(F)(F)F)CC1)c1cnc2cc(C3CC3)ncc2c1]

N,N-Diisopropylethylamine (0.092 mL, 0.525 mmol) was added to a stirred solution of 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, (R)-2-((trans-4-aminocyclohexyl)amino)-3,3,3-trifluoropropan-1-ol (103 mg, 0.455 mmol, Intermediate 28) in N,N-dimethylformamide (0.5 mL) was added, followed by the addition of N,N-diisopropylethylamine (0.092 mL, 0.525 mmol) and the reaction mixture was stirred for eight hours. Then, the reaction mixture was concentrated to dryness under vacuum. The resulting residue was purified via reverse phase chromatography, eluting with acetonitrile:water with 0.1% ammonium hydroxide (0:1 to 1:0) to give 7-cyclopropyl-N-((trans)-4-(((R)-1,1,1-trifluoro-3-hydroxypropan-2-yl)amino)cyclohexyl)-1,6-naphthyridine-3-carboxamide (0.035 g, 0.079 mmol, 22.5% yield) as an off white solid. $^1$H NMR (400 MHz, CD$_3$SOCD$_3$) δ 1.02-1.10 (m, 4H), 1.12 (q, J=13 Hz, 2H), 1.36 (q, J=13 Hz, 2H), 1.84-2.00 (m, 4H), 2.30-2.38 (m, 1H), 2.44-2.56 (m, 1H), 3.22-3.34 (m, 2H), 3.44-3.52 (m, 1H), 3.58-3.66 (m, 1H), 3.72-3.84 (m, 1H), 5.01 (t, J=6 Hz, 1H), 7.86 (s, 1H), 8.62 (d, J=8 Hz, 1H), 8.88 (d, J=2 Hz, 1H), 9.33 (s, 1H), 9.37 (d, J=2 Hz, 1H); LC-MS (LC-ES) M+H=423.

Example 38

7-Cyclopropyl-N-(trans-4-(3,3-difluoroazetidin-1-yl)cyclohexyl)-1,6-naphthyridine-3-carboxamide

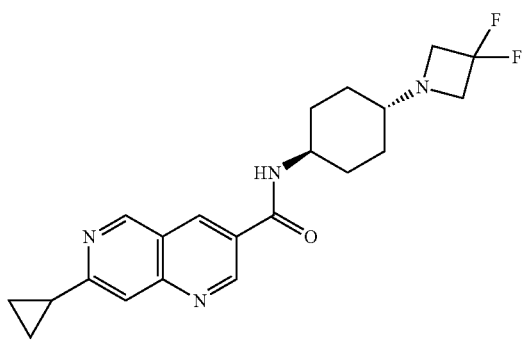 [SMILES: O=C(N[C@H]1CC[C@H](N2CC(F)(F)C2)CC1)c1cnc2cc(C3CC3)ncc2c1]

N,N-Diisopropylethylamine (0.092 mL, 0.525 mmol) was added to 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, trans-4-(3,3-difluoroazetidin-1-yl)cyclohexan-1-amine (87 mg, 0.455 mmol, Intermediate 30) was added, followed by the addition of N,N-diisopropylethylamine (0.092 mL, 0.525 mmol) and the reaction mixture was stirred for fifteen hours. Then, the reaction mixture was purified via reverse phase chromatography, eluting with acetonitrile:water with 0.1% ammonium hydroxide (0:1 to 1:0) to give 7-cyclopropyl-N-(trans-4-(3,3-difluoroazetidin-1-yl)cyclohexyl)-1,6-naphthyridine-3-carboxamide (0.095 g, 0.234 mmol, 66.7% yield) as an off white solid. $^1$H NMR (400 MHz, CD$_3$SOCD$_3$) δ 1.00-1.10 (m, 4H), 1.07 (q, J=11 Hz, 2H), 1.36 (q, J=14 Hz, 2H), 1.77 (br d, J=11 Hz, 2H), 1.89 (br d, J=10 Hz, 2H), 2.13 (t, J=11 Hz, 1H), 2.30-2.38 (m, 1H), 3.54 (t, J=12 Hz, 4H), 3.72-3.84 (m, 1H), 7.85 (s, 1H), 8.63 (d, J=8 Hz, 1H), 8.88 (d, J=2 Hz, 1H), 9.33 (s, 1H), 9.37 (d, J=2 Hz, 1H); LC-MS (LC-ES) M+H=387.

Example 39

Racemic 7-Cyclopropyl-N-(trans-4-(0,1-difluoropropan-2-yl)amino)cyclohexyl)-1,6-naphthyridine-3-carboxamide

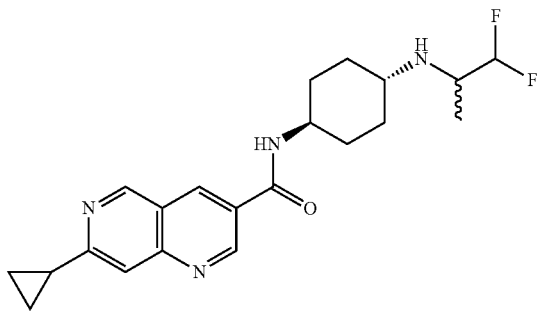 [SMILES: CC(N[C@H]1CC[C@H](NC(=O)c2cnc3cc(C4CC4)ncc3c2)CC1)C(F)F]

N,N-Diisopropylethylamine (0.092 mL, 0.525 mmol) was added to 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, trans-N1-(1,1-difluoropropan-2-yl)cyclohexane-1,4-diamine hydrochloride (104 mg, 0.455 mmol, Intermediate 31) was added, followed by the addition of N,N-diisopropylethylamine (0.092 mL, 0.525 mmol) and the reaction mixture was stirred for eighteen hours. Then, the reaction mixture was concentrated to dryness under vacuum. The resulting residue was purified via reverse phase chromatography, eluting with acetonitrile:water with 0.1% ammonium hydroxide (0:1 to 1:0) to give racemic 7-cyclopropyl-N-(trans-4-((1,1-difluoropropan-2-yl)amino)cyclohexyl)-1,6-naphthyridine-3-carboxamide (0.095 g, 0.232 mmol, 66.4% yield) as an off white solid. $^1$H NMR (400 MHz, CD$_3$SOCD$_3$) δ 1.02-1.10 M, 4H), 1.32 (d, J=6 Hz, 3H), 1.43 (q, J=12 Hz, 2H), 1.58 (q, J=14 Hz, 2H), 1.98 (br d, J=11 Hz, 2H), 2.17 (br t, J=12 Hz, 2H), 2.34 (quin, J=6 Hz, 1H), 3.10-3.24 (m, 1H), 3.72-3.92 (m, 2H), 6.44 (t, J=54 Hz, 1H), 7.86 (s, 1H), 8.78 (d, J=7 Hz, 1H), 8.92 (d, J=2 Hz, 1H), 9.33 (s, 1H), 9.39 (d, J=2 Hz, 1H); LC-MS (LC-ES) M+H=389.

Example 40

7-Cyclopropyl-N-((1s,3s)-3-hydroxy-3-(trifluoromethyl)cyclobutyl)-1,6-naphthyridine-3-carboxamide

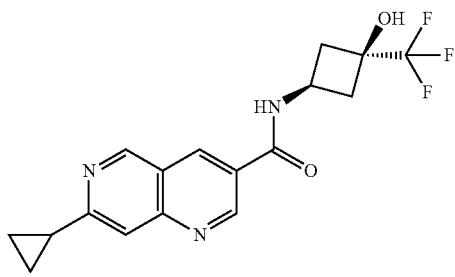 [SMILES: O=C(N[C@H]1C[C@](O)(C(F)(F)F)C1)c1cnc2cc(C3CC3)ncc2c1]

N,N-Diisopropylethylamine (0.061 mL, 0.350 mmol) was added to 7-cyclopropyl-1,6-naphthyridine-3-carboxylic acid (50 mg, 0.233 mmol, Intermediate 1) in N,N-dimethylformamide (1.0 mL) at room temperature. Then, 1-[bis(dimethylamino)methylene]-1H-1,2,3-triazolo[4,5-b]pyridinium 3-oxide hexafluorophosphate (133 mg, 0.350 mmol) was added. After stirring for 15 minutes, (1s,3s)-3-amino-1-(trifluoromethyl)cyclobutan-1-ol hydrochloride (44.7 mg, 0.233 mmol) was added, followed by the addition of N,N-diisopropylethylamine (0.061 mL, 0.350 mmol) and the reaction mixture was stirred for eighteen hours. Then, the reaction mixture was concentrated to dryness under vacuum. The resulting residue was purified via reverse phase chromatography, eluting with acetonitrile:water with 0.1% ammonium hydroxide (0:1 to 1:0) to give 7-cyclopropyl-N-((1s,3s)-3-hydroxy-3-(trifluoromethyl)cyclobutyl)-1,6-naphthyridine-3-carboxamide (0.070 g, 0.189 mmol, 81.0% yield) as an off white solid. $^1$H NMR (400 MHz, CD$_3$SOCD$_3$) δ 1.02-1.10 (m, 4H), 2.30-2.44 (m, 3H), 2.76-2.86 (m, 2H), 4.20 (sex, J=8 Hz, 1H), 6.72 (s, 1H), 7.86 (s, 1H), 8.93 (d, J=2 Hz, 1H), 9.21 (d, J=7 Hz, 1H), 9.33 (s, 1H), 9.39 (d, J=2 Hz, 1H); LC-MS (LC-ES) M+H=352.

Example 41

7-Cyclopropyl-N-((1r,3s)-3-hydroxy-3-methylcyclobutyl)-1,6-naphthyridine-3-carboxamide

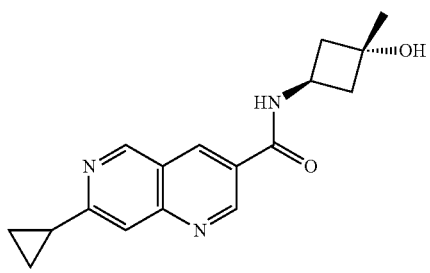 [SMILES: C[C@]1(O)C[C@H](NC(=O)c2cnc3cc(C4CC4)ncc3c2)C1]

N,N-Diisopropylethylamine (0.122 mL, 0.700 mmol) was added to 7-cyclopropyl-1,6-naphthyridine-3-carboxylic acid (75 mg, 0.350 mmol, Intermediate 1) in N,N-dimethylformamide (1.5 mL) at room temperature. Then, 1-[bis(dimethylamino)methylene]-1H-1,2,3-triazolo[4,5-b]pyridinium 3-oxide hexafluorophosphate (200 mg, 0.525 mmol) was added. After stirring for 15 minutes, (1r,3r)-3-amino-1-methylcyclobutan-1-ol (53.1 mg, 0.525 mmol, Intermediate 11, Astatech) was added, followed by the addition of N,N-diisopropylethylamine (0.122 mL, 0.700 mmol) and the reaction mixture was stirred for eight hours. Then, the reaction mixture was concentrated to dryness under vacuum. The resulting residue was purified via reverse phase chromatography, eluting with acetonitrile:water with 0.1% ammonium hydroxide (0:1 to 1:0) to give 7-cyclo propyl-N-((1r,3r)-3-hydroxy-3-methylcyclobutyl)-1,6-naphthyridine-3-carboxamide (0.070 g, 0.224 mmol, 63.9% yield) as an off white solid. $^1$H NMR (400 MHz, CD$_3$SOCD$_3$) δ 1.02-1.10 (m, 4H), 1.29 (s, 3H), 2.04-2.14 (m, 2H), 2.26-2.38 (m, 3H), 4.54 (sex, J=8 Hz, 1 H), 4.90 (s, 1H), 7.86 (s, 1H), 8.89 (d, J=2 Hz, 1H), 8.95 (d, J=7 Hz, 1H), 9.33 (s, 1H), 9.37 (d, J=2 Hz, 1H); LC-MS (LC-ES) M+H=298.

Example 42 & 43

7-Cyclopropyl-N-(cis-3-(((R)-1,1,1-trifluoro-3-hydroxypropan-2-yl)amino)cyclobutyl)-1,6-naphthyridine-3-carboxamide and 7-Cyclopropyl-N-(trans-3-(((R)-1,1,1-trifluoro-3-hydroxypropan-2-yl)amino)cyclobutyl)-1,6-naphthyridine-3-carboxamide

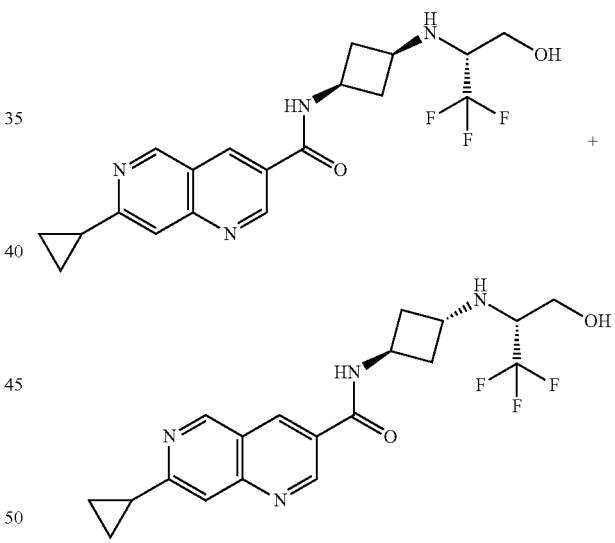

1-[bis(dimethylamino)methylene]-1H-1,2,3-triazolo[4,5-b]pyridinium 3-oxide hexafluorophosphate (213 mg, 0.560 mmol) was added to 7-cyclopropyl-1,6-naphthyridine-3-carboxylic acid (100 mg, 0.467 mmol, Intermediate 1) in N,N-dimethylformamide (3 mL) at room temperature. Then, N,N-diisopropylethylamine (0.122 mL, 0.700 mmol) was added. After stirring for 15 minutes, a cis/trans mixture of (2R)-2-((3-aminocyclobutyl)amino)-3,3,3-trifluoropropan-1-ol (139 mg, 0.700 mmol, Intermediate 32) was added, followed by the addition of more N,N-diisopropylethylamine (0.122 mL, 0.700 mmol) and the reaction mixture was stirred for eight hours. Then, the reaction mixture was concentrated under vacuum. The resulting residue was purified via reverse phase chromatography, eluting with acetonitrile:water with 0.1% ammonium hydroxide (0:1 to 1:0) to give an off white solid as a mixture of cis/trans isomers. The isomers were separated by chiral super critical fluid chromatography, eluting with 40% ethyl alcohol in carbon dioxide on a chiral IG column to give 7-cyclopropyl-N-(cis-3-(((R)-1,1,1-trifluoro-3-hydroxypropan-2-yl)amino)cyclobutyl)-1,6-naphthyridine-3-carboxamide (0.041 g, 0.099 mmol, 21.2% yield) and 7-cyclopropyl-N-(trans-3-(((R)-1,1,1-trifluoro-3-hydroxypropan-2-yl)amino)cyclobutyl)-1,6-naphthyridine-3-carboxamide (0.051 g, 0.123 mmol, 26.3% yield). The isomers were assigned via ROESY NMR.

7-Cyclopropyl-N-(cis-3-(((R)-1,1,1-trifluoro-3-hydroxypropan-2-yl)amino)cyclobutyl)-1,6-naphthyridine-3-carboxamide $^1$H NMR (400 MHz, CD$_3$SOCD$_3$) δ 1.02-1.10 (m, 4H), 1.78-1.92 (m, 2H), 2.22 (dd, J=8, 7 Hz, 1H), 2.30-2.38 (m, 1H), 2.50-2.64 (m, 2H), 3.02-3.22 (m, 2H), 3.42-3.52 (m, 1H), 3.58-3.66 (m, 1H), 4.08 (sex, J=8 Hz, 1H), 5.07 (t, J=6 Hz, 1H), 7.86 (s, 1H), 8.90 (d, J=2 Hz, 1H), 8.96 (d, J=8 Hz, 1H), 9.32 (s, 1H), 9.38 (d, J=2 Hz, 1H); LC-MS (LC-ES) M+H=395.

7-Cyclopropyl-N-(trans-3-(((R)-1,1,1-trifluoro-3-hydroxypropan-2-yl)amino)cyclobutyl)-1,6-naphthyridine-3-carboxamide $^1$H NMR (400 MHz, CD$_3$SOCD$_3$) δ 1.02-1.10 (m, 4H), 2.08-2.18 (m, 2H), 2.20-2.30 (m, 2H), 2.30-2.38 (m, 1H), 2.40 (t, J=7 Hz, 1H), 3.02-3.14 (m, 1H), 3.46-3.54 (m, 1H), 3.52-3.60 (m, 1H), 3.58-3.68 (m, 1H), 4.49 (sex, J=7 Hz, 1H), 5.03 (t, J=6 Hz, 1H), 7.86 (s, 1H), 8.91 (d, J=2 Hz, 1H), 9.02 (d, J=7 Hz, 1H), 9.33 (s, 1H), 9.39 (d, J=2 Hz, 1H); LC-MS (LC-ES) M+H=395.

Example 44

(S)-7-Cyclopropyl-N-(2-oxopyrrolidin-3-yl)-1,8-naphthyridine-3-carboxamide

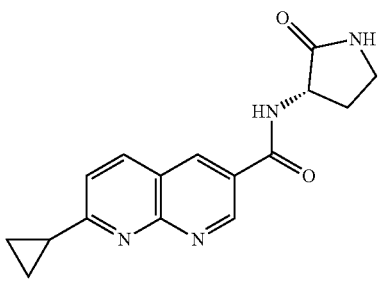

N,N-Diisopropylethylamine (0.265 mL, 1.520 mmol) was added to 7-cyclopropyl-1,8-naphthyridine-3-carboxylic acid (0.0814 g, 0.380 mmol, Intermediate 4F) in N,N-dimethylformamide (1.3 mL) at room temperature. Then, (S)-3-aminopyrrolidin-2-one (0.038 g, 0.380 mmol) was added and the reaction mixture was stirred for five minutes. Then, n-propylphosphonic acid anhydride (0.452 mL, 0.760 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 3:2) to give (S)-7-cyclopropyl-N-(2-oxopyrrolidin-3-yl)-1,8-naphthyridine-3-carboxamide (0.0510 g, 0.164 mmol, 43.0% yield). $^1$H NMR (400 MHz, CD$_3$SOCD$_3$) δ 1.10-1.22 (m, 4H), 1.96-2.10 (m, 1H), 2.32-2.44 (m, 2H), 3.20-3.30 (m, 2H), 4.62 (q, J=9 Hz, 1H), 7.66 (d, J=8 Hz, 1H), 7.93 (s, 1H), 8.41 (d, J=8 Hz, 1H), 8.83 (d, J=2 Hz, 1H), 9.06 (d, J=8 Hz, 1H), 9.35 (d, J=2 Hz, 1H); LC-MS (LC-ES) M+H=297.

Example 45

7-Cyclopropyl-N-((1s,3s)-3-hydroxy-3-methylcyclobutyl)-1,8-naphthyridine-3-carboxamide

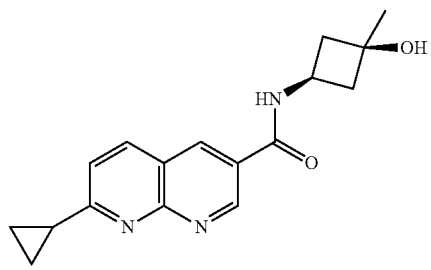 [SMILES: C[C@]1(O)C[C@@H](NC(=O)c2cnc3nc(C4CC4)ccc3c2)C1]

N,N-Diisopropylethylamine (0.249 mL, 1.428 mmol) was added to 7-cyclopropyl-1,8-naphthyridine-3-carboxylic acid (0.0765 g, 0.357 mmol, Intermediate 4F) in N,N-dimethylformamide (1.2 mL) at room temperature. Then, (1s,3s)-3-amino-1-methylcyclobutan-1-ol (0.036 g, 0.357 mmol, Intermediate 10) was added and the reaction mixture was stirred for five minutes. Then, n-propylphosphonic acid anhydride (0.425 mL, 0.714 mmol) was added and the reaction mixture was stirred for sixty-six hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give 7-cyclopropyl-N-((1s,3s)-3-hydroxy-3-methylcyclobutyl)-1,8-naphthyridine-3-carboxamide (0.0710 g, 0.227 mmol, 63.5% yield). $^1$H NMR (400 MHz, CD$_3$SOCD$_3$) δ 1.08-1.20 (m, 4H), 1.28 (s, 3H), 2.13 (t, J=8 Hz, 2H), 2.28-2.42 (m, 3H), 4.02 (h, J=8 Hz, 1H), 5.02 (s, 1H), 7.64 (d, J=8 Hz, 1H), 8.38 (d, J=8 Hz, 1H), 8.81 (d, J=2 Hz, 1H), 8.95 (d, J=7 Hz, 1H), 9.33 (d, J=2 Hz, 1H); LC-MS (LC-ES) M+H=298.

Example 46

7-Cyclopropyl-N-((1r,3s)-3-hydroxy-3-methylcyclobutyl)-1,8-naphthyridine-3-carboxamide

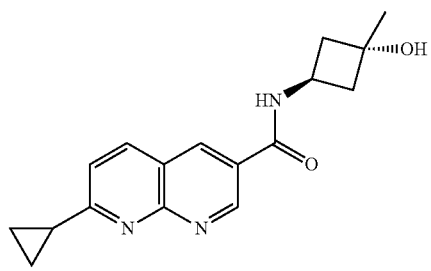 [SMILES: C[C@]1(O)C[C@H](NC(=O)c2cnc3nc(C4CC4)ccc3c2)C1]

N,N-Diisopropylethylamine (0.288 mL, 1.647 mmol) was added to 7-cyclopropyl-1,8-naphthyridine-3-carboxylic acid (0.0882 g, 0.412 mmol, Intermediate 4F) in N,N-dimethylformamide (1.4 mL) at room temperature. Then, (1r,3s)-3-amino-1-methylcyclobutan-1-ol (0.042 g, 0.412 mmol, Intermediate 11) was added and the reaction mixture was stirred for five minutes. Then, n-propylphosphonic acid anhydride (0.490 mL, 0.823 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give 7-cyclopropyl-N-((1r,3r)-3-hydroxy-3-methylcyclobutyl)-1,8-naphthyridine-3-carboxamide (0.0986 g, 0.315 mmol, 77% yield). $^1$H NMR (400 MHz, CD$_3$SOCD$_3$) δ 1.10-1.20 (m, 4H), 1.29 (s, 3H), 2.04-2.14 (m, 2H), 2.26-2.42 (m, 3H), 4.54 (h, J=8 Hz, 1H), 4.89 (s, 1H), 7.64 (d, J=8 Hz, 1H), 8.39 (d, J=8 Hz, 1H), 8.78 (d, J=2 Hz, 1H), 8.91 (d, J=7 Hz, 1H), 9.32 (d, J=2 Hz, 1H); LC-MS (LC-ES) M+H=298.

Example 47

7-Cyclopropyl-N-(trans-3-(2-hydroxypropan-2-yl)cyclobutyl)-1,8-naphthyridine-3-carboxamide

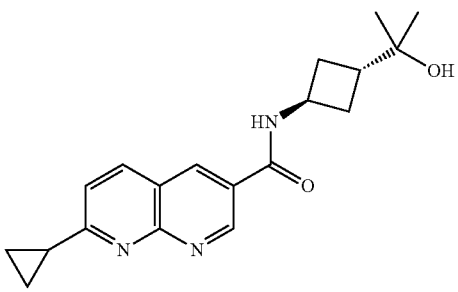 [SMILES: CC(C)(O)[C@H]1C[C@H](NC(=O)c2cnc3nc(C4CC4)ccc3c2)C1]

N,N-Diisopropylethylamine (0.280 mL, 1.602 mmol) was added to 7-cyclopropyl-1,8-naphthyridine-3-carboxylic acid (0.0858 g, 0.401 mmol, Intermediate 4F) in N,N-dimethylformamide (1.3 mL) at room temperature. Then, 2-(trans-3-aminocyclobutyl)propan-2-ol hydrochloride (0.066 g, 0.401 mmol) was added and the reaction mixture was stirred for five minutes. Then, n-propylphosphonic acid anhydride (0.477 mL, 0.801 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 3:2) to give 7-cyclopropyl-N-(trans-3-(2-hydroxypropan-2-yl)cyclobutyl)-1,8-naphthyridine-3-carboxamide (0.0630 g, 0.184 mmol, 45.9% yield). $^1$H NMR (400 MHz, CD$_3$SOCD$_3$) δ 1.05 (s, 6H), 1.08-1.20 (m, 4H), 2.02-2.12 (m, 2H), 2.18-2.42 (m, 4H), 4.26 (s, 1H), 4.37 (h, J=7 Hz, 1H), 7.64 (d, J=8 Hz, 1H), 8.39 (d, J=8 Hz, 1H), 8.81 (d, J=2 Hz, 1H), 8.96 (d, J=7 Hz, 1H), 9.34 (d, J=2 Hz, 1H); LC-MS (LC-ES) M+H=326.

Example 48

7-Cyclopropyl-N-((1r,4r)-4-hydroxy-4-methylcyclohexyl)-1,8-naphthyridine-3-carboxamide

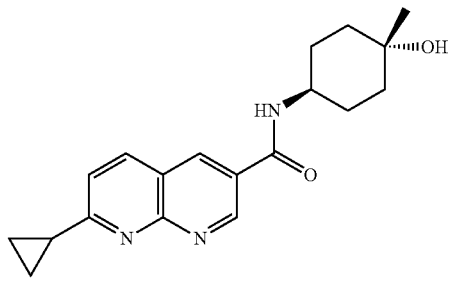 [SMILES: C[C@]1(O)CC[C@H](NC(=O)c2cnc3nc(C4CC4)ccc3c2)CC1]

N,N-Diisopropylethylamine (0.252 mL, 1.441 mmol) was added to 7-cyclopropyl-1,8-naphthyridine-3-carboxylic acid (0.0772 g, 0.360 mmol, Intermediate 4F) in N,N-dimethylformamide (1.2 mL) at room temperature. Then, (1r,4r)-4-amino-1-methylcyclohexan-1-ol (0.047 g, 0.360 mmol, Intermediate 21) was added and the reaction mixture was stirred for five minutes. Then, n-propylphosphonic acid anhydride (0.429 mL, 0.721 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give 7-cyclopropyl-N-((1r,4r)-4-hydroxy-4-methylcyclohexyl)-1,8-naphthyridine-3-carboxamide (0.0679 g, 0.198 mmol, 55.0% yield). $^1$H NMR (400 MHz, CD$_3$SOCD$_3$) δ 1.16 (s, 3H), 1.10-1.22 (m, 4H), 1.40-1.56 (m, 4H), 1.56-1.64 (m, 2H), 1.74-1.86 (m, 2H), 2.30-2.40 (m, 1H), 3.80-3.92 (m, 1H), 4.31 (s, 1H), 7.63 (s, 1H), 8.39 (d, J=8 Hz, 1H), 8.53 (d, J=8 Hz, 1H), 8.78 (d, J=2 Hz, 1H), 9.30 (d, J=2 Hz, 1H); LC-MS (LC-ES) M+H=326.

Example 49

Racemic 7-Cyclopropyl-N-(6-(2-hydroxypropan-2-yl)spiro[3.3]heptan-2-yl)-1,8-naphthyridine-3-carboxamide

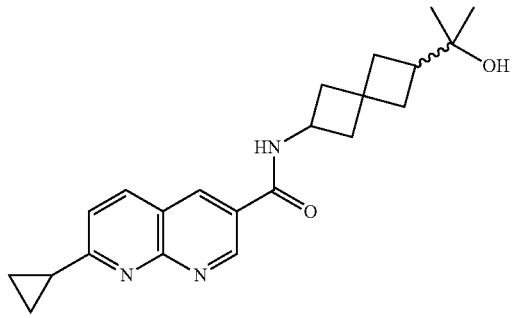 [SMILES: CC(C)(O)C1CC2(CC(NC(=O)c3cnc4nc(C5CC5)ccc4c3)C2)C1]

N,N-Diisopropylethylamine (0.255 mL, 1.460 mmol) was added to 7-cyclopropyl-1,8-naphthyridine-3-carboxylic acid (0.0782 g, 0.365 mmol, Intermediate 4F) in N,N-dimethylformamide (1.2 mL) at room temperature. Then, racemic 2-(6-aminospiro[3.3]heptan-2-yl)propan-2-ol (0.062 g, 0.365 mmol, Intermediate 24) was added and the reaction mixture was stirred for five minutes. Then, n-propylphosphonic acid anhydride (0.435 mL, 0.730 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-cyclopropyl-N-(6-(2-hydroxypropan-2-yl)spiro[3.3]heptan-2-yl)-1,8-naphthyridine-3-carboxamide (0.0886 g, 0.230 mmol, 63.1% yield). $^1$H NMR (400 MHz, CD$_3$SOCD$_3$) δ 0.94 (s, 3H), 0.95 (s, 3H), 1.08-1.20 (m, 4H), 1.16-1.26 (m, 1H), 1.84-2.04 (m, 4H), 2.06-2.22 (m, 3H), 2.30-2.46 (m, 2H), 4.01 (s, 1H), 4.33 (h, J=8 Hz, 1H), 7.64 (d, J=9 Hz, 1H), 8.38 (d, J=8 Hz, 1H), 8.78 (d, J=2 Hz, 1H), 8.90 (d, J=8 Hz, 1H), 9.31 (d, J=2 Hz, 1H); LC-MS (LC-ES) M+H=366.

Example 50

N-(trans-4-(2-Hydroxypropan-2-yl)cyclohexyl)-7-methoxy-1,8-naphthyridine-3-carboxamide

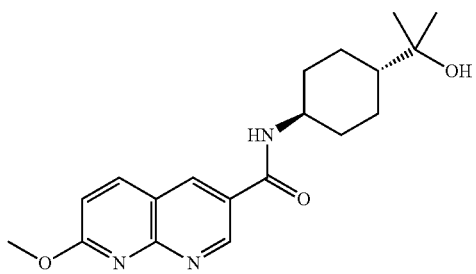 [SMILES: COc1ccc2cc(C(=O)N[C@H]3CC[C@H](C(C)(C)O)CC3)cnc2n1]

7-Methoxy-1,8-naphthyridine-3-carboxylic acid (0.110 g, 0.539 mmol, Intermediate 33) was added to 2-(trans-4-aminocyclohexyl)propan-2-ol (0.081 g, 0.515 mmol) in N,N-dimethylformamide (5 mL) at room temperature. Then, N,N-diisopropylethylamine (0.23 mL, 1.320 mmol) was added, followed by 1-[bis(dimethylamino)methylene]-1H-1,2,3-triazolo[4,5-b]pyridinium 3-oxide hexafluorophosphate (0.235 g, 0.618 mmol) and the reaction mixture was stirred for 150 minutes. The reaction mixture was concentrated and the resulting residue was purified by silica gel chromatography, eluting with (ethyl acetate:ethanol (3:1)): hexanes (0:1 to 1:0) to give a residue which was triturated/sonicated with ethyl acetate and filtered to give N-(trans-4-(2-hydroxypropan-2-yl)cyclohexyl)-7-methoxy-1,8-naphthyridine-3-carboxamide (0.127 g, 0.370 mmol, 71.8% yield) as an off-white powder. $^1$H NMR (400 MHz, CD$_3$SOCD$_3$) δ 1.04 (s, 6H), 1.06-1.24 (m, 3H), 1.31 (q, J=12 Hz, 2H), 1.83 (br d, J=12 Hz, 2H), 1.93 (br d, J=10 Hz, 2H), 3.68-3.80 (m, 1H), 4.03 (s, 3H), 4.06 (s, 1H), 7.19 (d, J=9 Hz, 1H), 8.40 (d, J=9 Hz, 1H), 8.54 (d, J=8 Hz, 1H), 8.78 (d, J=2 Hz, 1H), 9.27 (d, J=2 Hz, 1H); LC-MS (LC-ES) M+H=344.

Example 51

N-(trans-4-(2-Hydroxypropan-2-yl)cyclohexyl)-7-methoxy-1,6-naphthyridine-3-carboxamide

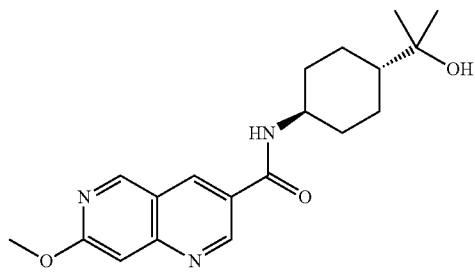 [SMILES: COc1cc2ncc(C(=O)N[C@H]3CC[C@H](C(C)(C)O)CC3)cc2cn1]

7-Methoxy-1,6-naphthyridine-3-carboxylic acid (0.110 g, 0.539 mmol, Intermediate 34) was added to 2-(trans-4-aminocyclohexyl)propan-2-ol (0.079 g, 0.502 mmol) in N,N-dimethylformamide (5 mL) at room temperature. Then, N,N-diisopropylethylamine (0.22 mL, 1.263 mmol) was added, followed by 1-[bis(dimethylamino)methylene]-1H-1,2,3-triazolo[4,5-b]pyridinium 3-oxide hexafluorophosphate (0.232 g, 0.610 mmol) and the reaction mixture was stirred for 150 minutes. The reaction mixture was concentrated and the resulting residue was purified by silica gel chromatography, eluting with (ethyl acetate:ethanol (3:1)): hexanes (0:1 to 1:0) to give a residue which was triturated/sonicated with ethyl acetate and filtered to give N-(trans-4-(2-hydroxypropan-2-yl)cyclohexyl)-7-methoxy-1,6-naphthyridine-3-carboxamide (0.123 g, 0.358 mmol, 71.3% yield) as a pale yellow powder. $^1$H NMR (400 MHz, CD$_3$SOCD$_3$) δ 1.04 (s, 6H), 1.06-1.24 (m, 3H), 1.31 (q, J=10 Hz, 2H), 1.84 (br d, J=12 Hz, 2H), 1.94 (br d, J=10 Hz, 2H), 3.68-3.80 (m, 1H), 4.01 (s, 3H), 4.06 (s, 1H), 7.27 (s, 1H), 8.58 (d, J=8 Hz, 1H), 8.90 (dd, J=2, 1 Hz, 1H), 9.25 (d, J=1 Hz, 1H), 9.34 (d, J=2 Hz, 1H); LC-MS (LC-ES) M+H=344.

Example 52

7-Cyclopropyl-N-((1r,4r)-4-(difluoromethyl)-4-hydroxycyclohexyl)-1,8-naphthyridine-3-carboxamide

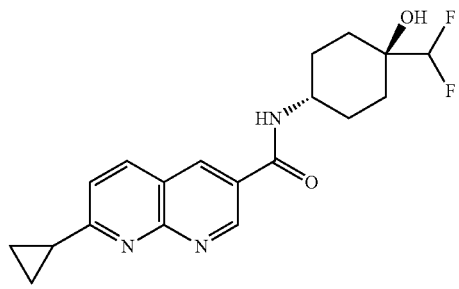 [SMILES: O=C(N[C@H]1CC[C@@](O)(C(F)F)CC1)c1cnc2nc(C3CC3)ccc2c1]

N,N-Diisopropylethylamine (0.098 mL, 0.560 mmol) was added to 7-cyclopropyl-1,8-naphthyridine-3-carboxylic acid (0.0300 g, 0.140 mmol, Intermediate 4F) in N,N-dimethylformamide (0.47 mL) at room temperature. Then, (1r,4r)-4-amino-1-(difluoromethyl)cyclohexan-1-ol (0.023 g, 0.140 mmol, Intermediate 23) was added and the reaction mixture was stirred for five minutes. Then, n-propylphosphonic acid anhydride (0.167 mL, 0.280 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-cyclopropyl-N-((1r,4r)-4-(difluoromethyl)-4-hydroxycyclohexyl)-1,8-naphthyridine-3-carboxamide (0.0164 g, 0.043 mmol, 30.8% yield). $^1$H NMR (400 MHz, CD$_3$SOCD$_3$) δ 1.12-1.20 (m, 4H), 1.38-1.50 (m, 2H), 1.66-1.74 (m, 2H), 1.78-1.92 (m, 4H), 2.32-2.40 (m, 1H), 4.02-4.12 (m, 1H), 5.08 (s, 1H), 5.73 (t, J=56 Hz, 1H), 7.63 (d, J=8 Hz, 1H), 8.40 (d, J=8 Hz, 1H), 8.48 (d, J=7 Hz, 1H), 8.77 (d, J=2 Hz, 1H), 9.29 (d, J=2 Hz, 1H); LC-MS (LC-ES) M+H=362.

Example 53

7-Cyclopropyl-N-(1s,3s)-3-hydroxy-3-(trifluoromethyl)cyclobutyl)-1,8-naphthyridine-3-carboxamide

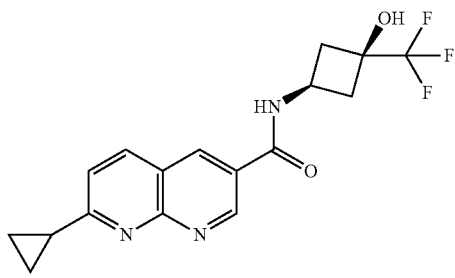 [SMILES: O=C(N[C@H]1C[C@](O)(C(F)(F)F)C1)c1cnc2nc(C3CC3)ccc2c1]

N,N-Diisopropylethylamine (0.252 mL, 1.443 mmol) was added to 7-cyclopropyl-1,8-naphthyridine-3-carboxylic acid (0.0773 g, 0.361 mmol, Intermediate 4F) in N,N-dimethylformamide (1.2 mL) at room temperature. Then, (1s,3s)-3-amino-1-(trifluoromethyl)cyclobutan-1-ol hydrochloride (0.069 g, 0.361 mmol) was added and the reaction mixture was stirred for five minutes. Then, n-propylphosphonic acid anhydride (0.430 mL, 0.722 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 7-cyclopropyl-N-((1s,3s)-3-hydroxy-3-(trifluoromethyl)cyclobutyl)-1,8-naphthyridine-3-carboxamide (0.0212 g, 0.057 mmol, 15.89% yield). $^1$H NMR (400 MHz, CD$_3$SOCD$_3$) δ 1.06-1.22 (m, 4H), 2.30-2.46 (m, 3H), 2.76-2.86 (m, 2H), 4.19 (h, J=9 Hz, 1H), 6.70 (s, 1H), 7.65 (d, J=8 Hz, 1H), 8.40 (d, J=8 Hz, 1H), 8.82 (d, J=2 Hz, 1H), 9.17 (d, J=7 Hz, 1H), 9.35 (d, J=2 Hz, 1H); LC-MS (LC-ES) M+H=352.

Example 54

7-Cyclopropyl-N-(trans-4-(3,3-difluoroazetidin-1-yl)cyclohexyl)-1,8-naphthyridine-3-carboxamide

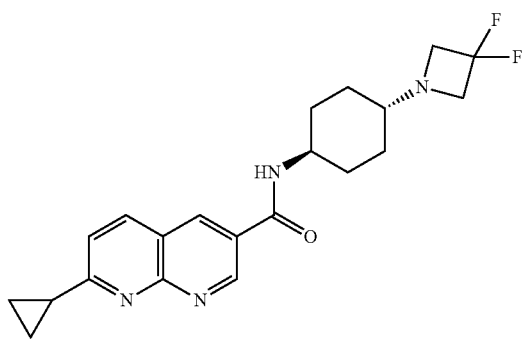 [SMILES: O=C(N[C@H]1CC[C@H](N2CC(F)(F)C2)CC1)c1cnc2nc(C3CC3)ccc2c1]

N,N-Diisopropylethylamine (0.239 mL, 1.369 mmol) was added to 7-cyclopropyl-1,8-naphthyridine-3-carboxylic acid (0.0733 g, 0.342 mmol, Intermediate 4F) in N,N-dimethylformamide (1.1 mL) at room temperature. Then, trans-4-(3,3-difluoroazetidin-1-yl)cyclohexan-1-amine (0.065 g, 0.342 mmol, Intermediate 30) was added and the reaction mixture was stirred for five minutes. Then, n-propylphosphonic acid anhydride (0.407 mL, 0.684 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give 7-cyclopropyl-N-(trans-4-(3,3-difluoroazetidin-1-yl)cyclohexyl)-1,8-naphthyridine-3-carboxamide (0.0596 g, 0.147 mmol, 42.8% yield). $^1$H NMR (400 MHz, CD$_3$SOCD$_3$) δ 1.07 (q, J=14 Hz, 2H), 1.08-1.20 (m, 4H), 1.36 (q, J=14 Hz, 2H), 1.77 (br d, J=12 Hz, 2H), 1.88 (br d, J=11 Hz, 2H), 2.06-2.18 (m, 1H), 2.28-2.42 (m, 1H), 3.54 (t, J=12 Hz, 4H), 3.72-3.84 (m, 1H), 7.63 (d, J=8 Hz, 1H), 8.39 (d, J=8 Hz, 1H), 8.59 (d, J=8 Hz, 1H), 8.78 (d, J=2 Hz, 1H), 9.32 (d, J=2 Hz, 1H); LC-MS (LC-ES) M+H=387.

Example 55 & 56

N-(trans-4-(2-Hydroxypropan-2-yl)cyclohexyl)-7-(2,2,2-trifluoroethoxy)-1,8-naphthyridine-3-carboxamide and 7-Ethoxy-N-(trans-4-(2-hydroxypropan-2-yl)cyclohexyl)-1,8-naphthyridine-3-carboxamide

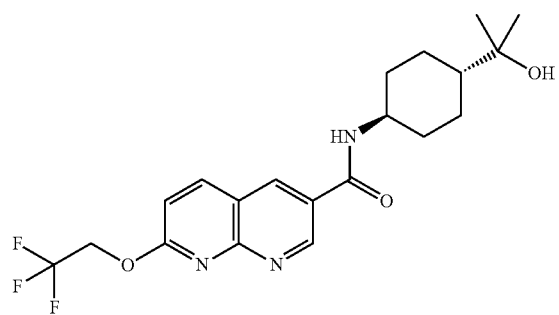

-continued

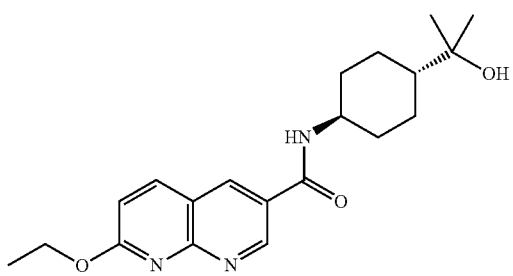

2-(trans-4-Aminocyclohexyl)propan-2-ol (0.144 g, 0.916 mmol) was added to a mixture of 7-(2,2,2-trifluoroethoxy)-1,8-naphthyridine-3-carboxylic acid and 7-ethoxy-1,8-naphthyridine-3-carboxylic acid (0.249 g, 0.913 mmol, Intermediate 35) in N,N-dimethylformamide (10 mL) at room temperature. Then, N,N-diisopropylethylamine (0.40 mL, 2.296 mmol) was added, followed by 1-[bis(dimethylamino)methylene]-1H-1,2,3-triazolo[4,5-b]pyridinium 3-oxide hexafluorophosphate (0.418 g, 1.099 mmol) and the reaction mixture was stirred for four hours. The reaction mixture was concentrated and the resulting residue was purified by silica gel chromatography, eluting with (ethyl acetate:ethanol (3:1)):hexanes (0:1 to 1:0). The mixed fractions were repurified by silica gel chromatography, eluting with (ethyl acetate:ethanol (3:1)):hexanes (0:1 to 3:1) and the mixed fractions were repurified by silica gel chromatography, eluting with (ethyl acetate:ethanol (3:1)):hexanes (0:1 to 3:1), then combined with the appropriate fractions to give residues which were triturated/sonicated with ethyl acetate and filtered to give N-(trans-4-(2-hydroxypropan-2-yl)cyclohexyl)-7-(2,2,2-trifluoroethoxy)-1,8-naphthyridine-3-carboxamide (0.188 g, 0.457 mmol, 49.95 yield) as a white powder and 7-ethoxy-N-(trans-4-(2-hydroxypropan-2-yl)cyclohexyl)-1,8-naphthyridine-3-carboxamide (0.045 g, 0.126 mmol, 13.7% yield) as an off-white powder.

N-(trans-4-(2-Hydroxypropan-2-yl)cyclohexyl)-7-(2,2,2-trifluoroethoxy)-1,8-naphthyridine-3-carboxamide $^1$H NMR (400 MHz, CD$_3$SOCD$_3$) δ 1.04 (s, 6H), 1.06-1.24 (m, 3H), 1.32 (q, J=12 Hz, 2H), 1.84 (br d, J=11 Hz, 2H), 1.94 (br d, J=10 Hz, 2H), 3.68-3.80 (m, 1H), 4.06 (s, 1H), 5.21 (q, J=9 Hz, 2H), 7.19 (d, J=9 Hz, 1H), 8.40 (d, J=9 Hz, 1H), 8.54 (d, J=8 Hz, 1H), 8.78 (d, J=2 Hz, 1H), 9.27 (d, J=2 Hz, 1H); LC-MS (LC-ES) M+H=412. 7-Ethoxy-N-(trans-4-(2-hydroxypropan-2-yl)cyclohexyl)-1,8-naphthyridine-3-carboxamide $^1$H NMR (400 MHz, CD$_3$SOCD$_3$) δ 1.04 (s, 6H), 1.06-1.24 (m, 3H), 1.31 (q, J=12 Hz, 2H), 1.40 (t, J=7 Hz, 3H), 1.83 (br d, J=12 Hz, 2H), 1.93 (br d, J=10 Hz, 2H), 3.68-3.80 (m, 1H), 4.06 (s, 1H), 4.51 (q, J=7 Hz, 2H), 7.16 (d, J=9 Hz, 1H), 8.39 (d, J=9 Hz, 1H), 8.53 (d, J=8 Hz, 1H), 8.76 (d, J=2 Hz, 1H), 9.26 (d, J=2 Hz, 1H); LC-MS (LC-ES) M+H=358.

Example 57

Racemic 7-Cyclopropyl-N-(trans-4-((1,1-difluoropropan-2-yl)amino)cyclohexyl)-1,8-naphthyridine-3-carboxamide

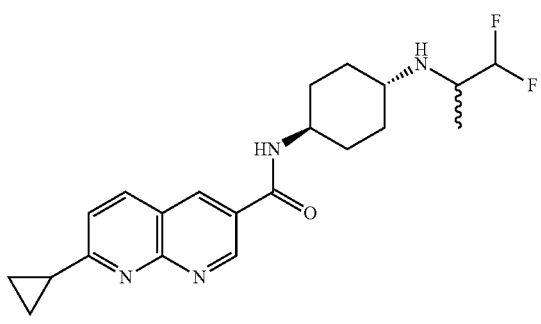 [SMILES: CC(N[C@H]1CC[C@H](NC(=O)c2cnc3nc(C4CC4)ccc3c2)CC1)C(F)F]

N,N-Diisopropylethylamine (0.384 mL, 2.201 mmol) was added to 7-cyclopropyl-1,8-naphthyridine-3-carboxylic acid (0.1179 g, 0.550 mmol, Intermediate 4F) in N,N-dimethylformamide (1.8 mL) at room temperature. Then, trans-N1-(1,1-difluoropropan-2-yl)cyclohexane-1,4-diamine (0.106 g, 0.550 mmol, Intermediate 31) was added and the reaction mixture was stirred for five minutes. Then, n-propylphosphonic acid anhydride (0.655 mL, 1.101 mmol) was added and the reaction mixture was stirred for sixty-six hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 3:2), then further purified by silica gel chromatography, eluting with methanol:dichloromethane (0:1 to 2:3) to give racemic 7-cyclopropyl-N-(trans-4-((1,1-difluoropropan-2-yl)amino)cyclohexyl)-1,8-naphthyridine-3-carboxamide (0.0523 g, 0.128 mmol, 23.24% yield). $^1$H NMR (400 MHz, CD$_3$SOCD$_3$) δ 1.02 (d, J=6 Hz, 3H), 1.06-1.20 (m, 6H), 1.30-1.46 (m, 2H), 1.82-2.00 (m, 4H), 2.30-2.40 (m, 1H), 2.42-2.50 (m, 1H), 2.90-3.08 (m, 1H), 3.68-3.84 (m, 1H), 5.77 (dt, J=57, 4 Hz, 1H), 7.63 (d, J=8 Hz, 1H), 8.39 (d, J=8 Hz, 1H), 8.58 (d, J=8 Hz, 1H), 8.78 (d, J=2 Hz, 1H), 9.31 (d, J=2 Hz, 1H); LC-MS (LC-ES) M+H=389.

Example 58

6-Chloro-N-(trans-4-(2-hydroxypropan-2-yl)cyclohexyl)-7-((S)-2-methylazetidin-1-yl)-1,8-naphthyridine-3-carboxamide

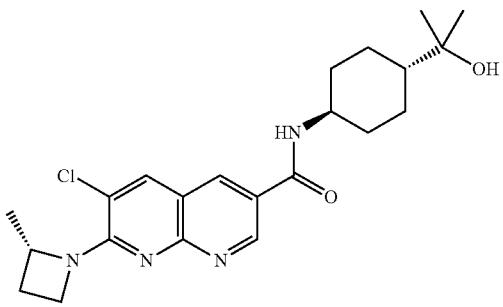 [SMILES: C[C@H]1CCN1c1nc2ncc(C(=O)N[C@H]3CC[C@H](C(C)(C)O)CC3)cc2cc1Cl]

N,N-Diisopropylethylamine (0.162 mL, 0.927 mmol) was added to lithium (S)-6-chloro-7-(2-methylazetidin-1-yl)-1,8-naphthyridine-3-carboxylate (0.0657 g, 0.232 mmol, Intermediate 36) in N,N-dimethylformamide (0.77 mL) at room temperature. Then, 2-(trans-4-aminocyclohexyl)propan-2-ol (0.055 g, 0.347 mmol) was added and the reaction mixture was stirred for five minutes. Then, n-propylphosphonic acid anhydride (0.276 mL, 0.463 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 6-chloro-N-(trans-4-(2-hydroxypropan-2-yl)cyclohexyl)-7-((S)-2-methylazetidin-1-yl)-1,8-naphthyridine-3-carboxamide (0.0560 g, 0.128 mmol, 55.1% yield). $^1$H NMR (400 MHz, CD$_3$SOCD$_3$) δ 1.04 (s, 6H), 1.06-1.24 (m, 3H), 1.30 (q, J=12 Hz, 2H), 1.48 (d, J=6 Hz, 3H), 1.83 (br d, J=11 Hz, 2H), 1.91 (br d, J=10 Hz, 2H), 1.90-2.02 (m, 1H), 2.42-2.54 (m, 1H), 3.66-3.78 (m, 1H), 4.05 (s, 1H), 4.24 (dt, J=9, 7 Hz, 1H), 4.53 (dt, J=9, 6 Hz, 1H), 4.79 (h, J=8 Hz, 1H), 8.33 (s, 1H), 8.44 (d, J=8 Hz, 1H), 8.54 (d, J=2 Hz, 1H), 9.14 (d, J=2 Hz, 1H); LC-MS (LC-ES) M+H=417.

Example 59

6-Chloro-N-((1r,4s)-4-hydroxy-4-methylcyclohexyl)-7-((S)-2-methylazetidin-1-yl)-1,8-naphthyridine-3-carboxamide

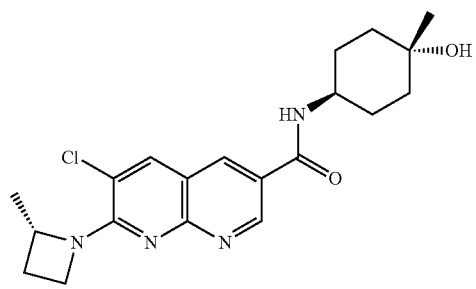 [SMILES: C[C@H]1CCN1c1nc2ncc(C(=O)N[C@H]3CC[C@](C)(O)CC3)cc2cc1Cl]

N,N-Diisopropylethylamine (0.158 mL, 0.907 mmol) was added to lithium (S)-6-chloro-7-(2-methylazetidin-1-yl)-1,8-naphthyridine-3-carboxylate (0.0643 g, 0.227 mmol, Intermediate 36) in N,N-dimethylformamide (0.76 mL) at room temperature. Then, (1r,4r)-4-amino-1-methylcyclohexan-1-ol (0.044 g, 0.340 mmol, Intermediate 21) was added and the reaction mixture was stirred for five minutes. Then, n-propylphosphonic acid anhydride (0.270 mL, 0.453 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 3:7) to give 6-chloro-N-((1r,4S)-4-hydroxy-4-methylcyclohexyl)-7-((S)-2-methylazetidin-1-yl)-1,8-naphthyridine-3-carboxamide (0.0712 g, 0.174 mmol, 77% yield). $^1$H NMR (400 MHz, CD$_3$SOCD$_3$) δ 1.15 (s, 3H), 1.48 (d, J=6 Hz, 3H), 1.38-1.54 (m, 4H), 1.54-1.62 (m, 2H), 1.72-1.82 (m, 2H), 1.90-2.02 (m, 1H), 2.42-2.54 (m, 1H), 3.76-3.88 (m, 1H), 4.24 (dt, J=9, 7 Hz, 1H), 4.31 (s, 1H), 4.53 (dt, J=9, 6 Hz, 1H), 4.79 (h, J=8 Hz, 1H), 8.33 (s, 1H), 8.39 (d, J=8 Hz, 1H), 8.53 (d, J=2 Hz, 1H), 9.13 (d, J=2 Hz, 1H); LC-MS (LC-ES) M+H=389.

Example 60

6-Chloro-7-((S)-2-methylazetidin-1-yl)-N—((S)-2-oxopyrrolidin-3-yl)-1,8-naphthyridine-3-carboxamide

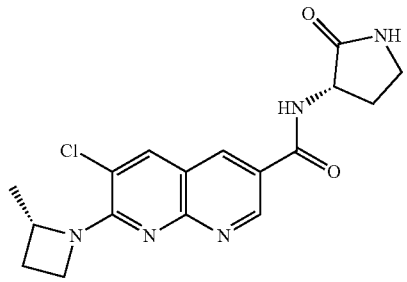 [SMILES: C[C@H]1CCN1c1nc2ncc(C(=O)N[C@H]3CCNC3=O)cc2cc1Cl]

N,N-Diisopropylethylamine (0.166 mL, 0.951 mmol) was added to lithium (S)-6-chloro-7-(2-methylazetidin-1-yl)-1,8-naphthyridine-3-carboxylate (0.0674 g, 0.238 mmol, Intermediate 36) in N,N-dimethylformamide (0.79 mL) at room temperature. Then, (S)-3-aminopyrrolidin-2-one (0.029 g, 0.285 mmol) was added and the reaction mixture was stirred for five minutes. Then, n-propylphosphonic acid anhydride (0.283 mL, 0.475 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 3:2) to give 6-chloro-7-((S)-2-methylazetidin-1-yl)-N—((S)-2-oxopyrrolidin-3-yl)-1,8-naphthyridine-3-carboxamide (0.0604 g, 0.159 mmol, 67.1% yield). $^1$H NMR (400 MHz, CD$_3$SOCD$_3$) δ 1.49 (d, J=6 Hz, 3H), 1.92-2.08 (m, 2H), 2.30-2.42 (m, 1H), 2.42-2.54 (m, 1H), 3.18-3.28 (m, 2H), 4.26 (dt, J=9, 7 Hz, 1H), 4.54 (dt, J=9, 6 Hz, 1H), 4.60 (dt, J=9, 8 Hz, 1H), 4.79 (h, J=8 Hz, 1H), 7.91 (br s, 1H), 8.36 (s, 1H), 8.58 (d, J=2 Hz, 1H), 8.93 (d, J=8 Hz, 1H), 9.17 (d, J=2 Hz, 1H); LC-MS (LC-ES) M+H=360.

Example 61

(S)-6-Chloro-N-(6-(2-hydroxypropan-2-yl)spiro[3.3]heptan-2-yl)-7-(2-methylazetidin-1-yl)-1,8-naphthyridine-3-carboxamide

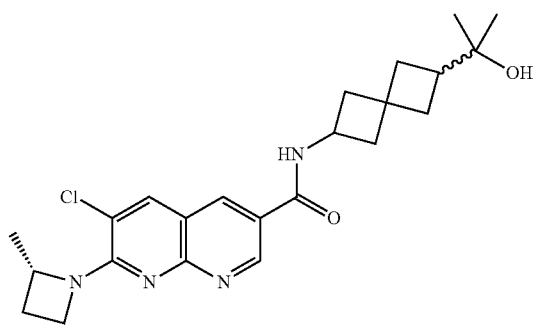 [SMILES: C[C@H]1CCN1c1nc2ncc(C(=O)NC3CC4(C3)CC(C(C)(C)O)C4)cc2cc1Cl]

N,N-Diisopropylethylamine (0.166 mL, 0.951 mmol) was added to lithium (S)-6-chloro-7-(2-methylazetidin-1-yl)-1,8-naphthyridine-3-carboxylate (0.0674 g, 0.238 mmol, Intermediate 36) in N,N-dimethylformamide (0.79 mL) at room temperature. Then, racemic 2-(6-aminospiro[3.3]heptan-2-yl)propan-2-ol (0.048 g, 0.285 mmol, Intermediate 24) was added and the reaction mixture was stirred for five minutes. Then, n-propylphosphonic acid anhydride (0.283 mL, 0.475 mmol) was added and the reaction mixture was stirred for sixty-six hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give (S)-6-chloro-N-(6-(2-hydroxypropan-2-yl)spiro[3.3]heptan-2-yl)-7-(2-methylazetidin-1-yl)-1,8-naphthyridine-3-carboxamide (0.0687 g, 0.152 mmol, 64.0% yield). $^1$H NMR (400 MHz, CD$_3$SOCD$_3$) δ 0.94 (s, 3H), 0.95 (s, 3H), 1.48 (d, J=6 Hz, 3H), 1.66-1.74 (m, 1H), 1.84-2.02 (m, 5H), 2.04-2.20 (m, 3H), 22.36-2.44 (m, 1H), 2.42-2.54 (m, 1H), 4.01 (s, 1H), 4.24 (dt, J=9, 7 Hz, 1H), 4.31 (h, J=8 Hz, 1H), 4.53 (dt, J=9, 6 Hz, 1H), 4.78 (h, J=8 Hz, 1H), 8.32 (s, 1H), 8.53 (d, J=2 Hz, 1H), 8.77 (d, J=8 Hz, 1H), 9.14 (d, J=2 Hz, 1H); LC-MS (LC-ES) M+H=429.

Example 62

6-Chloro-N-(trans-4-(2-hydroxypropan-2-yl)cyclohexyl)-7-methoxy-1,8-naphthyridine-3-carboxamide

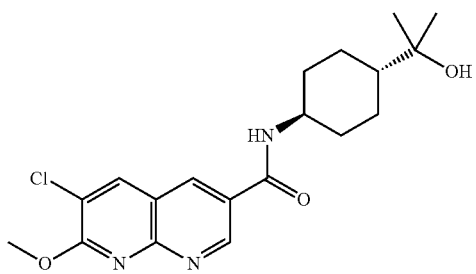 [SMILES: COc1nc2ncc(C(=O)N[C@H]3CC[C@H](C(C)(C)O)CC3)cc2cc1Cl]

2-(trans-4-Aminocyclohexyl)propan-2-ol (0.061 g, 0.388 mmol) was added to 6-chloro-7-methoxy-1,8-naphthyridine-3-carboxylic acid (0.096 g, 0.402 mmol, Intermediate 37) N,N-dimethylformamide (4 mL) at room temperature. Then, N,N-diisopropylethylamine (0.09 mL, 0.517 mmol) was added to the suspension, followed by 1-[bis(dimethylamino)methylene]-1H-1,2,3-triazolo[4,5-b]pyridinium 3-oxide hexafluorophosphate (0.189 g, 0.497 mmol) and the reaction mixture was stirred for fourteen hours. The reaction mixture was concentrated and the residue was purified via silica gel chromatography, eluting with ethyl acetate:ethanol (3:1):hexanes (0:1 to 3:1). Ethyl acetate (2 mL) was added to the solid residue and it was triturated/sonicated, then filtered and dried to give 6-chloro-N-(trans-4-(2-hydroxypropan-2-yl)cyclohexyl)-7-methoxy-1,8-naphthyridine-3-carboxamide (0.119 g, 0.315 mmol, 81% yield) as an off white powder. $^1$H NMR (400 MHz, CD$_3$SOCD$_3$) δ 1.04 (s, 6H), 1.06-1.24 (m, 3H), 1.31 (q, J=12 Hz, 2H), 1.83 (br d, J=11 Hz, 2H), 1.93 (br d, J=10 Hz, 2H), 3.68-3.80 (m, 1H), 4.06 (s, 1H), 4.12 (s, 3H), 8.60 (d, J=8 Hz, 1H), 8.69 (s, 1H), 8.75 (d, J=2 Hz, 1H), 9.30 (d, J=2 Hz, 1H); LC-MS (LC-ES) M+H=378.

Example 63

6-Chloro-N-((1s,3R)-3-hydroxy-3-methylcyclobutyl)-7-US)-2-methylazetidin-1-yl)-1,8-naphthyridine-3-carboxamide

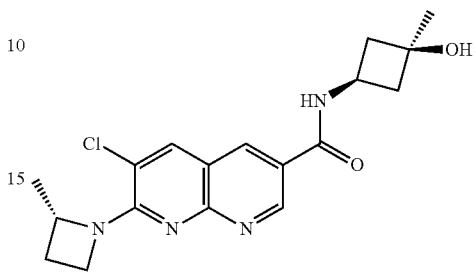

N,N-Diisopropylethylamine (0.150 mL, 0.859 mmol) was added to lithium (S)-6-chloro-7-(2-methylazetidin-1-yl)-1,8-naphthyridine-3-carboxylate (0.0609 g, 0.215 mmol, Intermediate 36) in N,N-dimethylformamide (0.72 mL) at room temperature. Then, (1s,3s)-3-amino-1-methylcyclobutan-1-ol (0.026 g, 0.258 mmol, Intermediate 10) was added and the reaction mixture was stirred for five minutes. Then, n-propylphosphonic acid anhydride (0.256 mL, 0.429 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give 6-chloro-N-((1s,3R)-3-hydroxy-3-methylcyclobutyl)-7-((S)-2-methylazetidin-1-yl)-1,8-naphthyridine-3-carboxamide (0.0686 g, 0.181 mmol, 84% yield). $^1$H NMR (400 MHz, CD$_3$SOCD$_3$) δ 1.27 (s, 3H), 1.48 (d, J=6 Hz, 3H), 1.90-2.02 (m, 1H), 2.06-2.16 (m, 2H), 2.26-2.34 (m, 2H), 2.42-2.54 (m, 1H), 4.00 (h, J=7 Hz, 1H), 4.24 (dt, J=9, 7 Hz, 1H), 4.53 (dt, J=9, 6 Hz, 1H), 4.78 (h, J=8 Hz, 1H), 5.00 (s, 1H), 8.32 (s, 1H), 8.55 (d, J=2 Hz, 1H), 8.81 (d, J=7 Hz, 1H), 9.16 (d, J=2 Hz, 1H); LC-MS (LC-ES) M+H=361.

Example 64

6-Chloro-N-((1r,3S)-3-hydroxy-3-methylcyclobutyl)-7-((S)-2-methylazetidin-1-yl)-1,8-naphthyridine-3-carboxamide

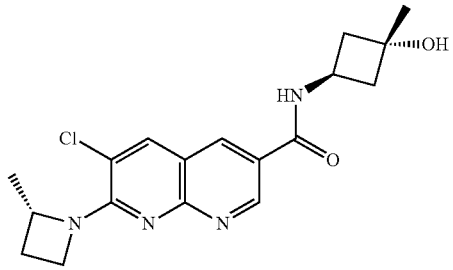 [SMILES: C[C@H]1CCN1c1nc2ncc(C(=O)N[C@H]3C[C@](C)(O)C3)cc2cc1Cl]

N,N-Diisopropylethylamine (0.165 mL, 0.942 mmol) was added to lithium (S)-6-chloro-7-(2-methylazetidin-1-yl)-1,8-naphthyridine-3-carboxylate (0.0668 g, 0.236 mmol, Intermediate 36) in N,N-dimethylformamide (0.78 mL) at room temperature. Then, (1r,3r)-3-amino-1-methylcyclobutan-1-ol (0.029 g, 0.283 mmol, Intermediate 11) was added and the reaction mixture was stirred for five minutes. Then, n-propylphosphonic acid anhydride (0.280 mL, 0.471 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 6-chloro-N-((1r,3S)-3-hydroxy-3-methylcyclobutyl)-7-((S)-2-methylazetidin-1-yl)-1,8-naphthyridine-3-carboxamide (0.0712 g, 0.187 mmol, 80% yield). $^1$H NMR (400 MHz, CD$_3$SOCD$_3$) δ 1.28 (s, 3H), 1.48 (d, J=6 Hz, 3H), 1.92-2.02 (m, 1H), 2.04-2.12 (m, 2H), 2.24-2.34 (m, 2H), 2.42-2.54 (m, 1H), 4.24 (dt, J=9, 7 Hz, 1H), 4.46-4.58 (m, 2H), 4.79 (h, J=8 Hz, 1H), 4.87 (s, 1H), 8.32 (s, 1 H), 8.53 (d, J=2 Hz, 1H), 8.78 (d, J=7 Hz, 1H), 9.14 (d, J=2 Hz, 1H); LC-MS (LC-ES) M+H=361.

Example 65

6-Chloro-N-(trans-3-(2-hydroxypropan-2-yl)cyclobutyl)-7-((S)-2-methylazetidin-1-yl)-1,8-naphthyridine-3-carboxamide

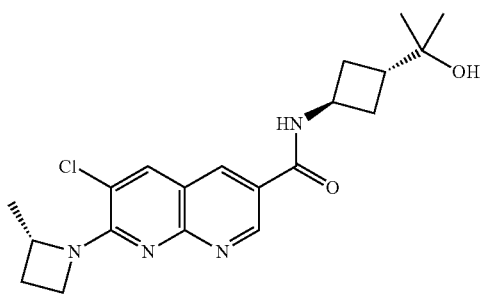 [SMILES: C[C@H]1CCN1c1nc2ncc(C(=O)N[C@H]3C[C@H](C(C)(C)O)C3)cc2cc1Cl]

N,N-Diisopropylethylamine (0.152 mL, 0.872 mmol) was added to lithium (S)-6-chloro-7-(2-methylazetidin-1-yl)-1,8-naphthyridine-3-carboxylate (0.0618 g, 0.218 mmol, Intermediate 36) in N,N-dimethylformamide (0.73 mL) at room temperature. Then, 2-(trans-3-aminocyclobutyl)propan-2-ol hydrochloride (0.043 g, 0.261 mmol) was added and the reaction mixture was stirred for five minutes. Then, n-propylphosphonic acid anhydride (0.259 mL, 0.436 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give 6-chloro-N-(trans-3-(2-hydroxypropan-2-yl)cyclobutyl)-7-((S)-2-methylazetidin-1-yl)-1,8-naphthyridine-3-carboxamide (0.0627 g, 0.153 mmol, 70.3% yield). $^1$H NMR (400 MHz, CD$_3$SOCD$_3$) δ 1.04 (s, 6H), 1.48 (d, J=6 Hz, 3H), 1.90-2.10 (m, 3H), 2.18-2.34 (m, 3H), 2.42-2.54 (m, 1H), 4.24 (s, 1H), 4.24 (dt, J=9, 7 Hz, 1H), 4.34 (h, J=7 Hz, 1H), 4.53 (dt, J=9, 6 Hz, 1H), 4.79 (h, J=8 Hz, 1H), 8.33 (s, 1H), 8.56 (d, J=2 Hz, 1H), 8.83 (d, J=7 Hz, 1H), 9.17 (d, J=2 Hz, 1H); LC-MS (LC-ES) M+H=389.

Example 66

6-Chloro-N-((1s,3R)-3-hydroxy-3-(trifluoromethyl)cyclobutyl)-7-((S)-2-methylazetidin-1-yl)-1,8-naphthyridine-3-carboxamide

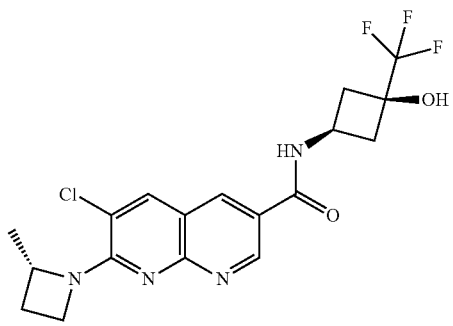 [SMILES: C[C@H]1CCN1c1nc2ncc(C(=O)N[C@H]3C[C@](O)(C(F)(F)F)C3)cc2cc1Cl]

N,N-Diisopropylethylamine (0.164 mL, 0.941 mmol) was added to lithium (S)-6-chloro-7-(2-methylazetidin-1-yl)-1,8-naphthyridine-3-carboxylate (0.0667 g, 0.235 mmol, Intermediate 36) in N,N-dimethylformamide (0.78 mL) at room temperature. Then, (1s,3s)-3-amino-1-(trifluoromethyl)cyclobutan-1-ol hydrochloride (0.054 g, 0.282 mmol) was added and the reaction mixture was stirred for five minutes. Then, n-propylphosphonic acid anhydride (0.280 mL, 0.470 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:4) to give 6-chloro-N-((1s,3R)-3-hydroxy-3-(trifluoromethyl)cyclobutyl)-7-((S)-2-methylazetidin-1-yl)-1,8-naphthyridine-3-carboxamide (0.0644 g, 0.147 mmol, 62.7% yield). $^1$H NMR (400 MHz, CD$_3$SOCD$_3$) δ 1.48 (d, J=6 Hz, 3H), 1.90-2.02 (m, 1H), 2.30-2.42 (m, 2H), 2.44-2.54 (m, 1H), 2.76-2.84 (m, 2H), 4.17 (h, J=8 Hz, 1H), 4.25 (dt, J=9, 7 Hz, 1H), 4.54 (dt, J=9, 6 Hz, 1H), 4.79 (h, J=8 Hz, 1H), 6.69 (s, 1H), 8.33 (s, 1H), 8.57 (d, J=2 Hz, 1H), 9.04 (d, J=7 Hz, 1H), 9.17 (d, J=2 Hz, 1H); LC-MS (LC-ES) M+H=415.

Example 67

6-Chloro-N-((3S,4R)-4-methyl-2-oxopyrrolidin-3-yl)-7-((S)-2-methylazetidin-1-yl)-1,8-naphthyridine-3-carboxamide

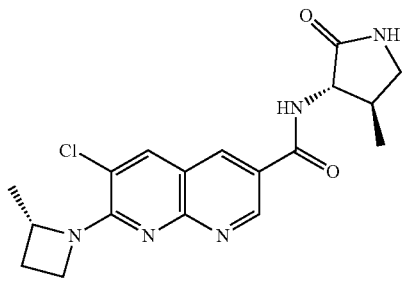 [SMILES: C[C@@H]1CNC(=O)[C@H]1NC(=O)c1cnc2nc(N3CC[C@@H]3C)c(Cl)cc2c1]

N,N-Diisopropylethylamine (0.160 mL, 0.918 mmol) was added to lithium (S)-6-chloro-7-(2-methylazetidin-1-yl)-1, 8-naphthyridine-3-carboxylate (0.0651 g, 0.230 mmol, Intermediate 36) in N,N-dimethylformamide (0.76 mL) at room temperature. Then, (3S,4R)-3-amino-4-methylpyrrolidin-2-one (0.031 g, 0.275 mmol, Intermediate 20) was added and the reaction mixture was stirred for five minutes. Then, n-propylphosphonic acid anhydride (0.273 mL, 0.459 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 2:3) to give 6-chloro-N-((3S,4R)-4-methyl-2-oxopyrrolidin-3-yl)-7-((S)-2-methylazetidin-1-yl)-1,8-naphthyridine-3-carboxamide (0.0579 g, 0.147 mmol, 64.1% yield). $^1$H NMR (400 MHz, CD$_3$SOCD$_3$) δ 1.08 (d, J=7 Hz, 3H), 1.49 (d, J=6 Hz, 3H), 1.92-2.02 (m, 1H), 2.34-2.54 (m, 2H), 2.88 (t, J=9 Hz, 1H), 3.33 (t, J=8 Hz, 1H), 4.26 (dt, J=9, 7 Hz, 1H), 4.29 (dd, J=10, 8 Hz, 1H), 4.54 (dt, J=9, 6 Hz, 1H), 4.79 (h, J=8 Hz, 1H), 7.85 (br s, 1H), 8.36 (s, 1H), 8.59 (d, J=2 Hz, 1H), 8.85 (d, J=8 Hz, 1H), 9.19 (d, J=2 Hz, 1H); LC-MS (LC-ES) M+H=374.

Example 68 & 69

7-Cyclopropyl-N-(cis-3-(((R)-1,1,1-trifluoro-3-hydroxypropan-2-yl)amino)cyclobutyl)-1,8-naphthyridine-3-carboxamide and 7-Cyclopropyl-N-trans-3-(((R)-1,1,1-trifluoro-3-hydroxypropan-2-yl)amino) cyclobutyl)-1,8-naphthyridine-3-carboxamide

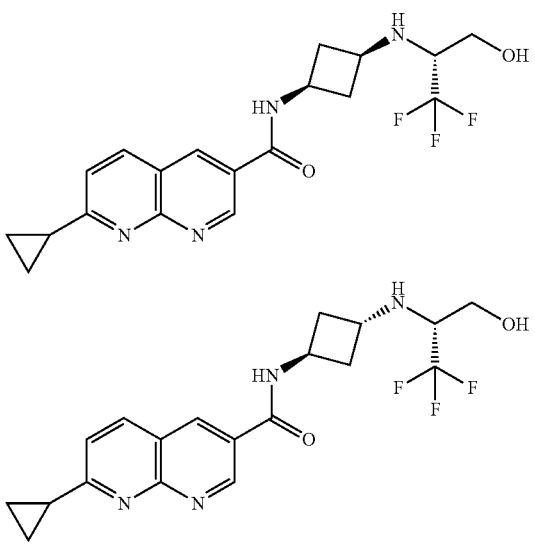

N,N-Diisopropylethylamine (0.206 mL, 1.180 mmol) was added to 7-cyclopropyl-1,8-naphthyridine-3-carboxylic acid (0.0632 g, 0.295 mmol, Intermediate 4F) in N,N-dimethylformamide (0.98 mL) at room temperature. Then, (R)-2-((3-aminocyclobutyl)amino)-3,3,3-trifluoropropan-1-ol (0.058 g, 0.295 mmol, Intermediate 32) was added and the reaction mixture was stirred for five minutes. Then, n-propylphosphonic acid anhydride (0.351 mL, 0.590 mmol) was added and the reaction mixture was stirred for forty hours. The reaction mixture was concentrated. The resulting residue was purified by RP HPLC, eluting with acetonitrile:water with 0.1% ammonium hydroxide (5:95:100:0), then further purified by silica gel chromatography, eluting with methanol:dichloromethane (1:19 to 1:4) to give a 1:1.6 mixture of cis/trans isomers (0.0375 g, 0.090 mmol, 30.6% yield). The isomers were separated via chiral chromatography on a CC4 column, eluting with ethanol:heptane (3:1) with 0.1% isopropylamine to give 7-cyclopropyl-N-(cis-3-(((R)-1,1,1-trifluoro-3-hydroxypropan-2-yl)amino)cyclobutyl)-1,8-naphthyridine-3-carboxamide (0.0143 g, 0.034 mmol, 11.68% yield) and 7-cyclopropyl-N-(trans-3-(((R)-1,1,1-trifluoro-3-hydroxypropan-2-yl)amino)cyclo butyl)-1,8-naphthyridine-3-carboxamide (0.0208 g, 0.050 mmol, 16.98% yield).

7-Cyclopropyl-N-(cis-3-(((R)-1,1,1-trifluoro-3-hydroxypropan-2-yl)amino)cyclobutyl)-1,8-naphthyridine-3-carboxamide $^1$H NMR (400 MHz, CD$_3$SOCD$_3$) δ 1.10-1.20 (m, 4H), 1.78-1.92 (m, 2H), 2.22 (dd, J=8, 7 Hz, 1H), 2.30-2.42 (m, 1H), 2.50-2.64 (m, 1H), 3.02-3.30 (m, 2H), 3.47 (dt, J=12, 6 Hz, 1H), 3.61 (dt, J=11, 6 Hz, 1H), 4.08 (h, J=8 Hz, 1H), 5.07 (t, J=6 Hz, 1H), 7.14 (br s, 1H), 7.64 (d, J=8 Hz, 1H), 8.38 (d, J=8 Hz, 1H), 8.80 (d, J=2 Hz, 1H), 8.92 (d, J=8 Hz, 1H), 9.32 (d, J=2 Hz, 1H); LC-MS (LC-ES) M+H=395.

7-Cyclopropyl-N-(trans-3-(((R)-1,1,1-trifluoro-3-hydroxypropan-2-yl)amino)cyclobutyl)-1,8-naphthyridine-3-carboxamide $^1$H NMR (400 MHz, CD$_3$SOCD$_3$) δ 1.10-1.20 (m, 4H), 2.06-2.18 (m, 2H), 2.20-2.30 (m, 2H), 2.32-2.44 (m, 1H), 3.02-3.14 (m, 1H), 3.20-3.30 (m, 1H), 3.49 (dt, J=12, 6 Hz, 1H), 3.62 (dt, J=9, 5 Hz, 1H), 4.49 (h, J=7 Hz, 1H), 5.03 (t, J=6 Hz, 1H), 7.25 (br s, 1H), 7.64 (d, J=8 Hz, 1H), 8.39 (d, J=8 Hz, 1H), 8.81 (d, J=2 Hz, 1H), 8.99 (d, J=7 Hz, 1H), 9.33 (d, J=2 Hz, 1H); LC-MS (LC-ES) M+H=395.

Example 70

N-(trans-4-(2-Hydroxypropan-2-yl)cyclohexyl)-2-(methylthio)pyrido[2,3-d]pyrimidine-6-carboxamide

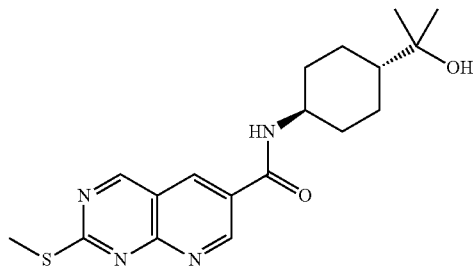

To a thick, stirred suspension of 2-(methylthio)pyrido[2,3-d]pyrimidine-6-carboxylic acid (32 mg, 0.145 mmol, Intermediate 38) and 2-((trans)-4-aminocyclohexyl)propan-2-ol (30 mg, 0.191 mmol) in N,N-dimethylformamide (1 mL) was added N,N-diisopropylethylamine (0.100 mL, 0.573 mmol), followed by n-propylphosphonic acid anhydride (0.170 mL, 0.289 mmol). The mixture quickly became homogeneous and was allowed to stir overnight. Then, the reaction mixture was loaded onto a pre-packed Celite® cartridge and purified by reverse phase chromatography, eluting with acetonitrile:water (0:1 to 1:0) with 0.1% ammonium hydroxide to give N-(trans-4-(2-hydroxypropan-2-yl)

cyclohexyl)-2-(methylthio)pyrido[2,3-d]pyrimidine-6-carboxamide (38 mg, 0.105 mmol, 73% yield) as a light beige solid. $^1$H NMR (400 MHz, CD$_3$SOCD$_3$) δ 1.04 (s, 6H), 1.06-1.24 (m, 3H), 1.31 (q, J=12 Hz, 2H), 1.84 (br d, J=11 Hz, 2H), 1.94 (br d, J=10 Hz, 2H), 2.65 (s, 3H), 3.68-3.80 (m, 1H), 4.07 (s, 1H), 8.68 (d, J=8 Hz, 1H), 8.94 (d, J=2 Hz, 1H), 9.48 (d, J=2 Hz, 1H), 9.56 (s, 1H); LC-MS (LC-ES) M+H=361.

Example 71

(S)-6-Chloro-7-cyclopropyl-N-(2-oxopyrrolidin-3-yl)-1,8-naphthyridine-3-carboxamide

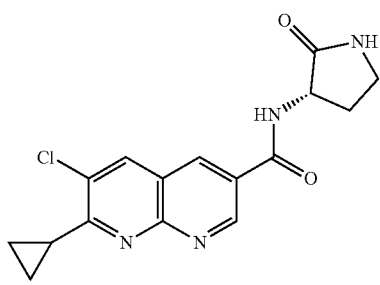 [SMILES: O=C(N[C@H]1CCNC1=O)c1cnc2nc(C3CC3)c(Cl)cc2c1]

(S)-3-Aminopyrrolidin-2-one (0.024 g, 0.240 mmol) was added to 6-chloro-7-cyclopropyl-1,8-naphthyridine-3-carboxylic acid (0.053 g, 0.213 mmol, Intermediate 18) in N,N-dimethylformamide (2.5 mL), followed by N,N-diisopropylethylamine (0.05 mL, 0.287 mmol). Then, 1-[bis(dimethylamino)methylene]-1H-1,2,3-triazolo[4,5-b]pyridinium 3-oxide hexafluorophosphate (0.105 g, 0.276 mmol) was added and the reaction mixture was stirred for 150 minutes and concentrated. Dichloromethane and methanol were added to the residue and it was purified via silica gel chromatography, eluting with (3:1 ethyl acetate:ethanol):hexanes (0:1 to 24:1) to give a material which was triturated/sonicated with ethyl acetate and the solids collected by filtration, air-dried, then dried under vacuum overnight to give (S)-6-chloro-7-cyclopropyl-N-(2-oxopyrrolidin-3-yl)-1,8-naphthyridine-3-carboxamide (0.035 g, 0.106 mmol, 49.6% yield) as a pale tan powder. $^1$H NMR (400 MHz, CD$_3$SOCD$_3$) δ 1.18-1.28 (m, 4H), 1.96-2.10 (m, 1H), 2.34-2.46 (m, 1H), 2.68-2.78 (m, 1H), 3.22-3.28 (m, 2H), 4.62 (q, J=9 Hz, 1H), 7.94 (br s, 1H), 8.71 (s, 1H), 8.82 (d, J=2 Hz, 1H), 9.13 (d, J=8 Hz, 1H), 9.36 (d, J=2 Hz, 1H); LC-MS (LC-ES) M+H=331.

Example 72

7-Cyclobutyl-N-(trans-4-(2-hydroxypropan-2-yl)cyclohexyl)-1,8-naphthyridine-3-carboxamide

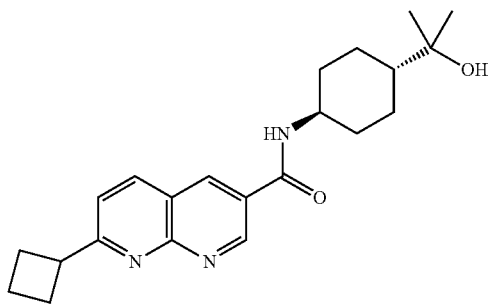 [SMILES: CC(C)(O)[C@H]1CC[C@H](NC(=O)c2cnc3nc(C4CCC4)ccc3c2)CC1]

2-(trans-4-Aminocyclohexyl)propan-2-ol (0.040 g, 0.254 mmol) was added to 7-cyclobutyl-1,8-naphthyridine-3-carboxylic acid (0.057 g, 0.250 mmol, Intermediate 39) in N,N-dimethylformamide (2.5 mL). Then, N,N-diisopropylethylamine (0.05 mL, 0.287 mmol) was added, followed by 1-[bis(dimethylamino)methylene]-1H-1,2,3-triazolo[4,5-b]pyridinium 3-oxide hexafluorophosphate (0.117 g, 0.308 mmol) and the reaction mixture was stirred for five hours and concentrated. Dichloromethane and methanol were added to the residue and it was purified via silica gel chromatography, eluting with (3:1 ethyl acetate:ethanol):hexanes (0:1 to 7:3) to give a material which was triturated/sonicated with ethyl acetate and the solids collected by filtration, air-dried, then dried under vacuum overnight to give 7-cyclobutyl-N-(trans-4-(2-hydroxypropan-2-yl)cyclohexyl)-1,8-naphthyridine-3-carboxamide (0.068 g, 0.185 mmol, 74.1% yield) as a cream colored powder. $^1$H NMR (400 MHz, CD$_3$SOCD$_3$) δ 1.04 (s, 6H), 1.06-1.24 (m, 3H), 1.32 (q, J=12 Hz, 2H), 1.84 (br d, J=12 Hz, 2H), 1.86-1.98 (m, 3H), 2.00-2.14 (m, 1H), 2.30-2.48 (m, 4H), 3.70-3.82 (m, 1H), 3.90 (p, J=9 Hz, 1H), 4.06 (s, 1H), 7.58 (d, J=8 Hz, 1H), 8.45 (d, J=8 Hz, 1H), 8.61 (d, J=8 Hz, 1H), 8.82 (d, J=2 Hz, 1H), 9.37 (d, J=2 Hz, 1H); LC-MS (LC-ES) M+H=368.

Example 73

6-Chloro-7-cyclopropyl-N-(trans-3-(2-hydroxypropan-2-yl)cyclobutyl)-1,8-naphthyridine-3-carboxamide

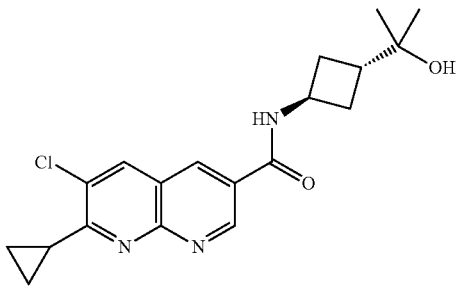 [SMILES: CC(C)(O)[C@H]1C[C@H](NC(=O)c2cnc3nc(C4CC4)c(Cl)cc3c2)C1]

2-(trans-3-Aminocyclobutyl)propan-2-ol hydrochloride (0.037 g, 0.223 mmol) was added 6-chloro-7-cyclopropyl-1,8-naphthyridine-3-carboxylic acid (0.053 g, 0.213 mmol, Intermediate 18) in N,N-dimethylformamide (2.5 mL). Then, N,N-diisopropylethylamine (0.10 mL, 0.574 mmol) was added, followed by 1-[bis(dimethylamino)methylene]-1H-1,2,3-triazolo[4,5-b]pyridinium 3-oxide hexafluorophosphate (0.099 g, 0.260 mmol) and the reaction mixture was stirred for 2.5 hours and concentrated. Dichloromethane and methanol were added to the residue and it was purified via silica gel chromatography, eluting with (3:1 ethyl acetate:ethanol):hexanes (0:1 to 3:2) to give a material which was dissolved in ethyl acetate. Once crystals formed, the mixture was partially concentrated via a stream of nitrogen and the solids collected by filtration, air-dried, then dried under vacuum overnight to give 6-chloro-7-cyclopropyl-N-(trans-3-(2-hydroxypropan-2-yl)cyclobutyl)-1,8-naphthyridine-3-carboxamide (0.049 g, 0.136 mmol, 63.9% yield) as a pale yellow solid. $^1$H NMR (400 MHz, CD$_3$SOCD$_3$) δ 1.04 (s, 6H), 1.20-1.26 (m, 4H), 2.00-2.12 (m, 2H), 2.20-2.36 (m, 3H), 2.68-2.78 (m, 1H), 4.26 (s, 1H), 4.36 (sex, J=7 Hz, 1H), 8.68 (s, 1H), 8.79 (d, J=2 Hz, 1H), 9.02 (d, J=7 Hz, 1H), 9.36 (d, J=2 Hz, 1H); LC-MS (LC-ES) M+H=360.

Example 74

6-Chloro-7-cyclopropyl-N-((1r,4r)-4-hydroxy-4-methylcyclohexyl)-1,8-naphthyridine-3-carboxamide ethyl acetate solvate

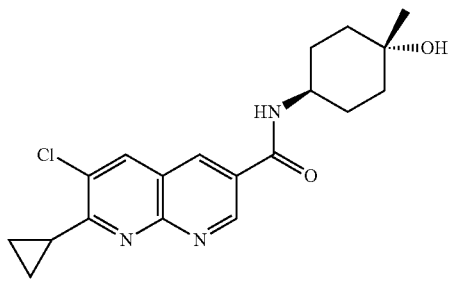 [SMILES: C[C@]1(O)CC[C@H](NC(=O)c2cnc3nc(C4CC4)c(Cl)cc3c2)CC1]

(1r,4r)-4-Amino-1-methylcyclohexan-1-ol (0.031 g, 0.240 mmol, Intermediate 21) was added 6-chloro-7-cyclopropyl-1,8-naphthyridine-3-carboxylic acid (0.053 g, 0.213 mmol, Intermediate 18) in N,N-dimethylformamide (2.5 mL). Then, N,N-diisopropylethylamine (0.05 mL, 0.287 mmol) was added, followed by 1-[bis(dimethylamino)methylene]-1H-1,2,3-triazolo[4,5-b]pyridinium 3-oxide hexafluorophosphate (0.098 g, 0.258 mmol) and the reaction mixture was stirred for 2.5 hours and concentrated. Dichloromethane and methanol were added to the residue and it was purified via silica gel chromatography, eluting with (3:1 ethyl acetate:ethanol):hexanes (0:1 to 3:2) to give a material which was dissolved in ethyl acetate. Once crystals formed, the mixture was partially concentrated via a stream of nitrogen and the solids collected by filtration, air-dried, then dried under vacuum overnight to give 6-chloro-7-cyclopropyl-N-((1r,4r)-4-hydroxy-4-methylcyclohexyl)-1,8-naphthyridine-3-carboxamide ethyl acetate solvate (0.058 g, 0.129 mmol, 60.7% yield) as an off-white crystalline solid. $^1$H NMR (400 MHz, CD$_3$SOCD$_3$) δ 1.15 (s, 3H), 1.20-1.26 (m, 4H), 1.40-1.54 (m, 4H), 1.56-1.64 (m, 2H), 1.74-1.86 (m, 2H), 2.68-2.78 (m, 1H), 3.80-3.92 (m, 1H), 4.32 (s, 1H), 8.59 (d, J=8 Hz, 1H), 8.69 (s, 1H), 8.76 (d, J=3 Hz, 1H), 9.32 (d, J=3 Hz, 1H); LC-MS (LC-ES) M+H=360.

Example 75

6-Chloro-7-cyclopropyl-N-((1r,3r)-3-hydroxy-3-methylcyclobutyl)-1,8-naphthyridine-3-carboxamide

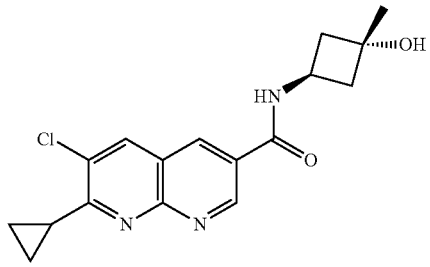 [SMILES: C[C@]1(O)C[C@H](NC(=O)c2cnc3nc(C4CC4)c(Cl)cc3c2)C1]

(1r,3r)-3-Amino-1-methylcyclobutan-1-ol (0.029 g, 0.287 mmol, Intermediate 11) was added to 6-chloro-7-cyclopropyl-1,8-naphthyridine-3-carboxylic acid (0.055 g, 0.221 mmol, Intermediate 18) in N,N-dimethylformamide (2.5 mL). Then, N,N-diisopropylethylamine (0.05 mL, 0.287 mmol) was added, followed by 1-[bis(dimethylamino)methylene]-1H-1,2,3-triazolo[4,5-b]pyridinium 3-oxide hexafluorophosphate (0.105 g, 0.276 mmol) and the reaction mixture was stirred for 145 minutes and concentrated. Dichloromethane and methanol were added to the residue and it was purified via silica gel chromatography, eluting with (3:1 ethyl acetate:ethanol):hexanes (0:1 to 7:3) to give a material which was dissolved in ethyl acetate. Once crystals formed, the mixture was partially concentrated via a stream of nitrogen and the solids collected by filtration, air-dried, then dried under vacuum overnight to give 6-chloro-7-cyclopropyl-N-((1r,3s)-3-hydroxy-3-methylcyclobutyl)-1,8-naphthyridine-3-carboxamide (0.040 g, 0.121 mmol, 54.5% yield) as an off-white powder. $^1$H NMR (400 MHz, CD$_3$SOCD$_3$) δ 1.20-1.26 (m, 4H), 1.29 (s, 3H), 2.04-2.14 (m, 2H), 2.26-2.34 (m, 2H), 2.68-2.78 (m, 1H), 4.53 (sex, J=8 Hz, 1H), 4.90 (s, 1H), 8.68 (s, 1H), 8.77 (d, J=2 Hz, 1H), 8.97 (d, J=7 Hz, 1H), 9.34 (d, J=2 Hz, 1H); LC-MS (LC-ES) M+H=332.

Example 76

6-Chloro-7-cyclopropyl-N-((1s,3s)-3-hydroxy-3-methylcyclobutyl)-1,8-naphthyridine-3-carboxamide

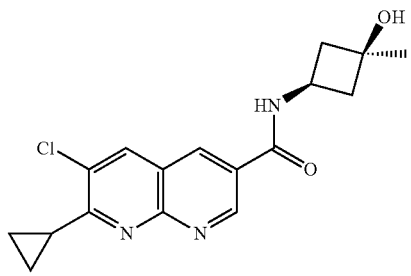 [SMILES: C[C@]1(O)C[C@@H](NC(=O)c2cnc3nc(C4CC4)c(Cl)cc3c2)C1]

(1s,3s)-3-Amino-1-methylcyclobutan-1-ol (0.027 g, 0.267 mmol, Intermediate 10) was added to 6-chloro-7-cyclopropyl-1,8-naphthyridine-3-carboxylic acid (0.053 g, 0.213 mmol, Intermediate 18) in N,N-dimethylformamide (2.5 mL). Then, N,N-diisopropylethylamine (0.05 mL, 0.287 mmol) was added, followed by 1-[bis(dimethylamino)methylene]-1H-1,2,3-triazolo[4,5-b]pyridinium 3-oxide hexafluorophosphate (0.097 g, 0.255 mmol) and the reaction mixture was stirred for 145 minutes and concentrated. Dichloromethane and methanol were added to the residue and it was purified via silica gel chromatography, eluting with (3:1 ethyl acetate:ethanol):hexanes (0:1 to 3:2) to give a material which was triturated/sonicated with ethyl acetate and the solids collected by filtration, air-dried, then dried under vacuum overnight to give 6-chloro-7-cyclopropyl-N-((1s,3s)-3-hydroxy-3-methylcyclobutyl)-1,8-naphthyridine-3-carboxamide (0.051 g, 0.154 mmol, 72.1% yield) as a cream-colored powder. $^1$H NMR (400 MHz, CD$_3$SOCD$_3$) δ 1.20-1.26 (m, 4H), 1.28 (s, 3H), 2.08-2.18 (m, 2H), 2.28-2.36 (m, 2H), 2.68-2.78 (m, 1H), 4.01 (sex, J=7 Hz, 1H), 5.02 (s, 1H), 8.67 (s, 1H), 8.79 (d, J=2 Hz, 1H), 9.01 (d, J=7 Hz, 1H), 9.35 (d, J=2 Hz, 1H); LC-MS (LC-ES) M+H=332.

Example 77

6-Chloro-7-cyclopropyl-N-((1s,3s)-3-hydroxy-3-(trifluoromethyl)cyclobutyl)-1,8-naphthyridine-3-carboxamide

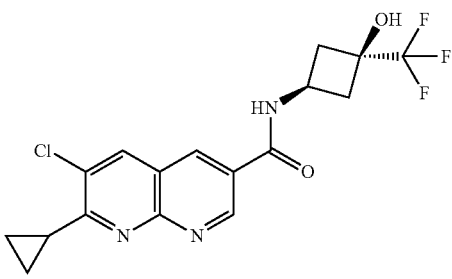 [SMILES: O=C(N[C@H]1C[C@](O)(C(F)(F)F)C1)c1cnc2nc(C3CC3)c(Cl)cc2c1]

(1s,3s)-3-Amino-1-(trifluoromethyl)cyclobutan-1-ol hydrochloride (0.042 g, 0.219 mmol) was added to 6-chloro-7-cyclopropyl-1,8-naphthyridine-3-carboxylic acid (0.052 g, 0.209 mmol, Intermediate 18) in N,N-dimethylformamide (2.5 mL). Then, N,N-diisopropylethylamine (0.10 mL, 0.574 mmol) was added, followed by 1-[bis(dimethylamino)methylene]-1H-1,2,3-triazolo[4,5-b]pyridinium 3-oxide hexafluorophosphate (0.098 g, 0.258 mmol) and the reaction mixture was stirred for 145 minutes and concentrated. Dichloromethane and methanol were added to the residue and it was purified via silica gel chromatography, eluting with (3:1 ethyl acetate:ethanol):hexanes (0:1 to 3:2) to give a material which was triturated/sonicated with ethyl acetate and the solids collected by filtration, air-dried, then dried under vacuum overnight to give 6-chloro-7-cyclopropyl-N-((1s,3s)-3-hydroxy-3-(trifluoromethyl)cyclobutyl)-1,8-naphthyridine-3-carboxamide (0.054 g, 0.140 mmol, 66.9% yield) as a cream-colored powder. $^1$H NMR (400 MHz, CD$_3$SOCD$_3$) δ 1.20-1.26 (m, 4H), 2.34-2.44 (m, 2H), 2.68-2.76 (m, 1H), 2.76-2.84 (m, 2H), 4.19 (sex, J=8 Hz, 1H), 6.71 (s, 1H), 8.69 (s, 1H), 8.81 (d, J=2 Hz, 1H), 9.23 (d, J=7 Hz, 1H), 9.37 (d, J=2 Hz, 1H); LC-MS (LC-ES) M+H=386.

Example 78

N—((S)-4,4-Dimethyl-2-oxopyrrolidin-3-yl)-7-((S)-2-methylazetidin-1-yl)-1,6-naphthyridine-3-carboxamide

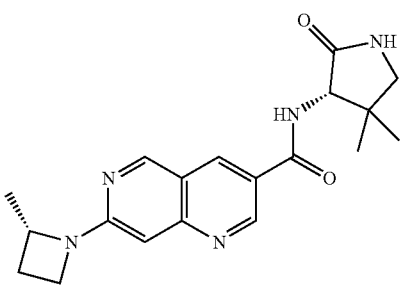

N,N-Diisopropylethylamine (0.169 ml, 0.970 mmol) was added to lithium (S)-7-(2-methylazetidin-1-yl)-1,6-naphthyridine-3-carboxylate (0.0604 g, 0.242 mmol, Intermediate 15) in dichloromethane (1.212 mL) at room temperature. Then, (S)-3-amino-4,4-dimethylpyrrolidin-2-one (0.047 g, 0.364 mmol, Intermediate 40) was added and the reaction mixture was stirred for five minutes. Then, n-propylphosphonic acid anhydride (0.289 mL, 0.485 mmol) was added and the reaction mixture was stirred for sixteen hours. The reaction mixture was concentrated. The resulting residue was purified by RP HPLC, eluting with acetonitrile:water with 0.1% ammonium hydroxide (5:95 to 100:0), then further purified by silica gel chromatography, eluting with methanol:ethyl acetate (0:1 to 1:1) to give N—((S)-4,4-dimethyl-2-oxopyrrolidin-3-yl)-7-((S)-2-methylazetidin-1-yl)-1,6-naphthyridine-3-carboxamide (0.0394 g, 0.106 mmol, 43.7% yield). $^1$H NMR (400 MHz, CD$_3$SOCD$_3$) δ 0.99 (s, 3H), 1.13 (s, 3H), 1.51 (d, J=6 Hz, 3H), 2.04 (p, J=8 Hz, 1H), 2.40-2.48 (m, 1H), 2.97 (dd, J=9, 2 Hz, 1H), 3.09 (d, J=9 Hz, 1H), 3.88 (q, J=8 Hz, 1H), 4.05 (dt, J=8, 4 Hz, 1H), 4.45 (h, J=8 Hz, 1H), 4.56 (d, J=9 Hz, 1H), 6.56 (s, 1H), 7.90 (br s, 1H), 8.71 (d, J=9 Hz, 1H), 8.81 (t, J=2 Hz, 1H), 9.06 (d, J=1 Hz, 1H), 9.23 (t, J=2 Hz, 1H); LC-MS (LC-ES) M+H=354.

Example 79

2-(Azetidin-1-yl)-N-((trans)-4-(2-hydroxypropan-2-yl)cyclohexyl)pyrido[2,3-d]pyrimidine-6-carboxamide

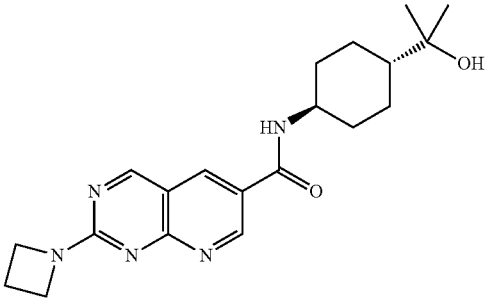 [SMILES: CC(C)(O)[C@H]1CC[C@H](NC(=O)c2cnc3nc(N4CCC4)ncc3c2)CC1]

To a thick, stirred suspension of lithium 2-(azetidin-1-yl)pyrido[2,3-d]pyrimidine-6-carboxylate (15 mg, 0.064 mmol, Intermediate 41) and 2-((trans)-4-aminocyclohexyl)propan-2-ol (15 mg, 0.095 mmol) in N,N-dimethylformamide (1 mL) was added N,N-diisopropylethylamine (0.055 mL, 0.318 mmol), followed by n-propylphosphonic acid anhydride (0.075 mL, 0.127 mmol). The mixture became homogeneous and was allowed to stir overnight. The mixture was loaded onto a pre-packed Celite® cartridge and purified by reverse phase chromatography, eluting with acetonitrile:water with 0.1% ammonium hydroxide (0:1 to 4:1) to give 2-(azetidin-1-yl)-N-((trans)-4-(2-hydroxypropan-2-yl)cyclohexyl)pyrido[2,3-d]pyrimidine-6-carboxamide (19.5 mg, 0.053 mmol, 83% yield) as a yellow solid. $^1$H NMR (400 MHz, CD$_3$SOCD$_3$) δ 1.04 (s, 6H), 1.04-1.24 (m, 3H), 1.29 (q, J=12 Hz, 2H), 1.83 (br d, J=12 Hz, 2H), 1.91 (br d, J=12 Hz, 2H), 2.37 (p, J=8 Hz, 2H), 3.66-3.78 (m, 1H), 4.21 (t, J=7 Hz, 4H), 8.41 (d, J=8 Hz, 1H), 8.67 (d, J=2 Hz, 1H), 9.25 (d, J=2 Hz, 1H), 9.29 (s, 1H); LC-MS (LC-ES) M+H=370.

Example 80

N-((trans)-4-(2-Hydroxypropan-2-yl)cyclohexyl)-2-methoxypyrido[2,3-d]pyrimidine-6-carboxamide

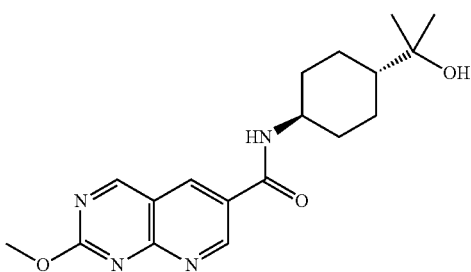 [SMILES: COc1ncc2cc(C(=O)N[C@H]3CC[C@H](C(C)(C)O)CC3)cnc2n1]

To a thick, stirred suspension of 2-methoxypyrido[2,3-d]pyrimidine-6-carboxylic acid (16 mg, 0.078 mmol, Intermediate 42) and 2-((trans)-4-aminocyclohexyl)propan-2-ol (15 mg, 0.095 mmol) in N,N-dimethylformamide (1 mL) was added N,N-diisopropylethylamine (0.050 mL, 0.286 mmol), followed by n-propylphosphonic acid anhydride (0.095 mL, 0.161 mmol). The mixture quickly became homogeneous and was allowed to stir overnight and concentrated. The mixture was purified by reverse phase chromatography, eluting with acetonitrile-water with 0.1% ammonium hydroxide (0:1 to 7:3) to give N-((trans)-4-(2-hydroxypropan-2-yl)cyclohexyl)-2-methoxypyrido[2,3-d]pyrimidine-6-carboxamide (10 mg, 0.029 mmol, 37% yield) as a white solid. $^1$H NMR (400 MHz, CD$_3$SOCD$_3$) δ 1.04 (s, 6H), 1.04-1.24 (m, 3H), 1.31 (q, J=12 Hz, 2H), 1.84 (br d, J=12 Hz, 2H), 1.94 (br d, J=11 Hz, 2H), 3.68-3.80 (m, 1H), 4.08 (s, 3H), 8.65 (d, J=8 Hz, 1H), 8.96 (d, J=2 Hz, 1H), 9.47 (d, J=2 Hz, 1H), 9.64 (s, 1H); LC-MS (LC-ES) M+H=345.

Example 81

2-Cyclopropyl-N-(trans-4-(2-hydroxypropan-2-yl)cyclohexyl)pyrido[2,3-d]pyrimidine-6-carboxamide

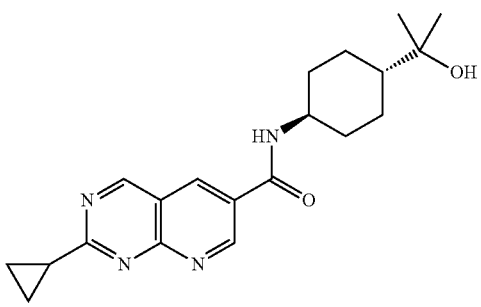

To a stirred solution of lithium 2-cyclopropylpyrido[2,3-d]pyrimidine-6-carboxylate (75 mg, 0.253 mmol maximum, Intermediate 43) and 2-((trans)-4-aminocyclohexyl)propan-2-ol (60 mg, 0.382 mmol) in N,N-dimethylformamide (2 mL) was added N,N-diisopropylethylamine (0.23 mL, 1.317 mmol), followed by n-propylphosphonic acid anhydride (0.30 mL, 0.509 mmol) and the reaction mixture was allowed to stir overnight. The reaction mixture was purified by reverse phase chromatography, eluting with acetonitrile-water with 0.1% ammonium hydroxide (0:1 to 4:1), then repurified by silica gel chromatography, eluting with ethyl acetate:ethanol (3:1):hexanes (1:9 to 3:1), then repurified by silica gel chromatography, eluting with methanol:dichloromethane (0:1 to 1:9) to give 2-cyclopropyl-N-(trans-4-(2-hydroxypropan-2-yl)cyclohexyl)pyrido[2,3-d]pyrimidine-6-carboxamide (18.5 mg, 0.52 mmol, 21% yield) as a white solid. $^1$H NMR (400 MHz, CD$_3$SOCD$_3$) δ 1.04 (s, 6H), 0.90-1.22 (m, 7H), 1.31 (q, J=12 Hz, 2H), 1.84 (br d, J=12 Hz, 2H), 1.94 (br d, J=10 Hz, 2H), 2.36-2.46 (m, 1H), 3.68-3.80 (m, 1H), 4.06 (s, 1H), 8.68 (d, J=8 Hz, 1H), 8.94 (d, J=2 Hz, 1H), 9.51 (d, J=2 Hz, 1H), 9.63 (s, 1H); LC-MS (LC-ES) M+H=355.

Example 82—Capsule Composition

An oral dosage form for administering the present invention is produced by filing a standard two piece hard gelatin capsule with the ingredients in the proportions shown in Table 1, below.

TABLE 1

| INGREDIENTS | AMOUNTS |
| --- | --- |
| 7-(3-Fluoroazetidin-1-yl)-N-(trans-4-(2-hydroxypropan-2-yl)cyclohexyl)-1,6-naphthyridine-3-carboxamide (Compound of Example 3) | 7 mg |
| Lactose | 53 mg |
| Talc | 16 mg |
| Magnesium Stearate | 4 mg |

Example 83—Injectable Parenteral Composition

An injectable form for administering the present invention is produced by stirring 1.7% by weight of 7-Cyclopropyl-N-((trans)-4-(2-hydroxypropan-2-yl)cyclohexyl)-1,6-naphthyridine-3-carboxamide (Compound of Example 10) in 10% by volume propylene glycol in water.

Example 84 Tablet Composition

The sucrose, calcium sulfate dihydrate and a H-PGDS inhibitor as shown in Table 2 below, are mixed and granulated in the proportions shown with a 10% gelatin solution. The wet granules are screened, dried, mixed with the starch, talc and stearic acid, screened and compressed into a tablet.

TABLE 2

| INGREDIENTS | AMOUNTS |
| --- | --- |
| (S)-7-(Azetidin-1-yl)-N-(2-oxopyrrolidin-3-yl)-1,6-naphthyridine-3-carboxamide (Compound of Example 20) | 12 mg |
| calcium sulfate dihydrate | 30 mg |
| sucrose | 4 mg |
| starch | 2 mg |
| talc | 1 mg |
| stearic acid | 0.5 mg |

Biological Assays

H-PGDS RapidFire™ High Throughput Mass Spectrometry Assay

The H-PGDS RapidFire™ mass spectrometric assay monitors conversion of prostaglandin H$_2$ (PGH$_2$) to prostaglandin D$_2$ (PGD$_2$) by haematopoietic prostaglandin D synthase (H-PGDS). In the assay format described here, the substrate (PGH$_2$) is formed in situ by the action of cyclooxygenase-2 on arachidonic acid. This first step is set up to be fast, and generates a burst of PGH$_2$ at ~10 µM. The PGH$_2$ is then further converted to PGD$_2$ by the H-PGDS enzyme. The reaction is quenched with tin (II) chloride in citric acid, which converts any remaining PGH$_2$ to the more stable PGF$_{2\alpha}$. Plates are then read on the RapidFire™ high throughput solid phase extraction system (Agilent) which incorporates a solid phase extraction step coupled to a triple quadrupole mass spectrometer (AB SCIEX). Relative levels of PGD$_2$ and PGF$_{2\alpha}$, which acts as a surrogate for substrate, are measured and a percent conversion calculated. Inhibitors are characterised as compounds which lower the conversion of PGH$_2$ to PGD$_2$.

Expression and Purification of H-PGDS Protein

Full length human H-PGDS cDNA (Invitrogen Ultimate ORF IOH13026) was amplified by PCR with the addition of a 5' 6-His tag and TEV protease cleavage site. The PCR product was digested with NdeI and XhoI and ligated into pET22b+ (Merck Novagen®). Expression was carried out in *E. coli* strain BL21 (DE3*) using auto-induction Overnight Express™ Instant TB medium (Merck Novagen®) supplemented with 1% glycerol. The culture was first grown at 37° C. and the temperature was reduced to 25° C. when OD600 reached 2.0. Cells were harvested by centrifugation after a further 18 hours. 10 g of *E. coli* cell pellet was suspended to a total volume of 80 mL in lysis buffer (20 mM Tris-Cl pH 7.5, 300 mM NaCl, 20 mM imidazole, 5 mM β-mercaptoethanol, 10% glycerol). 1 mg/mL protease inhibitors (Protease Inhibitor Cocktail Set III, Merck Calbiochem®) and 1 mg/mL lysozyme were added to the cell suspension. The suspension was then sonicated for 5 min (UltraSonic Processor VCX 750, Cole-Parmer Instrument Co.) with a micro probe (50% amplitude, 10 sec on/off) and then centrifuged at 100,000 g for 90 minutes (at 4° C.). The supernatant was loaded onto a Ni-NTA HiTrap column (5 mL, GE Healthcare, pre-equilibrated in lysis buffer). The column was washed with 10 column volumes of lysis buffer and eluted with lysis buffer containing 500 mM imidazole. The pooled protein peak fractions were concentrated using a 10 kDa centrifugal filter at 3500 g and 4° C. (Amicon Ultra-15 centrifugal filter unit with Ultracel-10 membrane from Millipore). Further purification of the concentrated protein was carried out using gel filtration chromatography on a HiLoad 26/600 Superdex 75 preparative grade column (GE Healthcare Life Sciences) using 50 mM Tris pH 7.5, 50 mM NaCl, 1 mM dithiothreitol, 1 mM MgCl$_2$. Fractions containing the protein were pooled, concentrated as described above, and stored at −80° C.

Expression and Purification of Cyclooxygenase-2 (COX-2) Protein

The full length human COX-2 gene (accession number L15326) was amplified by PCR to generate an EcoRI—HindIII fragment containing an in-frame FLAG tag. This was subcloned into pFastBac 1 (Invitrogen). The COX-2 FLAG plasmid was recombined into the baculovirus genome according to the BAC-to-BAC protocol described by Invitrogen. Transfection into *Spodoptera frugiperda* (Sf9) insect cells was performed using Cellfectin (Invitrogen), according to the manufacturer's protocol. Super Sf9 cells were cultured in EX420 media (SAFC Biosciences) to a density of approximately 1.5×106 cells/mL within a wave bioreactor. Recombinant virus was added at a Multiplicity of Infection (MOI) of 5 and the culture was allowed to continue for 3 days. Cells were harvested using a continuous feed centrifuge run at 2500 g at a rate of approximately 2 L/min with cooling. The resultant cell slurry was re-centrifuged in pots (2500 g, 20 min, 4° C.) and the cell paste was stored at −80° C. 342 g of cell paste was re-suspended to a final volume of 1600 mL in a buffer of 20 mM Tris-Cl pH 7.4, 150 mM NaCl, 0.1 mM EDTA, 1.3% w/v n-octyl-6-D-glucopyranoside containing 20 Complete EDTA-free Protease Inhibitor Cocktail tablets (Roche Applied Science). The suspension was sonicated in 500 mL batches for 8×5 seconds at 10 u amplitude with the medium tip of an MSE probe sonicator and subsequently incubated at 4° C. for 90 minutes with gentle stirring. The lysate was centrifuged at 12000 rpm for 45 minutes at 4° C. in a Sorvall SLA1500 rotor. The supernatant (1400 mL) was added to 420 mL of 20 mM Tris-Cl pH 7.4, 150 mM NaCl, 0.1 mM EDTA to reduce the concentration of n-octyl-6-D-glucopyranoside to 1% w/v. The diluted supernatant was incubated overnight at 4° C. on a roller with 150 mL of anti-FLAG M2 agarose affinity gel (Aldrich-Sigma) which had been pre-equilibrated with 20 mM Tris-Cl pH 7.4, 150 mM NaCl, 0.1 mM EDTA, 1% w/v n-octyl-β-D-glucopyranoside (purification buffer). The anti-Flag M2 agarose beads were pelleted by centrifugation in 500 mL conical Corning centrifuge pots at 2000 rpm for 10 min at 4° C. in a Sorvall RC3 swing-out rotor. The supernatant (unbound fraction) was discarded and the beads were re-suspended to half the original volume in purification buffer and re-centrifuged as above. The beads were then packed into a BioRad Econo Column (5 cm diameter) and washed with 1500 mL of purification buffer at 4° C. Bound proteins were eluted with 100 µg/mL triple FLAG peptide (Aldrich-Sigma) in purification buffer. Six fractions each of 0.5 column volume were collected. After each 0.5 column volume of purification buffer was added into the column the flow was held for 10 minutes before elution. Fractions containing COX-2 were pooled resulting in a protein concentration of ~1 mg/mL. The protein was further concentrated on Vivaspin 20 centrifugal concentrators (10 kDa cut-off) to 2.4 mg/mL and then stored at −80° C.

Test Compound Plate Preparation

Test compounds were diluted to 1 mM in DMSO and a 1:3, 11 point serial dilution was performed across a 384 well HiBase plate (Greiner Bio-one). 100 nL of this dilution series was then transferred into a 384 well v-base plate (Greiner Bio-one) using an Echo™ acoustic dispenser (Labcyte Inc) to create the assay plate. 100 nL of DMSO was added to each well in columns 6 and 18 for use as control columns.

Assay Method

5 µL of an enzyme solution containing 10 nM H-PGDS enzyme, 1.1 µM COX-2 enzyme and 2 mM reduced glutathione (Sigma-Aldrich), diluted in a buffer of 50 mM Tris-Cl pH 7.4, 10 mM MgCl$_2$ and 0.1% Pluronic F-127 (all Sigma-Aldrich) was added to each well of the plate except column 18 using a Multidrop Combi® dispenser (Thermo Fisher Scientific). 5 µL of enzyme solution without H-PGDS was added to each well in column 18 of the assay plate to generate 100% inhibition control wells.

Immediately after the addition of enzyme solution, 2.5 µL of a co-factor solution containing 4 µM Hemin (Sigma-Aldrich) diluted in buffer of 50 mM Tris-Cl pH 7.4 and 10 mM MgCl$_2$ (all Sigma-Aldrich), was added to each well using a Multidrop Combi® dispenser. 2.5 µL of substrate solution containing 80 µM arachidonic acid (Sigma-Aldrich) and 1 mM sodium hydroxide (Sigma-Aldrich) diluted in HPLC grade water (Sigma-Aldrich) was then added to each well using a Multidrop Combi® dispenser, to initiate the reaction.

The assay plates were incubated at room temperature for the duration of the linear phase of the reaction (usually 1 min 30 s 2 min, this timing should be checked on a regular basis). Precisely after this time, the reaction was quenched by the addition of 30 μL of quench solution containing 32.5 mM $SnCl_2$ (Sigma-Aldrich) in 200 mM citric acid (adjusted to pH 3.0 with 0.1 mM NaOH solution) to all wells using a Multidrop Combi® dispenser (Thermo Fisher Scientific). The $SnCl_2$ was initially prepared as a suspension at an equivalent of 600 mM in HPLC water (Sigma-Aldrich) and sufficient concentrated hydrochloric acid (Sigma-Aldrich) was added in small volumes until dissolved. The assay plates were centrifuged at 1000 rpm for 5 min prior to analysis.

The assay plates were analysed using a RapidFire™ high throughput solid phase extraction system (Agilent) coupled to a triple quadrupole mass spectrometer (AB SCIEX) to measure relative peak areas of $PGF_{2\alpha}$ and $PGD_2$ product. Peaks were integrated using the RapidFire™ integrator software before percentage conversion of substrate to $PGD_2$ product was calculated as shown below:

% Conversion=(($PGD_2$ peak area)/($PGD_2$ peak area+ $PGF_{2\alpha}$ peak area))×100.

Data were further analysed within Activitybase software (IDBS) using a four parameter curve fit of the following form:

$$y = \frac{a-d}{1 + (x/c)^b} + d$$

where a is the minimum, b is the Hill slope, c is the $IC_{50}$ and d is the maximum. Data are presented as the mean $pIC_{50}$.

TABLE 3

| Example # | Potency Range |
|---|---|
| 1 | * |
| 2 | * |
| 3 | *** |
| 4 | **** |
| 5 | **** |
| 6 | *** |
| 7 | *** |
| 8 | ** |
| 9 | **** |
| 10 | *** |
| 11 | *** |
| 12 | ** |
| 13 | **** |
| 14 | *** |
| 15 | *** |
| 16 | ** |
| 17 | ** |
| 18 | ** |
| 19 | *** |
| 20 | *** |
| 21 | **** |
| 22 | *** |
| 23 | ** |
| 24 | *** |
| 25 | **** |
| 26 | *** |
| 27 | **** |
| 28 | *** |
| 29 | *** |
| 30 | ** |
| 31 | ** |
| 32 | *** |
| 33 | ** |
| 34 | **** |
| 35 | *** |
| 36 | ** |
| 37 | *** |
| 38 | *** |
| 39 | *** |
| 40 | ** |
| 41 | ** |
| 42 | ** |
| 43 | ** |
| 44 | *** |
| 45 | ** |
| 46 | ** |
| 47 | *** |
| 48 | *** |
| 49 | *** |
| 50 | *** |
| 51 | *** |
| 52 | ** |
| 53 | ** |
| 54 | *** |
| 55 | ** |
| 56 | *** |
| 57 | *** |
| 58 | **** |
| 59 | **** |
| 60 | **** |
| 61 | **** |
| 62 | **** |
| 63 | **** |
| 64 | **** |
| 65 | **** |
| 66 | **** |
| 67 | **** |
| 68 | ** |
| 69 | *** |
| 70 | **** |
| 71 | **** |
| 72 | *** |
| 73 | **** |
| 74 | **** |
| 75 | *** |
| 76 | **** |
| 77 | **** |
| 78 | ** |
| 79 | *** |
| 80 | ** |
| 81 |  |

Legend
* = $pIC_{50}$ 5.0-5.9
** = $pIC_{50}$ 6.0-7.0,
*** = $pIC_{50}$ 7.1-8.0,
**** = $pIC_{50}$ > 8.0

In Vivo Assays for Functional Response to Muscle Injury

Under anesthesia, the right hind limb of a mouse is restrained at the knee and the foot attached to a motorized footplate/force transducer. Needle electrodes are inserted into the upper limb, either side of the sciatic nerve and a current sufficient to elicit a maximal muscle contraction is applied. Muscle tension is produced by moving the footplate to lengthen the plantarflexor muscles while the limb is under maximal stimulation. This is repeated 60 times to fatigue the muscles of the lower limb. Anesthesia, limb immobilization and limb stimulation are then repeated at regular intervals to measure maximal isometric force in the recovering limb. 7 to 9 animals are tested for each test condition.

Eccentric contraction-induced muscle fatigue in vehicle-treated male $C_{57}Bl/6N$ mice, 10-12 weeks of age, significantly reduced (~35%) maximal isometric torque 24 hours after injury and took ~5 weeks for full functional restoration.

In contrast, animals (PO) dosed with 3 and 10 mg/kg QD of the compound of Example 21 beginning 10 min prior to eccentric contraction challenge exhibited an acceleration in the kinetics of recovery. And 3 and 10 mg/kg QD of the compound of Example 21 also reduced the initial magnitude of the injury, as determined by isometric limb force 24 hours following protocol initiation. See FIG. 1.

In Vivo Mast Cell Activation

Mice were randomized by body weight into 8 groups (n=8): Vehicle (0.5% HPML with 0.1% Tween80)+phosphate buffered saline (PBS), vehicle+compound 48/80 (0.75 mg/ml) and compound 48/80+Example 21 at various doses ranging from 0.1 mg/kg to 10 mg/kg.

C57BL mice were dosed orally with vehicle, or Example 21 at 0.1, 0.3, 1, 3, & 10 mg/kg. One hour later, blood samples were withdrawn via tail snip for measurement of drug levels, and mice were then terminally anesthetized with 2% isoflurane and given an intraperitoneal injection of 0.2 mL PBS or compound 48/80 solution (0.75 mg/mL, Sigma), followed by gentle massage of the abdomen. Mice were kept under anesthesia for 7 minutes prior to euthanasia. The abdominal cavity was then opened with a small incision and filled with 2 mL PBS and the abdomen was gently massaged for several seconds. One mL of peritoneal lavage fluid was removed, spun down (12,000 rpm for 2 min) and the supernatant was kept on dry ice and later used for measurement of $PGD_2$ and $PGE_2$ levels.

$PGD_2$ and $PGE_2$ LC/MS/MS Assay

Samples were thawed at room temperature and vortex-mixed. Standard stock solutions of $PGD_2$ and $PGE_2$ (Cayman Chemical, Ann Arbor, Mich.) were prepared at a concentration of 1 mg/mL in methanol. The stock solutions were used to prepare an intermediate standard stock solution containing both $PGD_2$ and $PGE_2$ at a concentration of 0.1 mg/mL in methanol. The intermediate standard stock solution was further diluted with methanol to obtain intermediate standard solutions (1-10,000 ng/mL). Standards of $PGD_2$ and $PGE_2$ (0.05-50 ng/mL) were prepared from the intermediate standard solutions in phosphate buffered saline pH=7.4 (1X) (Thermo Fisher Scientific, Waltham, Mass.). Acetonitrile (75 µL) containing internal standards ($PGD_2$-d9 and $PGE_2$-d9) (Cayman Chemical, Ann Arbor, Mich.) at a concentration of 1 ng/mL was added to a 96-well plate. An aliquot (75 µL) of each sample and standard was pipetted into the plate then vortex-mixed at 1500 rpm for 1 minute and centrifuged at 1840×g for 20 minutes. The supernatant (100 µL) was transferred to a clean 96-well plate containing 50 µL water. The plate was vortex-mixed for 30 seconds at 1000 rpm and analyzed by LC/MS/MS.

The analytical system consisted of a CTC HTS PAL autoinjector (Leap, Carrboro, N.C.), an Agilent 1290 Infinity binary pump and thermostated column compartment (Agilent Technologies, Santa Clara, Calif.) and an AB Sciex QTRAP 5500 mass spectrometer (AB Sciex, Framingham, Mass.). Samples (20 µL) were injected onto a 100×2.1 mm, 1.8 micron, Waters Acquity UPLC HSS T3 column (Agilent, Santa Clara, Calif.) maintained at 50° C. The mobile phase consisted of water containing 0.1% formic acid (Solvent A) and 100% acetonitrile containing 0.1% formic acid (Solvent B). An isocratic gradient elution at 0.750 mL/minute was used with a composition of 65% A:35% B over 4.0 minutes. Total run time was 4.0 minutes. $PGD_2$ eluted at 2.57 min and $PGE_2$ at 2.22 min. The internal standards $PGD_2$-d9 eluted at 2.51 min and $PGE_2$-d9 at 2.16 min. The analytes were detected by multiple reaction monitoring (MRM) in negative mode using Turbolon spray with the transitions of m/z 351/271 amu for $PGD_2/PGE_2$ and m/z 360/280 amu for $PGD_2$-d9/$PGE_2$-d9. Data were acquired, analyzed and quantified using Analyst software version 1.6.2 (AB Sciex, Framingham, Mass.).

The calibration curves for the $PGD_2$ and $PGE_2$ samples ranged from 0.05 to 50 ng/mL (10 concentrations with an n=2/concentration) and 20/20 were within the acceptable accuracy limits of ±20% of the nominal concentration. For the $PGD_2$ calibration curve, the correlation coefficient was 0.9991 using a $1/x^2$ weighted linear regression analysis. For the $PGE_2$ calibration curve, the correlation coefficient was 0.9995 using a $1/x^2$ weighted linear regression analysis.

Figure 2:
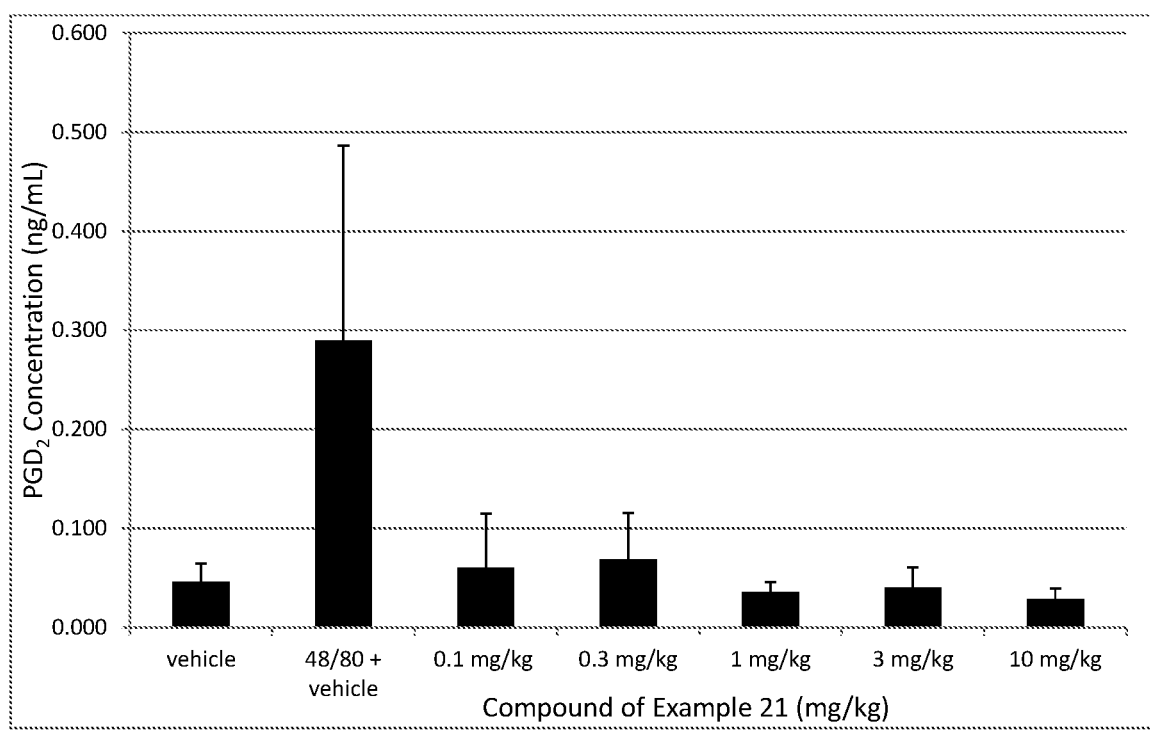
FIG. 2 depicts the effects of different doses of the H-PGDS inhibitor of Example 21 on prostaglandin $D_2$ generation following 48/80-induced mast cell degranulation in normal C57Bl6/N mice.

The effect of different doses of the H-PGDS inhibitor of Example 21 on prostaglandin $D_2$ generation following 48/80-induced mast cell degranulation in normal $C_{571316}/N$ mice is depicted in FIG. 2. Doses were administered ~1 hour prior to 48/80 (i.p.) injection, with peritoneal lavage collected 7-minutes afterwards. The data in FIG. 2 indicates that PGDS inhibition prevents 48/80-induced $PGD_2$ generation in lavage fluid of normal mice.

While the preferred embodiments of the invention are illustrated by the above, it is to be understood that the invention is not limited to the precise instructions herein disclosed and that the right to all modifications coming within the scope of the following claims is reserved.

The invention claimed is:

1. A compound according to Formula (I)

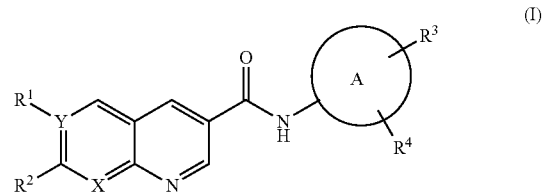

wherein:
either X is N and Y is C, X is CH and Y is N, or X is N and Y is N;
$R^1$ is absent or selected from hydrogen, fluoro, chloro, bromo, iodo, cyano, —$OR^5$, $C_{1-5}$alkyl, substituted $C_{1-5}$alkyl, $C_{3-5}$-cycloalkyl, substituted $C_{3-5}$ cycloalkyl, and heterocycloalkyl;
$R^2$ is selected from hydrogen, fluoro, chloro, bromo, iodo, cyano, —$OR^5$, —$SR^6$, $C_{1-5}$-alkyl, substituted $C_{1-5}$alkyl, $C_{3-5}$cycloalkyl, $C_{3-5}$cycloalkyl (substituted with from 1 to 4 substituents independently selected from: fluoro, chloro, bromo, iodo, $C_{1-4}$alkyloxy, —OH, $C_{1-4}$alkyl, oxo, —COOH, —$NO_2$, —$NH_2$ and —CN), amino, —$NHR^7$, —$NR^7R^8$, azetidinyl, and azetidinyl (substituted with from 1 to 4 substituents independently selected from: fluoro, chloro, bromo, iodo, $C_{1-4}$alkyloxy, —OH, $C_{1-4}$alkyl, oxo, —COOH, —$NO_2$, —$NH_2$ and CN), and heterocycloalkyl;
A is selected from:
$C_{4-7}$cycloalkyl,
a 4-, 5-, or 6-membered heterocycloalkyl containing one or two heteroatoms independently selected from O and N,
and
a 5-12 membered heteroaryl containing one or two heteroatoms, wherein at least one heteroatom is nitrogen and the second heteroatom, if present, is selected from N and S;

$R^3$ and $R^4$ are independently selected from:
hydrogen,
—OS(O)$_2$NH$_2$,
—S(O)$_2$CH$_3$,
—OH,
—C≡N,
F,
Cl,
Br,
I,
tetrazolyl,
methyl-tetrazolyl,
ethyl-tetrazolyl,
cycloalkyl,
cycloalkyl substituted with one or two substituents independently selected from; fluoro, —OH, —OCH$_3$, and —CH$_3$,
morpholinyl,
azetidinyl,
azetidinyl substituted with one or two substituents independently selected from: fluoro, chloro, bromo, iodo, —OH, —CF$_3$, and —CH$_3$,
pyridinyl,
pyridinyl substituted with —C≡N,
oxazolyl,
oxazolyl substituted with —C(O)OCH$_2$CH$_3$,
oxazolyl substituted with —C≡N,
—N(H)oxazolyl,
—N(H)oxazolyl substituted with —C(O)OCH$_2$CH$_3$,
—N(H)oxazolyl substituted with —C≡N,
—N(H)S(O)$_2$CH$_3$,
oxo,
C$_{1-8}$alkyl,
C$_{1-8}$alkyl substituted with from one to six substituents independently selected from: —OH, oxo, fluoro, chloro, bromo, iodo, C$_{1-4}$alkoxy, cycloalkyl, morpholinyl, methylpiperazinyl, —NH$_2$, —N(H)C$_{1-4}$alkyl, —N(H)C$_{1-4}$alkyl where alkyl is substituted with from 1 to 5 fluoro, —N(C$_{1-4}$alkyl)$_2$, and —N(C$_{1-4}$alkyl)$_2$ where the alkyls are independently substituted with from 1 to 7 fluoro,
C$_{1-8}$alkoxy,
C$_{1-8}$alkoxy substituted with from one to six substituents independently selected from: —OH, oxo, fluoro, chloro, bromo, iodo, C$_{1-4}$alkoxy, cycloalkyl, —NH$_2$, —N(H)C$_{1-4}$alkyl, —N(H)C$_{1-4}$alkyl where the alkyl is substituted with from 1 to 5 fluoro, —N(C$_{1-4}$alkyl)$_2$, —N(C$_{1-4}$alkyl)$_2$ where the alkyls are independently substituted with from 1 to 7 fluoro, —S(O)$_2$CH$_3$, —S(O)$_2$NH$_2$, and —S(O)$_2$N(H)C$_{1-4}$alkyl,
dimethylamine oxide,
N(C$_{1-6}$alkyl)$_2$, where each alkyl is optionally substituted with from one to six substituents independently selected from: —OH, oxo, fluoro, chloro, bromo, iodo, and —S(O)$_2$CH$_3$,
N(H)C$_{1-6}$alkyl, and
N(H)C$_{1-6}$alkyl substituted with from one to six substituents independently selected from: —OH, oxo, fluoro, chloro, bromo, iodo, CF$_3$, CHF$_2$, CH$_2$F, and —S(O)$_2$CH$_3$;
$R^5$ is selected from hydrogen, C$_{3-5}$cycloalkyl, C$_{3-5}$cycloalkyl (substituted with from 1 to 4 substituents independently selected from: fluoro, chloro, bromo, iodo, C$_{1-4}$alkyloxy, —OH, C$_{1-4}$alkyl, oxo, —COOH, —NO$_2$, —NH$_2$ and —CN), C$_{1-6}$alkyl, and C$_{1-6}$alkyl (substituted with from 1 to 6 substituents independently selected from: fluoro, chloro, bromo, iodo, C$_{1-4}$alkyloxy, —OH, C$_{1-4}$alkyl, oxo, —COOH, —NO$_2$, —NH$_2$ and —CN);
$R^6$ is selected from hydrogen, C$_{3-5}$cycloalkyl, C$_{3-5}$cycloalkyl (substituted with from 1 to 4 substituents independently selected from: fluoro, chloro, bromo, iodo, C$_{1-4}$alkyloxy, —OH, C$_{1-4}$alkyl, oxo, —COOH, —NO$_2$, —NH$_2$ and —CN), C$_{1-6}$alkyl, and C$_{1-6}$alkyl (substituted with from 1 to 6 substituents independently selected from: fluoro, chloro, bromo, iodo, C$_{1-4}$alkyloxy, —OH, C$_{1-4}$alkyl, oxo, —COOH, —NO$_2$, —NH$_2$ and —CN);
$R^7$ is selected from aryl, heteroaryl, C$_{3-6}$cycloalkyl, heterocycloalkyl, —OC$_{1-6}$alkyl, —OC$_{1-6}$alkyl (substituted with from 1 to 6 substituents independently selected from: fluoro, chloro, oxo, and —OH), —C$_{1-6}$alkyl, and C$_{1-6}$alkyl (substituted with from 1 to 6 substituents independently selected from: fluoro, chloro, oxo, —OH, —OC$_{1-6}$alkyl, —COOH, —NH$_2$, —NHcycloalkyl, and —CN); and
$R^8$ is selected from aryl, heteroaryl, C$_{3-6}$cycloalkyl, heterocycloalkyl, —OC$_{1-6}$alkyl, —OC$_{1-6}$alkyl (substituted with from 1 to 6 substituents independently selected from: fluoro, chloro, oxo, and —OH), —C$_{1-6}$alkyl, and C$_{1-6}$alkyl (substituted with from 1 to 6 substituents independently selected from: fluoro, chloro, oxo, —OH, —OC$_{1-6}$alkyl, —COOH, —NH$_2$, —NHcycloalkyl, and —CN);
provided $R^1$ is absent when Y is N, and
provided $R^2$, $R^3$ and $R^4$ are not all hydrogen;
or a pharmaceutically acceptable salt thereof.

2. A compound of claim 1 represented by the following Formula (II):

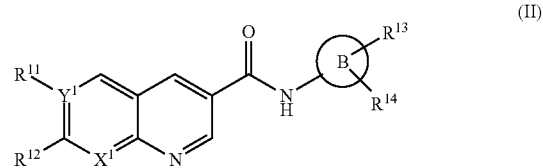

(II)

wherein:
either $X^1$ is N and $Y^1$ is C, $X^1$ is CH and $Y^1$ is N, or $X^1$ is N and $Y^1$ is N;
$R^{11}$ is absent or selected from hydrogen, fluoro, chloro, bromo, iodo, cyano, —OR$^{15}$, C$_{1-5}$alkyl, C$_{1-5}$alkyl substituted from 1 to 6 times by fluoro, C$_{3-5}$cycloalkyl, and C$_{3-5}$cycloalkyl substituted from 1 to 4 times by fluoro;
$R^{12}$ is selected from hydrogen, —OR$^{15}$, —SR$^{16}$, C$_{1-5}$alkyl, C$_{1-5}$alkyl substituted from 1 to 6 times by fluoro, C$_{3-5}$-cycloalkyl, C$_{3-5}$-cycloalkyl substituted from 1 to 4 times by fluoro, amino, —NHR$^{17}$, —NR$^{17}$R$^{18}$, azetidinyl, and azetidinyl (substituted with from 1 to 3 substituents independently selected from: fluoro, chloro, C$_{1-4}$alkyl, and C$_{1-4}$alkyl substituted from 1 to 4 times by fluoro);
B is selected from:
C$_{4-7}$cycloalkyl, and
a 4-, 5-, or 6-membered heterocycloalkyl containing one or two heteroatoms independently selected from O and N;
$R^{13}$ and $R^{14}$ are independently selected from:
hydrogen,
—OH,
—C≡N,
F,
Cl, C$_{3-6}$cycloalkyl,
C$_{3-6}$cycloalkyl substituted with one or two substituents independently selected from; fluoro, —OH, —OCH$_3$, and —CH$_3$,
azetidinyl,
azetidinyl substituted with one or two substituents independently selected from: fluoro, chloro, bromo, iodo, —OH, —CF$_3$, and —CH$_3$,
oxo,
C$_{1-6}$alkyl,
  C$_{1-6}$alkyl substituted with from one to six substituents independently selected from: —OH, oxo, fluoro, chloro, bromo, iodo, C$_{1-4}$alkoxy, cycloalkyl, morpholinyl, methylpiperazinyl, —NH$_2$, —N(H)C$_{1-4}$alkyl, —N(H)C$_{1-4}$alkyl where alkyl is substituted with from 1 to 5 fluoro, —N(C$_{1-4}$alkyl)$_2$, and —N(C$_{1-4}$alkyl)$_2$ where the alkyls are independently substituted with from 1 to 7 fluoro,
C$_{1-8}$alkoxy,
  C$_{1-8}$alkoxy substituted with from one to six substituents independently selected from: —OH, oxo, fluoro, chloro, bromo, iodo, C$_{1-4}$alkoxy, cycloalkyl, —NH$_2$, —N(H)C$_{1-4}$alkyl, —N(H)C$_{1-4}$alkyl where the alkyl is substituted with from 1 to 5 fluoro, —N(C$_{1-4}$alkyl)$_2$, —N(C$_{1-4}$alkyl)$_2$ where the alkyls are independently substituted with from 1 to 7 fluoro, —S(O)$_2$CH$_3$, —S(O)$_2$NH$_2$, and —S(O)$_2$N(H)C$_{1-4}$alkyl,
N(C$_{1-6}$alkyl)$_2$, where each alkyl is optionally substituted with from one to six substituents independently selected from: —OH, oxo, fluoro, chloro, bromo, iodo, and —S(O)$_2$CH$_3$,
N(H)C$_{1-6}$alkyl,
N(H)C$_{1-6}$alkyl substituted with from one to six substituents independently selected from: —OH, oxo, fluoro, chloro, bromo, iodo, and —S(O)$_2$CH$_3$;
R$^{15}$ is selected from: hydrogen, C$_{3-5}$cycloalkyl, C$_{3-5}$cycloalkyl substituted from 1 to 4 times by fluoro, C$_{1-5}$alkyl, and C$_{1-5}$alkyl substituted with from 1 to 6 substituents independently selected from: fluoro, chloro, C$_{1-3}$alkyloxy, —OH, oxo, —COOH, —NH$_2$ and —CN;
R$^{16}$ is selected from: hydrogen, C$_{3-5}$cycloalkyl, C$_{3-5}$cycloalkyl substituted from 1 to 4 times by fluoro, C$_{1-5}$alkyl, and C$_{1-5}$alkyl substituted with from 1 to 6 substituents independently selected from: fluoro, chloro, C$_{1-3}$alkyloxy, —OH, oxo, —COOH, —NH$_2$ and —CN;
R$^{17}$ is selected from: C$_{3-6}$cycloalkyl, —OC$_{1-6}$alkyl, —OC$_{1-6}$alkyl (substituted with from 1 to 6 substituents independently selected from: fluoro, chloro, oxo, and —OH), C$_{1-6}$alkyl, and C$_{1-6}$alkyl (substituted with from 1 to 6 substituents independently selected from: fluoro, chloro, oxo, and —OH);
and
R$^{18}$ is selected from: C$_{3-6}$cycloalkyl, —OC$_{1-6}$alkyl, —OC$_{1-6}$alkyl (substituted with from 1 to 6 substituents independently selected from: fluoro, chloro, oxo, and —OH), C$_{1-6}$alkyl, and C$_{1-6}$alkyl (substituted with from 1 to 6 substituents independently selected from: fluoro, chloro, oxo, and —OH);
provided R$^{11}$ is absent when Y$^1$ is N, and
provided R$^{12}$, R$^{13}$ and R$^{14}$ are not all hydrogen;
or a pharmaceutically acceptable salt thereof.

3. A compound of claim 1 represented by the following Formula (III):

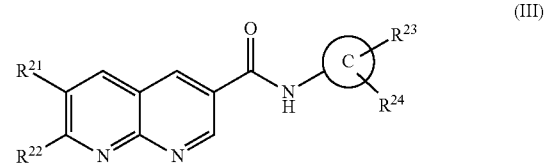

(III)

wherein:
  R$^{21}$ is selected from: hydrogen and chloro;
  R$^{22}$ is selected from hydrogen, —OR$^{25}$, —SR$^{26}$, cyclopropyl, cyclobutyl, —NHR$^{27}$, azetidinyl, and azetidinyl substituted with 1 or 2
substituents independently selected from: fluoro, and —CH$_3$;
where:
  R$^{25}$ is selected from hydrogen, C$_{1-2}$alkyl, and C$_{1-2}$alkyl substituted from 1 to 3 times by: fluoro,
  R$^{26}$ is selected from hydrogen, and C$_{1-2}$alkyl, and
  R$^{27}$ is selected from C$_{1-2}$alkyl, and C$_{1-2}$alkyl substituted from 1 to 3 times by fluoro;
C is selected from: cyclohexyl, cyclobutyl, pyrrolidinyl, piperidinyl, spiro[3.3]heptanyl, and azetidinyl; and
R$^{23}$ and R$^{24}$ are independently selected from:
  hydrogen,
  —OH,
  F,
  azetidinyl,
  azetidinyl substituted one or two times by fluoro,
  oxo,
  C$_{1-6}$alkyl,
    C$_{1-6}$alkyl substituted with from one to five substituents independently selected from: —OH, oxo, and fluoro,
  N(H)C$_{1-3}$alkyl, and
  N(H)C$_{1-3}$alkyl substituted with from one to five substituents independently selected from: —OH, and fluoro;
provided R$^{22}$, R$^{23}$ and R$^{24}$ are not all hydrogen;
or a pharmaceutically acceptable salt thereof.

4. A compound of claim 1 represented by the following Formula (V):

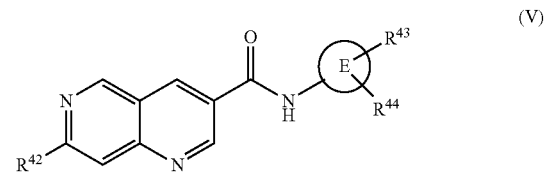

(V)

wherein:
  R$^{42}$ is selected from hydrogen, —OR$^{45}$, —SR$^{46}$, cyclopropyl, cyclobutyl, —NHR$^{47}$, azetidinyl, and azetidinyl substituted with 1 or 2
substituents independently selected from: fluoro, and —CH$_3$;
where:
  R$^{45}$ is selected from hydrogen, C$_{1-2}$alkyl, and C$_{1-2}$alkyl substituted from 1 to 3 times by: fluoro,
  R$^{46}$ is selected from hydrogen, and C$_{1-2}$alkyl, and
  R$^{47}$ is selected from C$_{1-2}$alkyl, and C$_{1-2}$alkyl substituted from 1 to 3 times by fluoro;
E is selected from: cyclohexyl, cyclobutyl, pyrrolidinyl, piperidinyl, spiro[3.3]heptanyl, and azetidinyl; and $R^{43}$ and $R^{44}$ are independently selected from:
hydrogen,
—OH,
F,
azetidinyl,
azetidinyl substituted one or two times by fluoro,
oxo,
$C_{1-6}$alkyl,
$C_{1-6}$alkyl substituted with from one to five substituents independently selected from: —OH, oxo, and fluoro,
$N(H)C_{1-3}$alkyl, and
$N(H)C_{1-3}$alkyl substituted with from one to five substituents independently selected from: —OH, and fluoro;
provided $R^{42}$, $R^{43}$ and $R^{44}$ are not all hydrogen;
or a pharmaceutically acceptable salt thereof.

5. A compound of claim 1 selected from:
N-(trans-4-(2-Hydroxypropan-2-yl)cyclohexyl)-1,6-naphthyridine-3-carboxamide;
N-(trans-4-(2-Hydroxypropan-2-yl)cyclohexyl)-1,8-naphthyridine-3-carboxamide;
7-(3-Fluoroazetidin-1-yl)-N-(trans-4-(2-hydroxypropan-2-yl)cyclohexyl)-1,6-naphthyridine-3-carboxamide;
7-(Azetidin-1-yl)-N-(trans-4-(2-hydroxypropan-2-yl)cyclohexyl)-1,6-naphthyridine-3-carboxamide;
7-(Azetidin-1-yl)-N-(trans-4-(2-hydroxypropan-2-yl)cyclohexyl)-1,8-naphthyridine-3-carboxamide;
7-(3-Fluoroazetidin-1-yl)-N-(trans-4-(2-hydroxypropan-2-yl)cyclohexyl)-1,8-naphthyridine-3-carboxamide;
N-(trans-4-(2-Hydroxypropan-2-yl)cyclohexyl)-7-(2-methylazetidin-1-yl)-1,8-naphthyridine-3-carboxamide;
N-(trans-4-(2-Hydroxypropan-2-yl)cyclohexyl)-7-((R)-2-methylazetidin-1-yl)-1,8-naphthyridine-3-carboxamide;
N-(trans-4-(2-Hydroxypropan-2-yl)cyclohexyl)-7-((S)-2-methylazetidin-1-yl)-1,8-naphthyridine-3-carboxamide;
7-Cyclopropyl-N-((trans)-4-(2-hydroxypropan-2-yl)cyclohexyl)-1,6-naphthyridine-3-carboxamide;
N-(trans-4-(2-Hydroxypropan-2-yl)cyclohexyl)-7-(2-methylazetidin-1-yl)-1,6-naphthyridine-3-carboxamide;
N-(trans-4-(2-Hydroxypropan-2-yl)cyclohexyl)-7-((R)-2-methylazetidin-1-yl)-1,6-naphthyridine-3-carboxamide;
N-(trans-4-(2-Hydroxypropan-2-yl)cyclohexyl)-7-((S)-2-methylazetidin-1-yl)-1,6-naphthyridine-3-carboxamide;
7-(Cyclopropylamino)-N-(trans-4-(2-hydroxypropan-2-yl)cyclohexyl)-1,6-naphthyridine-3-carboxamide;
7-(Azetidin-1-yl)-N-((1s,3s)-3-hydroxy-3-methyl cyclobutyl)-1,6-naphthyridine-3-carboxamide;
7-(2,2-Difluoroethyl)amino)-N-(trans-4-(2-hydroxypropan-2-yl)cyclohexyl)-1,8-naphthyridine-3-carboxamide;
N-(trans-4-(2-Hydroxypropan-2-yl)cyclohexyl)-7-(2,2,2-trifluoroethyl)amino)-1,8-naphthyridine-3-carboxamide;
7-(Azetidin-1-yl)-N-((1s,3s)-3-hydroxy-3-methylcyclobutyl)-1,8-naphthyridine-3-carboxamide;
(S)-7-(Azetidin-1-yl)-N-(2-oxopyrrolidin-3-yl)-1,8-naphthyridine-3-carboxamide;
(S)-7-(Azetidin-1-yl)-N-(2-oxopyrrolidin-3-yl)-1,6-naphthyridine-3-carboxamide;
7-Cyclopropyl-N-((trans)-4-(2-hydroxypropan-2-yl)cyclohexyl)-1,8-naphthyridine-3-carboxamide;
7-((S)-2-Methylazetidin-1-yl)-N—((S)-2-oxopyrrolidin-3-yl)-1,6-naphthyridine-3-carboxamide;
N-((1s,3R)-3-Hydroxy-3-methylcyclobutyl)-7-((S)-2-methylazetidin-1-yl)-1,6-naphthyridine-3-carboxamide;
(S)—N-(1-(2-Hydroxy-2-methylpropanoyl)piperidin-4-yl)-7-(2-methylazetidin-1-yl)-1,6-naphthyridine-3-carboxamide;
7-(Azetidin-1-yl)-6-chloro-N-(trans-4-(2-hydroxypropan-2-yl)cyclohexyl)-1,8-naphthyridine-3-carboxamide;
N-(trans-3-(2-Hydroxypropan-2-yl)cyclobutyl)-7-((S)-2-methylazetidin-1-yl)-1,6-naphthyridine-3-carboxamide;
6-Chloro-7-cyclopropyl-N-((trans)-4-(2-hydroxypropan-2-yl)cyclohexyl)-1,8-naphthyridine-3-carboxamide;
N-((3 S,4R)-4-Methyl-2-oxopyrrolidin-3-yl)-7-((S)-2-methylazetidin-1-yl)-1,6-naphthyridine-3-carboxamide;
(S)-7-Cyclopropyl-N-(2-oxopyrrolidin-3-yl)-1,6-naphthyridine-3-carboxamide;
7-Cyclopropyl-N-((1r,4-4-hydroxy-4-methylcyclohexyl)-1,6-naphthyridine-3-carboxamide;
7-Cyclopropyl-N-((1s,3s)-3-hydroxy-3-methylcyclobutyl)-1,6-naphthyridine-3-carboxamide;
7-Cyclopropyl-N-(trans-3-(2-hydroxypropan-2-yl)cyclobutyl)-1,6-naphthyridine-3-carboxamide;
7-Cyclopropyl-N-((1 r,4-4-(difluoromethyl)-4-hydroxycyclohexyl)-1,6-naphthyridine-3-carboxamide;
7-Cyclopropyl-N-(6-(2-hydroxypropan-2-yl)spiro[3.3]heptan-2-yl)-1,6-naphthyridine-3-carboxamide;
7-Cyclopropyl-N-(trans-4-(3-fluoroazetidin-1-yl)cyclohexyl)-1,6-naphthyridine-3-carboxamide;
7-Cyclopropyl-N-((1s,4 s)-4-(difluoromethyl)-4-hydroxycyclohexyl)-1,6-naphthyridine-3-carboxamide;
7-Cyclopropyl-N-((trans)-4-(((R)-1,1,1-trifluoro-3-hydroxypropan-2-yl)amino)cyclohexyl)-1,6-naphthyridine-3-carboxamide;
7-Cyclopropyl-N-(trans-4-(3,3-difluoroazetidin-1-yl)cyclohexyl)-1,6-naphthyridine-3-carboxamide;
7-Cyclopropyl-N-(trans-4-((1,1-difluoropropan-2-yl)amino)cyclohexyl)-1,6-naphthyridine-3-carboxamide;
7-Cyclopropyl-N-((1s,3s)-3-hydroxy-3-(trifluoromethyl)cyclobutyl)-1,6-naphthyridine-3-carboxamide;
7-Cyclopropyl-N-((1r,3r)-3-hydroxy-3-methylcyclobutyl)-1,6-naphthyridine-3-carboxamide;
7-Cyclopropyl-N-(cis-3-(((R)-1,1,1-trifluoro-3-hydroxypropan-2-yl)amino)cyclobutyl)-1,6-naphthyridine-3-carboxamide;
7-Cyclopropyl-N-(trans-3-(((R)-1,1,1-trifluoro-3-hydroxypropan-2-yl)amino)cyclobutyl)-1,6-naphthyridine-3-carboxamide;
(S)-7-Cyclopropyl-N-(2-oxopyrrolidin-3-yl)-1,8-naphthyridine-3-carboxamide;
7-Cyclopropyl-N-((1s,3s)-3-hydroxy-3-methylcyclobutyl)-1,8-naphthyridine-3-carboxamide;
7-Cyclopropyl-N-((1 r,3 r)-3-hydroxy-3-methylcyclobutyl)-1,8-naphthyridine-3-carboxamide;
7-Cyclopropyl-N-(trans-3-(2-hydroxypropan-2-yl)cyclobutyl)-1,8-naphthyridine-3-carboxamide;
7-Cyclopropyl-N-((1 r,4r)-4-hydroxy-4-methylcyclohexyl)-1,8-naphthyridine-3-carboxamide;
7-Cyclopropyl-N-(6-(2-hydroxypropan-2-yl)spiro[3.3]heptan-2-yl)-1,8-naphthyridine-3-carboxamide;
N-(trans-4-(2-Hydroxypropan-2-yl)cyclohexyl)-7-methoxy-1,8-naphthyridine-3-carboxamide;

N-(trans-4-(2-Hydroxypropan-2-yl)cyclohexyl)-7-methoxy-1,6-naphthyridine-3-carboxamide;
7-Cyclopropyl-N-((1 r,4-4-(difluoromethyl)-4-hydroxycyclohexyl)-1,8-naphthyridine-3-carboxamide;
7-Cyclopropyl-N-((1s,3s)-3-hydroxy-3-(trifluoromethyl)cyclobutyl)-1,8-naphthyridine-3-carboxamide;
7-Cyclopropyl-N-(trans-4-(3,3-difluoroazetidin-1-yl)cyclohexyl)-1,8-naphthyridine-3-carboxamide;
N-(trans-4-(2-Hydroxypropan-2-yl)cyclohexyl)-7-(2,2,2-trifluoroethoxy)-1,8-naphthyridine-3-carboxamide;
7-Ethoxy-N-(trans-4-(2-hydroxypropan-2-yl)cyclohexyl)-1,8-naphthyridine-3-carboxamide;
7-Cyclopropyl-N-(trans-4-((1,1-difluoropropan-2-yl)amino)cyclohexyl)-1,8-naphthyridine-3-carboxamide;
6-Chloro-N-(trans-4-(2-hydroxypropan-2-yl)cyclohexyl)-7-((S)-2-methylazetidin-1-yl)-1,8-naphthyridine-3-carboxamide;
6-Chloro-N-((1r,4 S)-4-hydroxy-4-methylcyclohexyl)-7-((S)-2-methylazetidin-1-yl)-1,8-naphthyridine-3-carboxamide;
6-Chloro-7-((S)-2-methylazetidin-1-yl)-N—((S)-2-oxopyrrolidin-3-yl)-1,8-naphthyridine-3-carboxamide;
(S)-6-Chloro-N-(6-(2-hydroxypropan-2-yl)spiro[3.3]heptan-2-yl)-7-(2-methylazetidin-1-yl)-1,8-naphthyridine-3-carboxamide;
6-Chloro-N-(trans-4-(2-hydroxypropan-2-yl)cyclohexyl)-7-methoxy-1,8-naphthyridine-3-carboxamide;
6-Chloro-N-((1s,3R)-3-hydroxy-3-methylcyclobutyl)-7-((S)-2-methylazetidin-1-yl)-1,8-naphthyridine-3-carboxamide;
6-Chloro-N-((1r,3S)-3-hydroxy-3-methylcyclobutyl)-7-((S)-2-methylazetidin-1-yl)-1,8-naphthyridine-3-carboxamide;
6-Chloro-N-(trans-3-(2-hydroxypropan-2-yl)cyclobutyl)-7-((S)-2-methylazetidin-1-yl)-1,8-naphthyridine-3-carboxamide;
6-Chloro-N-((1s,3R)-3-hydroxy-3-(trifluoromethyl)cyclobutyl)-74(S)-2-methylazetidin-1-yl)-1,8-naphthyridine-3-carboxamide;
6-Chloro-N-((3 S,4R)-4-methyl-2-oxopyrrolidin-3-yl)-7-((S)-2-methylazetidin-1-yl)-1,8-naphthyridine-3-carboxamide;
7-Cyclopropyl-N-(cis-3-(((R)-1,1,1-trifluoro-3-hydroxypropan-2-yl)amino)cyclobutyl)-1,8-naphthyridine-3-carboxamide;
7-Cyclopropyl-N-(trans-3-(((R)-1,1,1-trifluoro-3-hydroxypropan-2-yl)amino)cyclobutyl)-1,8-naphthyridine-3-carboxamide;
N-(trans-4-(2-Hydroxypropan-2-yl)cyclohexyl)-2-(methylthio)pyrido [2,3-d]pyrimidine-6-carboxamide;
(S)-6-Chloro-7-cyclopropyl-N-(2-oxopyrrolidin-3-yl)-1,8-naphthyridine-3-carboxamide;
7-Cyclobutyl-N-(trans-4-(2-hydroxypropan-2-yl)cyclohexyl)-1,8-naphthyridine-3-carboxamide;
6-Chloro-7-cyclopropyl-N-(trans-3-(2-hydroxypropan-2-yl)cyclobutyl)-1,8-naphthyridine-3-carboxamide;
6-Chloro-7-cyclopropyl-N-((1 r,4r)-4-hydroxy-4-methylcyclohexyl)-1,8-naphthyridine-3-carboxamide;
6-Chloro-7-cyclopropyl-N-((1r,3r)-3-hydroxy-3-methylcyclobutyl)-1,8-naphthyridine-3-carboxamide;
6-Chloro-7-cyclopropyl-N-((1s,3s)-3-hydroxy-3-methylcyclobutyl)-1,8-naphthyridine-3-carboxamide;
6-Chloro-7-cyclopropyl-N-((1s,3s)-3-hydroxy-3-(trifluoromethyl)cyclobutyl)-1,8-naphthyridine-3-carboxamide;
N—((S)-4,4-Dimethyl-2-oxopyrrolidin-3-yl)-7-((S)-2-methylazetidin-1-yl)-1,6-naphthyridine-3-carboxamide;
2-(Azetidin-1-yl)-N-((trans)-4-(2-hydroxypropan-2-yl)cyclohexyl)pyrido [2,3-d]pyrimidine-6-carboxamide;
N-((trans)-4-(2-Hydroxypropan-2-yl)cyclohexyl)-2-methoxypyrido [2,3-d]pyrimidine-6-carboxamide; and
2-Cyclopropyl-N-(trans-4-(2-hydroxypropan-2-yl)cyclohexyl)pyrido [2,3-d]pyrimidine-6-carboxamide;

or a pharmaceutically acceptable salt thereof.

6. A method for the treatment of disorders in which inhibition of H-PGDS is beneficial in a human comprising administering to the human in need thereof a therapeutically effective amount of a compound of Formula (I) or a pharmaceutically acceptable salt thereof according to claim 1.

7. A method for the treatment of conditions selected from asthma, aspirin-exacerbated respiratory disease (AERD), cough, chronic obstructive pulmonary disease, bronchoconstriction, allergic rhinitis, vasomotor rhinitis, rhinoconjunctivitis, allergic conjunctivitis, food allergy, hypersensitivity lung diseases, eosinophilic asthma, eosinophilic pneumonitis, eosinophilic oesophagitis, eosinophilic granuloma, delayed-type hypersensitivity disorders, atherosclerosis, rheumatoid arthritis, pancreatitis, gastritis, inflammatory bowel disease, osteoarthritis, psoriasis, sarcoidosis, pulmonary fibrosis, respiratory distress syndrome, bronchiolitis, sinusitis, cystic fibrosis, actinic keratosis, skin dysplasia, chronic urticaria, eczema, atopic dermatitis or contact dermatitis in a human comprising administering to the human in need thereof a therapeutically effective amount of a compound of Formula (I) or a pharmaceutically acceptable salt thereof according to claim 1.

8. A method for the treatment or prophylaxis of asthma in a human comprising administering to the human in need thereof a therapeutically effective amount of a compound of Formula (I) or a pharmaceutically acceptable salt thereof according to claim 1.

9. A method for the treatment of Duchenne muscular dystrophy in a human comprising administering to the human in need thereof a therapeutically effective amount of a compound of Formula (I) or a pharmaceutically acceptable salt thereof according to claim 1.

10. A pharmaceutical composition comprising a compound of Formula (I) or a pharmaceutically acceptable salt thereof according to claim 1 and one or more pharmaceutically acceptable carriers or excipients.

11. A pharmaceutical composition as claimed in claim 10 for the treatment of a disorder in which inhibition of H-PGDS is beneficial.

12. A pharmaceutical composition as claimed in claim 11 for the treatment or prophylaxis of asthma.

13. A pharmaceutical composition as claimed in claim 11 for the treatment or prophylaxis of Duchenne muscular dystrophy.

14. A method for the treatment of neuromuscular-related conditions selected from: Duchenne muscular dystrophy (MD), Becker MD, congenital MD (Fukuyama), Dreifuss MD, limb girdle MD, fascioscapulohumeral MD, myotonic dystrophy type I, myotonic dystrophy type II, congenital myotonia, polymyositis, dermatomyositis, amyotrophic lateral sclerosis (ALS), muscle injury, surgery-related muscle injury, traumatic muscle injury, work-related skeletal muscle injury, overtraining-related muscle injury, muscle damage due to knee replacement, muscle damage due to anterior cruciate ligament (ACL) repair, muscle damage due to plastic surgery, muscle damage due to hip replacement surgery, muscle damage due to joint replacement surgery, muscle damage due to tendon repair surgery, muscle damage due to surgical repair of rotator cuff disease, muscle damage due to surgical repair of rotator cuff injury, muscle damage due to amputation, battlefield muscle injuries, auto accident-related muscle injuries, sports-related muscle injuries, muscle lacerations, traumatic injury due to blunt force contusions, traumatic injury due to shrapnel wounds, muscle pulls or tears, traumatic injury due to burns, acute muscle strains, chronic muscle strains, weight or force stress muscle injuries, repetitive stress muscle injuries, avulsion muscle injury, compartment syndrome, muscle injuries caused by highly repetitive motions, muscle injuries caused by forceful motions, muscle injuries caused by awkward postures, muscle injuries caused by prolonged and forceful mechanical coupling between the body and an object, muscle injuries caused by vibration, muscle injuries due to unrepaired or under-repaired muscle damage coincident with a lack of recovery or lack of an increase of physical work capacity, exercise-induced delayed onset muscle soreness (DOMS), wound healing and disuse atrophy in a human comprising administering to the human in need thereof a therapeutically effective amount of a compound of Formula (I) or a pharmaceutically acceptable salt thereof according to claim 1.

15. A pharmaceutical composition as claimed in claim 10 for the treatment of neuromuscular-related conditions selected from: Duchenne muscular dystrophy (MD), Becker MD, congenital MD (Fukuyama), Dreifuss MD, limb girdle MD, fascioscapulohumeral MD, myotonic dystrophy type I, myotonic dystrophy type II, congenital myotonia, polymyositis, dermatomyositis, amyotrophic lateral sclerosis (ALS), muscle injury, surgery-related muscle injury, traumatic muscle injury, work-related skeletal muscle injury, overtraining-related muscle injury, muscle damage due to knee replacement, muscle damage due to anterior cruciate ligament (ACL) repair, muscle damage due to plastic surgery, muscle damage due to hip replacement surgery, muscle damage due to joint replacement surgery, muscle damage due to tendon repair surgery, muscle damage due to surgical repair of rotator cuff disease, muscle damage due to surgical repair of rotator cuff injury, muscle damage due to amputation, battlefield muscle injuries, auto accident-related muscle injuries, sports-related muscle injuries, muscle lacerations, traumatic injury due to blunt force contusions, traumatic injury due to shrapnel wounds, muscle pulls or tears, traumatic injury due to burns, acute muscle strains, chronic muscle strains, weight or force stress muscle injuries, repetitive stress muscle injuries, avulsion muscle injury, compartment syndrome, muscle injuries caused by highly repetitive motions, muscle injuries caused by forceful motions, muscle injuries caused by awkward postures, muscle injuries caused by prolonged and forceful mechanical coupling between the body and an object, muscle injuries caused by vibration, muscle injuries due to unrepaired or under-repaired muscle damage coincident with a lack of recovery or lack of an increase of physical work capacity, exercise-induced delayed onset muscle soreness (DOMS), wound healing and disuse atrophy.

16. A pharmaceutical composition comprising from 0.5 to 1,000 mg of a compound or pharmaceutically acceptable salt thereof as defined in claim 1, and from 0.5 to 1,000 mg of a pharmaceutically acceptable excipient.

\* \* \* \* \*